(12) United States Patent
Amino et al.

US011369670B2

(10) Patent No.: US 11,369,670 B2
(45) Date of Patent: Jun. 28, 2022

(54) MULTIPLE MALARIA PRE-ERYTHROCYTIC ANTIGENS AND THEIR USE IN THE ELICITATION OF A PROTECTIVE IMMUNE RESPONSE IN A HOST

(71) Applicants: INSTITUT PASTEUR, Paris (FR); CENTRE NATIONAL DE LA RECHERCHE SCIENTIFIQUE, Paris (FR)

(72) Inventors: Rogerio Amino, Bagneux (FR); Pierre Charneau, Paris (FR); Anne-Sophie Beignon, Paris (FR); Catherine Blanc, Chantilly (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 16/483,031

(22) PCT Filed: Feb. 1, 2018

(86) PCT No.: PCT/EP2018/052574
§ 371 (c)(1),
(2) Date: Aug. 1, 2019

(87) PCT Pub. No.: WO2018/141874
PCT Pub. Date: Aug. 9, 2018

(65) Prior Publication Data
US 2020/0121776 A1    Apr. 23, 2020

(30) Foreign Application Priority Data

Feb. 2, 2017 (EP) ..................... 17305122

(51) Int. Cl.
*A61K 39/015* (2006.01)
*C07K 14/445* (2006.01)
*C12N 7/00* (2006.01)
*C12N 15/86* (2006.01)
*A61K 39/00* (2006.01)

(52) U.S. Cl.
CPC .......... *A61K 39/015* (2013.01); *C07K 14/445* (2013.01); *C12N 7/00* (2013.01); *C12N 15/86* (2013.01); *A61K 2039/5256* (2013.01); *C12N 2740/15043* (2013.01)

(58) Field of Classification Search
None
See application file for complete search history.

(56) References Cited

PUBLICATIONS

Bauza et al. Infect Immun, Mar. 2016; 84(3):622-634.*
Speake et al. PLoS One Jul. 19, 2016;11(7):e0159449 doi:10.1371/journal.pone.0159449. eCollection 2016.*

* cited by examiner

*Primary Examiner* — Oluwatosin A Ogunbiyi
(74) *Attorney, Agent, or Firm* — Arrigo, Lee, Guttman & Mouta-Bellum LLP

(57) ABSTRACT

The invention relates to *Plasmodium* antigenic polypeptides identified through the use of a specifically devised functional immunization screening assay. In particular, the invention relates to antigenic polypeptides of malaria parasites wherein said antigenic polypeptides that exhibit a protective effect, especially that of eliciting a protective immune response in a host against challenge by *Plasmodium* sporozoites. The invention relates to a combination of compounds, comprising at least 2 distinct active ingredients wherein each active ingredient consists of an antigenic polypeptide of a *Plasmodium* parasite, a polynucleotide encoding the antigenic polypeptide, or a vector, in particular a viral vector, especially a lentiviral vector, expressing such antigenic polypeptide of a *Plasmodium* parasite, wherein one antigenic polypeptide is the circumsporozoite protein (CSP) or a polypeptidic derivative thereof and another antigenic polypeptide is either protein Ag40 (11-09) or protein Ag45 (11-10).

Figure 1:
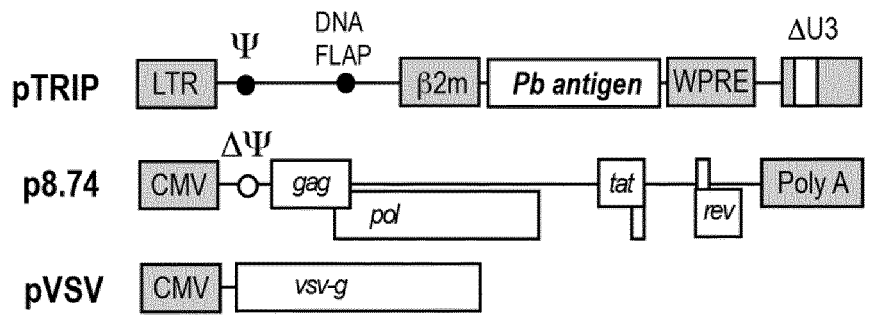

21 Claims, 13 Drawing Sheets
Specification includes a Sequence Listing.

Fig. 23

Plasmid map: pCMV-VSV-G NJco — 5158 nt

- bGH PA 4841...5068
- WPRE 4203...4801
- 86...877 Kan/neoR
- VSV NJco 2604...4157
- 1181...1809 ColE1 origin
- 1893...2509 CMVprom

MULTIPLE MALARIA PRE-ERYTHROCYTIC ANTIGENS AND THEIR USE IN THE ELICITATION OF A PROTECTIVE IMMUNE RESPONSE IN A HOST

The invention relates to *Plasmodium* antigenic polypeptides identified through the use of a specifically devised functional immunization screening assay. In particular, the invention relates to antigenic polypeptides of malaria parasites wherein said antigenic polypeptides that exhibit a protective effect, especially that of eliciting a protective immune response in a host against challenge by *Plasmodium* sporozoites. Such identified antigenic polypeptides may thus constitute active ingredients suitable for the design of a vaccine candidate, in particular a vaccine suitable for a human host. In the last 15 years, malaria control measures reduced by 48% the global deaths caused by this mosquito-borne disease. Despite this significant decrease in mortality, the WHO estimated ~215 millions of malaria clinical episodes, resulting in more than 400,000 deaths in 2015. Actual malaria control programs rely mainly on the use of insecticides and antiplasmodial medicines, but the emergence and spreading of resistant mosquitos and parasites put the efficacy of these interventions at risk[1]. In this scenario, an efficient malaria vaccine could be an important additional tool to control and eventually eliminate malaria.

Since the 60's, it has been known that multiple immunizations using, irradiated sporozoites can elicit sterile protection against malaria infection. However, during the last 50 years only a few protective antigens were identified, but none of them, individually or in combination, could match the robust protection induced by irradiated parasites.

The most advanced malaria vaccine, RTS,S (Mosquirix, GSK), targets the *Plasmodium falciparum* circumsporozoite protein (CSP), the major surface protein of sporozoites, the motile stage inoculated in the skin during an infective mosquito bite. This subunit vaccine reduced the clinical cases of malaria in African infants and children by 26-36%[2]. This partial protection is mainly associated with high titers of anti-CSP antibodies[3], and albeit significant, it is far from achieving the standards established by the WHO malaria vaccine road map, which preconizes the development of a vaccine with at least 75% of efficacy against clinical malaria, and ideally targeting morbidity, mortality and parasite transmission[4].

On the other hand, live irradiated sporozoites can invade but are arrested as early liver-stages inside hepatocytes, conferring sterile immunity against a homologous sporozoite challenge[5]. Unfortunately, technical and economical impediments associated with the production, storage and delivery of these live parasites still hinder their use for mass vaccination in poor tropical countries. This sterile protection seems to be mainly dependent on CD8+ T cells, since their depletion abolishes sterile immunity in several experimental models, however, the identity of the antigens conferring such robust protection is still elusive[6]. So far, the number of known protective antigens among the thousands of possible proteins expressed by pre-erythrocytic (PE) stages, sporozoite and the ensuing liver-stage, is extremely limited, and these antigens only confer weaker protection than CSP alone or in multi-antigenic formulations in human[7]. To date the attempts to identify new protective antigens from live attenuated sporozoites have not yielded suitable candidates, despite the screening of thousands of PE peptides, minigenes and genes[8-10].

The Antigenic Polypeptides Provided as Active Ingredients According to the Invention To identify critical protective antigens, the invention provides a lentiviral-based immunization screen designed to select plasmodial-conserved antigens capable of protecting susceptible mice against a stringent sporozoite challenge. Using this functional screen as illustrated in the examples the inventors identified 8 protective antigens, including the known vaccine candidates CSP and TRAP, out of 55 tested antigens. Notably, the inventors showed that a combination of 7 antigens sterile protected more than 85% (18/21) of challenged animals versus 5% (1/20) in the CSP immunized group. In addition, a core of 5 antigens was identified as the source of this potent sterile protection. These findings applied to antigens originating from *Plasmodium* parasites infecting human pave the way for the development of a multi-antigenic, second-generation PE malaria vaccine.

Accordingly, the invention relates to a combination of compounds, comprising at least 2 distinct active ingredients wherein each active ingredient consists of an antigenic polypeptide of a *Plasmodium* parasite, a polynucleotide encoding the antigenic polypeptide, or a vector, in particular a viral vector, especially a lentiviral vector wherein such vector expresses such antigenic polypeptide of a *Plasmodium* parasite, wherein one antigenic polypeptide is the circumsporozoite protein (CSP) or a polypeptidic derivative thereof and another antigenic polypeptide is either protein Ag40(11-09) having one of the sequences of SEQ ID No. 67, 68, 70, 71, 73 or 74 or a polypeptidic derivative thereof, or protein Ag45 (11-10) having one of the sequences of SEQ ID No. 76, 77, 79, 80, 82 or 83 or independently of each other, a polypeptidic derivatives thereof, provided each polypeptidic derivative keeps protective properties of the antigen from which it derives in the combination of compounds.

In a particular embodiment of the invention, the combination of compounds further comprises as active ingredients one or more antigenic polypeptide(s) of a *Plasmodium* parasite a polynucleotide encoding the antigenic polypeptide, or a vector, in particular a viral vector, especially a lentiviral vector, wherein such vector expresses such antigenic polypeptide(s) of a *Plasmodium* parasite, wherein each antigenic polypeptide is selected from the group of the thrombospondin related anonymous protein (TRAP), the inhibitor of cysteine protease (ICP), the metallopeptidase (Bergheilysin/Falcilysin), the GPI-anchored protein P113, the pore-forming like protein SPECT2, or respectively and independently of each other a polypeptidic derivative of any of these antigenic polypeptides wherein said polypeptidic derivative keeps protective properties of the antigen from which it derives in the combination of compounds of the invention. Accordingly, the combination of compounds comprises 2, 3, 4, 5, 6, 7 or 8 antigens or polynucleotides encoding such antigenic polypeptides, or a vector, in particular a viral vector, especially lentiviral vector(s), wherein such vector expresses the same or alternatively consists in a combination of 2, 3, 4, 5, 6, 7 or 8 antigens or viral, especially lentiviral vector(s) expressing the same. In a particular embodiment wherein the combination of compounds comprises at least 3 antigens or viral vector(s) expressing at least 3 antigens, these antigens at least consist of the circumsporozoite protein (CSP), protein Ag40(11-09) and/or protein Ag45 (11-10), or derivatives thereof as disclosed herein.

In a particular embodiment of the invention, a combination of compounds is a set of distinct active ingredients wherein each active ingredient consists of an antigenic polypeptide of a *Plasmodium* parasite or apolynucleotide encoding this antigenic polypeptide or the active ingredient consists of a vector, in particular a viral vector, especially a lentiviral vector, expressing such antigenic polypeptide of a *Plasmodium* parasite, wherein said set of active ingredients encompasses PE stage antigens of a *Plasmodium* parasite or viral vector, in particular lentiviral vectors expressing such PE stage antigens of a *Plasmodium* parasite which include the circumsporozoite protein (CSP), the thrombospondin related anonymous protein (TRAP), the inhibitor of cysteine protease (ICP), the metallopeptidase (Bergheilysin/Falcilysin), the GPI-anchored protein P113, the pore-forming like protein SPECT2, the protein Ag40 (11-09) having the sequence of SEQ ID No. 67, 68, 70, 71, 73, 74 or variants thereof, the protein Ag45 (11-10) having the sequence of SEQ ID No. 76, 77, 79, 80, 82 or 83 or a variant thereof, or a polypeptidic derivative of any of these antigenic polypeptides wherein said polypeptidic derivative that keeps protective properties of the antigen from which it derives in the combination of compounds of the invention.

Said ingredients whether they are provided for administration as polypeptides (native, recombinant or synthetic), polynucleotides such as RNA and DNA molecules (modified or not), or as vectors, in particular viral vectors, especially lentiviral vectors capable of expressing said antigenic polypeptides are described as distinct "active ingredients" which means according to the invention, that they individually elicit the immune response against the parasite or that they modulate and in particular broaden and/or enhance qualitatively or quantitatively the immune response which is raised in the host by other antigenic polypeptides provided by or expressed from the combination of compounds and hence have their own activity or effect on the qualitative and/or quantitative immune response elicited by the combination, in such a way that the combination of compounds elicits a protective response against a *Plasmodium* infection or against the parasite-induced condition or disease. In addition to being distinct active ingredients, the antigenic polypeptides defined herein are collectively an active ingredient to elicit a protective immune response against a *Plasmodium* infection or against the parasite-induced condition or disease.

The expression "vector" relates to biological or chemical entities suitable for the delivery of the polynucleotides encoding the antigenic polypeptides of the combination of compounds to the cells of the host administered with such vectors. Vectors are well known in the art and may be viral vectors such as adenovirus vectors, especially a vector prepared using Chimpanzee Adenovirus, vectors obtained using modified vaccinia virus, measles virus or Yellow Fever virus. Vectors obtained from these viruses are disclosed in the art in a way that would enable the person skilled in the art to prepare them. Alternatively and preferably lentivirus vectors are suitable for the preparation of the combination of compounds of the invention, in particular vectors obtained using lentiviruses which infect human, or depending on the host concerned by the protection sought lentiviruses that infect animals. Examples of such lentivivuses are disclosed herein and the invention relates in particular to the use of HIV vectors, especially HIV-1 vectors. Details for the construction for HIV-1 vectors are provided herein and each disclosed embodiment in this regard is intended to be provided for application with each embodiment relating to the disclosure of the antigenic polypeptides.

The expressions "*Plasmodium* parasite" and "malaria parasite" are used interchangeably in the present application. They designate every and all forms of the parasite that are associated with the various stages of the parasite cycle in the mammalian, especially human host, including in particular sporozoites, especially sporozoites inoculated in the host skin and present in the blood flow after inoculation, or sporozoites developing in the hepatocytes (liver-stages), merozoites, including especially merozoites produced in the hepatocytes and merozoites produced in the red-blood cells, or merozoites developing in the red-blood cells (blood-stages). These various forms of the parasite are characterized by multiple specific antigens many of which are well known and identified in the art and some of which are still unknown and to which no biological function has yet been assigned. The antigens can often be designated or classified in groups by reference to their expression according to the stage of the infection. *Plasmodium* parasites according to the present disclosure encompass parasites infecting human hosts and parasites infecting non-human mammals especially rodents and in particular mice. Accordingly, *Plasmodium falciparum*, *Plasmodium vivax*, *Plasmodium yoelii* and *Plasmodium berghei* are particular examples of these parasites. *Plasmodium cynomolgi* and *Plasmodium knowlesi* are primarily infectious for macaques, but can also cause human infection. By the expression "antigenic polypeptide", it is intended according to the present invention a polypeptide which may be a native antigen of a *Plasmodium* parasite, or expression product of a gene, codon-optimized or not, of a *Plasmodium* parasite, in particular of *P. berghei*, *P. cynomolgi* or of a *Plasmodium* parasite infecting humans such as *P. falciparum* or *P. vivax*. The application also relates to modified version of such antigenic polypeptides designated as "polypeptidic derivative thereof" which can be a fragment of the native antigen of the parasite and especially a truncated version of such native antigen or a modified version thereof as a result of post-translational modifications. A derivative polypeptide has an amino acid sequence which is sufficient to provide one or several epitope(s) and which keeps the protective properties leading to the protective activity of the antigenic polypeptide from which it derives and/or exhibits such protective properties when encompassed in the combination of compounds of the invention. the protective properties of the reference antigen may even be improved with the derivative. Various examples of derivatives of the antigenic disclosed herein are illustrated in the examples. In particular derivatives of Ag40 and Ag45 are provided (such as derivative 18-10 illustrated in the examples that has improved properties with respect to Ag45). It may accordingly have a length of at least about 4 amino acid for B epitopes or at least about 8 amino acid residues and in particular from about 8 to about 19 amino acid residues for sequential T epitopes. In a particular embodiment, the recombinant polynucleotide of the lentiviral vector encodes a fragment of an antigen of the malaria parasite, especially a fragment which results from the deletion of contiguous amino acid residues of the full-length (i.e., native) antigen, provided it keeps the capacity of the native antigen to elicit an immune response in a host. The polypeptidic derivative as defined hereabove should be considered an alternative to the recited antigenic polypeptide in any definitions or embodiments of the invention unless it appears irrelevant in the context of the disclosure.

The expressions "T-epitope" and "B-epitope" refer to antigenic determinants that are involved respectively in the adaptive immune response driven by T cells and in the immune response driven by B cells. In particular said T-epitopes and respectively B-epitopes elicit T cell, respectively B cell immune response when delivered to the host in suitable conditions. According to a particular embodiment the antigenic polypeptides targeted according to the invention and the polypeptide derivatives of these antigenic polypeptides comprise epitope(s) mediating CD8+ T cell response. In a particular embodiment, alternatively or cumulatively, the antigenic polypeptides of the invention and the polypeptide derivatives of these antigenic polypeptides comprise epitope(s) mediating an antibody response.

In a particular embodiment of the invention, the combination of compounds comprises, at least one, preferably at least two antigenic polypeptide(s) or when provided as a polynucleotide or as a recombinant vector, especially lentiviral vector the combination of compounds comprises at least one, preferably at least two recombinant polynucleotide(s) which encodes an antigenic polypeptide(s) wherein said antigenic polypeptide(s) is or encompasses the circumsporozoite protein (CSP) of a *Plasmodium* parasite selected from the group of *Plasmodium falciparum, Plasmodium malariae, Plasmodium vivax, Plasmodium ovale* or *Plasmodium knowlesi* and *Plasmodium berghei*, in particular the group of *Plasmodium falciparum* and *Plasmodium vivax*. It is especially a truncated version of the CSP and in particular a polypeptide devoid of the GPI anchoring motif of the CSP. In such combination of compounds, the additional polypeptide(s) or polynucleotide(s) contained in the viral, especially lentiviral vector(s) are also selected in the above disclosed groups of *Plasmodium* parasites.

In a particular embodiment of the combination of compounds of the invention, the active ingredients are provided as polynucleotides or as vectors, In particular lentiviral vectors expressing antigenic polypeptides are provided wherein the vectors have or comprise in their genome (vector genome) a recombinant polynucleotide which encodes at least a polypeptide of the CSP of *Plasmodium berghei* as illustrated in the examples or advantageously an orthologous sequence of *Plasmodium falciparum*, or *Plasmodium vivax* as disclosed or illustrated herein e.g., a polypeptide corresponding to a fragment of said CSP-antigen devoid of the GPI-anchoring motif (polypeptide derivative of CSP). Said GPI motif corresponds to the last 12 amino acid residues in the C-terminal part in the native amino acid sequence of the CSP antigen, In a particular embodiment of the invention, the combination of compounds comprises or consists in separate active ingredients or separate compositions of single or of multiple active ingredients. These active ingredients provided as separate compositions or packages in the combination may be used for separate administration to the host or to the contrary for combined administration.

In another particular embodiment of the invention, the combination of compounds comprises or consists in an admixture of all the active ingredients, otherwise stated consist in a single composition of said active ingredients.

Accordingly antigenic polypeptides disclosed herein may especially be provided as the expression product of a collection of vectors, in particular as a collection of lentiviral vectors, in particular HIV-1 based vectors, wherein each vector expresses one or a plurality of the antigenic polypeptides and the collection expresses all the antigenic polypeptides. This collection of vectors may be provided as a single composition for administration or as separate compositions for administration to the host simultaneously or separately in time.

When used together as a combination these antigenic polypeptides (especially when provided as vectors expressing the same) have proved suitable for the elicitation of a protective immune response, especially a sterile protection against stringent challenge of immunized non-human mammal with *Plasmodium* parasite from which the polypeptides originate. Accordingly the combination of compounds of the invention provides a response to the need for efficient alternative against *Plasmodium* infection by devising active ingredients which may be used for the elaboration of a vaccine candidate in human host.

Whatever its presentation as one or more compositions, the combination of compounds of the invention provides individual and collective active ingredients (as antigenic polypeptides or as vector particles especially lentiviral vector particles) which constitute collectively the qualitative composition for a dose of a candidate medicine product.

In a particular embodiment of the combination of compounds of the invention, the active ingredients consist of antigenic polypeptides of a human-infecting *Plasmodium* parasite or consist of lentiviral vector(s) expressing antigenic polypeptides of a human-infecting *Plasmodium* parasite, or consist in a mixture or an association of such antigenic polypeptides and viral vectors, especially lentiviral vectors, in particular wherein the *Plasmodium* parasite is *Plasmodium falciparum* or *Plasmodium vivax*.

In a particular embodiment of a specific combination of compounds according to the invention the circumsporozoite protein (CSP) is a representative of the worldwide distributed variants of the protein such as CSP VK210 (reference in GenBank: AAKM01000017.1 and protein ID XP_001613068) or CSP VK247 (reference in GenBank: GU339076.1 and Protein ID: ADB92545.1).

A specific combination of compounds according to the invention is characterized in that the active ingredients comprise or consist of the following antigens: circumsporozoite protein (CSP) characterized by the sequence of SEQ ID No. 11, 12, 14, 15, 17 or 18, the thrombospondin related anonymous protein (TRAP) characterized by the sequence of SEQ ID No. 20, 21, 23, 24, 26 or 27, the inhibitor of cysteine protease (ICP) characterized by the sequence of SEQ ID No. 29, 30, 32, 33, 35 or 36, the metallopeptidase (Bergheilysin/Falcilysin) characterized by the sequence of SEQ ID No. 38, 39, 41, 42, 44, 45, or 47, the GPI-anchored protein P113 characterized by the sequence of SEQ ID No. 58, 59, 61, 62, 64 or 65, the pore-forming like protein SPECT2 characterized by the sequence of SEQ ID No. 49, 50, 52, 53, 55 or 56, a protein Ag40(11-09) characterized by the sequence of SEQ ID No. 67, 68, 70, 71, 73, 74 or variants thereof, and a protein Ag45(11-10) characterized by the sequence of SEQ ID No. 76, 77, 79, 80, 82 or 83 or a variant thereof, or a polypeptidic derivative thereof which consists of an amino acid sequence with at least 86% of identity in amino acids, preferably at least 95% amino acid identity with the antigenic polypeptide from which it derives (*P. falciparum* or *P. vivax*) and which keeps the protective properties of the polypeptide from which it derives when it is encompassed within the combination od compounds of the invention. This threshold of 86% amino acid identity corresponds to the average identity of the three most dissimilar Pf protective antigens (PfCSP; Query cover of 100%, and amino acid identity of 86%) obtained when comparing the 8 *P. falciparum* pre-erythrocytic antigens of the reference strain known as 3D7 strain (the amino acid sequence of its relevant antigens are those provided herein) with sequences of other *P falciparum* parasites in the Genbank database identified above.

The specific polypeptidic derivatives thus disclosed are in particular obtained by substitution of amino acid residues in the original sequence of the *Plasmodium* antigen and/or by point mutations (such as substitution, insertion or deletion) or deletion(s) of short sequence(s) in said original sequence, to the extent that the derived polypeptide keeps essentially the immunogenic properties of the polypeptide from which it derives. Derivatives can thus be illustrated by the polypeptides including in their sequence residues originating from the polynucleotide construct from which they are obtained such as amino acid residues resulting from the presence of a Kozak sequence in the polynucleotide. Other derivatives may be obtained by conservative substitution of amino acid residue(s), especially amino acid substitution of less than 20% in particular less than 15% or less than 5%, in particular less than 3% or less than 2% of the original amino acid residues of the sequence of the antigen. Without considering the optional addition of functional amino acid sequence(s) to the natural or mutated ORF (Open Reading Frame) of the antigenic polypeptide, such derivatives obtained by substitution, in particular conservative substitutions of amino acid residues, have in particular the same length as the original sequence from which they derive. Alternatively, when the derivative polypeptide has an ORF which consists in a mutant by deletion or by addition with respect to the original ORF, the length of the mutated ORF determined in respect of the number of amino acid residues in the expressed polypeptide derivative is advantageously at least 95% of the length of the original sequence, preferably at least 97%; 98% or 99% identical to the original sequence.

In a particular embodiment of the combination of compounds wherein the active ingredients comprise or consist of human lentiviral vector(s) expressing the antigenic polypeptides or polypeptidic derivatives thereof, in particular HIV-1 lentiviral vector(s), wherein the antigenic polypeptides or polypeptidic derivatives thereof are expressed:
  either individually from separate vectors and/or,
  from one or more vectors wherein at least one vector expresses more than one antigenic polypeptide or polypeptide derivatives thereof.

In a particular embodiment of such combination of compounds wherein the active ingredients are lentiviral vectors, especially HIV-1 based vectors, each lentiviral vector is a replication-incompetent pseudotyped lentiviral vector, in particular a replication-incompetent pseudotyped HIV-1 lentiviral vector, wherein said vector contains a genome comprising a mammal codon-optimized synthetic nucleic acid, in particular a human-codon optimized synthetic nucleic acid, wherein said synthetic nucleic acid encodes the antigenic polypeptide(s) of a *Plasmodium* parasite infecting a mammal, in particular a human host, or a polypeptidic derivative thereof. The malaria parasite may be in particular *Plasmodium falciparum, Plasmodium vivax, P. knowlesi, P cynomolgi, P malariae, P ovale*.

Use of codon-optimized sequences in the genome of the vector particles allows in particular strong expression of the antigenic polypeptide in the cells of the host administered with the vector, especially by improving mRNA stability or reducing secondary structures. In addition the expressed antigenic polypeptide undergoes post translational modifications which are suitable for processing of the antigenic polypeptide in the cells of the host, in particular by modifying translation modification sites (such as glycosylation sites) in the encoded polypeptide. Codon optimization tools are well known in the art, including algorithms and services such as those made available by GeneArt (Life technologies-USA) and DNA2.0 (Menlo Park, Calif.—USA). In a particular embodiment codon-optimization is carried out on the ORF sequence encoding the antigenic polypeptide or its derivative and the optimization is carried out prior to the introduction of the sequence encoding the ORF into the plasmid intended for the preparation of the vector genome.

In another embodiment additional sequences of the vector genome are also codon-optimized.

The active ingredients consisting of the viral vectors may be integrative pseudotyped lentiviral vectors, especially replication-incompetent integrative pseudotyped lentiviral vectors, in particular a HIV-1 vector. Such lentiviral vectors may in addition contain a genome comprising a mammal-codon optimized synthetic nucleic acid, in particular a human-codon optimized synthetic nucleic acid, wherein said synthetic nucleic acid encodes the antigenic polypeptide(s) of a *Plasmodium* parasite infecting a mammal such as disclosed herein, in particular a parasite infecting a human host, or a polypeptidic derivative thereof as disclosed herein.

Alternatively the lentiviral vector and in particular the HIV-1 based vector may be a non-integrative replication-incompetent pseudotyped lentiviral vector.

A particular embodiment of a lentiviral vector suitable to achieve the invention relates to a lentiviral vector whose genome is obtained from the pTRIP vector plasmid wherein the *Plasmodium* synthetic nucleic acid encoding the antigenic polypeptide or polypeptidic derivative thereof has been cloned under control of a promoter functional in mammalian cells, in particular the human beta-2 microglobulin promoter, and optionally under the control of post-transcriptional regulatory element of the woodchuck hepatitis virus (WPRE).

In a further embodiment of the invention, the lentiviral vector expressing the antigenic polypeptide(s) according to the features herein described is pseudotyped with the glycoprotein G from a Vesicular Stomatitis Virus (V-SVG) of Indiana or of New-Jersey serotype.

The particular features of such lentiviral vectors will be further discussed in detail below.

The antigenic polypeptides encompassed in the combination of compounds of the invention may advantageously be expressed from nucleic acid molecules characterized by the following sequences, and in particular are expressed from mammalian codon-optimized synthetic nucleic acids:
  SEQ ID No. 10 for CSP of *P. berghei*, SEQ ID No. 19 for TRAP of *P. berghei*, SEQ ID No. 28 for ICP of *P. berghei*, SEQ ID No. 37 for Falcilysin of *P. berghei*, SEQ ID No. 57 for GPI-anchored protein P113 of *P. berghei*, SEQ ID No. 48 for pore-forming like protein SPECT2 of *P. berghei*, SEQ ID No. 66 for protein Ag40 11-09 of *P. berghei*, and SEQ ID No. 75 for protein Ag45 11-10 of *P. berghei*, or,
  SEQ ID No. 13 for CSP of *P. falciparum*, SEQ ID No. 22 for TRAP of *P. falciparum*, SEQ ID No. 31 for ICP of *P. falciparum*, SEQ ID No. 40 for Falcilysin of *P. falciparum*, SEQ ID No. 51 for pore-forming like protein SPECT2 of *P. falciparum*, SEQ ID No. 60 for GPI-anchored protein P113 of *P. falciparum*, SEQ ID No. 69 for protein 11-09 of *P. falciparum*, and SEQ ID No. 78 for protein 11-10 of *P. falciparum* or,
  SEQ ID No. 16 for CSP of *P. vivax*, SEQ ID No. 25 for TRAP of *P. vivax*, SEQ ID No. 34 for ICP of *P. vivax*, SEQ ID No. 43 for Falcilysin of *P. vivax*, SEQ ID No. 54 for pore-forming like protein SPECT2 of *P. vivax*, SEQ ID No. 63 for GPI-anchored protein P113 of *P. vivax*, SEQ ID No. 72 for protein 11-09 of *P. vivax*, and SEQ ID No. 81 for protein 11-10 of *P. vivax*.

Codon optimization of the polynucleotide may influence post translational modifications of the encoded polypeptide, in particular when it is expressed in mammalian cells and therefore enables the expression of polypeptides which harbor structural features which distinguish over those of the polypeptide encoded by the corresponding non-optimized sequence (Mauro V. P. and Chappell S. A. Trends Mol Med-2014 November; 20(11): 604-613).

Similarly the lentiviral vectors expressing the antigenic polypeptides in the combination of compounds may advantageously contain in their genome nucleic acid molecules which are mammalian codon-optimized synthetic nucleic acids characterized by the following sequences:

SEQ ID No. 10 for CSP of *P. berghei*, SEQ ID No. 19 for TRAP of *P. berghei*, SEQ ID No. 28 for ICP of *P. berghei*, SEQ ID No. 37 for Falcilysin of *P. berghei*, SEQ ID No. 57 for GPI-anchored protein P113 of *P. berghei*, SEQ ID No. 48 for pore-forming like protein SPECT2 of *P. berghei*, SEQ ID No. 66 for protein Ag40 11-09 of *P. berghei*, and SEQ ID No. 75 for protein Ag45 11-10 of *P. berghei*, or, SEQ ID No. 13 for CSP of *P. falciparum*, SEQ ID No. 22 for TRAP of *P. falciparum*, SEQ ID No. 31 for ICP of *P. falciparum*, SEQ ID No. 40 for Falcilysin of *P. falciparum*, SEQ ID No. 51 for pore-forming like protein SPECT2 of *P. falciparum*, SEQ ID No. 60 for GPI-anchored protein P113 of *P. falciparum*, SEQ ID No. 69 for protein 11-09 of *P. falciparum*, and SEQ ID No. 78 for protein 11-10 of *P. falciparum* or, SEQ ID No. 16 for CSP of *P. vivax*, SEQ ID No. 25 for TRAP of *P. vivax*, SEQ ID No. 34 for ICP of *P. vivax*, SEQ ID No. 43 for Falcilysin of *P. vivax*, SEQ ID No. 54 for pore-forming like protein SPECT2 of *P. vivax*, SEQ ID No. 63 for GPI-anchored protein P113 of *P. vivax*, SEQ ID No. 72 for protein 11-09 of *P. vivax*, and SEQ ID No. 81 for protein 11-10 of *P. vivax*.

The invention also relates to a formulation suitable for administration to a mammalian host comprising a combination of compounds according to any one of the definitions provided herein as active ingredient for protection against a *Plasmodium* infection or against the parasite-induced condition or disease, together with excipient(s) suitable for administration to a host in need thereof, in particular a human host.

In another aspect of the invention the combination of compounds of the invention or the formulation comprising the same is for use in the protective immunisation against malaria parasite infection or against parasite-induced condition or disease, in a mammalian host, especially a human host, optionally in association with an appropriate delivery vehicle and optionally with an adjuvant component and/or with an immunostimulant component.

Accordingly, the combination of compounds in particular lentiviral vector particles of the invention, when administered to a host in needs thereof, especially to a mammalian in particular to a human host, elicits an immune response, encompassing activation of naïve lymphocytes and generation of effector T-cell response and generation of immune memory antigen-specific T-cell response against antigen(s) of the malaria parasite. The immune response may additionally involve a humoral response against antigenic polypeptides delivered to or expressed in the host following administration of the combination of compounds. The immune response may either prevent the infection by the malaria parasite when such parasite is inoculated as sporozoite to the host or may prevent the onset or the development of a pathological state resulting from inoculation of malaria parasite in the form of sporozoite or prevent the onset or the development of the consequences of the generation of further forms of said parasite such a merozoite forms.

Accordingly, the active ingredients of the combination of compounds of the invention are suitable for the elicitation of a protective immune response against the parasite infection or against the parasite-induced disease or condition. Such response enables in particular, control or inhibition of the onset of the pathology caused by inoculation of the parasite or by the induction of the exo-erythrocytic i.e., hepatic, stage of the cycle of the malaria parasite and in an advantageous embodiment this response is suitable to prevent, alleviate or inhibit the onset or development of the erythrocytic stage of said parasite. Advantageously, it has been observed that the combination of compounds of the invention especially when the active ingredients are provided as lentiviral vector particles used in a single administration regimen or in a prime-boost regimen of administration enable the development of a protective immunity and especially enable a sterilizing protection against the malaria parasite-induced pathology. Such a sterilizing protection may result from controlling the consequences of the infection at the stage of liver infection, if not before, in the cycle of the parasite. In a particular embodiment of the invention, the combination of compounds, especially when the active ingredients are provided as lentiviral vector(s) is a suspension formulated with a suitable administration vehicle for administration to the host. Physiologically acceptable vehicles may be chosen with respect to the administration route of the immunization composition. In a preferred embodiment administration may be carried out by injection, in particular intramuscularly or, for children by intranasal administration or topical skin application.

A combination of compounds of the invention is used for protective immunisation against malaria parasite infection or against parasite-induced disease or condition in a mammalian host, especially in a human host, said use involving an immunisation pattern comprising administering an effective amount of the active ingredients to elicit the cellular and/or humoral immune response of the host, possibly as a prime and where appropriate later in time administering an effective amount of said active ingredients to boost the cellular immune response of the host, and optionally repeating (once or several times) said administration step for boosting, wherein if the active ingredients are provided as the lentiviral particles administered in each of the priming or boosting steps they are pseudotyped with distinct pseudotyping envelope protein(s) which do not cross-neutralise with each other, and wherein said priming and boosting steps are separated in time by at least 6 weeks, in particular by at least 8 weeks. Details on the administration regimen will be discussed further below.

The combination of compounds of the invention especially as lentiviral vector is especially used in a particular embodiment for the protective immunization against malaria parasite infection or against parasite-induced pathology in mammalian, host, especially in a human host to obtain at least a cellular immune response (T-cell immune response), particularly a CD8-mediated cellular immune response or a CD4-mediated cellular immune response i.e., an immune response which is mediated by activated cells harbouring CD8 or CD4 receptors, preferably Cytotoxic T lymphocytes (CTL) and memory T cell response are advantageously targeted when defining the immunization regimen of the lentiviral particles of the invention.

The immune response can also involve a humoral response i.e., antibodies, elicited by said compounds, produced against said at least one antigenic polypeptide. In a particular embodiment, said humoral response is a protective humoral response. The protective humoral response results mainly in maturated antibodies, having a high affinity for their antigen, such as IgG or IgM. In a particular aspect, the protective humoral response is T-cell dependent. In a particular embodiment, the protective humoral response induces the production of neutralizing antibodies.

In a particular embodiment of the invention, the combination of compounds of the invention especially when the active ingredients are lentiviral vectors, even when used in a form which has defective integrase, is able to elicit an early immune response. The expression "early immune response" refers to a protective immune response (protection against the parasite or against the parasite-induced pathology) that is conferred within about one week after the administration of the product.

In another particularly advantageous embodiment, the immune response conferred by the combination of compounds of the invention especially as lentiviral particles is a long-lasting immune response i.e., said immune response encompasses memory cells response and in particular central memory cells response; in a particular embodiment it can be still detected at least several months.

When the immune response includes a humoral response, the long-lasting response can be shown by the detection of specific antibodies, by any suitable methods such as ELISA, immunofluorescence (IFA), focus reduction neutralization tests (FRNT), immunoprecipitation, or Western blotting.

According to a particular aspect of the use of the combination of compounds of the invention, the active ingredients are designed to enable performing a prime-boost administration in a host in need thereof, where the first administration step elicits an immune, especially cellular, immune response and the later administration step(s) boost(s) the immune reaction including the cellular immune response. For each step of administration, it is preferred that the pseudotyping envelope protein(s) of the vector particles is(are) different from the one used in the other step(s), especially originate from different viruses, in particular different VSVs. In the prime-boost regimen, the administered combination of compounds of each step comprises lentiviral vectors as defined herein which collectively express all the antigenic polypeptides. Accordingly, combinations of compounds may be provided to perform the prime-boost regimen which comprise compounds that are distinct lentiviral particles at least due to the difference in their pseudotyping envelope proteins.

Accordingly, when a prime-boost regimen is selected, combinations of compounds containing said lentiviral vectors can be provided in separate packages or can be presented in a common package for a separate use thereof.

Therefore, the notice included in the packages and comprising the directions for use, may indicate the sequence order for the administration of the combinations of compounds and the time slot for their administration, for priming and subsequently boosting an immune reaction in a host.

In accordance with the invention when the combination of compound is used in a prime-boost regimen, a first combination of compounds is provided which contains lentiviral vector particles pseudotyped with a first determined pseudotyping envelope G protein obtained from the VSV, strain New-Jersey, and a second combination of compounds is provided which contains lentiviral viral vector particles pseudotyped with a second determined pseudotyping envelope G protein obtained from a VSV, strain Indiana. The order of use in the prime-boost regimen of the first and second combinations thus described may alternatively be inversed. Thus, the lentiviral vector particles contained in the separate compounds of the combinations of the invention when intended for use in a prime-boost regiment are distinct from each other, at least due to the particular pseudotyping envelope protein(s) used for pseudotyping the vector particles.

In the examples which follow where mice models have been treated according to the prime-boost regimen with lentiviral vector particles of the invention, it has been shown by the inventors that mice immunized according to such a regimen and challenged after the last immunization step exhibit a sterile protection for a significant proportion of the vaccinated mice (more than 80%) which illustrates that the combination of compounds of the invention elicit an effective protection in a host, and would therefore constitute a suitable candidate vaccine for immunization especially in a human host. The invention relates, in a particular embodiment, to the combination of compounds of the invention especially as lentiviral vector particles as defined herein, for the protective immunization against malaria parasite infection or against parasite-induced pathology in a mammalian host, especially in a human host, in a dosage regimen comprising separately provided active ingredients of said combination of compounds wherein the dose of the active ingredients intended for priming and boosting the cellular immune response is a moderate dose and the dose intended for boosting the cellular immune response is higher than the dose for priming.

Accordingly, the dose of lentiviral vectors intended for priming and boosting the cellular immune response which is used in the administration pattern, comprises from $10^5$ TU to $10^{10}$ TU of each type of viral particles especially from $10^5$ to $10^7$, when integrative vectors are used. The dose intended for priming and boosting comprises from $10^7$ to $10^{10}$ of each type of lentiviral particles when integrative-incompetent vectors are used. The invention also concerns the use of the combination of compounds of the invention especially as lentiviral vector according to the definitions given herein, for the manufacture of an immunogenic composition for prophylactic immunisation against malaria parasite infection or against parasite-induced pathology in a mammalian host, especially in a human host.

The invention also concerns a method of providing immunization in a mammalian host, especially in a human host, comprising the step of administering the combination of compounds of the invention especially as lentiviral vectors of the invention to elicit the immune response, and optionally repeating the administration steps one or several times, to boost said response, in accordance with the present disclosure.

In a particular embodiment of the invention, the combination of compounds especially provided as lentiviral vector(s) may be used in association with an adjuvant compound suitable for administration to a mammalian, especially a human host, and/or with an immunostimulant compound, together with an appropriate delivery vehicle.

The combination of compounds quoted above can be injected in a host via different routes: subcutaneous (s.c.), intradermal (i.d.), intramuscular (i.m.) or intravenous (i.v.) injection, oral administration and mucosal or skin administration, especially intranasal administration or inhalation. The quantity to be administered (dosage) depends on the subject to be treated, including considering the condition of the patient, the state of the individual's immune system, the route of administration and the size of the host. Suitable dosages range expressed with respect to the content in equivalent transducing units of vector particles (for HIV-1 lentiviral vectors) can be determined. Other examples and features of the invention will be apparent when reading the examples and the figures which illustrate the preparation and application of the lentiviral vector particles with features that may be individually combined with the definitions given in the present description.

Detailed Description of the Lentiviral Vectors for Use According to the Invention The invention accordingly involves lentiviral vector which are lentiviral particles (i.e. vector particles), and which may be replication-incompetent lentiviral vectors, especially replication-incompetent HIV-1 based vectors characterized in that (i) they are pseudotyped with a determined heterologous viral envelope protein or viral envelope proteins originating from a RNA virus which is not HIV and (ii) they comprise in their genome at least one recombinant polynucleotide encoding at least one antigenic polypeptide (or polypeptide derivative thereof) carrying epitope(s) of a pre-erythrocytic stage antigen of a *Plasmodium* parasite or a polypeptidic derivative thereof wherein the parasite is capable of infecting a mammalian host, and wherein said epitope(s) encompass(es) T-epitope(s).

In a particular embodiment of the invention, the encoded antigenic polypeptide of a pre-erythrocytic stage antigen of a *Plasmodium* parasite further comprises B-epitope(s).

The antigenic polypeptides or derivatives thereof expressed by the vectors are those disclosed herein in any aspects of the invention, in particular in the description of the combination of compounds of the invention.

According to a particular embodiment of the invention, the lentiviral vectors are either designed to express proficient (i.e., integrative-competent) or deficient (i.e., integrative-incompetent) particles.

The preparation of the lentiviral vectors is well known from the skilled person and has been extensively disclosed in the literature (confer for review Sakuma T. et al (Biochem. J. (2012) 443, 603-618). The preparation of such vectors is also illustrated herein in the Examples.

In a particular embodiment of the invention, the polynucleotide(s) encoding the antigenic polypeptides (ORF) of the lentiviral vector has(have) been mammal-codon optimized (CO) in particular human-codon optimized. Optionally the lentiviral sequences of the genome of said particles have also a mammal-codon optimized nucleotide sequence. In a particular aspect of the invention the codon optimization has been carried out for expression in mouse cells. In another embodiment the sequence the polynucleotide(s) encoding the antigenic polypeptides of the lentiviral vector has(have) been human-codon optimized (CO).

It has been observed that codon optimized nucleotide sequences, especially when optimized for expression in mammalian and in particular in human cells, enable the production of higher yield of particles in such mammalian or human cells. Production cells are illustrated in the examples. Accordingly, when lentiviral vector particles of the invention are administered to a mammalian, especially to a human host, higher amounts of particles are produced in said host which favour the elicitation of a strong immune response.

The lentiviral vector (i.e., lentiviral vectors particles or lentiviral-based vector particles) defined in the present invention are pseudotyped lentiviral vectors consisting of vector particles bearing envelope protein or envelope proteins which originate from a virus different from the particular lentivirus (especially a virus different from HIV, in particular HIV-1), which provides the vector genome of the lentiviral vector particles. Accordingly, said envelope protein or envelope proteins, are "heterologous" viral envelope protein or viral envelope proteins with respect to the vector genome of the particles. In the following pages, reference will also be made to "envelope protein(s)" to encompass any type of envelope protein or envelope proteins suitable to perform the invention. When reference is made to "lentiviral" vectors (lentiviral-based vectors) in the application, it relates in particular, to HIV-based vectors and especially HIV-1-based vectors.

The lentiviral vectors suitable to perform the invention are so-called replacement vectors, meaning that the sequences of the original lentivirus encoding the lentiviral proteins are essentially deleted in the genome of the vector or, when present, are modified, and especially mutated, especially truncated, to prevent expression of biologically active lentiviral proteins, in particular, in the case of HIV, to prevent the expression by said transfer vector, of functional ENV, GAG, and POL proteins and optionally of further structural and/or accessory and/or regulatory proteins of the lentivirus, especially of HIV. In a particular embodiment, the lentiviral vector is a first-generation vector, in particular a first-generation of a HIV-based vector which is characterized in that it is obtained using separate plasmids to provide (i) the packaging construct, (ii) the envelope and (iii) the transfer vector genome. Alternatively it may be a second-generation vector, in particular a second-generation of a HIV-based vector which in addition, is devoid of viral accessory proteins (such as in the case of HIV-1, Vif, Vpu, Vpr or Nef) and therefore includes only four out of nine HIV full genes: gag, pol, tat and rev. In another embodiment, the vector is a third-generation vector, in particular a third-generation of a HIV-based vector which is furthermore devoid of said viral accessory proteins and also is Tat-independent; these third-generation vectors may be obtained using 4 plasmids to provide the functional elements of the vector, including one plasmid encoding the Rev protein of HIV when the vector is based on HIV-1. Such vector system comprises only three of the nine genes of HIV-1. The structure and design of such generations of HIV-based vectors is well known in the art.

The "vector genome" of the vector particles is a recombinant nucleic acid which also comprises comprises as a recombined sequence the polynucleotide or transgene of interest encoding one or more antigenic polypeptide(s) or polypeptide derivative thereof of malaria parasite as disclosed herein. The lentiviral-based sequence and polynucleotide/transgene of the vector genome are borne by a plasmid vector thus giving rise to the "transfer vector" also referred to as "sequence vector". Accordingly, these expressions are used interchangeably in the present description. According to a particular embodiment, a vector genome prepared for the invention comprises a nucleic acid having a sequence selected in the group of SEQ ID No. 10, 13, 16, 19, 22, 25, 28, 31, 34, 37, 40, 43, 46, 48, 51, 54, 57, 60, 63, 66, 69, 72, 75, 78, 81 or comprises a plurality of these sequences encoding antigenic polypeptides or derivatives thereof.

The vector genome as defined herein accordingly contains, apart from the so-called recombinant polynucleotide(s) encoding the antigenic polypeptide(s) or polypeptide derivative thereof of malaria parasite placed under control of proper regulatory sequences for its expression, the sequences of the original lentiviral genome which are non-coding regions of said genome, and are necessary to provide recognition signals for DNA or RNA synthesis and processing (mini-viral genome). These sequences are cis-acting sequences necessary for packaging (ψ), reverse transcription (LTRs possibly mutated with respect to the original ones) and transcription and optionally integration (RRE) and furthermore for the particular purpose of the invention, they contain a functional sequence favouring nuclear import in cells and accordingly transgene transfer efficiency in said cells, which element is described as a DNA Flap element that contains or consists of the so-called central cPPT-CTS nucleotidic domain present in lentiviral genome sequences especially in HIV-1 or in some retroelements such as those of yeasts.

The structure and composition of the vector genome used to prepare the lentiviral vectors of the invention are based on the principles described in the art and on examples of such lentiviral vectors primarily disclosed in (Zennou et al, 2000; Firat H. et al, 2002; VandenDriessche T. et al). Constructs of this type have been deposited at the CNCM (Institut Pasteur, France) as will be referred to herein. In this respect reference is also made to the disclosure, including to the deposited biological material, in patent applications WO 99/55892, WO 01/27300 and WO 01/27304.

According to a particular embodiment of the invention, a vector genome may be a replacement vector in which all the viral protein coding sequences between the 2 long terminal repeats (LTRs) have been replaced by the recombinant polynucleotide encoding the polypeptide of the malaria parasite, and wherein the DNA-Flap element has been re-inserted in association with the required cis-acting sequences described herein. Further features relating to the composition of the vector genome are disclosed in relation to the preparation of the particles.

In a particular embodiment of the invention one lentiviral vector encodes one antigenic polypeptide of the *Plasmodium* parasite.

In a particular embodiment, a lentiviral vector of the invention may comprise in its genome one or more than one recombinant polynucleotide encoding at least one antigenic polypeptide carrying epitope(s) of a pre-erythrocytic stage antigen as disclosed herein. In particular, said vector genome comprises two polynucleotides which are consecutive or separated on the genome and which encode different polypeptides of either the same or distinct antigens of the pre-erythrocytic stage of a *Plasmodium* parasite or different antigenic polypeptidic derivatives of distinct antigens of the parasite.

In a particular embodiment, the vector genome contains two or more recombinant polynucleotides, each of them encoding a distinct antigenic polypeptide and each polypeptide originating from a different antigen of the pre-erythrocytic stage as disclosed herein, including the CSP antigen and at least one of the Ag40 or Ag45 antigens, and optionally one or more, including all the antigenic polypeptides selected from the group of the thrombospondin related anonymous protein (TRAP), the inhibitor of cysteine protease (ICP), the metallopeptidase (Falcilysin), the GPI-anchored protein P113, the pore-forming like protein SPECT2 of the *Plasmodium* parasites disclosed herein or derivatives thereof.

The description made herein in respect to antigenic polypeptides similarly applies to polypeptidic derivatives thereof.

Particular features of the lentiviral vectors used in accordance with the various embodiments of the invention are also disclosed in the Examples, such features being either taken alone or in combination to produce the vectors.

According to the invention, the lentiviral vector particles are pseudotyped with a heterologous viral envelope protein or viral polyprotein of envelope originating from a RNA virus which is not the lentivirus providing the lentiviral sequences of the genome of the lentiviral particles.

As examples of typing envelope proteins for the preparation of the lentiviral vector, the invention relates to viral transmembrane glycosylated (so-called G proteins) envelope protein(s) of a Vesicular Stomatitis Virus (VSV), which is(are) for example chosen in the group of VSV-G protein(s) of the Indiana strain and VSV-G protein(s) of the New Jersey strain.

The envelope glycoprotein of the vesicular stomatitis virus (VSV-G) is a transmembrane protein that functions as the surface coat of the wild type viral particles. It is also a suitable coat protein for engineered lentiviral vectors. Presently, nine virus species are definitively classified in the VSV gender, and nineteen rhabdovirus are provisionally classified in this gender, all showing various degrees of cross-neutralisation. When sequenced, the protein G genes indicate sequence similarities. The VSV-G protein presents a N-terminal ectodomain, a transmembrane region and a C-terminal cytoplasmic tail. It is exported to the cell surface via the transGolgi network (endoplasmic reticulum and Golgi apparatus).

Vesicular stomatitis Indiana virus (VSIV) and Vesicular stomatitis New Jersey virus (VSNJV) are preferred strains to pseudotype the lentiviral vectors of the invention, or to design recombinant envelope protein(s) to pseudotype the lentiviral vectors. Their VSV-G proteins are disclosed in GenBank, where several strains are presented. For VSV-G New Jersey strain reference is especially made to the sequence having accession number V01214. For VSV-G of the Indiana strain, reference is made to the sequence having accession number AAA48370.1 in Genbank corresponding to strain JO2428.

Said viral envelope protein(s) are capable of uptake by antigen presenting cells and especially by dendritic cells including by liver dendritic cells by mean of fusion and/or of endocytosis. In a particular embodiment, the efficiency of the uptake may be used as a feature to choose the envelope of a VSV for pseudotyping. In this respect the relative titer of transduction (Titer DC/Titer of other transduced cells e.g. 293T cells) may be considered as a test and envelope having a relative good ability to fuse with DC would be preferred.

Antigen Presenting Cells (APC) and especially Dentritic cells (DC) are proper target cells for pseudotyped lentiviral vectors which are used as immune compositions accordingly.

The VSV-G envelope protein(s) are expressed from a polynucleotide containing the coding sequence for said protein(s), which polynucleotide is inserted in a plasmid (designated envelope expression plasmid or pseudotyping env plasmid) used for the preparation of the lentiviral vector particles of the invention. The polynucleotide encoding the envelope protein(s) is under the control of regulatory sequences for the transcription and/or expression of the coding sequence (including optionally post-transcriptional regulatory elements (PRE) especially a polynucleotide such as the element of the Woodchuck hepatitis virus, i.e. the WPRE sequence, obtainable from Invitrogen).

Accordingly, a nucleic acid construct is provided which comprises an internal promoter suitable for the use in mammalian cells, especially in human cells in vivo and the nucleic acid encoding the envelope protein under the control of said promoter. A plasmid containing this construct is used for transfection or for transduction of cells suitable for the preparation of vector particles. Promoters may in particular be selected for their properties as constitutive promoters, tissue-specific promoters, or inducible promoters. Examples of suitable promoters encompass the promoters of the following genes: MHC Class1 promoters, human beta-2 microglobulin gene (β2M promoter), EF1α, human PGK, PPI (preproinsulin), thiodextrin, HLA DR invariant chain (P33), HLA DR alpha chain, Ferritin L chain or Ferritin H chain, Chymosin beta 4, Chymosin beta 10, Cystatin Ribosomal Protein L41, CMVie or chimeric promoters such as GAG (CMV early enhancer/chicken β actin) disclosed in Jones S. et al (Jones S. et al Human Gene Therapy, 20:630-640(June 2009)).

These promoters may also be used in regulatory expression sequences involved in the expression of gag-pol derived proteins from the encapsidation plasmids, and/or to express the antigenic polypeptides from the transfer vector.

Alternatively, when the envelope expression plasmid is intended for expression in stable packaging cell lines, especially for stable expression as continuously expressed viral particles, the internal promoter to express the envelope protein(s) is advantageously an inducible promoter such as one disclosed in Cockrell A. S. et al. (Mol. Biotechnol. (2007) 36:184-204). As examples of such promoters, reference is made to tetracycline and ecdysone inducible promoters. The packaging cell line may be the STAR packaging cell line (ref Cockrell A. S. et al (2007), Ikedia Y. et al (2003) Nature Biotechnol. 21: 569-572) or a SODk packaging cell line, such as SODk0 derived cell lines, including SODk1 and SODk3 (ref Cockrell A. S. et al (2007), Cockrell A; S. et al (2006) Molecular Therapy, 14: 276-284, Xu K. et al. (2001), Kafri T. et al (1999) Journal of Virol. 73:576-584).

According to the invention, the lentiviral vector are the product recovered from co-transfection of mammalian cells, with:
- a vector plasmid comprising (i) lentiviral, especially HIV-1, cis-active sequences necessary for packaging, reverse transcription, and transcription and further comprising a functional lentiviral, especially derived from HIV-1, DNA flap element and (ii) a polynucleotide encoding one or more antigenic polypeptide(s) (or polypeptide derivative thereof) of a malaria parasite as disclosed herein under the control of regulatory expression sequences, and optionally comprising sequences for integration into the genome of the host cell;
- an expression plasmid encoding a pseudotyping envelope derived from a RNA virus, said expression plasmid comprising a polynucleotide encoding an envelope protein or proteins for pseudotyping, wherein said envelope pseudotyping protein is advantageously from a VSV and is in particular a VSV-G of the Indianan strain or of the New Jersey strain and,
- an encapsidation plasmid, which either comprises lentiviral, especially HIV-1, gag-pol packaging sequences suitable for the production of integration-competent vector particles or modified gag-pol packaging sequences suitable for the production of integration-deficient vector particles.

The invention thus also concerns lentiviral vector particles as described above, which are the product recovered from a stable cell line transfected with:
- a vector plasmid comprising (i) lentiviral, especially HIV-1, cis-active sequences necessary for packaging, reverse transcription, and transcription and further comprising a functional lentiviral, especially HIV-1, DNA flap element and optionally comprising cis-active sequences necessary for integration, said vector plasmid further comprising (ii) a polynucleotide of a codon-optimized sequence for murine or for human of the gene encoding the antigenic polypeptide (or a derivative thereof) of a *Plasmodium* parasite as disclosed herein, under the control of regulatory expression sequences, especially a promoter;
- a VSV-G envelope expression plasmid comprising a polynucleotide encoding a VSV-G envelope protein in particular VSV-G of the Indiana strain or of the New Jersey strain, wherein said polynucleotide is under the control of regulating expression sequences, in particular regulatory expression sequences comprising an inducible promoter, and;
- an encapsidation plasmid, wherein the encapsidation plasmid either comprises lentiviral, especially HIV-1, gag-pol coding sequences suitable for the production of integration-competent vector particles or modified gag-pol coding sequences suitable for the production of integration-deficient vector particles, wherein said gag-pol sequences are from the same lentivirus sub-family as the DNA flap element, wherein said lentiviral gag-pol or modified gag-pol sequence is under the control of regulating expression sequences.

The stable cell lines expressing the vector particles of the invention are in particular obtained by transduction of the plasmids.

The polynucleotide encodes at least one antigenic polypeptide of a malaria parasite according to any embodiment disclosed in the present specification. In particular, it encodes a polypeptide which is a truncated mammalian, especially human, codon-optimized sequence coding for such antigenic polypeptide of *Plasmodium falciparum, Plasmodium vivax* or *Plasmodium berghei*.

In a particular embodiment, the polynucleotide encodes two or more antigenic polypeptides of the malaria parasite which originate and/or are derived from distinct antigens of said parasite as disclosed in the various embodiments. Accordingly, the vector plasmid may comprise several expression cassettes for the expression of the various antigenic polypeptides or may comprise bicistronic or multicistronic expression cassettes where the polynucleotides encoding the various polypeptides are separated by an IRES sequence of viral origin (Internal Ribosome Entry Site), or it may encode fusion protein(s).

The internal promoter contained the vector genome and controlling the expression of the polynucleotide encoding an antigenic polypeptide of the malaria parasite (as a transgene or in an expression cassette) may be selected from the promoters of the following genes: human beta-2 microglobuline gene (β2M promoter), EF1α, human PGK, PPI (preproinsulin), thiodextrin, HLA DR invariant chain (P33), HLA DR alpha chain, Ferritin L chain or Ferritin H chain, Chymosin beta 4, Chimosin beta 10, or Cystatin Ribosomal Protein L41 CMVie or chimeric promoters such as GAG (CMV early enhancer/chicken β actin) disclosed in Jones S. et al (2009).

A promoter among the above cited internal promoters may also be selected for the expression of the envelope protein(s) and packaging (gag-pol derived) proteins. Alternatively, vector particles can be produced from co-transfection of the plasmids disclosed herein, in stable packaging cell lines which thus become capable of continuously secreting vector particles. Promoters used in the regulatory expression sequences involved for the expression of the envelope protein(s) are advantageously inducible promoters.

The following particular embodiments may be carried out when preparing the lentiviral vector based on human lentivirus, and especially based on HIV-1 virus.

According to the invention, the genome of the lentiviral vector is derived from a human lentivirus, especially from the HIV lentivirus. In particular, the pseudotyped lentiviral vector is an HIV-based vector, such as an HIV-1, or HIV-2 based vector, in particular is derived from HIV-1M, for example from the BRU or LAI isolates. Alternatively, the lentiviral vector providing the necessary sequences for the vector genome may be originating from lentiviruses such as EIAV, CAEV, VISNA, FIV, BIV, SIV, HIV-2, HIV-O which are capable of transducing mammalian cells.

As stated above, when considering it apart from the recombinant polynucleotide that it finally contains, the vector genome is a replacement vector in which the nucleic acid between the 2 long terminal repeats (LTRs) in the original lentivirus genome have been restricted to cis-acting sequences for DNA or RNA synthesis and processing, including for the efficient delivery of the transgene to the nuclear of cells in the host, or at least are deleted or mutated for essential nucleic acid segments that would enable the expression of lentiviral structure proteins including biological functional GAG polyprotein and possibly POL and ENV proteins.

In a particular embodiment, the 5' LTR and 3' LTR sequences of the lentivirus are used in the vector genome, but the 3'-LTR at least is modified with respect to the 3'LTR of the original lentivirus at least in the U3 region which for example can be deleted or partially deleted for the enhancer. The 5'LTR may also be modified, especially in its promoter region where for example a Tat-independent promoter may be substituted for the U3 endogenous promoter.

In a particular embodiment the vector genome comprises one or several of the coding sequences for Vif-, Vpr, Vpu- and Nef-accessory genes (for HIV-1 lentiviral vectors). Alternatively, these sequences can be deleted independently or each other or can be non-functional (second-generation lentiviral vector).

The vector genome of the lentiviral vector particles comprises, as an inserted cis-acting fragment, at least one polynucleotide consisting in the DNA flap element or containing such DNA flap element. In a particular embodiment, the DNA flap is inserted upstream of the polynucleotide encoding the antigenic polypeptide of *Plasmodium* parasite, and is advantageously—although not necessarily—located in an approximate central position in the vector genome. A DNA flap suitable for the invention may be obtained from a retrovirus, especially from a lentivirus, in particular a human lentivirus especially a HIV-1 retrovirus, or from a retrovirus-like organism such as retrotransposon. It may be alternatively obtained from the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. The DNA flap may be either prepared synthetically (chemical synthesis) or by amplification of the DNA providing the DNA Flap from the appropriate source as defined above such as by Polymerase chain reaction (PCR). In a more preferred embodiment, the DNA flap is obtained from an HIV retrovirus, for example HIV-1 or HIV-2 virus including any isolate of these two types.

The DNA flap (also designated cPPT/CTS) (defined in Zennou V. et al. ref 27, 2000, Cell vol 101, 173-185 or in WO 99/55892 and WO 01/27304), is a structure which is central in the genome of some lentiviruses especially in HIV, where it gives rise to a 3-stranded DNA structure normally synthesized during especially HIV reverse transcription and which acts as a cis-determinant of HIV genome nuclear import. The DNA flap enables a central strand displacement event controlled in cis by the central polypurine tract (cPPT) and the central termination sequence (CTS) during reverse transcription. When inserted in lentiviral-derived vectors, the polynucleotide enabling the DNA flap to be produced during reverse-transcription, stimulates gene transfer efficiency and complements the level of nuclear import to wild-type levels (Zennou et al., Cell, 2000 Cell vol 101, 173-185 or in WO 99/55892 and WO 01/27304).

Sequences of DNA flaps have been disclosed in the prior art, especially in the above cited patent applications. These sequences are also disclosed in the sequence of SEQ ID Not from position 2056 to position 2179. They are preferably inserted as a fragment, optionally with additional flanking sequences, in the vector genome, in a position which is preferably near the centre of said vector genome. Alternatively they may be inserted immediately upstream from the promoter controlling the expression of the polynucleotide(s) encoding the antigenic polypeptide. Said fragments comprising the DNA flap, inserted in the vector genome may have a sequence of about 80 to about 200 bp, depending on its origin and preparation.

According to a particular embodiment, a DNA flap has a nucleotide sequence of about 90 to about 140 nucleotides.

In HIV-1, the DNA flap is a stable 99-nucleotide-long plus strand overlap. When used in the genome vector of the lentiviral vector of the invention, it may be inserted as a longer sequence, especially when it is prepared as a PCR fragment. A particular appropriate polynucleotide comprising the structure providing the DNA flap is a 124-base pair polymerase chain reaction (PCR) fragment encompassing the cPPT and CTS regions of the HIV-1 DNA (as disclosed in SEQ ID N No. 1).

It is specified that the DNA flap used in the genome vector and the polynucleotides of the encapsidation plasmid encoding the GAG and POL polyproteins should originate from the same lentivirus sub-family or from the same retrovirus-like organism.

Preferably, the other cis-activating sequences of the genome vector also originate from the same lentivirus or retrovirus-like organism, as the one providing the DNA flap. The vector genome may further comprise one or several unique restriction site(s) for cloning the recombinant polynucleotide.

In a preferred embodiment, in said vector genome, the 3' LTR sequence of the lentiviral vector genome is devoid of at least the activator (enhancer) and possibly the promoter of the U3 region. In another particular embodiment, the 3' LTR region is devoid of the U3 region (delta U3). In this respect, reference is made to the description in WO 01/27300 and WO 01/27304.

In a particular embodiment, in the vector genome, the U3 region of the LTR 5' is replaced by a non lentiviral U3 or by a promoter suitable to drive tat-independent primary transcription. In such a case, the vector is independent of tat transactivator (third generation vector).

The vector genome also comprises the psi (ψ) packaging signal. The packaging signal is derived from the N-terminal fragment of the gag ORF. In a particular embodiment, its sequence could be modified by frameshift mutation(s) in order to prevent any interference of a possible transcription/translation of gag peptide, with that of the transgene.

The vector genome may optionally also comprise elements selected among a splice donor site (SD), a splice acceptor site (SA) and/or a Rev-responsive element (RRE). According to a particular embodiment, the vector plasmid (or added genome vector) comprises the following cis-acting sequences for a transgenic expression cassette:

1. The LTR sequence (Long-Terminal Repeat), required for reverse transcription, the sequences required for transcription and including optionally sequences for viral DNA integration. The 3' LTR is deleted in the U3 region at least for the promoter to provide SIN vectors (Self-inactivating), without perturbing the functions necessary for gene transfer, for two major reasons: first, to avoid trans-activation of a host gene, once the DNA is integrated in the genome and secondly to allow self-inactivation of the viral cis-sequences after retrotranscription. Optionally, the tat-dependent U3 sequence from the 5'-LTR which drives transcription of the genome is replaced by a non endogenous promoter sequence. Thus, in target cells only sequences from the internal promoter will be transcribed (transgene).
2. The ψ region, necessary for viral RNA encapsidation.
3. The RRE sequence (REV Responsive Element) allowing export of viral messenger RNA from the nucleus to the cytosol after binding of the Rev protein.
4. The DNA flap element (cPPT/CTS) to facilitate nuclear import.
5. Optionally post-transcriptional regulatory elements, especially elements that improve the expression of the antigenic polypeptides in dendritic cells, such as the WPRE cis-active sequence (Woodchuck hepatitis B virus Post-Responsive Element) also added to optimize stability of mRNA (Zufferey et al., 1999), the matrix or scaffold attachment regions (SAR and MAR sequences) such as those of the immunoglobulin-kappa gene (Park F. et al Mol Ther 2001; 4: 164-173).

The lentiviral vector of the invention is non replicative (replication-incompetent) i.e., the vector and lentiviral vector genome are regarded as suitable to alleviate concerns regarding replication competent lentiviruses and especially are not able to form new particles budding from the infected host cell after administration. This may be achieved in well known ways as the result of the absence in the lentiviral genome of the gag, pol or env genes, or their absence as "functional genes". The gag and pol genes are thus, only provided in trans. This can also be achieved by deleting other viral coding sequence(s) and/or cis-acting genetic elements needed for particles formation.

By "functional" it is meant a gene that is correctly transcribed, and/or correctly expressed. Thus, if present in the lentiviral vector genome of the invention in this embodiment contains sequences of the gag, pol, or env are individually either not transcribed or incompletely transcribed; the expression "incompletely transcribed" refers to the alteration in the transcripts gag, gag-pro or gag-pro-pol, one of these or several of these being not transcribed. Other sequences involved in lentiviral replication may also be mutated in the vector genome, in order to achieve this status. The absence of replication of the lentiviral vector should be distinguished from the replication of the lentiviral genome. Indeed, as described before, the lentiviral genome may contain an origin of replication ensuring the replication of the lentiviral vector genome without ensuring necessarily the replication of the vector particles.

In order to obtain lentiviral vectors according to the invention, the vector genome (as a vector plasmid) must be encapsidated in particles or pseudo-particles. Accordingly, lentiviral proteins, except the envelope proteins, have to be provided in trans to the vector genome in the producing system, especially in producing cells, together with the vector genome, having recourse to at least one encapsidation plasmid carrying the gag gene and either the pol lentiviral gene or an integrative-incompetent pol gene, and preferably lacking some or all of the coding sequences for Vif-, Vpr, Vpu- and Nef-accessory genes and optionally lacking Tat (for HIV-1 lentiviral vectors).

A further plasmid is used, which carries a polynucleotide encoding the envelope pseudotyping protein(s) selected for pseudotyping lentiviral vector particles.

In a preferred embodiment, the packaging plasmid encodes only the lentiviral proteins essential for viral particle synthesis. Accessory genes whose presence in the plasmid could raise safety concerns are accordingly removed. Accordingly, viral proteins brought in trans for packaging are respectively as illustrated for those originating from HIV-1:
1. GAG proteins for building of the matrix (MA, with apparent Molecular Weight p17), the capsid (CA, p24) and nucleocapsid (NC, p6).
2. POL encoded enzymes: integrase, protease and reverse transcriptase.
3. TAT and REV regulatory proteins, when TAT is necessary for the initiation of LTR-mediated transcription; TAT expression may be omitted if the U3 region of 5'LTR is substituted for a promoter driving tat-independent transcription. REV may be modified and accordingly used for example in a recombinant protein which would enable recognition of a domain replacing the RRE sequence in the vector genome, or used as a fragment enabling binding to the RRE sequence through its RBD (RNA Binding Domain).

In order to avoid any packaging of the mRNA generated from the genes contained in the packaging plasmid in the viral particles, the ψ region is removed from the packaging plasmid. A heterologous promoter is inserted in the plasmid to avoid recombination issues and a poly-A tail is added 3' from the sequences encoding the proteins. Appropriate promoters have been disclosed above.

The envelope plasmid encodes the envelope protein(s) for pseudotyping which are disclosed herein, under the control of an internal promoter, as disclosed herein.

Any or all the described plasmids for the preparation of the lentiviral vector particles of the invention may be codon optimized (CO) in the segment encoding proteins. Codon optimization according to the invention is preferably performed to improve translation of the coding sequences contained in the plasmids, in mammalian cells, murine or especially human cells. According to the invention, codon optimization is especially suited to directly or indirectly improve the preparation of the vector particles or to improve their uptake by the cells of the host to whom they are administered, or to improve the efficiency of the transfer of the polynucleotide encoding the antigenic polypeptide of the malaria parasite (transgene) in the genome of the transduced cells of the host. Methods for optimizing codons are well known in the art and codon optimization is especially performed using available programs to that effect. Codon optimization is illustrated for the coding sequences used in the examples.

In a particular embodiment of the invention, the pseudotyped lentiviral vector is also, or alternatively, integrative-competent, thus enabling the integration of the vector genome and of the recombinant poly nucleotide which it contains into the genome of the transduced cells or in the cells of the host to whom it has been administered.

In another particular embodiment of the invention, the pseudotyped lentiviral vector is also, or alternatively, integrative-incompetent. In such a case, the vector genome and thus the recombinant polynucleotide which it contains do not integrate into the genome of the transduced cells or in the cells of the host to whom it has been administered.

The present invention relates to the use of a lentiviral vector wherein the expressed integrase protein is defective and which further comprises a polynucleotide especially encoding at least one antigenic polypeptide carrying epitope(s) of a pre-erythrocytic stage antigen of a *Plasmodium* parasite, in an immunogenic composition.

By "integration-incompetent", it is meant that the integrase, preferably of lentiviral origin, is devoid of the capacity of integration of the lentiviral genome into the genome of the host cells i.e., an integrase protein mutated to specifically alter its integrase activity.

Integration-incompetent lentiviral vectors are obtained by modifying the pol gene encoding the Integrase, resulting in a mutated pol gene encoding an integrative deficient integrase, said modified pol gene being contained in the encapsidation plasmid. Such integration-incompetent lentiviral vectors have been described in patent application WO 2006/010834. Accordingly the integrase capacity of the protein is altered whereas the correct expression from the encapsidation plasmid of the GAG, PRO and POL proteins and/or the formation of the capsid and hence of the vector particles, as well as other steps of the viral cycle, preceding or subsequent to the integration step, such as the reverse transcription, the nuclear import, stay intact. An integrase is said defective when the integration that it should enable is altered in a way that an integration step takes place less than 1 over 1000, preferably less than 1 over 10000, when compared to a lentiviral vector containing a corresponding wild-type integrase.

In a particular embodiment of the invention, the defective integrase results from a mutation of class 1, preferably amino acid substitutions (one-amino acid substitution) or short deletions fulfilling the requirements of the expression of a defective integrase. The mutation is carried out within the pol gene. These vectors may carry a defective integrase with the mutation D64V in the catalytic domain of the enzyme, which specifically blocks the DNA cleaving and joining reactions of the integration step. The D64V mutation decreases integration of pseudotyped HIV-1 up to $1/10,000$ of wild type, but keep their ability to transduce non dividing cells, allowing efficient transgene expression.

Other mutations in the pol gene which are suitable to affect the integrase capacity of the integrase of HIV-1 are the following: H12N, H12C, H16C, H16V, S81 R, D41A, K42A, H51A, Q53C, D55V, D64E, D64V, E69A, K71A, E85A, E87A, D116N, D116I, D116A, N120G, N120I, N120E, E152G, E152A, D-35-E, K156E, K156A, E157A, K159E, K159A, K160A, R166A, D167A, E170A, H171A, K173A, K186Q, K186T, K188T, E198A, R199C, R199T, R199A, D202A, K211A, Q214L, Q216L, Q221 L, W235F, W235E, K236S, K236A, K246A, G247W, D253A, R262A, R263A and K264H. In a particular embodiment, mutation in the pol gene is performed at either of the following positions D64, D116 or E152, or at several of these positions which are in the catalytic site of the protein. Any substitution at these positions is suitable, including those described above.

Another proposed substitution is the replacement of the amino acids residues RRK (positions 262 to 264) by the amino acids residues AAH.

In a particular embodiment of the invention, when the lentiviral vector is integration-incompetent, the lentiviral genome further comprises an origin of replication (ori), whose sequence is dependent on the nature of cells where the lentiviral genome has to be expressed. Said origin of replication may be from eukaryotic origin, preferably of mammalian origin, most preferably of human origin. It may alternatively be of viral origin, especially coming from DNA circular episomic viruses, such as SV40 or RPS. It is an advantageous embodiment of the invention to have an origin or replication inserted in the lentiviral genome of the lentiviral vector of the invention. Indeed, when the lentiviral genome does not integrate into the cell host genome (because of the defective integrase), the lentiviral genome is lost in cells that undergo frequent cell divisions; this is particularly the case in immune cells, such as B or T cells. The presence of an origin of replication ensures that at least one lentiviral genome is present in each cell, even after cell division, accordingly maximazing the efficiency of the immune response.

The lentiviral vector genome of said lentiviral vectors of the invention may especially be derived from HIV-1 plasmid pTRIPΔU3.CMV-GFP deposited at the CNCM (Paris, France) on Oct. 11, 1999 under number 1-2330 (also described in WO01/27300) or variants thereof. The sequence of such variants are provided as SEQ ID No. 1 or 2. When the vector genome is derived from these particular plasmids, a sequence of a recombinant polynucleotide encoding an antigenic polypeptide of a *Plasmodium* parasite as disclosed in the present application is inserted therein, in addition or in replacement of the GFP coding fragment. The GFP coding sequence may also be substituted by a different marker. The CMV promoter may also be substituted by another promoter, especially one of the promoters disclosed above, especially in relation to the expression of the transgene.

The WPRE sequence also contained in the particular deposited pTRIP vectors may optionally be deleted.

Vector particles may be produced after transfection of appropriate cells (such as mammalian cells or human cells, such as Human Embryonic Kidney cells illustrated by 293 T cells) by said plasmids, or by other processes. In the cells used for the expression of the lentiviral particles, all or some of the plasmids may be used to stably express their coding polynucleotides, or to transiently or semi-stably express their coding polynucleotides.

The concentration of particles produced can be determined by measuring the P24 (capsid protein for HIV-1) content of cell supernatants.

The lentiviral vector of the invention, once administered into the host, infects cells of the host, possibly specific cells, depending on the envelope proteins it was pseudotyped with. The infection leads to the release of the lentiviral vector genome into the cytoplasm of the host cell where the retrotranscription takes place. Once under a triplex form (via the DNA flap), the lentiviral vector genome is imported into the nucleus, where the polynucleotide(s) encoding polypeptide(s) of antigen(s) of the malaria parasite is (are) expressed via the cellular machinery. When non-dividing cells are transduced (such as DC), the expression may be stable. When dividing cells are transduced, such as B cells, the expression is temporary in absence of origin of replication in the lentiviral genome, because of nucleic acid dilution and cell division. The expression may be longer by providing an origin of replication ensuring a proper diffusion of the lentiviral vector genome into daughter cells after cell division. The stability and/or expression may also be increased by insertion of MAR (Matrix Associated Region) or SAR (Scaffold Associated Region) elements in the vector genome.

Indeed, these SAR or MAR regions are AT-rich sequences and enable to anchor the lentiviral genome to the matrix of the cell chromosome, thus regulating the transcription of the polynucleotide encoding at least one antigenic polypeptide, and particularly stimulating gene expression of the transgene and improving chromatin accessibility.

If the lentiviral genome is non integrative, it does not integrate into the host cell genome. Nevertheless, the at least one polypeptide encoded by the transgene is sufficiently expressed and longer enough to be processed, associated with MHC molecules and finally directed towards the cell surface. Depending on the nature of the polynucleotide(s) encoding antigenic polypeptide(s) of a malaria parasite, the at least one polypeptide epitope associated with the MHC molecule triggers a humoral or a cellular immune response.

Unless otherwise stated, or unless technically not relevant, the characteristics disclosed in the present application with respect to any of the various features, embodiments or examples of the structure or use of the lentiviral particles, especially regarding their envelope protein(s), or the recombinant polynucleotide, may be combined according to any possible combinations.

The invention further relates to a combination of compounds for separate administration to a mammalian host, which comprises at least:

(i) lentiviral vector particles of the invention which are pseudotyped with a first determined heterologous viral envelope pseudotyping protein or viral envelope pseudotyping proteins; such first pseudotyping protein may be from the New-Jersey strain of VSV;

(ii) provided separately from lentiviral vector particles in (i), lentiviral vector particles of the invention which are pseudotyped with a second determined heterologous viral envelope pseudotyping protein or viral envelope pseudotyping proteins distinct from said first heterologous viral envelope pseudotyping protein(s); such second pseudotyping protein may be from the Indiana strain of VSV.

The invention also relates to a polynucleotide which is a mouse codon-optimized nucleic acid encoding a pre-erythrocytic stage antigen of a *Plasmodium* parasite, wherein said polynucleotide is selected from the group of:

a/ SEQ ID No. 10 for CSP of *P. berghei*, SEQ ID No. 19 for TRAP of *P. berghei*, SEQ ID No. 28 for ICP of *P. berghei*, SEQ ID No. 37 for Falcilysin of *P. berghei*, SEQ ID No. 57 for GPI-anchored protein P113 of *P. berghei*, SEQ ID No. 48 for pore-forming like protein SPECT2 of *P. berghei*, SEQ ID No. 66 for protein Ag40 11-09 of *P. berghei*, and SEQ ID No. 75 for protein Ag45 11-10 of *P. berghei*, or, b/ SEQ ID No. 13 for CSP of *P. falciparum*, SEQ ID No. 22 for TRAP of *P. falciparum*, SEQ ID No. 31 for ICP of *P. falciparum*, SEQ ID No. 40 for Falcilysin of *P. falciparum*, SEQ ID No. 51 for pore-forming like protein SPECT2 of *P. falciparum*, SEQ ID No. 60 for GPI-anchored protein P113 of *P. falciparum*, SEQ ID No. 69 for protein 11-09 of *P. falciparum*, and SEQ ID No. 78 for protein 11-10 of *P. falciparum* or, c/ SEQ ID No. 16 for CSP of *P. vivax*, SEQ ID No. 25 for TRAP of *P. vivax*, SEQ ID No. 34 for ICP of *P. vivax*, SEQ ID No. 43 for Falcilysin of *P. vivax*, SEQ ID No. 54 for pore-forming like protein SPECT2 of *P. vivax*, SEQ ID No. 63 for GPI-anchored protein P113 of *P. vivax*, SEQ ID No. 72 for protein 11-09 of *P. vivax*, and SEQ ID No. 81 for protein 11-10 of *P. vivax*.

Codon optimisation reflected in the above sequences has been carried out for expression in mice when polynucleotides encoding antigens of *P. berghei* are concerned. It has been carried out for expression in human cells when polynucleotides encoding antigens of *P. falciparum* or of *P. vivax* are concerned.

The invention also concerns the use of the above polynucleotides for the design of alternative forms of nucleic acids also suitable for the preparation of the vectors of the invention, wherein the thus obtained nucleic acids are RNAs of modified DNAs such as threose nucleic acids (TNAs), glycol nucleic acids (GNAs), peptide nucleic acids (PNAs), locked nucleic acids (LNAs) with either known configuration or ethylene nucleic acids (ENA) or cyclohexenyl nucleic acids (CeNA) or hybrids or combinations thereof. In particular when carrying out the preparation of the vector genome of the invention, hybrid molecules can be used wherein the polynucleotide encoding the antigenic polypeptide of the malaria parasite as disclosed herein is expressed from one of the above disclosed forms of sequences. According to an embodiment of the invention, the nucleotide sequence of the vector genome is a chimeric sequence encompassing a modified nucleic acid for the transcription of the antigenic polypeptide. In another embodiment of the invention, possibly in combination with the above disclosed alternative forms of the nucleic acid, the polynucleotide encoding the antigenic polypeptide is structurally modified and/or chemically modified. Illustrative thereof a polynucleotide comprises a Kozak consensus sequence in its 5' region. Such polynucleotides encompassing Kozak consensus sequences are especially illustrated herein. Other nucleic acid sequences that are not of lentiviral origin may be present in the vector genome are IRES sequence(s) (Internal Ribosome entry site) suitable to initiate polypeptide synthesis WPRE sequence as post-transcriptional regulatory element to stabilize the produced RNA.

According to another embodiment of the invention, if multiple heterologous polypeptides are encoded by one vector genome, the coding sequences may optionally be separated by a linker moiety which is either a nucleic acid based molecule or a non-nucleic acid based molecule. Such a molecule may be a functionalized linker molecule aimed at recognizing a 3' functionalized nucleic acid to which it shall be linked. A sequence suitable to function as a linker may alternatively be a nucleic acid which encodes a self-cleaving peptide, such as a 2A peptide.

The invention relates to a collection of polynucleotides thus described wherein each polynucleotide encodes one or more of the antigenic polypeptides of the malaria parasite as described herein for the purpose of the invention, provided the collection of these polynucleotides is suitable for the preparation of the active ingredients of the combination of compounds of the invention.

The invention also relates to the use of the polynucleotides thus disclosed, for the preparation of a collection of lentiviral vectors, in particular HIV-1 based vectors, wherein a vector comprises in its genome, at least one of these polynucleotides, provided the collection of lentiviral vectors enables the expression of all antigenic polypeptides encoded by the polynucleotides of one subgroup selected among a/, b/, and c/.

Further features and properties of the present invention, including features to be used in the embodiments described above will be described in the examples and figures which follow and may accordingly be used to characterise the invention.

LEGENDS OF THE FIGURES

FIG. 1. Schema of plasmids used in the production of Lentiviral Particles.

Figure 2:
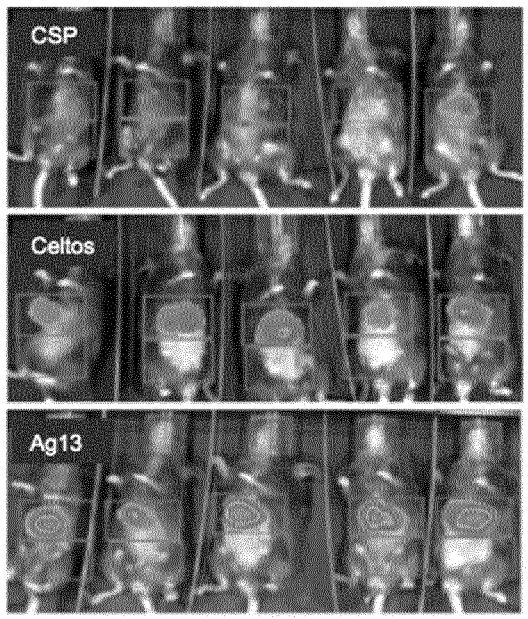
Figure 2:
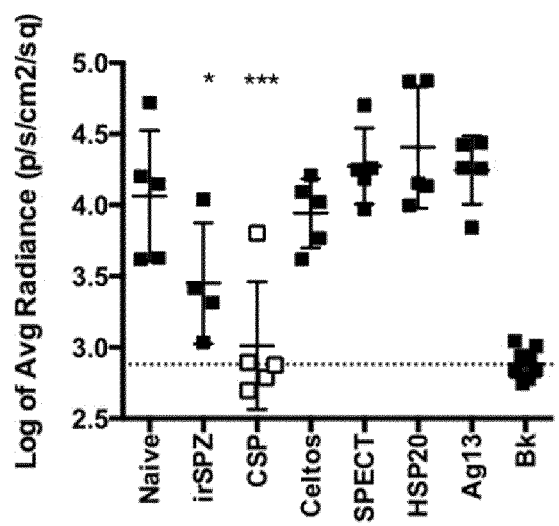

FIG. 2. C57BL/6 mice (n=5) were immunized intramuscularly with $5 \times 10^7$ TU of VSV$^{IND}$ pseudotyped lentiviral particles coding for the antigens, CSP, Celtos SPECT, HSP20 and Ag13. As a positive control of protection, mice were immunized with 50 k irradiated sporozoites via intravenous injection. Thirty days after immunization, the animals were challenged with 10,000 bioluminescent sporozoites micro-injected subcutaneously in the mice footpad. The parasite load in the liver was quantified two days later by bioluminescence as shown in the picture for CSP, Celtos and Ag13. The graph shows the quantification of the liver infection represented as the log of average radiance (squares). Dotted line represents the average of background signal (Bk) of a non-infected region. *P<0.05 and ***P<0.001 (ANOVA).

Figure 3:
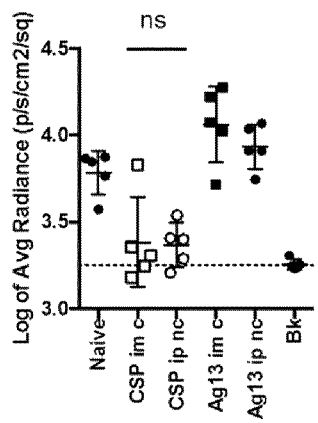

FIG. 3. C57BL/6 mice (n=5 per group) were immunized or not (naïve) with 5×10$^7$ TU of VSV$^{IND}$ LPs carrying Ag13 (negative control) and CSP (positive control). The groups receiving concentrated LPs were inoculated intramuscularly in the thigh muscle with 50 uL of vector (Ag13 im c and CSP im c). The groups receiving non-concentrated LPs were inoculated intraperitoneally with 700 uL of vector (Ag13 ip nc and CSP ip nc). Thirty days after immunization, the animals were challenged with 5,000 luciferase-expressing sporozoites, micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). ns, not significant (ANOVA).

Figure 4:
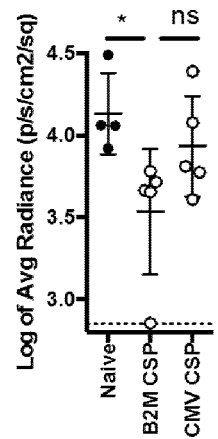

FIG. 4. C57BL/6 mice (n=4-5 per group) were intraperitoneally immunized or not (naïve) with 1×10$^7$ TU of non concentrated VSV$^{IND}$ CSP LPs under the control of CMV or B2M promoters (CMV CSP and B2M CSP, respectively). Thirty days after immunization, the animals were challenged with 5,000 luciferase-expressing sporozoites micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). *P<0.05; ns, not significant (ANOVA).

Figure 5:
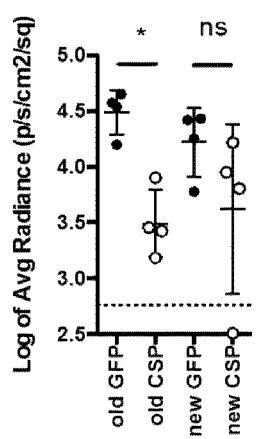

FIG. 5. 4 and 7 weeks-old C57BL/6 mice (n=4-per group) were acclimated for 3 weeks (old groups) and 3 days (new groups). These age-matched groups were then intraperitoneally immunized with 1×10$^7$ TU of non concentrated VSV$^{IND}$ B2M CSP or GFP LPs. Thirty days after immunization, the animals were challenged with 5,000 luciferase-expressing sporozoites micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). *P<0.05; ns, not significant (ANOVA).

Figure 6:
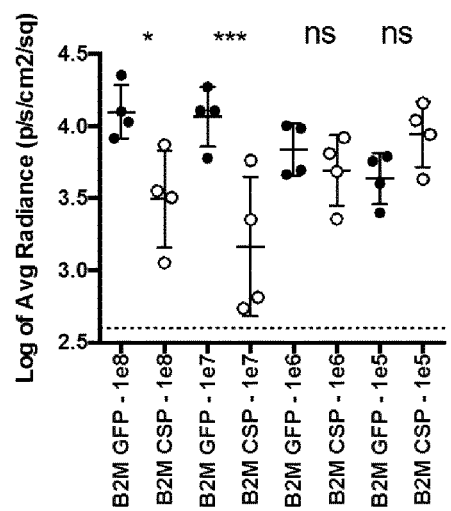

FIG. 6. 4 weeks-old C57BL/6 mice (n=4-per group) were acclimated for 3 weeks (old groups) and intraperitoneally immunized with different doses of non-concentrated VSV$^{IND}$ B2M CSP (black) or GFP (white) LPs. Thirty days after immunization, the animals were challenged with 5,000 luciferase-expressing sporozoites micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). *P<0.05; ***P<0.001; ns, not significant (ANOVA).

Figure 7:
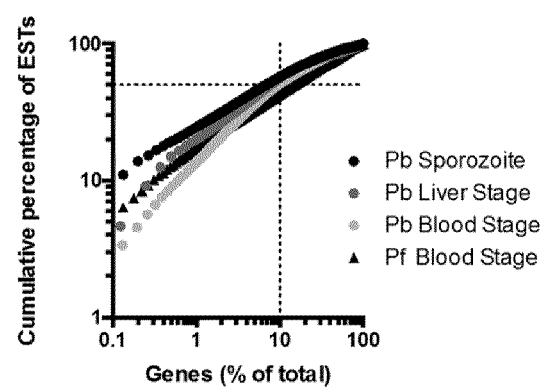

FIG. 7. Analysis of Sporozoite, Liver Stage and Blood Stage cDNA libraries of *Plasmodium berghei* (Pb) and *falciparum* (Pf) deposited in Plasmodb. The percentage of each expression sequence tag (EST) was normalized to the total number of ESTs and represented cumulatively. Each symbol represents one gene, ranked by EST abundance (higher to lower) and represented as % of total ESTs. Of note ~10% of genes (most abundant) are responsible for ~50% of total ESTs (dotted lines).

Figure 8:
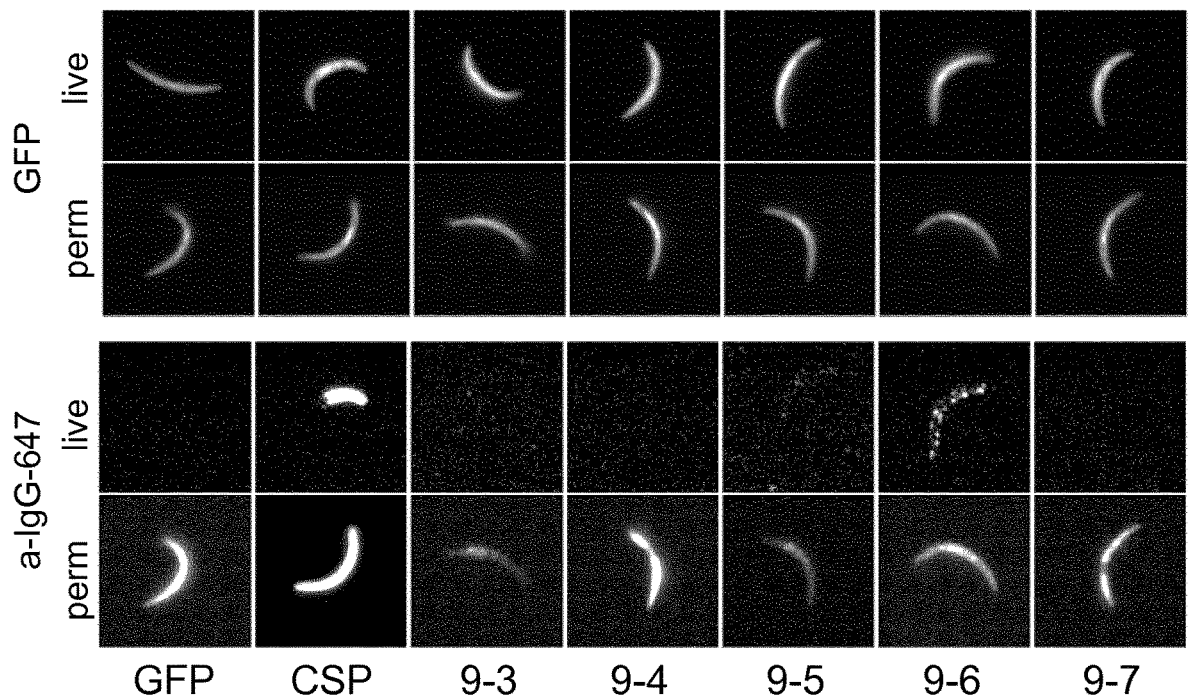
Figure 8:
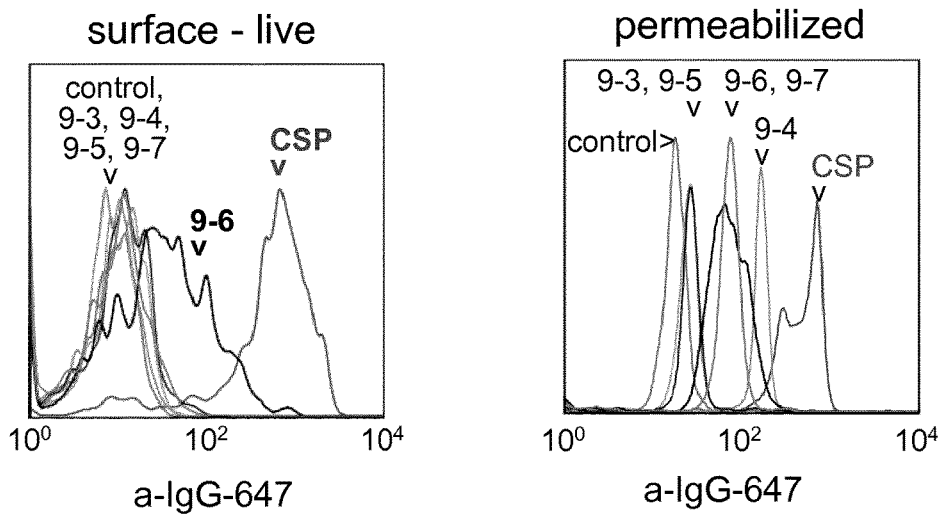

FIG. 8. Expression and surface localization of antigens. GFP-expressing Pb sporozoites were fixed with 2% of PFA and permeabilized with 0.1% of Triton X100 (perm) or not (live). Parasites were incubated with the indicated immune-sera (1/50) for one hour on ice, washed and revealed with goat anti-mouse secondary antibody labelled with AlexaFluor 647. Sporozoites were then analysed by cytometry as shown in the right histograms (surface, staining using live non-permeabilized SPZ; permeabilized, staining using fixed and permeabilized SPZ) or by fluorescence microscopy, as depicted in the pictures. Notice that CSP and antigen 9-6 present a surface pattern staining both by cytometry and microscopy.

Figure 9:
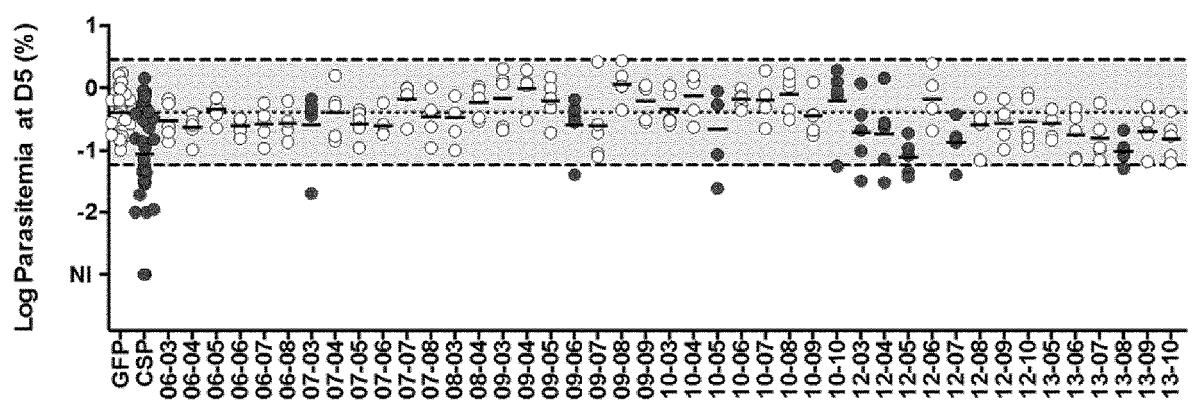

FIG. 9. Targeted screening of protective antigens. 4 weeks-old C57BL/6 mice (n=5 per group) were acclimated for 3 weeks and intraperitoneally immunized with a single dose of 1×10$^7$ TU of non-concentrated VSV$^{IND}$ B2M LPs. Thirty days after immunization, the animals were challenged with 5,000 GFP-expressing sporozoites micro-injected subcutaneously in the mice footpad. The parasite infection was measured by flow cytometry. The graph shows the average of the log of parasitemia (trace, individual mice represented by circles) immunized with the indicated plasmodial antigens. Bold dotted lines represent the 95% tolerance interval of GFP log normal distribution. Mice with parasitemia below the lower limit of the tolerance interval are considered protected. Top dotted line is the average of control and bottom dotted line represents non-infected (NI) mice.

Figure 10:
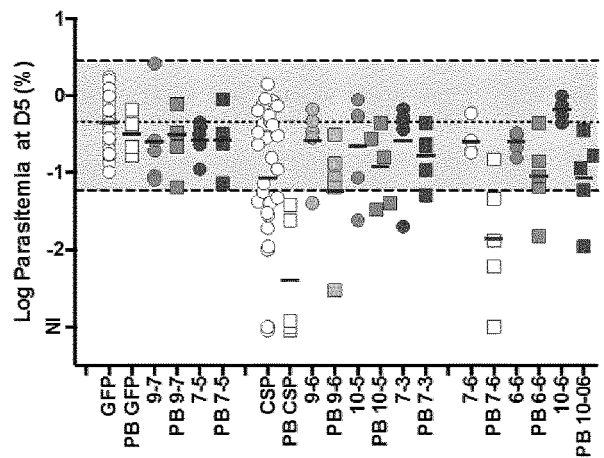

FIG. 10. Comparison of protection induced by one or two immunization doses. 4 weeks-old C57BL/6 mice (n=5 per group) were acclimated for 3 weeks and intraperitoneally immunized with a first dose of 5×10$^5$ TU of non-concentrated VSV$^{NJ}$ B2M LPs. Thirty days after the first immunization, the animals received a second dose of 1×10$^7$ TU of non-concentrated VSV$^{IND}$ B2M LPs. Thirty days later, mice were challenged with 5,000 GFP-expressing sporozoites micro-injected subcutaneously in the footpad. The parasite infection was measured by flow cytometry. The graph shows the log of parasitemia at day 5 post-inoculation of individual challenged mice that received two immunization doses (Squares, PB). Circles represent mice that received only one immunization dose of LPs (data from experiment shown in FIG. 9). Traces represents the average of the Log Parasitemia. Bold dotted lines represent the 95% tolerance interval of GFP log normal distribution. Mice below the lower limit of tolerance interval are considered protected. NI, non-infected mice.

Figure 11:
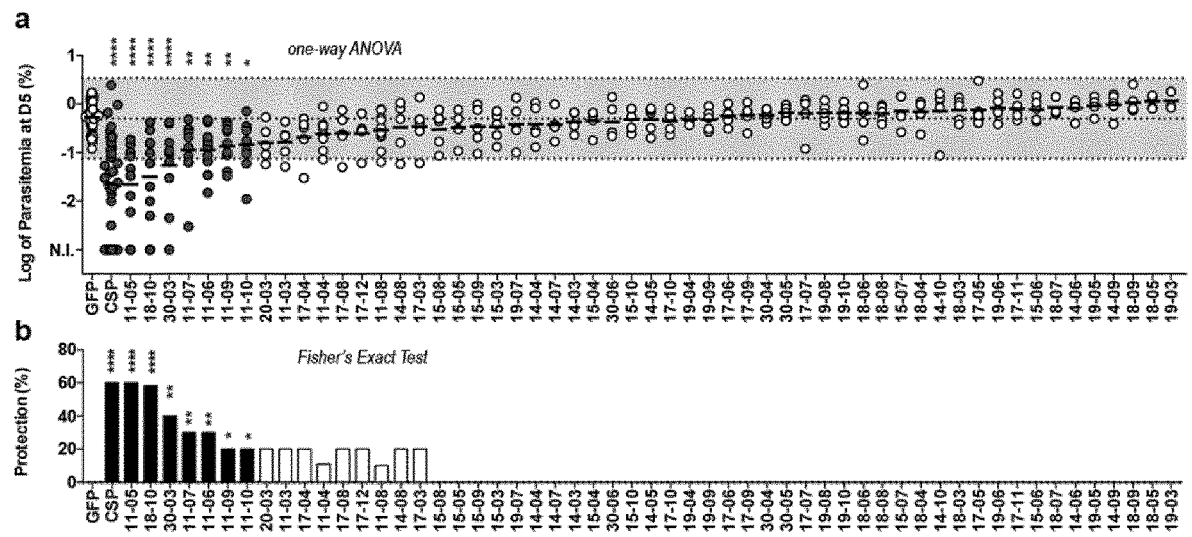

FIG. 11. Targeted Screening of Protective Antigens. 4 weeks-old C57BL/6 mice (n=5-10 per group) were acclimated for 3 weeks and intraperitoneally immunized with a first dose of 5×10$^5$ TU of non-concentrated VSV$^{NJ}$ B2M LPs. Thirty days after the first immunization, the animals received a second dose of 1×10$^7$ TU of non-concentrated VSV$^{IND}$ B2M LPs. Third days later, mice were challenged with 5,000 GFP-expressing sporozoites micro-injected subcutaneously in the footpad. The parasite blood infection was measured by flow cytometry. (a.) The upper graph shows the log of parasitemia of individual mouse at day 5 post-infection. Traces represent the mean of the log parasitemia. The average of the GFP group (control of protection) is represented by the dotted middle line. The superior and inferior dotted lines delineate the 95% tolerance interval (grey box) of the GFP control group. The CSP group is the positive control of protection. NI (not infected=no parasitemia at day 10 post-infection, located at the limit of detection of our method of parasitemia quantification). Black circles represent antigens where there was a significant decrease in the averaged log parasitemia and therefore are considered protective (ANOVA). (b) The bottom graph represents the percentage of protected mice (% of animals below the 95% tolerance interval). Black bars represent protective antigens (Fisher's Exact test). *P<0.05, P<0.01, **P<0.0001.

Figure 12:
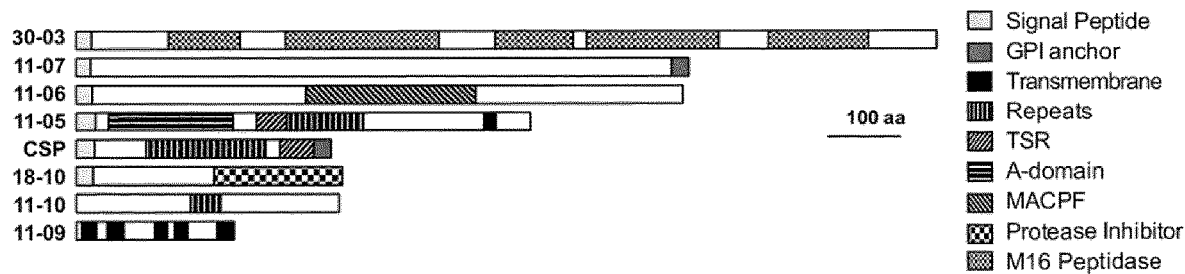

FIG. 12. Structure of *P. berghei* protective antigens. Conserved structural and functional domains are represented by boxes according to the code on the right. GPI (glycosylphosphatidylinositol), TSR (thrombospondin type I repeat), MACPF (membrane attack complex/perforin).

Figure 13:
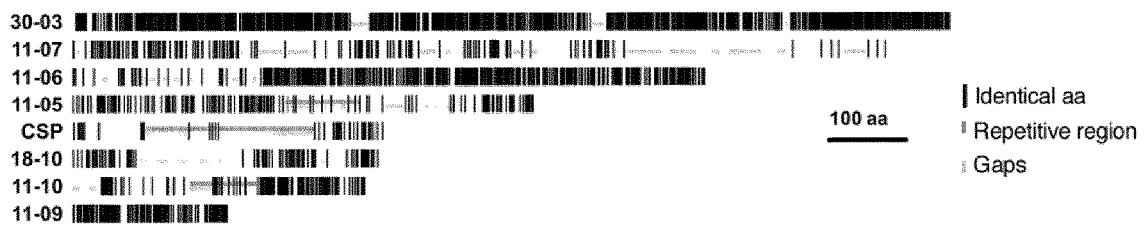

FIG. 13. Protective antigens are conserved among plasmodial species. Amino acid sequences of protective orthologous antigens from rodent-infecting *P. berghei*, macaque-infecting *P. cynomolgi*, and human-infecting *P. falciparum* and *P. vivax* parasites were aligned by MUltiple Sequence Comparison by Log-Expectation (MUSCLE). Vertical black bars represent identical amino acids conserved in the four plasmodial species, short dark gray bars represent repetitive regions and short light gray bars, insertional gaps used for the alignment.

Figure 14:
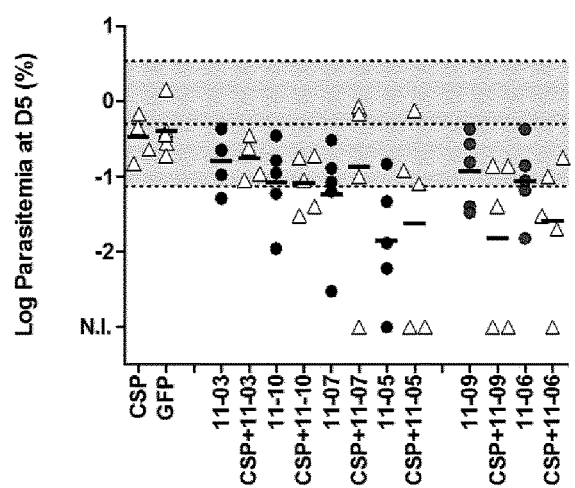

FIG. 14. Protection induced by combination of down-selected protective antigens with a sub-optimal dose of CSP. Mice were immunized twice, four weeks apart, with a sub-optimal dose of CSP ($5 \times 10^5$ TU of non-concentrated $VSV^{NJ}$ B2M LP in the first immunization and $5 \times 10^6$ TU of non-concentrated $VSV^{IND}$ B2M LP in the second immunization, white triangle, CSP) and the usual dose of protective plasmodial antigens (CSP+11-03, +11-05, +11-06, +11-07, +11-09 and +11-10; triangles). As negative control mice were immunized with the usual, two doses of GFP. 4 weeks after the second immunization dose, animals were challenged with 5,000 sporozoites.

Figure 15:
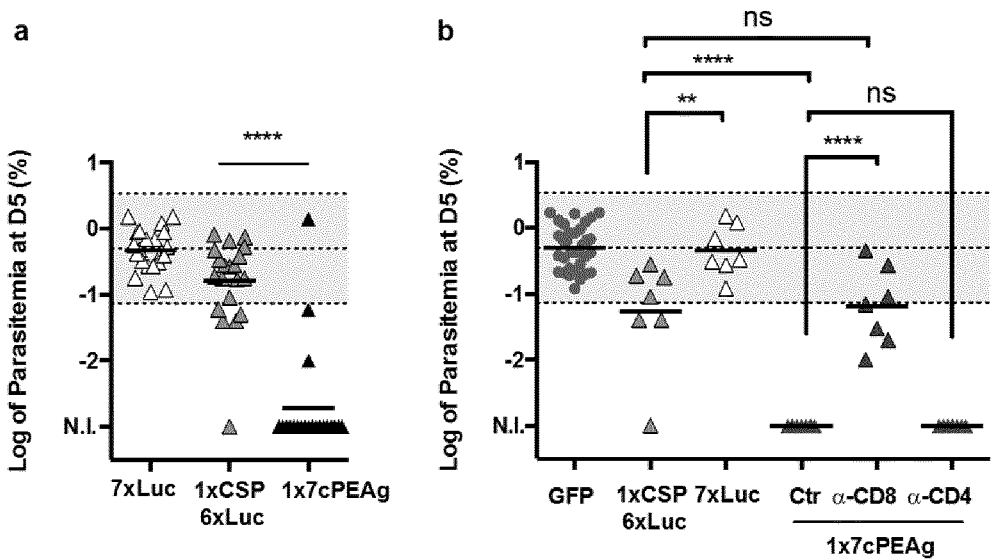

FIG. 15. Sterile protection induced by a multigenic combination. Mice were immunized twice, four weeks apart, with 7× the individual dose (1 dose=$5 \times 10^5$ TU of non-concentrated $VSV^{NJ}$ B2M LPs in the first immunization/1× $10^7$ TU of non-concentrated $VSV^{IND}$ B2M LPs in the second immunization) of the control antigen AL11-luciferase (Luc, white triangles), with the individual dose of CSP plus 6×Luc (gray triangles), or with the individual doses of CSP and of 6 conserved PE antigens (11-05, 11-06, 11-07, 11-09, 11-10 and 18-10; black triangles, 7cPEAg). 4 weeks after the second immunization dose, mice were challenged with 5,000 GFP SPZs. Both graphs show the individual log of parasitemia at day 5 post-challenge. (a) The graph shows the pooled results of three independent experiments. Number of sterile protected/challenged mice: 7×Luc (0/21), 1×CSP 6×Luc (1/20) and 1×7cPEAg (18/21). (b) Three and one day before sporozoite challenge, 1×7cPEAg immunized mice were injected with 400 μg of control (Ctr), CD4-depleting (a-CD4+, clone GK1.5) and CD8-depleting (a-CD8+, clone 2.43) monoclonal antibodies. GFP data comes from experiment showed in FIG. 11 (gray circles). Number of sterile protected/challenged mice: 7×Luc (0/7), 1×CSP 6×Luc (1/7) and 1×7cPEAg (ctr,7/7; a-CD8, 0/7 and a-CD4, 7/7). Notice that depletion of CD8+ cells abolished sterile protection. *P<0.05, P<0.01, **P<0.0001 (ANOVA).

Figure 16:
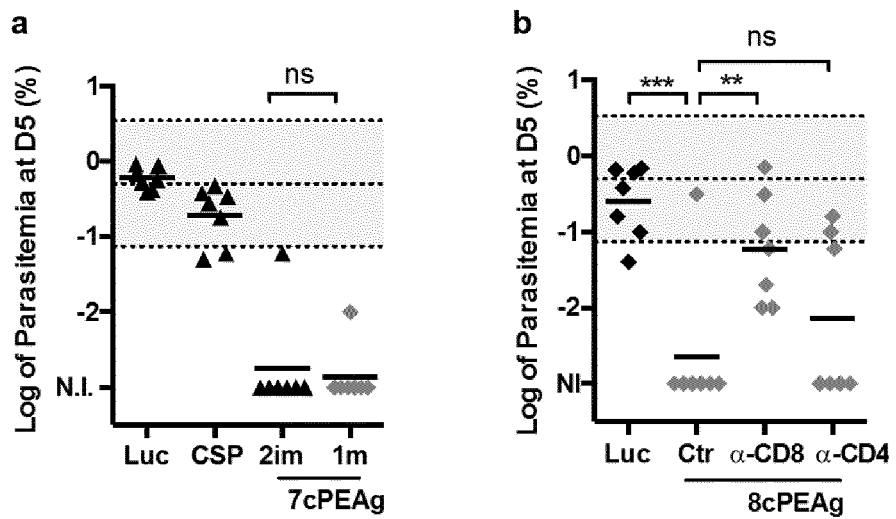

FIG. 16. Sterile protection induced by a multigenic combination in a single immunization dose. (a) Mice were immunized twice, four weeks apart, with 7× the individual dose (1 dose=$5 \times 10^5$ TU of non-concentrated $VSV^{NJ}$ B2M LPs in the first immunization/1×$10^7$ TU of non-concentrated $VSV^{IND}$ B2M LPs in the second immunization) of the control antigen AL11-luciferase (Luc, black triangles), with the individual dose of CSP plus 6×Luc (CSP, black triangles), or with the individual dose of CSP and of 6 conserved PE antigens (11-05, 11-06, 11-07, 11-09, 11-10 and 18-10; black triangles; 2 im 7cPEAg). Alternatively, mice were administered only with the second individual immunization dose (1×$10^7$ TU) of CSP and of 6 conserved PE antigens (11-05, 11-06, 11-07, 11-09, 11-10 and 18-10; grey diamonds; 1 im 7cPEAg). 4 weeks after the second immunization dose, mice were challenged with 5,000 GFP SPZs. The graph shows the individual log of parasitemia at day 5 post-challenge. Black bars are the average of log of parasitemia. Number of sterile protected/challenged mice: Luc (0/7), CSP (0/7), 2im 7cPEAg (6/7) and 1 m 7cPEAg (6/7). (b) Mice were immunized once with 9× the individual dose (1 dose=1×$10^7$ TU of non-concentrated $VSV^{IND}$ B2M LPs) of the control antigen AL11-luciferase (Luc, black diamonds), or with the individual doses of CSP+ of 7 conserved PE antigens (11-05, 11-06, 11-07, 11-09, 11-10, 18-10, 30-03A and 30-03B; grey diamonds; 8cPEAg). Three and one day before sporozoite challenge, 8cPEAg immunized mice were injected with 400 μg of control (Ctr), CD4-depleting (a-CD4+, clone GK1.5) and CD8-depleting (a-CD8+, clone 2.43) monoclonal antibodies. 4 weeks after the single immunization dose, mice were challenged with 5,000 GFP SPZs. The graph shows the individual log of parasitemia at day 5 post-challenge. Black bars are the average of log of parasitemia. Number of sterile protected/challenged mice: 7×Luc (0/7) and 8cPEAg (ctr,6/7; a-CD8, 0/7 and a-CD4, 4/7). Notice that depletion of CD8+ cells abolished protection. *P<0.05; P<0.01; **P<0.0001; ns, P>0.05 (ANOVA).

Figure 17:
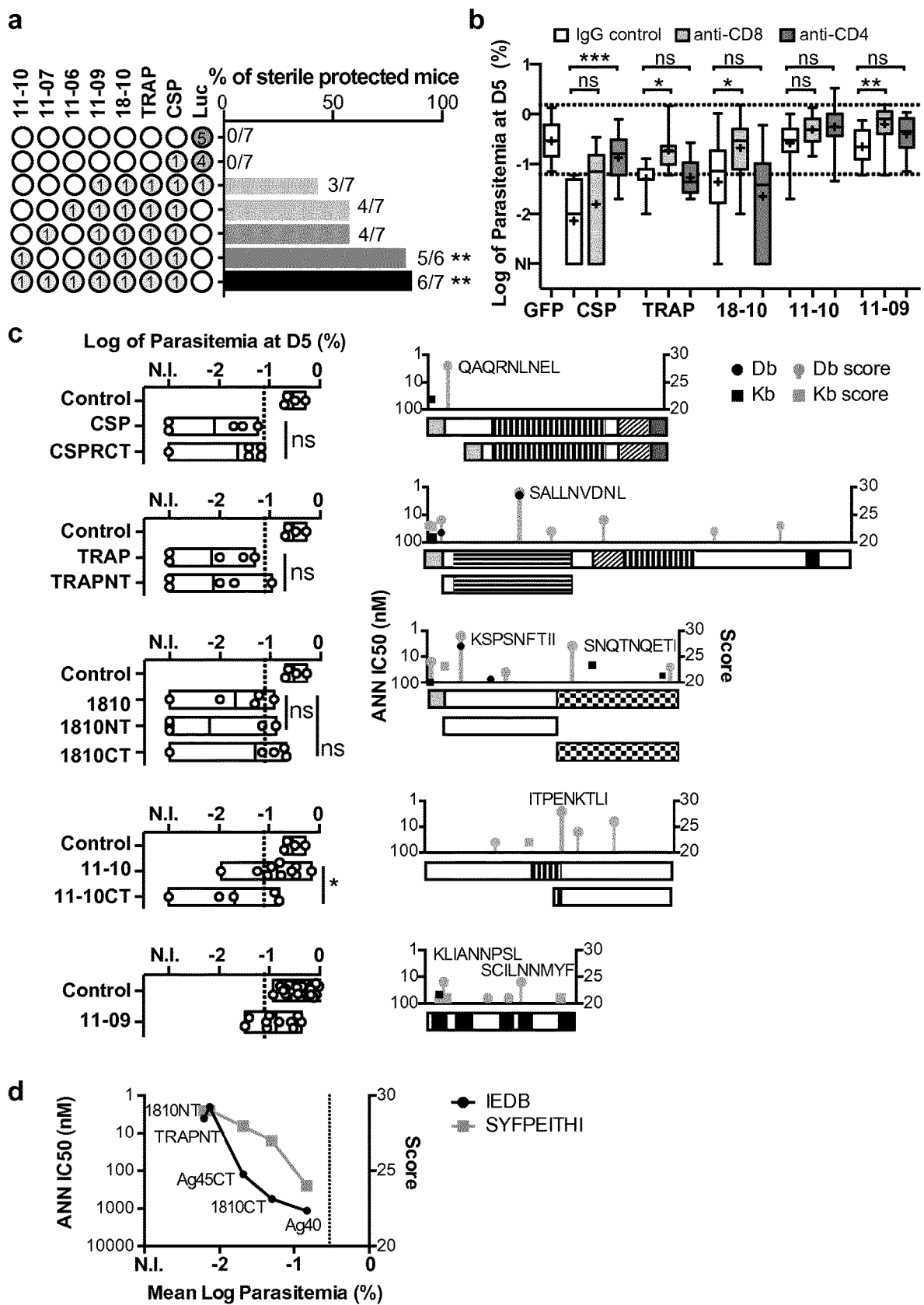

FIG. 17. Sterile protection induced by a minimal combination of 5 PE antigens. (a) Mice were immunized twice, four weeks apart, with the individual dose multiplied by the number indicated in the circles (1 dose=$5 \times 10^5$ TU of non-concentrated $VSV^{NJ}$ B2M LPs in the first immunization/1× $10^7$ TU of non-concentrated $VSV^{IND}$ B2M LPs in the second immunization). For example, for the control antigen AL11-luciferase (LUC), animals were immunized with 5× the individual dose. All groups received 5 doses, with exception of the positive control of protection that received 7 doses of LPs (7PEAg). 4 weeks after the second immunization dose, mice were challenged with 5,000 GFP SPZs. Bars represents the percentage of sterile protected mice. The numbers of sterile protected/challenged mice are shown at the right of bars. **P<0.01 (Fisher's Exact test). (b) Mice were immunized twice, four weeks apart, with the individual dose (1 dose=$5 \times 10^5$ TU of non-concentrated $VSV^{NJ}$ B2M LPs in the first immunization/1×$10^7$ TU of non-concentrated $VSV^{IND}$ B2M LPs in the second immunization) of the control antigen GFP (GFP, black circles) or with the individual dose of CSP, TRAP, 18-10, 11-09 or 11-10 (grey triangles). Three and one day before sporozoite challenge, immunized mice were injected with 400 μg of control (Ctr), CD4-depleting (a-CD4+, clone GK1.5) and CD8-depleting (a-CD8+, clone 2.43) monoclonal antibodies. 4 weeks after the second immunization dose, mice were challenged with 5,000 GFP SPZs. Graphs show the average±sd of log of parasitemia at day 5 post-challenge. *P<0.05; ns, P>0.05 (ANOVA). (c) The 5 down-selected protective antigens were split according the presence of predicted CD8 T cell epitopes and respecting conserved structural domains as depicted by the schematic representation of the antigens. The graphs above the schematic proteins represent the distribution of epitopes predicted to bind to H2Kb (8 aa) and H2Kd (9 aa) MHC class I molecules using SYFPEITHI (score) and IEDB ANN IC 50 (nM). The graphs on the left of schematic proteins represent the protection induced by these constructs, where bars are the average±sd of log of parasitemia at day 5 post-challenge. Data shown for antigen 11-09 come from FIG. 11. Dotted line represents the inferior limit of the tolerance interval of the control calculated in the FIG. 11. *P<0.05; ns, P>0.05 (ANOVA). (d) Correlation of the best epitope predicted to bind to MHC class I molecules in the segments of CD8+ T cell dependent PE antigens and mean protective activity obtained from 17c. Circles show the IC50 using IEDB ANN software and squares the score values using SYFPEITHI. Dotted line shows the average of Luc control.

Figure 18:
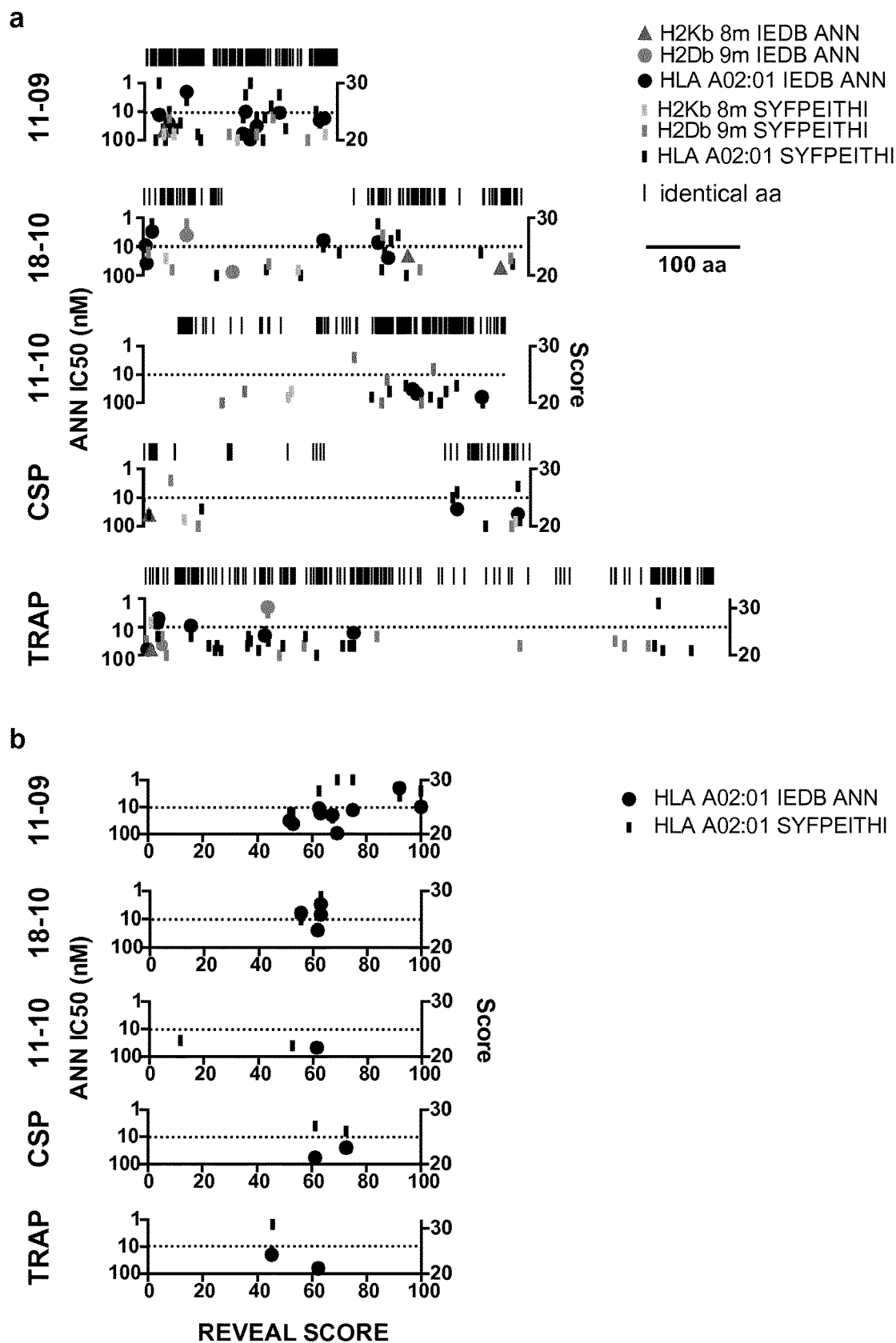

FIG. 18. Clustering of CD8 T cell epitopes in conserved amino acid regions and binding of predicted Pf epitopes to HLA A02:01. Amino acid sequences of protective orthologous antigens from rodent-infecting *P. berghei*, macaque-infecting *P. cynomolgi*, and human-infecting *P. falciparum* and *P. vivax* parasites were aligned by MUltiple Sequence Comparison by Log-Expectation (MUSCLE). Vertical black bars represent identical amino acids conserved in the four plasmodial species. The graph shows the distribution of Pb epitopes predicted to bind to H2Kb (8 aa) and H2Kd (9 aa) MHC class I molecules or of Pf epitopes predicted to bind to the HLA A02:01 (9 mers) using SYFPEITHI (score) and IEDB ANN IC50 (nM). The best predicted HLA binders were tested in the assay of stabilization of MHC class I molecule in the presence of peptide and β2-microglobulin (REVEAL® Score). The score of 100 corresponds to the binding of a positive control peptide. Notice the clustering of epitopes in regions of conserved amino acids.

Figure 19:
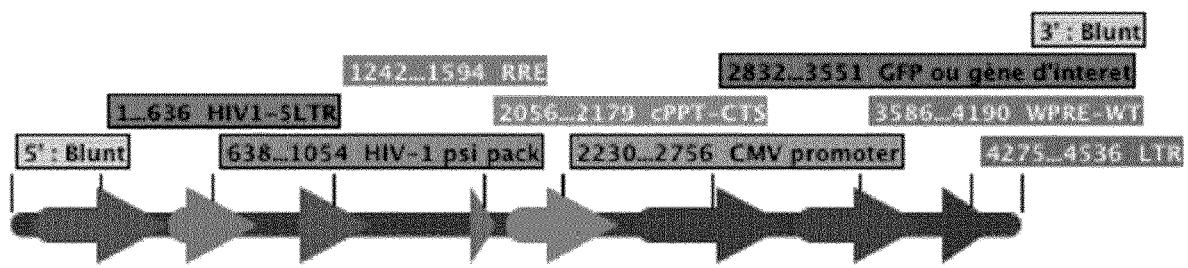

FIG. 19. plasmid used to produce VSV-pseutdotyped lentiviral particles: pTRIP CMV GFP The sequence of the plasmid is constituted by the following functional regions wherein the cis-active lentiviral regions are derived from the HIV genome, and the promoter driving the expression of the protein (GFP) is CMV:

The insert in the plasmid that provides the vector genome is composed as follows: LTR-ψ-RRE-cPPT/CTS-CMV-GFP-WPRE-ΔU3LTR, wherein LTR is Long Terminal Repeat
Psi (ψ) is Packaging signal
RRE is Rev Responsive Element
CMV is Immediate early CytoMegaloVirus promoter
cPPT is central PolyPurine Tract, and wherein the nucleotide segment from cPPT to CTS forms the flap sequence
CTS is Central Termination Sequence
WPRE is Woodchuck hepatitis virus Post Regulatory Element The nucleotide sequence is provided as SEQ ID No. 1

Figure 20:
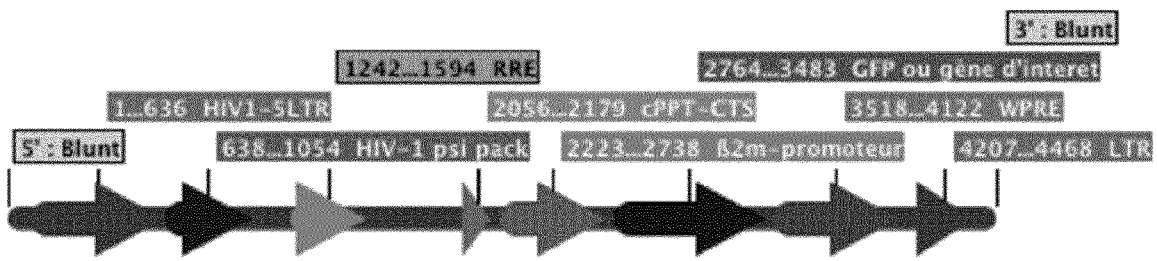

FIG. 20: alternative plasmid (to the plasmid of FIG. 19) used to produce VSV-pseutdotyped lentiviral particles: pTRIP B2M GFP The insert in the plasmid that provides the vector genome is composed as follows: LTR-ψ-RRE-cPPT/CTS-B2M-GFP-WPRE-ΔU3LTR.

The nucleotide sequence is provided as SEQ ID No. 2.

Figure 21:
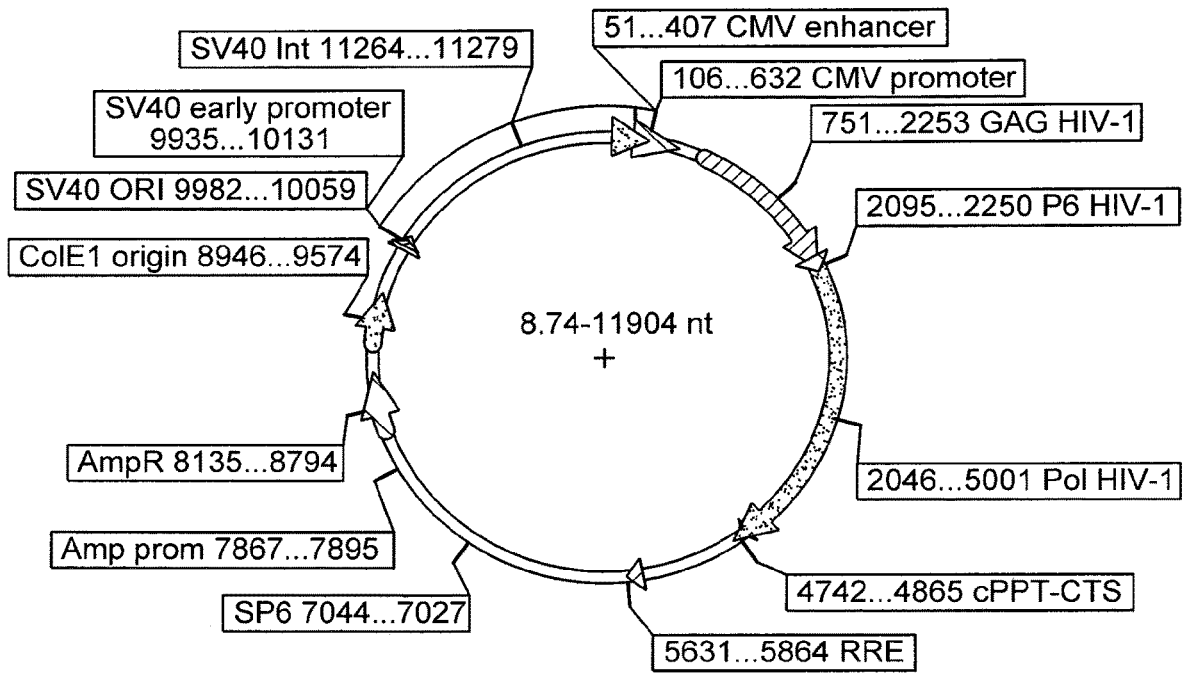

FIG. 21. plasmid used to produce VSV-pseutdotyped lentiviral particles: packaging 8.74 plasmid The plasmid provides the required GAG and POL coding sequences of the HIV-1 lentivirus under the control of the CMV promoter.

The nucleotide sequence is provided as SEQ ID No. 3.

Figure 22:
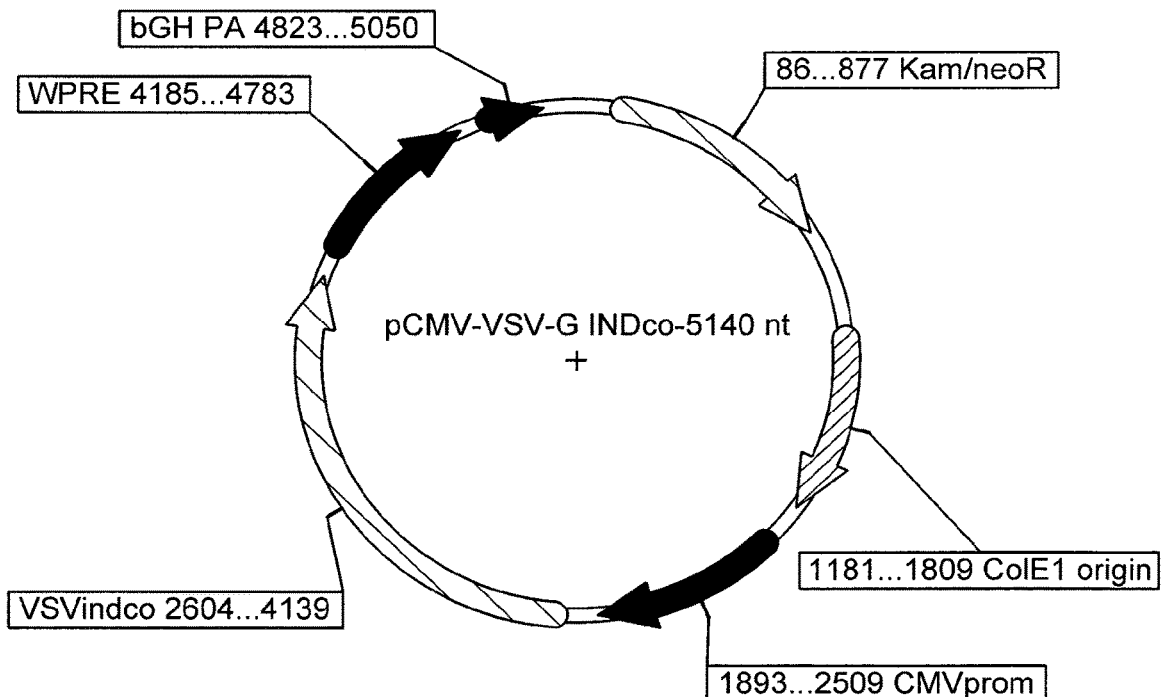

FIG. 22. plasmid used to produce VSV-pseutdotyped lentiviral particles: encapsidation plasmid pCMV-VSV-INDco The envelope protein is the VSV-G of the Indiana strain and the coding sequence has been mouse-codon optimized.

The nucleotide sequence is provided as SEQ ID No. 4.

FIG. 23. alternative plasmid (to plasmid of FIG. 22) used to produce VSV-pseutdotyped lentiviral particles: encapsidation plasmid pCMV-VSV-NJco The envelope protein is the VSV-G of the New-Jersey strain and the coding sequence has been mouse-codon optimized.

The nucleotide sequence is provided as SEQ ID No. 5.

The following table provides the list and identification of the sequences contained in the sequence listing.

| SEQ ID No. | Sequence designation | Origin | Type |
| --- | --- | --- | --- |
| 1 | pTRIP CMV GFP | | DNA |
| 2 | pTRIP B2M GFP | | DNA |
| 3 | PACKAGING 8.74 PLASMID | | DNA |
| 4 | pCMV-VSV-INDco | | DNA |
| 5 | pCMV-VSV-Njco | | DNA |
| 6 | eGFP | | DNA |
| 7 | eGFP protein | | protein |
| 8 | AL11-Luciferase | | protein |
| 9 | AL11-Luciferase | | protein |
| 10 | circumsporozoite (CS) protein (CSP) mouseCO + Kozak | *P. berghei* ANKA strain | DNA |
| 11 | PbCSP (mouseCO + Kozak) | *P. berghei* ANKA strain | protein |
| 12 | PbCSP | *P. berghei* ANKA strain | protein |
| 13 | PfCSP humanCO + Kozak | *P falciparum* 3D7 strain | DNA |
| 14 | PfCSP (humanC0 + Kozak) | *P falciparum* 3D7 strain | protein |
| 15 | PfCSP | *P falciparum* | protein |
| 16 | PvCSP humanCO + Kozak | *P vivax* Sal-1 strain | DNA |
| 17 | PvCSP (humanCO + Kozak) | *P vivax* Sal-1 strain | protein |
| 18 | PvCSP | *P vivax* Sal-1 strain | protein |
| 19 | thrombospondin-related anonymous protein (PbTRAP) mouseCO + Kozak | *P. berghei* ANKA strain | DNA |
| 20 | PbTRAP (mouseCO + Kozak) | *P. berghei* ANKA strain | protein |
| 21 | PbTRAP | *P. berghei* ANKA strain | protein |
| 22 | PfTRAP humanCO + Kozak | *P falciparum* 3D7 strain | DNA |
| 23 | PfTRAP (humanCO + Kozak) | *P falciparum* 3D7 strain | protein |
| 24 | PfTRAP | *P falciparum* | protein |
| 25 | PvTRAPhumanCO | *P vivax* Sal-1 strain | DNA |
| 26 | PvTRAP | *P vivax* Sal-1 strain | protein |
| 27 | PvTRAP | *P vivax* | protein |
| 28 | inhibitor of cysteine proteases (ICP) mouseCO + Kozak | *P. berghei* ANKA strain | DNA |
| 29 | PbICP (mouseCO + Kozak) | *P. berghei* ANKA strain | protein |
| 30 | PbICP | *P. berghei* ANKA strain | protein |
| 31 | PfICP humanCO | *P falciparum* 3D7 strain | DNA |
| 32 | PfICP | *P falciparum* 3D7 strain | protein |
| 33 | PfICP | *P falciparum* | protein |
| 34 | PvICP humanCO + Kozac | *P vivax* Sal-1 strain | DNA |
| 35 | PvICP (humanCO + Kozac) | *P vivax* Sal-1 strain | protein |
| 36 | PvICP | *P vivax* | protein |
| 37 | Bergheilysin-A-mouseCO + Kozak | *P. berghei* ANKA strain | DNA |

| SEQ ID No. | Sequence designation | Origin | Type |
|---|---|---|---|
| 38 | Bergheilysin-A (1-777, mouse CO + Kozak) | P. berghei ANKA strain | protein |
| 39 | Bergheilysin entire ORF (1-1149) | P. berghei ANKA strain | protein |
| 40 | Falcilysin human CO + Kozak | P falciparum 3D7 strain | DNA |
| 41 | Falcilysin (human CO + Kozak) | P falciparum 3D7 strain | protein |
| 42 | Falcilysin | P falciparum 3D7 strain | protein |
| 43 | PvFalcilysin human CO + Kozak | P vivax Sal-1 strain | DNA |
| 44 | PvFalcilysin (humanCO + Kozak) | P vivax Sal-1 strain | protein |
| 45 | PvFalcilysin | P vivax Sal-1 strain | protein |
| 46 | Bergheilysin-B-mouseCO + Kozak + signal peptide (SP) | P. berghei ANKA strain | DNA |
| 47 | Bergheilysin-B (SP + 778-1149, mouse CO + Kozak) | P. berghei ANKA strain | protein |
| 48 | perforin like protein 1 (SPECT2) mouseCO + Kozak | P. berghei ANKA strain | DNA |
| 49 | PbSPECT2 (mouseCO + Kozak) | P. berghei ANKA strain | protein |
| 50 | PbSPECT2 | P. berghei ANKA strain | protein |
| 51 | PfSPECT2 human CO + Kozak | P falciparum 3D7 strain | DNA |
| 52 | PfSPECT2 (humanCO + Kozak) | P falciparum 3D7 strain | protein |
| 53 | PfSPECT2 | P falciparum 3D7 strain | protein |
| 54 | PvSPECT2 human CO + Kozak | P vivax Sal-1 strain | DNA |
| 55 | PvSPECT2 (human CO + Kozak) | P vivax Sal-1 strain | protein |
| 56 | PvSPECT2 | P vivax | protein |
| 57 | GPI_P113 mouseCO + Kozak | P. berghei ANKA strain | DNA |
| 58 | Pb GPI_P113 (mouseCO + Kozak) | P. berghei ANKA strain | protein |
| 59 | Pb GPI_P113 | P. berghei ANKA strain | protein |
| 60 | PfP113 human CO + Kozak | P falciparum 3D7 strain | DNA |
| 61 | PfP113 (human CO + Kozak) | P falciparum 3D7 strain | protein |
| 62 | P113 | P falciparum | protein |
| 63 | PvP113 human CO + Kozak | P vivax Sal-1 strain | DNA |
| 64 | PvP113 (human CO + Kozak) | P vivax Sal-1 strain | protein |
| 65 | P113 | P vivax | protein |
| 66 | PbAg40 mouse CO + Kozak | P. berghei ANKA strain | DNA |
| 67 | PbAg40 (mouse CO + Kozak) | P. berghei ANKA strain | protein |
| 68 | PbAg40 | P. berghei ANKA strain | protein |
| 69 | PfAg40 human CO + Kozak | P falciparum 3D7 strain | DNA |
| 70 | PfAg40 (human CO + Kozak) | P falciparum 3D7 strain | protein |
| 71 | Ag40 | P falciparum | protein |
| 72 | PvAg40 human CO + Kozak | P vivax Sal-1 strain | DNA |
| 73 | PvAg40 (human CO + Kozak) | P vivax Sal-1 strain | protein |
| 74 | PvAg40 | P vivax Sal-1 strain | protein |
| 75 | PbAg45 mouse CO + Kozak | P. berghei ANKA strain | DNA |
| 76 | PbAg45 (mouse CO + Kozak) | P. berghei ANKA strain | protein |
| 77 | PbAg45 | P. berghei ANKA strain | protein |
| 78 | PfAg45 human CO + Kozak | P falciparum 3D7 strain | DNA |
| 79 | PfAg45 (human CO + Kozak) | P falciparum 3D7 strain | protein |
| 80 | PfAg45 | P falciparum | protein |
| 81 | PvAg45 human CO + Kozak | P vivax Sal-1 strain | DNA |
| 82 | PvAg45 (human CO + Kozak) | P vivax Sal-1 strain | protein |
| 83 | PvAg45 | P vivax | protein |
| 84 | Kozak consensus sequence | | DNA |
| 85 | Kozak consensus sequence | | DNA |
| 86 | BamHI site | | DNA |
| 87 | XhoI site | | DNA |
| 88-94 | CD8 T cell epitopes | | protein |

Additional information relating to some of the sequences disclosed in the above table are provided in the table below.

| SEQ ID | GenBank | strain | pubmed |
|---|---|---|---|
| 15 | BAM84930.1 | Plasmodium falciparum isolate Pal97-042 origin: Philippines | 23295064 |
| | ACO49323 | Plasmodium falciparum" isolate A5 origin: Thailand | 19460323 |
| 18 | AAA29535.1 | P.vivax (strain Thai; isolate NYU Thai) origin: Thailand | 2290443 |
| 24[(1)] | EWC74605.1 | Plasmodium falciparum UGT5.1 strain origin: Uganda | |
| 27 | AIU97014.1 | Plasmodium vivax isolate = "TMS38" origin: Thailand | |
| 36[(3)] | KMZ87332.1 | Plasmodium vivax Brazil I strain | |
| 56 | KMZ82648.1 | Plasmodium vivax India VII | |
| 65 | KMZ78214.1 | Plasmodium vivax India VII | |
| 83 | KMZ90984.1 | Plasmodium vivax Mauritania I | |

[(1)]Worldwide web: ncbi.nlm.nih.gov/biosample/SAMN01737342
[(2)]Worldwide web: ncbi.nlm.nih.gov/biosample/SAMEA2394724
[(3)]Worldwide web: ncbi.nlm.nih.gov/biosample/SAMN00710434

EXAMPLES

To approach the complex problem of identifying protective antigens, the inventors devised a functional screening to identify and combine novel PE protective antigens using a rodent malaria model where mice (C57BL/6) are extremely susceptible to Plasmodium berghei (Pb) sporozoite infection. In this model, sterilizing protection induced by live irradiated sporozoites is mediated by antibodies and mainly by CD8 T cell responses against sporozoites and liver stages, respectively. The inventors' screening strategy was designed based on four main features: i) parameterized selection of 55 PE antigens based on abundance, orthology, predicted topology and function, ii) synthesis of codon-optimized antigens to avoid AT-rich plasmodial sequences and maximize the expression in mammalian cells, iii) immunization using HIV-based lentiviral vector that elicits strong humoral and cellular responses[11, 12], and iv) measurement of protection after a stringent challenge of sporozoites inoculated subcutaneously in the immunized mice.

1. Setting Up the Parameters of the Screening.

In a proof-of-concept experiment aimed at validating the viability of the strategy to screen antigens at a mediumthroughput, the inventors ordered mouse-codon optimized synthetic genes of Pb CSP (SEQ ID No. 11), a known protective antigen, and of more 4 other sporozoite antigens (Celtos, SPECT, HSP20 and Ag13), which were previously correlated with protection[13]. The synthetic plasmodial genes were cloned in to the pTRIP vector plasmid, which drives their expression in mammalian cells via the immediate-early cytomegalovirus promoter (CMV) and the post-transcriptional regulatory element of woodchuck hepatitis virus (WPRE) (FIG. 1, SEQ ID No. 1). These two elements assure a strong expression of the antigen in a wide variety of mouse cells in vivo. HIV-1 derived lentiviral particles were produced by transient co-transfection of HEK 293T cells with three helper plasmids encoding separate packaging functions, the pTRIP vector plasmid containing the synthetic plasmodial gene, the envelope expression plasmid encoding the glycoprotein G from the Vesicular Stomatitis Virus, Indiana ($VSV^{IND}$) or New Jersey ($VSV^{NJ}$) serotypes, and the p8.74 encapsidation plasmid (FIG. 1). This co-transfection generates integrative but replication-incompetent pseudotyped lentiviral particles capable of transducing dividing and non-dividing cells—including dendritic cells— and inducing potent cellular[6] and humoral[7] memory responses. The particles were collected 48 hours after co-transfection and each batch of vector were titrated in HeLa cells by quantitative PCR. This functional titration assay gives the concentration of particles capable to transfer one copy of the gene per cell and will be expressed in Transducing Units (TU)/mL. Plasmid sequences are shown in the figures and their sequences are provided in the sequence listing.

Groups of five mice were immunized with a single intra-muscular dose of 5e7 TU of ultracentrifugation-concentrated $VSV^{IND}$ pseudotyped lentiviral particles (LPs). Thirty days after immunization, mice were challenged with 10,000 bioluminescent sporozoites inoculated sub-cutaneously in the footpad. Two days later, the parasite load in the liver was measured by bioluminescence. Surprisingly, CSP-immunization decreased 15×-fold the parasite load in the liver after a challenge using 10,000 bioluminescent sporozoites, versus a 5×-fold decrease in animals immunized intravenously with 50,000 irradiated sporozoites, our golden standard of protection (FIG. 2). This preliminary and promising result validated the high performance of the present method to functionally identify new protective antigens and showed the feasibility to scale-up our test samples.

The inventors next aimed at the transposition of these optimal experimental conditions to those of a larger screening. This transposition included the validation of the use of non-concentrated LPs, the choice of the best promoter driving the expression of the plasmodial antigens, and the dose of immunization.

The first parameter tested was the use of non-concentrated, instead of concentrated LPs, to avoid a costly and time consuming ultracentrifugation concentration step in the protocol of LP production, which requires large volumes of non-concentrated LP suspensions. FIG. 3 shows that there is no significant difference between protection induced by the same dose ($5 \times 10^7$ TU) of concentrated LPs injected intramuscularly (CS im c, 50 µL) and non-concentrated LPs injected intraperitoneally (CS ip nc, 700 µL). Protection was measured by reduction in the liver infection, as assessed by bioluminescence after a challenge of 5,000 sporozoites injected subcutaneously 30 days following immunization. As negative control of protection the inventors used mice immunized with Pb Ag13, determined previously as a non-protective antigen (FIG. 1).

Next two promoters were tested to identify which one induced the best protection using the codon optimized Pb CSP. The inventors compared the use of the strong and constitutive cytomegalovirus (CMV) promoter versus a human beta-2 microglobulin (B2M) promoter, which direct gene expression in many cell types, particularly in dendritic cells. FIG. 4 shows that CSP-induced protection was slightly better, although not statistically significant, using the B2M promoter at an immunization dose of $1 \times 10^7$ TU of non-concentrated LP. Therefore the inventors further adopted this promoter in our constructs.

During this period of optimization the inventors observed some variations in the CSP-induced protection using the same stock of LPs, as can be seen in the FIG. 4. The inventors asked if this variability could be due to the process of mouse acclimation, including the modification of mouse microbiota. To test this hypothesis a group of mice purchased from Elevage Janvier (4 weeks-old) was reared in the animal facility for 3 weeks before immunization (group old). A second group of mice (7 weeks-old) was purchased and put in cages 3 days before the immunization (group new). Both groups were intraperitoneally immunized with $1 \times 10^7$ TU of non-concentrated LPs. As shown in the FIG. 5, mouse acclimation of 3 weeks resulted in a significant and more homogeneous protection when compared to 3 days of acclimation. Consequently, the inventors adopted this period of acclimation in all our subsequent experiments.

Next, the best protective immunization dose was tested, ranging from $1 \times 10^8$ to $1 \times 10^5$ TU of B2M CSP non-concentrated LPs. As shown in FIG. 6, significant protection was observed using $10^7$ and $10^8$ TU, and the best protective activity was observed using an immunization dose of $1 \times 10^7$ TU. In this experiment the inventors also observed a gradual loss of SPZ infectivity over time, as evidenced in the GFP groups, due to the use of a single SPZ stock to challenge all animals. To reduce the multiple shocks of temperature due to the manipulation of the stock tube, kept on ice between injections, the inventors prepared a SPZ stock for each group in the subsequent challenges and this variation disappeared.

In summary, an immunization protocol was set up based on CSP that relied on a single intraperitoneal injection of $10^7$ TU of non-concentrated $VSV^{IND}$ B2M LP in C57BL/6 mice of 7 weeks-old, acclimated for 3 weeks in the animal facility. In the pooled data, this protocol leaded in average to a ~5-fold decrease in the parasite liver load, as assessed by bioluminescence imaging, using a subcutaneous challenge of 5,000 luciferase-expressing SPZ.

However, this bioluminescent method of detection of parasites presents some disadvantages such as the use and associated costs of anesthesia and luminescent substrate, limited capacity of analysis of a few animals per acquisition, being time-consuming and not sensible enough to predict sterile protection. Therefore, the inventors decided to use fluorescent parasites to check protection by measuring parasitemia at day 4, 5, 6 and 10 post-inoculation by flow cytometry. The inventors analyze at least 100,000 red blood cells, which gives the sensibility to detect a parasitemia of 0.001%. At day 4 to 6, parasites grow exponentially in the blood therefore the log transform of parasitemia can be fitted using a linear regression where the slope represents the time of parasite replication per day. Consequently, the inventors use this parameter to determine if the immunization impacts the parasite growth in the blood. For quantifying protection, the inventors used the log of parasitemia at day 5 post inoculation. This represents an indirect measure of liver infection and it is more robust than the measure at day 4 because more events of infected blood cells are registered.

Finally the inventors defined that immunized mice are sterile protected if infected red blood cells are not detected after 10 days post inoculation. After defining the protocol of immunization and the method for the quantification of parasite infection the inventors started to screen the protective activity of down-selected antigens.

2. Parameterized Selection of Antigens

By merging proteomic and transcriptomic data using PlasmoDB (Worldwide web: plasmodb.org), the inventors identified ~9000 genes expressed in plasmodial pre-erythrocytic stages—salivary gland sporozoites and liver-stages—of three different plasmodial species, with 3654 syntenic orthologs in *Plasmodium falciparum* (Pf), the most lethal human-infecting plasmodial species. By analyzing the repertoire of pathogen transcripts, as inferred by the amount of expressed sequence tags (ESTs) obtained in cDNA libraries of different stages and species of malaria parasites, the inventors have observed that ~50% of the total amount of ESTs are coming from only ~10% of genes represented in these libraries, corresponding to approximately 100 genes in these libraries (FIG. 7). Therefore, by focusing on the ~100 most abundant transcribed genes the inventors could target about 50% of the putative (to be translated) antigenic mass of a given parasite stage. Accordingly, the inventors selected ~50 abundantly transcribed genes coding for conserved proteins with high probability of being expressed/presented on the surface of the parasite/infected cell, giving priority to candidates containing T cell epitopes predicted by IEDB MHC binding algorithm (Worldwide web: tools.iedb.org/mhci/). A Kozak consensus sequence, a translational start site, was added to these down-selected genes, which were then mammalian codon-optimized and synthesized by MWG Eurofins (listed in the figures). These synthetic codon-optimized down-selected plasmodial genes were then cloned into the B2M pTRIP plasmid and produced as non-concentrated $VSV^{IND}$ LPs.

3. First Screening of Protective Antigens Using a Single Dose of LPs

Usually, 6-10 plasmodial antigens were tested by experiment, with a negative (GFP) and positive (CSP) control of protection. After three weeks post-immunization, the immune-sera were tested on permeabilized and non-permeabilized sporozoites, allowing the determination of (i) the efficiency of the host humoral response and therefore the immunogenicity of the lentivirus-delivered antigen, and (ii) the localization of the parasite antigen (surface vs intracellular). As shown in the FIG. 8, where the inventors immunized mice with putative GPI-anchored antigens, surface antigens were identified by flow cytometry and immunofluorescence (CSP and 9-6). The sera of GFP and CSP group served, respectively, as positive control for intracellular and surface antigen localization.

Four weeks post-immunization the animals were challenged with 5,000 GFP-expressing sporozoites, microinjected in the footpad of immunized mice. Parasitemia was determined by flow cytometry. To define protection, parasitemia of all GFP groups (day 5 post-infection, n=35) was log transformed, pooled and the 95% tolerance interval was calculated (FIG. 9). All animals below the inferior limit of the tolerance interval, which represents a ~8-fold decrease in parasitemia compared to the mean log of parasitemia of the GFP group, were considered protected. As positive control, 43% of animals (15/35) were protected by CSP immunization with a mean decrease of ~5 fold in comparison to the GFP group. 9% of them (3/35) became sterile protected after sporozoite challenge.

In the first set of 43 antigens tested (FIG. 9), we identified 9 PE antigens that protected at least one out of five immunized mice (black circles; 07-03, 09-06, 10-05, 10-10, 12-03, 12-04, 12-05, 12-07 and 13-08). Three of them were also identified as sporozoite surface antigens (09-06, 10-05 and 10-10).

To verify the robustness of our screening, the inventors selected 4 protective antigens (CSP, 09-06, 10-05 and 07-03), 6 non-protective antigens (GFP, 09-07, 07-05, 07-06, 06-06 and 10-06), and instead of only one immunization dose, the inventors administered one dose of $5 \times 10^5$ TU of non-concentrated $VSV^{NJ}$ B2M LPs and one month later, a second dose of $1 \times 10^7$ TU of $VSV^{IND}$ B2M LPs. As shown in the FIG. 10, the inventors observed three patterns of infection profile when the inventors compared one (circles, data from FIG. 9) and two immunization doses (squares, PB). For the non-protective antigens GFP, 09-07 and 07-05, the second dose of LP did not change the profile of infection, as expected. For the protective antigens CSP (***P<0.001), 09-06, 10-05 and 07-03, the second dose of LP increased the number of protected mice and/or decreased the average parasitemia, also, as expected. Notably, the non-protective antigens 07-06, 06-06 and 10-06 as assessed by one dose of LP immunization, showed a strong protective activity, including a sterile protected mice (PB 7-6), when administered twice in mice.

These results validated some of our protective antigens detected with a single immunization dose, but also showed that some good protective antigens were not detected in our first screen, leading to the decision of repeating the screening using two immunization doses.

4. Second Screening of Protective Antigens Using Two Doses of LP

By functionally screening the protective activity of 55 down-selected plasmodial PE antigens using the protocol of two immunization doses, the inventors identified 16 antigens that protected at least one immunized mice per group. Among these 16 antigens, 7 of them (black circles/bars in the FIG. 11) conferred significant protection when compared to animals immunized with the GFP, both when analysing the number of protected mice (Fisher's Exact test) or the mean of the log parasitemia (ANOVA).

All of them presented a similar or an inferior protective activity when compared individually to our standard of protection, the CSP (FIG. 11). Five of them are molecules with assigned function (11-05, 11-06, 11-07, 30-03 and 18-10) and two are proteins with no predicted function (11-09 and 11-10). The structure of these Pb protective antigens is shown in the FIG. 12 and the alignment of these proteins with their respective orthologs from human-infecting parasites, *P. falciparum* (Pf) and *P. vivax* (Pv), and macaque-infecting parasite *P. cynomolgi*, is represented in the FIG. 13. As shown in table I, the percentage of identical amino acids between orthologs varied from 75 to 38% (Pb vs Pf), 78 to 33% (Pb vs Pv) and 79 to 26% (Pf vs Pv). The most conserved genes (>50% identity) are 30-03, 11-09, 11-10 and 11-06 orthologs. Antigens with divergent repetitive sequences are penalized in the alignment by insertional gaps, presenting less percentage of identity.

TABLE I

Percent Identity Matrix created by CLUSTAL 2.1. Amino acid sequence of Pb antigens were pBlasted against Pf and Pv taxids (organism) and the best matched sequence was used to align the orthologous proteins using MUSCLE (Worldwide web: ebi.ac.uk/Tools/msa/muscle/). The table shows the percentage of identical amino acids between species. Raw data is presented in the figures.

| Antigen | Amino acid identity (%) | | |
| --- | --- | --- | --- |
| | Pb/Pf | Pb/Pv | Pf/Pv |
| 30-03 | 74.65 | 77.90 | 73 |
| 11-09 | 66.19 | 66.19 | 79.05 |
| 11-06 | 64.92 | 63.40 | 64.44 |
| 11-10 | 56.94 | 50.15 | 62.28 |
| CSP | 42.06 | 33.53 | 26.36 |
| 18-10 | 39.60 | 41.23 | 49.30 |
| 11-05 | 38.75 | 44.67 | 42.86 |
| 11-07 | 37.53 | 33.42 | 46.30 |

In a decreasing order of protection the first antigen identified is TRAP[14] (thrombospondin related anonymous protein; 11-05) (SEQ ID No. 20 and 21), which validated our method of screening since immunization with TRAP is known to induce protection both in rodents[15] and humans[16]. TRAP is a type I transmembrane protein harbouring two extracellular adhesive domains, a von Willebrand factor type A domain and a thrombospondin type 1 domain, followed by a proline-rich repetitive region. TRAP is stored in micronemal secretory vesicles and following parasite activation, the protein is translocated to the surface of sporozoites where it serves as a linker between a solid substrate and the cytoplasmic motor of sporozoites. Intriguingly, anti-TRAP antibodies do not impair parasite motility and infectivity[17] CD8+ T cells seem to mediate the protection mediated by TRAP immunization[10,15,16,18].

The second protective antigen identified is an inhibitor of cysteine protease (ICP, 18-10)[19] (SEQ ID No. 29, 30). ICP seems to be involved in the motility and infectivity capacity of sporozoites via the processing of CSP[20,21], as well as, in the parasite intra-hepatic development[22]. Although the protein does not present structural signatures of membrane localization, there is evidence that the protein is located on the surface of sporozoites[19,20]. Opposing results are published regarding the secretion of the protein following parasite activation[21,22]. Similarly, there are contradictory results regarding the inhibition of host cell invasion by sporozoites in vitro in the presence of anti-ICP immune sera[20,23].

The third protective antigen identified is a metallopeptidase (Falcilysin/Bergheilysin, 30-03)[24] (SEQ ID No. 38 for Bergheilysin A, No. 47 for Bergheilysin B, and No. 39 for the entire Bergheilysin ORF). This protease seems to be involved in the catabolism of hemoblobin in the parasite blood stages[25]. A $H-2K^b$-restricted CD8 T cell epitope was recently described during the parasite blood infection[25] suggesting that CD8 T cells could mediate the protection elicited by the antigen 30-03 during the hepatic infection.

The fourth protective antigen is a GPI-anchored protein (P113, 11-07) (SEQ ID No. 58 and 59) initially described in blood stages[16] and also expressed in PE stages. P113 seems to be important for liver infection, dispensable for blood infection, but its precise function is unclear[17].

The fifth antigen is the pore-forming like protein SPECT2 (11-06)[28] (SEQ ID No. 49 and 50). This protein has a membrane attack complex/perforin (MACPF) domain and is involved in the sporozoite cell traversal activity, being important for the progression of sporozoites in the dermis[29] and survival to phagocytosis in the liver[30].

The sixth antigen identified is a hypothetical protein that the inventors called 11-09 or Ag40 (SEQ ID No. 67 and 68). This protein has 4-5 annotated transmembrane domains. Deletion of the gene coding for the antigen 11-09 caused impairment of Pb parasite development in the liver.

The seventh antigen is also a hypothetical protein that the inventors called 11-10 or Ag45 (SEQ ID No. 76 and 77). This protein doesn't have annotated domains, but possesses a central region with negatively charged amino acids. Recently the 11-10 ortholog of Plasmodium yoelii, another rodent-infecting plasmodial species, was also identified as a protective antigen[21]. The deletion of the gene coding for the antigen 11-10 blocked the Pb sporozoite invasion of salivary glands and completely abolished the capacity of sporozoites to infect the liver.

To determine if CSP based protection could be additively or synergistically improved by the combination of antigens, the inventors assessed the protection elicited by a sub-optimal dose of CSP ($5 \times 10^5$ TU of $VSV^{NJ}$/$5 \times 10^6$ TU of $VSV^{IND}$ B2M LPs) in the absence or presence of a usual dose of protective antigens ($5 \times 10^5$ TU of $VSV^{NJ}$/$1 \times 10^7$ TU of $VSV^{IND}$ B2M LPs). This protection induced by CSP+ protective antigens was compared to the protection elicited by these antigens alone (data from FIG. 11). As negative control the inventors used animals immunized with the usual dose of GFP LPs. FIG. 14 shows that 4 antigens when combined with a sub-optimal dose of CSP (CSP+11-03, +11-10, +11-07 and +11-05, triangles) did not change the average of protection when compared to the protective activity elicited by these antigens administered alone. For two antigens, the antigen combination (CSP+11-09 and CSP+1-06) showed a tendency of better protection (~10 fold), but not statistically significant.

5. Identification of Multi-Antigenic Formulations Capable of Sterilizing Sporozoite Infection Via a CD8+ T Cell Response Since testing all possible combinations of antigens was technically unfeasible, the inventors decided to evaluate the protection elicited by the combination of these multiple protective antigens. Remarkably, two immunizations of mice with the combination of CSP and 6 of these antigens (11-05, 11-06, 11-07, 11-09, 11-10, 18-10) elicited sterile protection in the vast majority of challenged animals (7PEAg, 86-100%, FIG. 15). This percentage of sterile protection was far superior to the protection conferred by CSP in the same experimental conditions (0-14%). Depletion of CD8+ cells (α-CD8) just before the challenge, but not of CD4+ cells, decreased this protection to the level of that induced by CSP, suggesting that CD8+ T cells mediate the extra-protection elicited by the addition of these 6 PE antigens.

The same protective efficacy was observed using only a single immunization for the 7PEAg or for the 7PEAg+30-03 (FIGS. 16a and 16b, 8PEAg), as well as, the dependence on CD8+ T cells for the sterilizing immunity of 8PEAg (FIG. 16b). Since the antigen 30-03 is a large molecule and did not improve sterile protection when administered with the 7PEAg, the inventors excluded it from further analysis.

6. Design of a Chimeric Antigen Containing the Protective Domains of Down-Selected PE Antigens To determine a minimal antigenic composition capable of eliciting this additional protective CD8+ T cell response, the inventors first identified the antigens whose protective activity was dependent on these T cells. Protection induced by two immunizations using TRAP, 18-10 and 11-09 was significantly reduced after depletion of CD8+ cells, as shown in the FIG. 17b. Protection induced by two immunizations using 11-10 was reduced after depletion of CD8+ cells but it was not statistically significant (FIG. 17b). Therefore the inventors grouped CSP with the CD8+ dependent protective antigens, TRAP, 18-10 and 11-09 and added separately 11-10, 11-07 and 11-06 to identify a minimal antigenic combination capable of sterile protect immunized animals like the complete combination of antigens. As shown in FIG. 17a, the combination of 5 antigens, CSP+TRAP, 18-10, Ag40 and Ag45 induced comparable level of sterile protection elicited by the combination of the 7PEAg.

In order to combine the protective domains of each of these 5 antigens in a single chimeric molecule and thus avoid the costs associated with the production and delivery of five different antigens, the inventors mapped the protective regions of each antigen according to the localization of predicted epitopes binding to MHC class I molecules (FIGS. 17c and 18) and structural-functional conserved motifs (FIGS. 12, 13, 17c and 18).

As shown in the FIG. 17c, all tested domains presented either a better (11-10CT) or similar protective activity when compared to the entire antigen. The level of mean protection elicited by the domains of antigens inducing protective CD8+ T cells correlated with the score (P<0.01) or affinity (P=0.01) of CD8+ T cell epitopes respectively predicted by SYFPEITHI and IEDB (FIGS. 17c and 17d). Importantly, the mapping of protective domains allowed the reduction of ~2000 basepairs in the final chimeric PE antigen construct. Due to its small size, Ag40 was not split in domains and the data presented in the FIG. 17c comes from the experiment showed in the FIG. 11.

Analysis of the distribution of epitopes of Pb antigens predicted to bind to MHC class I molecules of C57BL/6 mice (H2-$K^b$, H2-$D^b$) or of the Pf orthologues predicted to bind to HLA A02:01, a high prevalent human HLA allele, revealed that most of predicted good binders are clustering in the regions that are conserved among different plasmodial species (Pb, Pc, Pv and Pf, FIG. 18). This renders possible the utilization of the Pb protective regions mapped in the FIG. 17 to select the correspondent regions in the Pf orthologues. In addition, the inventors validated the binding of the best predicted Pf epitopes to the HLA A02:01 class I molecule using the REVEAL® binding assay developed by Proimmune, which allows the quantification of the binding and stabilization of the complex formed by the tested peptide, HLA A02:01 and β2-microglobulin (FIG. 18).

In summary, using a parameterized selection of antigens, a screening based on lentiviral vaccination and a direct measurement of protection in vivo against a stringent sporozoite challenge, the inventors identified 8 protective antigens, including the vaccine candidates CSP and TRAP, out of 55 tested antigens. All these 8 antigens are conserved across several plasmodial species. Remarkably, immunization using a combination of seven or eight of these antigens elicited sterile protection in the vast majority of challenged mice, either using one or two immunizations. More importantly, this protection was far superior than the one elicited by CSP, so far the best protective PE antigen. Depletion of CD8+ T cells abolished sterilizing immunity, indicating that these cells are essential for this protective phenotype, similarly to the protection conferred by irradiated sporozoites. A minimal combination of 5 of these antigens was also capable of eliciting sterile protection in most of challenged animals. Mapping of the protective domains of these 5 antigens allowed the design of a chimeric antigen containing the fused protective domains of these 5 down-selected antigens. The human-infecting parasite orthologs of these protective antigens, or of their protective domains are potential candidates for being used in the development of a malaria vaccine formulation containing multiple protective antigens or multiple protective domains fused in a single molecule.

Material and Methods

Parasite Strains:

*Plasmodium berghei* ANKA strain constitutively expressing the GFP under the control of the hsp70 promoter (Ishino et al, 2006) was used in the challenges using parasitemia, quantified by flow cytometry, as protective readout. *Plasmodium berghei* ANKA strain constitutively expressing a GFP-luciferase fusion under the control of the eef-1alfa promoter (Franke-Fayard et al, 2008) was used in the challenges using liver infection, assessed by bioluminescence, as protective readout. Of note, parasitemia quantified using hsp70-gfp parasites was at least 10 times more sensible than using eef-1a gfp:luc parasites due to more intense expression level of GFP.

Ishino T, Orito Y, Chinzei Y, Yuda M (2006) A calcium-dependent protein kinase regulates *Plasmodium* ookinete access to the midgut epithelial cell. *Mol Microbiol* 59:1175-1184.

Franke-Fayard B, Djokovic D, Dooren M W, Ramesar J, Waters A P, et al. (2008) Simple and sensitive antimalarial drug screening in vitro and in vivo using transgenic luciferase expressing *Plasmodium berghei* parasites. *Int J Parasitol* 38:1651-1662.

Mouse Strains:

C57BL/6 Rj and Swiss mice were purchased from Elevage Janvier (France). All experiments were approved by the Animal Care and Use Committee of Institut Pasteur (CETEA 2013-0093) and were performed in accordance with European guidelines and regulations (MESR-01324).

Production of Lentiviral Particles Stock:

Down-selected plasmodial antigens were synthesized by Eurofins MWG as mouse codon-optimized genes with the addition of a Kozak consensus sequence (GCCACCATGGCT(C) (SEQ ID No. 85 and 86), representing the first 12 nucleotides in the coding sequences of the antigenic polypeptides), encompassing the first translated ATG. This modification adds an extra alanine after the first methionine. A BamHI (GGATCC-SEQ ID No. 87) and Xho I (CTCGAG-SEQ ID No. 88) restriction sites were also inserted in the 5' and 3' extremities of the construct, respectively. These synthetic codon-optimized genes were then cloned into the BamHI and Xho I restriction sites of the pTRIP plasmid harboring either the CMV or B2M promoter (FIGS. 16 and 17). Lentiviral particles were produced by transient calcium co-transfection of HEK 293T cells with three helper plasmids encoding separate packaging functions, the pTRIP vector plasmid containing the synthetic plasmodial gene, the envelope expression plasmid encoding the glycoprotein G from VSV (Vesicular Stomatitis Virus, Indiana (FIG. 19) or New Jersey (FIG. 20) serotypes) and the p8.74 encapsidation plasmid (FIG. 18), containing the structural, accessory and regulatory genes of HIV. This co-transfection will generate integrative but replication-incompetent pseudotyped lentiviral particles. At 24 hours post-transfection, the cell culture medium was replaced by serum-free DMEM. Supernatants were collected at 48 hours post-transfection, clarified by low-speed centrifugation, and stored at −80° C. The lentiviral vector stocks were titrated by real-time PCR on cell lysates from transduced HEK 293T cells and titer were expressed as transduction unit (TU) per ml.

Immunization Protocol:

For the screening using one single dose of LPs, 4 weeks-old C57BL/6 mice (n=5 per group per experiment) were acclimated for 3 weeks and intraperitoneally immunized with a single dose of $1\times10^7$ TU of non-concentrated VSV$^{IND}$ B2M LPs. For the protocol using two immunization doses. 4 weeks-old C57BL/6 mice (n=5 per group per experiment) were acclimated for 3 weeks and intraperitoneally immunized with a first dose of $5\times10^5$ TU of non-concentrated VSV$^{NJ}$ B2M LPs. Thirty days after the first immunization, the animals received a second dose of $1\times10^7$ TU of non-concentrated VSV$^{IND}$ B2M LPs. For testing combinations of a sub-optimal dose of CSP+ an optimal dose of down-selected antigens, mice were immunized twice, four weeks apart, with a sub-optimal dose of CSP ($5\times10^5$ TU of non-concentrated VSV$^{NJ}$ B2M LP in the first immunization and $5\times10^6$ TU of non-concentrated VSV$^{IND}$ B2M LP in the second immunization) and the usual dose of protective plasmodial antigens ($5\times10^5$ TU of non-concentrated VSV$^{NJ}$ B2M LP in the first immunization and $1\times10^7$ TU of non-concentrated VSV$^{IND}$ B2M LP in the second immunization). For testing the combination of multiple antigens, mice were immunized twice, four weeks apart, with 7× the individual dose (1 dose=$5\times10^5$ TU of non-concentrated VSV$^{NJ}$ B2M LPs in the first immunization/$1\times10^7$ TU of non-concentrated VSV$^{IND}$ B2M LPs in the second immunization) of the control antigen Al11-luciferase (Luc), with the individual dose of CSP plus 6 doses of Luc or with the individual doses of CSP and of the 6 conserved PE antigens (11-05, 11-06, 11-07, 11-09, 11-10 and 18-10). For this experiment the inventors used ultrafiltration and lenti-X (Clontech) concentrated stocks. The average volume of injection was 500 uL of LPs diluted in DMEM.

In all cases, thirty days after last immunization, mice were challenged with 5,000 GFP-expressing sporozoites micro-injected subcutaneously in the mice footpad.

Sporozoite Challenge:

*Anopheles stephensi* (Sda500 strain) mosquitoes were reared using standard procedures. 3-5 days after emergence, mosquitoes were fed on infected Swiss mice with a parasitemia superior to 2%, and kept as described in Amino et al, 2007. Between 20 and 23 days post-feeding, the salivary glands of infected mosquitoes were dissected in PBS, collected in 20 uL of sterile PBS on ice and disrupted using an eppendorf pestle. The suspension of parasites was filtered through a nylon mesh of 40 um, counted using Kova glasstic slide (Hycor) and adjusted to a concentration of 5,000 or 10,000 sporozoites/uL with sterile PBS. This suspension was divided in individual tubes, one for each group of immunized mice (n=4-7 per group), and kept on ice until the challenge. One microliter of parasite suspension was injected in the right footpad of mice using a Nanofil syringe (World Precision Instruments) with a 35 GA bevelled needle (NF35BV).

Amino R, Thiberge S, Blazquez S, Baldacci P, Renaud O, et al. (2007) Imaging malaria sporozoites in the dermis of the mammalian host. *Nat Protoc* 2:1705-1712.

Measurement of Parasite Infection:

Hepatic parasite loads were quantified at ~44 h by bioluminescence in fur shaved mice infected with GFP LUC parasites. Infected mice were first anesthetized with isoflurane and injected subcutaneously with D-luciferin (150 mg/kg, Caliper LifeSciences). After a 5 minutes incubation allowing the distribution of the substrate in the body of the anesthetized animals, mice were transferred to the stage of an intensified charge-coupled device photon-counting video camera box where anesthesia was maintained with 2.5% isoflurane delivered via nose cones. After 5 minutes of signal acquisition controlled by the Living Image software (Xenogen Corporation), animals were returned to their cage. Automated detection of bioluminescence signals by the system resulted in the generation of bioluminescence signal maps superimposed to the gray-scale photograph of the experimental mice. These images were then quantified using the Living Image software. Briefly, regions of interest (ROI) encompassing the liver were manually defined, applied to all animals and the average radiance within these ROIs was automatically calculated. Background signal was measured in the lower region of the abdomen, and the average values of background signal obtained.

Alternatively, blood infection was assessed by flow cytometry using hsp70-GFP parasites. At day 4, 5, 6 and >10 post-challenge, a millimetric excision was performed in the tail of mice allowing the collection of a drop of blood that was readily diluted in 500 uL of PBS. This diluted blood was analyzed using a flow cytometer. 500,000 events were analyzed at day 4 post-challenge and 100,000 events in the subsequent days. Non-infected mice after day 10 were considered as sterile protected.

Statistical Analysis:

Parasitemia data from GFP immunized control were log transformed and pooled for the calculation of 95% tolerance of interval with 95% of certitude. For the immunization protocol of one dose this limit comprised the interval of the mean value±2.49 SD (mean=−0.3906, SD=0.3392, n=35). Similarly, for the immunization protocol of two doses this limit comprised the interval of the mean value±2.51 (mean=−0.3002, SD=0.3305, n=33). All mice with a log parasitemia inferior to the lower limit (mean−2.5 SD) were considered as significantly different from the control mice (P<0.05), and therefore considered as protected. In the protocol using two immunization doses, the difference in the numbers of protected mice, following the definition above, between the test group and the GFP control group was assessed using the Fisher's exact test. The average of the log parasitemia of the groups with significant differences in the Fisher's Test were compared to the GFP group using one-way ANOVA (Holm-Sidak's multiple comparison test).

REFERENCES

1. Worldwide web: who.int/mediacentre/factsheets/fs094/en/
2. RTS,S Clinical Trials Partnership. Lancet. 2015; 4; 386 (9988):31-45.
3. Moorthy V S, Ballou W R. Malar J. 2009; 8: 312.
4. Worldwide web: who.int/immunization/topics/malaria/vaccine_roadmap/en/
5. Seder R A, et al. *Science*. 2013; 341:1359-65.
6. Amino R, Ménard R. *Nature*. 2012; 484(7395):S22-3
7. Kester K E, et al. 2014. pii: S0264-410X(14)00822-6.
8. Mishra S, et al. *Vaccine*. 2011; 29(43):7335-42.
9. Murphy S C, Kas A, Stone B C, Bevan M J. *Proc Natl Acad Sci USA*. 2013; 110(15):6055-60.
10. Hafalla J C, et al. PLoS Pathog. 2013; 9(5):e1003303.
11. Iglesias, M. C., et al. J Gene Med. 2006; 8, 265-274.
12. Firat, H., et al. J Gene Med. 2002; 4, 38-45.
13. Doolan D L, et al. Proc Natl Acad Sci USA. 2003; 100:9952-7.
14. Robson K J, et al. Nature. 1988; 335(6185):79-82.
15. Khusmith S, et al. Science. 1991; 252(5006):715-8.
16. Ewer K J, et al. Nat Commun. 2013; 4:2836.
17. Gantt S, et al. Infect Immun. 2000; 68(6):3667-73.

18. Khusmith S, Sedegah M, Hoffman S L. *Infect Immun.* 1994; 62(7):2979-83.
19. LaCrue A N, et al. Mol Biochem Parasitol. 2006; 148(2):199-209.
20. Rennenberg A et al. PLoS Pathog. 2010; 6(3):e1000825.
21. Boysen K E, Matuschewski K. MBio. 2013; 4(6): e00874-13.
22. Lehmann C, et al. PLoS Pathog. 2014; 10(8):e1004336.
23. Pei Y, et al. Cell Microbiol. 2013 September; 15(9): 1508-26.
24. Eggleson K K, Duffin K L, Goldberg D E. J Biol Chem.; 274(45):32411-7.
25. Poh C M, Howland S W, Grotenbreg G M, Rénia L. Infect Immun. 2014; 82(11):4854-64.
26. Gilson P R, et al. Mol Cell Proteomics. 2006; 5(7):1286-99.
27. Offeddu V, Rauch M, Silvie O, Matuschewski K. Mol Biochem Parasitol. 2014; 193(2):101-9.
28. Ishino T, Chinzei Y, Yuda M. Cell Microbiol. 2005; 7(2):199-208.
29. Amino R, et al. Cell Host Microbe. 2008 Feb. 14; 3(2):88-96.
30. Tavares J, et al. J Exp Med. 2013; 210(5):905-15.
31. Speake C, et al. PLoS One. 2016; 11(7):e0159449.

The invention claimed is:

1. A polynucleotide which is a mammalian codon-optimized synthetic nucleic acid encoding a pre-erythrocyte stage antigen of a *Plasmodium* parasite, wherein said polynucleotide is selected from the group of:
   a. SEQ ID No. 10 for CSP of *P. berghei*, SEQ ID No. 19 for TRAP of *P. berghei*, SEQ ID No.28 for ICP of *P. berghei*, SEQ ID No.37 for Falcilysin of *P. berghei*, SEQ ID No.57 for GPI-anchored protein P113 of *P. berghei*, SEQ ID No.48 for pore-forming like protein SPECT2 of *P. berghei*, SEQ ID No.66 for protein Ag40 11-09 of *P. berghei*, and SEQ ID No.75 for protein Ag45 11-10 of *P. berghei*, or, b. SEQ ID No.13 for CSP of *P. falciparum*, SEQ ID No.22 for TRAP of *P. falciparum*, SEQ ID No.31 for ICP of *P. falciparum*, SEQ ID No.40 for Falcilysin of *P. falciparum*, SEQ ID No.51 for pore-forming like protein SPECT2 of *P. falciparum*, SEQ ID No.60 for GPI-anchored protein P113 of *P. falciparum*, SEQ ID No.69 for protein 11-09 of *P. falciparum*, and SEQ ID No.78 for protein 11-10 of *P. falciparum* or, c. SEQ ID No.16 for CSP of *P. vivax*, SEQ ID No.25 for TRAP of *P. vivax*, SEQ ID No.34 for ICP of *P. vivax*, SEQ ID No.43 for Falcilysin of *P. vivax*, SEQ ID No.54 for pore-forming like protein SPECT2 of *P. vivax*, SEQ ID No.63 for GPI-anchored protein P113 of *P. vivax*, SEQ ID No.72 for protein 11-09 of *P. vivax*, and SEQ ID No.81 for protein 11-10 of *P. vivax*.

2. A method comprising administering to a subject a collection of lentiviral vectors comprising the polynucleotides according to claim 1 provided the collection of lentiviral vectors enables the expression of all antigenic polypeptides encoded by the polynucleotides of one subgroup selected among a/, b/, and c/.

3. A combination of compounds, comprising at least 2 distinct active ingredients, wherein each active ingredient comprises a polynucleotide encoding the antigenic polypeptide of a *Plasmodium* parasite, wherein the polynucleotides are mammalian codon-optimized synthetic nucleic acids selected from the group consisting of:

a. SEQ ID No. 10 for CSP of *P. berghei*, SEQ ID No.19 for TRAP of *P. berghei*, SEQ ID No.28 for ICP of *P. berghei*, SEQ ID No.37 and 46 for Falcilysin of *P. berghei*, SEQ ID No.57 for GPI-anchored protein P113 of *P. berghei*, SEQ ID No.48 for pore-forming like protein SPECT2 of *P. berghei*, SEQ ID No.66 for protein Ag40 11-09 of *P. berghei*, and SEQ ID No.75 for protein Ag45 11-10 of *P. berghei*, b. SEQ ID No.13 for CSP of *P. falciparum*, SEQ ID No.22 for TRAP of *P. falciparum*, SEQ ID No.31 for ICP of *P. falciparum*, SEQ ID No.40 for Falcilysin of *P. falciparum*, SEQ ID No.51 for pore-forming like protein SPECT2 of *P. falciparum*, SEQ ID No.60 for GPI-anchored protein P113 of *P. falciparum*, SEQ ID No.69 for protein Ag40 11-09 of *P. falciparum*, and SEQ ID No.78 for protein Ag40 11-10 of *P. falciparum*, and C. SEQ ID No.16 for CSP of *P. vivax*, SEQ ID No.25 for TRAP of *P. vivax*, SEQ ID No.34 for ICP of *P. vivax*, SEQ ID No.43 for Falcilysin of *P. vivax*, SEQ ID No.54 for pore-forming like protein SPECT2 of *P. vivax*, SEQ ID No.63 for GPI-anchored protein P113 of *P. vivax*, SEQ ID No.72 for protein Ag40 11-09 of *P. vivax*, and SEQ ID No.81 for protein Ag40 11-10 of *P. vivax*.

4. The combination of compounds according to claim 3, wherein one of the polynucleotides encodes the circumsporozoite protein (CSP) and one of the polynucleotides encodes protein Ag40 (11-09).

5. The combination of compounds according to claim 3, wherein one of the polynucleotides encodes the circumsporozoite protein (CSP) and one of the polynucleotides encodes protein Ag45 (11-10).

6. The combination of compounds according to claim 4, further comprising a polynucleotide encoding an antigenic polypeptide selected from the group consisting of thrombospondin related anonymous protein (TRAP), inhibitor of cysteine protease (ICP), metallopeptidase (Falcilysin), GPI-anchored protein P113, and pore-forming like protein SPECT2.

7. The combination of compounds according to claim 5, further comprising a polynucleotide encoding an antigenic polypeptide selected from the group consisting of thrombospondin related anonymous protein (TRAP), inhibitor of cysteine protease (ICP), metallopeptidase (Falcilysin), GPI-anchored protein P113, and pore-forming like protein SPECT2.

8. The combination of compounds according to claim 3, wherein the distinct active ingredients of *Plasmodium* are provided as separate active ingredients.

9. The combination of compounds according to claim 3, wherein the distinct active ingredients of *Plasmodium* are provided as separate compositions of multiple active ingredients in the combination of compounds.

10. The combination of compounds according to claim 3, wherein the distinct active ingredients of *Plasmodium* are provided as a single composition.

11. The combination of compounds according to claim 3, wherein the active ingredients are lentiviral vector(s).

12. The combination of compounds according to claim 11, wherein the active ingredients are HIV-1 lentiviral vector(s).

13. The combination of compounds according to claim 12, wherein each lentiviral vector is a replication-incompetent pseudotyped lentiviral vector, wherein said vector contains a genome comprising a human-codon optimized synthetic nucleic acid.

14. The combination of compounds according to claim 13, wherein each lentiviral vector is an integrative pseudotyped lentiviral vector.

15. The combination of compounds according to claim 14, wherein the genome of the lentiviral vector genome is obtained from the pTRIP vector plasmid wherein the *Plasmodium* synthetic nucleic acid encoding the antigenic polypeptide has been cloned under control of the human beta-2 microglobulin promoter, and under the control of post-transcriptional regulatory element of the woodchuck hepatitis virus (WPRE).

16. The combination of compounds according to claim 15, wherein the lentiviral vector is pseudotyped with the glycoprotein G from a Vesicular Stomatitis Virus (V-SVG) of Indiana or of New-Jersey serotype.

17. A formulation suitable for administration to human host comprising a combination of compounds according to claim 3 together with excipient(s) suitable for administration to a human host.

18. A method for the protective immunisation against malaria parasite infection or against malaria parasite-induced condition or disease, in a human host comprising administering the combination of compounds according to claim 3 to said human host.

19. The method of claim 18, wherein the active ingredients are lentiviral vector(s) and are administered in a priming and boosting steps, wherein the lentiviral vector(s) are pseudotyped with distinct envelope protein(s) which do not cross-seroneutralise, and wherein said priming and boosting steps are separated in time by at least 6 weeks.

20. The method of claim 19, comprising separately provided doses of the lentiviral vector(s), wherein the dose for boosting the cellular immune response is higher than the dose for priming.

21. The method of claim 19, wherein the dose for priming and the dose for boosting the cellular immune response each comprises from $10^5$ to $10^9$ transducing units (TU) when integrative-competent vector particles are used and the dose for priming and for boosting the cellular immune response comprises from $10^7$ to $10^{10}$ TU when integrative-incompetent vector particles are used.

* * * * *

SEQUENCE LISTING

<160> NUMBER OF SEQ ID NOS: 94

<210> SEQ ID NO 1
<211> LENGTH: 4536
<212> TYPE: DNA
<213> ORGANISM: Artificial Sequence
<220> FEATURE:
<223> OTHER INFORMATION: pTRIP CMV GFP

<400> SEQUENCE: 1

| | | | | | |
|---|---|---|---|---|---|
| tggaagggct | aattcactcc | caacgaagac | aagatatcct | tgatctgtgg | atctaccaca | 60 |
| cacaaggcta | cttccctgat | tagcagaact | acacaccagg | gccagggatc | agatatccac | 120 |
| tgacctttgg | atggtgctac | aagctagtac | cagttgagcc | agagaagtta | gaagaagcca | 180 |
| acaaaggaga | gaacaccagc | ttgttacaac | ctgtgagcct | gcatgggatg | gatgacccgg | 240 |
| agagagaagt | gttagagtgg | aggtttgaca | gccgcctagc | atttcatcac | ggtggcccga | 300 |
| gagctgcatc | cggagtactt | caagaactgc | tgatatcgag | cttgctacaa | gggactttcc | 360 |
| gctggggac | tttccaggga | ggcgtggcct | gggcgggact | ggggagtggc | gagccctcag | 420 |
| atcctgcata | taagcagctg | cttttttgcct | gtactgggtc | tctctggtta | gaccagatct | 480 |
| gagcctggga | gctctctggc | taactaggga | acccactgct | taagcctcaa | taaagcttgc | 540 |
| cttgagtgct | tcaagtagtg | tgtgcccgtc | tgttgtgtga | ctctggtaac | tagagatccc | 600 |
| tcagaccctt | ttagtcagtg | tggaaaatct | ctagcagtgg | cgcccgaaca | gggacttgaa | 660 |
| agcgaaaggg | aaaccagagg | agctctctcg | acgcaggact | cggcttgctg | aagcgcgcac | 720 |
| ggcaagaggc | gaggggcggc | gactggtgag | tacgccaaaa | attttgacta | gcggaggcta | 780 |
| gaaggagaga | gatgggtgcg | agagcgtcag | tattaagcgg | gggagaatta | gatcgcgatg | 840 |
| ggaaaaaatt | cggttaaggc | caggggggaaa | gaaaaaatat | aaattaaaac | atatagtatg | 900 |
| ggcaagcagg | gagctagaac | gattcgcagt | taatcctggc | ctgttagaaa | catcagaagg | 960 |
| ctgtagacaa | atactgggac | agctacaacc | atcccttcag | acaggatcag | aagaacttag | 1020 |
| atcattatat | aatacagtag | caaccctcta | ttgtgtgcat | caaaggatag | agataaaaga | 1080 |
| caccaaggaa | gctttagaca | agatagagga | agagcaaaac | aaaagtaaga | ccaccgcaca | 1140 |
| gcaagcggcc | gctgatcttc | agacctggag | gaggagatat | gagggacaat | tggagaagtg | 1200 |
| aattatataa | atataaagta | gtaaaaattg | aaccattagg | agtagcaccc | accaaggcaa | 1260 |
| agagaagagt | ggtgcagaga | gaaaaaagag | cagtgggaat | aggagctttg | ttccttgggt | 1320 |
| tcttgggagc | agcaggaagc | actatgggcg | cagcgtcaat | gacgctgacg | gtacaggcca | 1380 |
| gacaattatt | gtctggtata | gtgcagcagc | agaacaattt | gctgagggct | attgaggcgc | 1440 |
| aacagcatct | gttgcaactc | acagtctggg | gcatcaagca | gctccaggca | agaatcctgg | 1500 |
| ctgtggaaag | atacctaaag | gatcaacagc | tcctggggat | ttggggttgc | tctggaaaac | 1560 |

```
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccccac   2820
cggtcgccac catggtgagc aagggcgagg agctgttcac cggggtggtg cccatcctgg   2880
tcgagctgga cggcgacgta aacggccaca agttcagcgt gtccggcgag ggcgagggcg   2940
atgccaccta cggcaagctg accctgaagt tcatctgcac caccggcaag ctgcccgtgc   3000
cctggcccac cctcgtgacc accctgacct acggcgtgca gtgcttcagc cgctaccccg   3060
accacatgaa gcagcacgac ttcttcaagt ccgccatgcc cgaaggctac gtccaggagc   3120
gcaccatctt cttcaaggac gacggcaact acaagacccg cgccgaggtg aagttcgagg   3180
gcgacaccct ggtgaaccgc atcgagctga agggcatcga cttcaaggag gacggcaaca   3240
tcctggggca caagctggag tacaactaca acagccacaa cgtctatatc atggccgaca   3300
agcagaagaa cggcatcaag gtgaacttca agatccgcca caacatcgag gacggcagcg   3360
tgcagctcgc cgaccactac cagcagaaca cccccatcgg cgacggcccc gtgctgctgc   3420
ccgacaacca ctacctgagc acccagtccg ccctgagcaa agaccccaac gagaagcgcg   3480
atcacatggt cctgctggag ttcgtgaccg ccgcgggat cactctcggc atggacgagc   3540
tgtacaagta aagcggccgc gactctagct cgagctcaag cttcgaattc cgataatca   3600 acctctggat tacaaaattt gtgaaagatt gactggtatt cttaactatg ttgctccttt   3660
tacgctatgt ggatacgctg ctttaatgcc tttgtatcat gctattgctt cccgtatggc   3720
tttcattttc tcctccttgt ataaatcctg gttgctgtct ctttatgagg agttgtggcc   3780
cgttgtcagg caacgtggcg tggtgtgcac tgtgtttgct gacgcaaccc ccactggttg   3840
gggcattgcc accacctgtc agctcctttc cgggactttc gctttccccc tccctattgc   3900
```

```
cacggcggaa ctcatcgccg cctgccttgc ccgctgctgg acaggggctc ggctgttggg    3960
cactgacaat tccgtggtgt tgtcggggaa gctgacgtcc tttccatggc tgctcgcctg    4020
tgttgccacc tggattctgc gcgggacgtc cttctgctac gtcccttcgg ccctcaatcc    4080
agcggacctt ccttcccgcg gcctgctgcc ggctctgcgg cctcttccgc gtcttcgcct    4140
tcgccctcag acgagtcgga tctccctttg gccgcctcc ccgcatcggg aattctgcag    4200
tcgacggtac ctttaagacc aatgacttac aaggcagctg tagatcttag ccactttta    4260 aaagaaaagg ggggactgga agggctaatt cactcccaac gaagacaaga tcgtcgagag    4320
atgctgcata taagcagctg cttttgctt gtactgggtc tctctggtta gaccagatct    4380
gagcctggga gctctctggc taactaggga acccactgct taagcctcaa taaagcttgc    4440
cttgagtgct tcaagtagtg tgtgcccgtc tgttgtgtga ctctggtaac tagagatccc    4500
tcagacccct ttagtcagtg tggaaaatct ctagca                              4536

<210> SEQ ID NO 2
<211> LENGTH: 4468
<212> TYPE: DNA
<213> ORGANISM: Artificial Sequence
<220> FEATURE:
<223> OTHER INFORMATION: pTRIP B2M GFP

<400> SEQUENCE: 2
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180 acaaggaga gaacaccagc ttgttacaac ctgtgagcct gcatgggatg gatgacccgg     240
agagagaagt gttagagtgg aggtttgaca gccgcctagc atttcatcac ggtgcccga     300 gagctgcatc cggagtactt caagaactgc tgatatcgag cttgctacaa gggactttcc     360 gctggggac tttccaggga ggcgtggcct gggcggact ggggagtggc gagccctcag     420
atcctgcata taagcagctg cttttgcct gtactgggtc tctctggtta gaccagatct     480
gagcctggga gctctctggc taactaggga acccactgct taagcctcaa taaagcttgc     540
cttgagtgct tcaagtagtg tgtgcccgtc tgttgtgtga ctctggtaac tagagatccc     600
tcagacccct ttagtcagtg tggaaaatct ctagcagtgg cgcccgaaca gggacttgaa     660
agcgaaaggg aaaccagagg agctctctcg acgcaggact cggcttgctg aagcgcgcac     720
ggcaagaggc gaggggcggc gactggtgag tacgccaaaa attttgacta gcggaggcta     780
gaaggagaga gatgggtgcg agagcgtcag tattaagcgg gggagaatta gatcgcgatg     840
ggaaaaaatt cggttaaggc cagggggaaa gaaaaatat aaattaaaac atatagtatg     900
ggcaagcagg gagctagaac gattcgcagt taatcctggc ctgttagaaa catcagaagg     960
ctgtagacaa atactgggac agctacaacc atcccttcag acaggatcag aagaacttag    1020
atcattatat aatacagtag caaccctcta ttgtgtgcat caaaggatag ataaaaga    1080 caccaaggaa gctttagaca agatagagga agagcaaaac aaaagtaaga ccaccgcaca    1140
gcaagcggcc gctgatcttc agacctggag gaggagatat gagggacaat ggagaagtg    1200 aattatataa atataaagta gtaaaaattg aaccattagg agtagcaccc accaaggcaa    1260
agagaagagt ggtgcagaga gaaaaaagag cagtgggaat aggagctttg ttccttgggt    1320
tcttgggagc agcaggaagc actatgggcg cagcgtcaat gacgctgacg gtacaggcca    1380
gacaattatt gtctggtata gtgcagcagc agaacaattt gctgagggct attgaggcgc    1440
```

```
aacagcatct gttgcaactc acagtctggg gcatcaagca gctccaggca agaatcctgg    1500
ctgtggaaag atacctaaag gatcaacagc tcctggggat ttggggttgc tctggaaaac    1560
tcatttgcac cactgctgtg ccttggaatg ctagttggag taataaatct ctggaacaga    1620
tttggaatca cacgacctgg atggagtggg acagagaaat aacaattac acaagcttaa     1680 tacactcctt aattgaagaa tcgcaaaacc agcaagaaaa gaatgaacaa gaattattgg    1740
aattagataa atgggcaagt tgtggaatt ggtttaacat aacaaattgg ctgtggtata     1800
taaaattatt cataatgata gtaggaggct tggtaggttt aagaatagtt tttgctgtac    1860
tttctatagt gaatagagtt aggcagggat attcaccatt atcgtttcag acccacctcc    1920
caaccccgag gggacccgac aggcccgaag gaatagaaga agaaggtgga gagagagaca    1980
gagacagatc cattcgatta gtgaacggat ctcgacggta tcgccgaatt cacaaatggc    2040
agtattcatc cacaatttta aaagaaaagg ggggattggg gggtacagtg caggggaaag    2100
aatagtagac ataatagcaa cagacataca aactaaagaa ttacaaaaac aaattacaaa    2160
aattcaaaat tttcgggttt attacaggga cagcagagat ccactttggc tgatacgcgc    2220
cggaaaccct gcagggaatt ccccagctgt agttataaac agaagttctc cttctgctag    2280
gtagcattca aagatcttaa tcttctgggt ttccgttttc tcgaatgaaa aatgcaggtc    2340
cgagcagtta actggcgggg gcaccattag caagtcactt agcatctctg ggccagtct     2400 gcaaagcgag ggggcagcct taatgtgcct ccagcctgaa gtcctagaat gagcgcccgg    2460
tgtcccaagc tggggcgcgc acccagatc ggagggcgcc gatgtacaga cagcaaactc     2520
acccagtcta gtgcatgcct tcttaaacat cacgagactc taagaaaagg aaactgaaaa    2580
cgggaaagtc cctctctcta acctggcact gcgtcgctgg cttggagaca ggtgacggtc    2640
cctgcgggcc ttgtcctgat tggctgggca cgcgtttaat ataagtggag gcgtcgcgct    2700
ggcgggcatt cctgaagctg acagcattcg ggccgagcga tcggatcccc accggtcgcc    2760
accatggtga gcaagggcga ggagctgttc accggggtgg tgcccatcct ggtcgagctg    2820
gacggcgacg taaacggcca caagttcagc gtgtccggcg agggcgaggg cgatgccacc    2880
tacggcaagc tgaccctgaa gttcatctgc accaccggca agctgcccgt gccctggccc    2940
accctcgtga ccaccctgac ctacggcgtg cagtgcttca gccgctaccc cgaccacatg    3000
aagcagcacg acttcttcaa gtccgccatg cccgaaggct acgtccagga gcgcaccatc    3060
ttcttcaagg acgacggcaa ctacaagacc cgcgccgagg tgaagttcga gggcgacacc    3120
ctggtgaacc gcatcgagct gaagggcatc gacttcaagg aggacggcaa catcctgggg    3180
cacaagctgg agtacaacta caacagccac aacgtctata tcatggccga caagcagaag    3240
aacggcatca aggtgaactt caagatccgc cacaacatcg aggacggcag cgtgcagctc    3300
gccgaccact accagcagaa cacccccatc ggcgacggcc ccgtgctgct gcccgacaac    3360
cactacctga gcacccagtc cgccctgagc aaagacccca acgagaagcg cgatcacatg    3420
gtcctgctgg agttcgtgac cgccgccggg atcactctcg gcatggacga gctgtacaag    3480
taaagcggcc gcgactctag ctcgagctca agcttcgaat tccgataat caacctctgg     3540 attacaaaat ttgtgaaaga ttgactggta ttcttaacta tgttgctcct tttacgctat    3600
gtggatacgc tgctttaatg cctttgtatc atgctattgc ttcccgtatg gctttcattt    3660
tctcctcctt gtataaatcc tggttgctgt ctctttatga ggagttgtgg cccgttgtca    3720
ggcaacgtgg cgtggtgtgc actgtgtttg ctgacgcaac ccccactggt tggggcattg    3780
```

```
ccaccacctg tcagctcctt tccgggactt tcgctttccc cctccctatt gccacggcgg    3840
aactcatcgc cgcctgcctt gcccgctgct ggacaggggc tcggctgttg ggcactgaca    3900
attccgtggt gttgtcgggg aagctgacgt cctttccatg gctgctcgcc tgtgttgcca    3960
cctggattct gcgcgggacg tccttctgct acgtcccttc ggccctcaat ccagcggacc    4020
ttccttcccg cggcctgctg ccggctctgc ggcctcttcc gcgtcttcgc cttcgccctc    4080
agacgagtcg gatctccctt ggggccgcct cccgcatcg ggaattctgc agtcgacggt    4140
acctttaaga ccaatgactt acaaggcagc tgtagatctt agccactttt taaaagaaaa    4200 gggggggactg aagggctaa ttcactccca acgaagacaa gatcgtcgag agatgctgca    4260
tataagcagc tgcttttttgc ttgtactggg tctctctggt tagaccagat ctgagcctgg    4320
gagctctctg gctaactagg gaacccactg cttaagcctc aataaagctt gccttgagtg    4380
cttcaagtag tgtgtgcccg tctgttgtgt gactctggta actagagatc cctcagaccc    4440
ttttagtcag tgtggaaaat ctctagca                                       4468

<210> SEQ ID NO 3
<211> LENGTH: 11904
<212> TYPE: DNA
<213> ORGANISM: Artificial Sequence
<220> FEATURE:
<223> OTHER INFORMATION: PACKAGING 8.74 PLASMID

<400> SEQUENCE: 3
gggctgcagg aattaattcg agctcgcccg acattgatta ttgactagtt attaatagta      60
atcaattacg gggtcattag ttcatagccc atatatggag ttccgcgtta cataacttac     120
ggtaaatggc ccgcctggct gaccgcccaa cgacccccgc ccattgacgt caataatgac     180
gtatgttccc atagtaacgc caatagggac tttccattga cgtcaatggg tggagtattt     240
acggtaaact gcccacttgg cagtacatca agtgtatcat atgccaagta cgccccctat     300
tgacgtcaat gacggtaaat ggcccgcctg gcattatgcc cagtacatga ccttatggga     360
ctttcctact tggcagtaca tctacgtatt agtcatcgct attaccatgg tgatgcggtt     420
ttggcagtac atcaatgggc gtggatagcg gtttgactca cggggatttc caagtctcca     480
ccccattgac gtcaatggga gtttgttttg gcaccaaaat caacgggact ttccaaaatg     540
tcgtaacaac tccgccccat tgacgcaaat gggcggtagg cgtgtacggt gggaggtcta     600
tataagcaga gctcgtttag tgaaccgtca gatcgcctgg agacgccatc cacgctgttt     660
tgacctccat agaagacacc gggaccgatc agcctccgc ggccgcgttg acgcgcacgg     720
caagaggcga ggggcggcga ctggtgagag atgggtgcga gagcgtcagt attaagcggg     780
ggagaattag atcgatggga aaaaattcgg ttaaggccag ggggaaagaa aaatataaa     840 ttaaaacata tagtatgggc aagcagggag ctagaacgat tcgcagttaa tcctggcctg     900
ttagaaacat cagaaggctg tagacaaata ctgggacagc tacaaccatc ccttcagaca     960
ggatcagaag aacttagatc attatataat acagtagcaa ccctctattg tgtgcatcaa    1020
aggatagaga taaaagacac caaggaagct ttagacaaga tagaggaaga gcaaaacaaa    1080
agtaagaaaa aagcacagca agcagcagct gacacaggac acagcaatca ggtcagccaa    1140
aattacccta tagtgcagaa catccagggg caaatggtac atcaggccat atcacctaga    1200
actttaaatg catgggtaaa agtagtagaa gagaaggctt tcagcccaga agtgataccc    1260
atgttttcag cattatcaga aggagccacc ccacaagatt taaacaccat gctaaacaca    1320
gtggggggac atcaagcagc catgcaaatg ttaaaagaga ccatcaatga ggaagctgca    1380
```

```
gaatgggata gagtgcatcc agtgcatgca gggcctattg caccaggcca gatgagagaa    1440 ccaagggaa gtgacatagc aggaactact agtacccttc aggaacaaat aggatggatg    1500
acacataatc cacctatccc agtaggagaa atctataaaa gatggataat cctgggatta    1560
aataaaatag taagaatgta tagccctacc agcattctgg acataagaca aggaccaaag    1620
gaacccttta gagactatgt agaccgattc tataaaactc taagagccga gcaagcttca    1680
caagaggtaa aaaattggat gacagaaacc ttgttggtcc aaaatgcgaa cccagattgt    1740
aagactattt taaaagcatt gggaccagga gcgacactag aagaaatgat gacagcatgt    1800
cagggagtgg ggggacccgg ccataaagca agagttttgg ctgaagcaat gagccaagta    1860
acaaatccag ctaccataat gatacagaaa ggcaatttta ggaaccaaag aaagactgtt    1920
aagtgtttca attgtggcaa agaagggcac atagccaaaa attgcagggc ccctaggaaa    1980
aagggctgtt ggaaatgtgg aaaggaagga caccaaatga agattgtac tgagagacag    2040 gctaattttt tagggaagat ctggccttcc cacaagggaa ggccaggaa ttttcttcag    2100 agcagaccag agccaacagc cccaccagaa gagagcttca ggtttgggga agagacaaca    2160
actccctctc agaagcagga ccgatagac aaggaactgt atcctttagc ttccctcaga    2220
tcactctttg gcagcgaccc ctcgtcacaa taaagatagg ggggcaatta aaggaagctc    2280
tattagatac aggagcagat gatacagtat agaagaaat gaatttgcca ggaagatgga    2340
aaccaaaaat gatagggga attggaggtt ttatcaaagt aagacagtat gatcagatac    2400
tcatagaaat ctgcggacat aaagctatag gtacagtatt agtaggacct acacctgtca    2460
acataattgg aagaaatctg ttgactcaga ttggctgcac tttaaatttt cccattagtc    2520
ctattgagac tgtaccagta aaattaaagc caggaatgga tggcccaaaa gttaaacaat    2580
ggccattgac agaagaaaaa ataaaagcat tagtagaaat ttgtacagaa atggaaaagg    2640
aaggaaaaat ttcaaaaatt gggcctgaaa atccatacaa tactccagta tttgccataa    2700
agaaaaaaga cagtactaaa tggagaaaat tagtagattt cagagaactt aataagagaa    2760
ctcaagattt ctgggaagtt caattaggaa taccacatcc tgcagggtta aaacagaaaa    2820
aatcagtaac agtactggat gtgggcgatg catatttttc agttccctta gataaagact    2880
tcaggaagta tactgcattt accataccta gtataaacaa tgagacacca gggattagat    2940
atcagtacaa tgtgcttcca cagggatgga aaggatcacc agcaatattc cagtgtagca    3000
tgacaaaaat cttagagcct tttagaaaac aaaatccaga catagtcatc tatcaataca    3060
tggatgattt gtatgtagga tctgacttag aaatagggca gcatagaaca aaaatagagg    3120
aactgagaca acatctgttg aggtggggat ttaccacacc agacaaaaaa catcagaaag    3180
aacctccatt cctttggatg ggttatgaac tccatcctga taaatggaca gtacagccta    3240
tagtgctgcc agaaaaggac agctggactg tcaatgacat acagaaatta gtgggaaaat    3300
tgaattgggc aagtcagatt tatgcaggga ttaaagtaag gcaattatgt aaacttctta    3360
ggggaaccaa agcactaaca gaagtagtac cactaacaga agaagcagag ctagaactgg    3420
cagaaaacag ggagattcta aaagaaccgg tacatggagt gtattatgac ccatcaaaag    3480
acttaatagc agaaatacag aagcaggggc aaggccaatg gacatatcaa atttatcaag    3540
agccatttaa aaatctgaaa acaggaaagt atgcaagaat gaagggtgcc cacactaatg    3600
atgtgaaaca attaacagag gcagtacaaa aaatagccac agaaagcata gtaatatggg    3660
gaaagactcc taaatttaaa ttacccatac aaaaggaaac atgggaagca tggtggacag    3720
```

```
agtattggca agccacctgg attcctgagt gggagtttgt caatacccct cccttagtga    3780
agttatggta ccagttagag aaagaaccca taataggagc agaaactttc tatgtagatg    3840
gggcagccaa tagggaaact aaattaggaa aagcaggata tgtaactgac agaggaagac    3900
aaaaagttgt cccctaacg gacacaacaa atcagaagac tgagttacaa gcaattcatc    3960
tagctttgca ggattcggga ttagaagtaa acatagtgac agactcacaa tatgcattgg    4020
gaatcattca agcacaacca gataagagtg aatcagagtt agtcagtcaa ataatagagc    4080
agttaataaa aaggaaaaa gtctacctgg catgggtacc agcacacaaa ggaattggag    4140
gaaatgaaca gtagataaa ttggtcagtg ctggaatcag gaaagtacta ttttagatg    4200
gaatagataa ggcccaagaa gaacatgaga atatcacag taattggaga gcaatggcta    4260
gtgattttaa cctaccacct gtagtagcaa aagaaatagt agccagctgt gataaatgtc    4320
agctaaaagg ggaagccatg catggacaag tagactgtag cccaggaata tggcagctag    4380
attgtacaca tttagaagga aaagttatct tggtagcagt tcatgtagcc agtggatata    4440
tagaagcaga agtaattcca gcagagacag ggcaagaaac agcatacttc ctcttaaaat    4500
tagcaggaag atggccagta aaaacagtac atacagacaa tggcagcaat ttcaccagta    4560
ctacagttaa ggccgcctgt tggtgggcgg ggatcaagca ggaatttggc attccctaca    4620
atccccaaag tcaaggagta atagaatcta tgaataaaga attaagaaa attataggac    4680
aggtaagaga tcaggctgaa catcttaaga cagcagtaca aatggcagta ttcatccaca    4740
attttaaaag aaaaggggg attgggggt acagtgcagg ggaaagaata gtagacataa    4800
tagcaacaga catacaaact aaagaattac aaaaacaaat tacaaaaatt caaaattttc    4860
gggtttatta cagggacagc agagatccag tttggaaagg accagcaaag ctcctctgga    4920
aaggtgaagg ggcagtagta atacaagata atagtgacat aaaagtagtg ccaagaagaa    4980
aagcaaagat catcagggat tatggaaaac agatggcagg tgatgattgt gtggcaagta    5040
gacaggatga ggattaacac atggaattct gcaacaactg ctgtttatcc atttcagaat    5100
tgggtgtcga catagcagaa taggcgttac tcgacagagg agagcaagaa atggagccag    5160
tagatcctag actagagccc tggaagcatc caggaagtca gcctaaaact gcttgtacca    5220
attgctattg taaaaagtgt tgctttcatt gccaagtttg tttcatgaca aaagccttag    5280
gcatctccta tggcaggaag aagcggagac agcgacgaag agctcatcag aacagtcaga    5340
ctcatcaagc ttctctatca aagcagtaag tagtacatgt aatgcaacct ataatagtag    5400
caatagtagc attagtagta gcaataataa tagcaatagt tgtgtggtcc atagtaatca    5460
tagaatatag gaaaatggcc gctgatcttc agacctggag gaggagatat gagggacaat    5520
tggagaagtg aattatataa atataaagta gtaaaaattg aaccattagg agtagcaccc    5580
accaaggcaa agagaagagt ggtgcagaga gaaaaaagag cagtgggaat aggagctttg    5640
ttccttgggt tcttgggagc agcaggaagc actatgggcg cagcgtcaat gacgctgacg    5700
gtacaggcca gacaattatt gtctggtata gtgcagcagc agaacaattt gctgagggct    5760
attgaggcgc aacagcatct gttgcaactc acagtctggg gcatcaagca gctccaggca    5820
agaatcctgg ctgtggaaag atacctaaag gatcaacagc tcctggggat ttggggttgc    5880
tctggaaaac tcatttgcac cactgctgtg ccttggaatg ctagttggag taataaatct    5940
ctggaacaga tttggaatca cacgacctgg atggagtggg acagagaaat taacaattac    6000
acaagcttaa tacactcctt aattgaagaa tcgcaaaacc agcaagaaaa gaatgaacaa    6060
gaattattgg aattagataa atgggcaagt ttgtggaatt ggtttaacat aacaaattgg    6120
```

```
ctgtggtata taaaattatt cataatgata gtaggaggct tggtaggttt aagaatagtt      6180
tttgctgtac tttctatagt gaatagagtt aggcagggat attcaccatt atcgtttcag      6240
acccacctcc caaccccgag gggacccgac aggcccgaag gaatagaaga agaaggtgga      6300
gagagagaca gagacagatc cattcgatta gtgaacggat ccttggcact tatctgggac      6360
gatctgcgga gcctgtgcct cttcagctac caccgcttga gagacttact cttgattgta      6420
acgaggattg tggaacttct gggacgcagg ggtgggaag ccctcaaata ttggtggaat       6480
ctcctacaat attggagtca ggagctaaag aatagtgctg ttagcttgct caatgccaca      6540
gccatagcag tagctgaggg gacagatagg gttatagaag tagtacaagg agcttgtaga      6600
gctattcgcc acatacctag aagaataaga cagggcttgg aaaggatttt gctataagct      6660
cgagtgacct tcagaccttg gcactggagg tggcccggca gaagcgcggc atcgtggatc      6720
agtgctgcac cagcatctgc tctctctacc aactggagaa ctactgcaac taggcccacc      6780
actaccctgt ccacccctct gcaatgaata aaaccttga aagagcacta caagttgtgt       6840
gtacatgcgt gcatgtgcat atgtggtgcg gggggaacat gagtggggct ggctggagtg      6900
gcgatgataa gctgtcaaac atgagaatta attcttgaag acgaaagggc ctcgtgatac      6960
gcctattttt ataggttaat gtcatgataa taatggtttc ttagtctaga attaattccg      7020
tgtattctat agtgtcacct aaatcgtatg tgtatgatac ataaggttat gtattaattg      7080
tagccgcgtt ctaacgacaa tatgtacaag cctaattgtg tagcatctgg cttactgaag      7140
cagaccctat catctctctc gtaaactgcc gtcagagtcg gtttggttgg acgaaccttc      7200
tgagtttctg gtaacgccgt cccgcacccg gaaatggtca gcgaaccaat cagcagggtc      7260
atcgctagcc agatcctcta cgccggacgc atcgtggccg gcatcaccgg cgccacaggt      7320
gcggttgctg gcgcctatat cgccgacatc accgatgggg aagatcgggc tcgccacttc      7380
gggctcatga gcgcttgttt cggcgtgggt atggtggcag gccccgtggc cggggggactg     7440 ttgggcgcca tctccttgca tgcaccattc cttgcggcgg cggtgctcaa cggcctcaac      7500
ctactactgg gctgcttcct aatgcaggag tcgcataagg gagagcgtcg aatggtgcac      7560
tctcagtaca atctgctctg atgccgcata gttaagccag ccccgacacc cgccaacacc      7620
cgctgacgcg ccctgacggg cttgtctgct cccggcatcc gcttacagac aagctgtgac      7680
cgtctccggg agctgcatgt gtcagaggtt ttcaccgtca tcaccgaaac gcgcgagacg      7740
aaagggcctc gtgatacgcc tatttttata ggttaatgtc atgataataa tggtttctta      7800
gacgtcaggt ggcactttc ggggaaatgt gcgcggaacc cctatttgtt tatttttcta       7860
aatacattca aatatgtatc cgctcatgag acaataaccc tgataaatgc ttcaataata      7920
ttgaaaaagg aagagtatga gtattcaaca tttccgtgtc gcccttattc ccttttttgc      7980
ggcattttgc cttcctgttt ttgctcaccc agaaacgctg gtgaaagtaa aagatgctga     8040
agatcagttg ggtgcacgag tgggttacat cgaactggat ctcaacagcg gtaagatcct      8100
tgagagtttt cgccccgaag aacgttttcc aatgatgagc acttttaaag ttctgctatg      8160
tggcgcggta ttatcccgta ttgacgccgg gcaagagcaa ctcggtcgcc gcatacacta      8220
ttctcagaat gacttggttg agtactcacc agtcacagaa aagcatctta cggatggcat      8280
gacagtaaga gaattatgca gtgctgccat aaccatgagt gataacactg cggccaactt      8340
acttctgaca acgatcggag gaccgaagga gctaaccgct tttttgcaca acatggggga      8400
tcatgtaact cgccttgatc gttgggaacc ggagctgaat gaagccatac caaacgacga      8460
```

```
gcgtgacacc acgatgcctg tagcaatggc aacaacgttg cgcaaactat taactggcga   8520
actacttact ctagcttccc ggcaacaatt aatagactgg atggaggcgg ataaagttgc   8580
aggaccactt ctgcgctcgg cccttccggc tggctggttt attgctgata atctggagc   8640
cggtgagcgt gggtctcgcg gtatcattgc agcactgggg ccagatggta agccctcccg   8700
tatcgtagtt atctacacga cggggagtca ggcaactatg gatgaacgaa atagacagat   8760
cgctgagata ggtgcctcac tgattaagca ttggtaactg tcagaccaag tttactcata   8820
tatactttag attgatttaa aacttcattt ttaatttaaa aggatctagg tgaagatcct   8880
ttttgataat ctcatgacca aaatccctta acgtgagttt tcgttccact gagcgtcaga   8940
ccccgtagaa aagatcaaag gatcttcttg agatcctttt tttctgcgcg taatctgctg   9000
cttgcaaaca aaaaaaccac cgctaccagc ggtggtttgt ttgccggatc aagagctacc   9060
aactcttttt ccgaaggtaa ctggcttcag cagagcgcag ataccaaata ctgttcttct   9120
agtgtagccg tagttaggcc accacttcaa gaactctgta gcaccgccta catacctcgc   9180
tctgctaatc ctgttaccag tggctgctgc cagtggcgat aagtcgtgtc ttaccgggtt   9240
ggactcaaga cgatagttac cggataaggc gcagcggtcg ggctgaacgg ggggttcgtg   9300
cacacagccc agcttggagc gaacgaccta caccgaactg agatacctac agcgtgagct   9360
atgagaaagc gccacgcttc ccgaagggag aaaggcggac aggtatccgg taagcggcag   9420
ggtcggaaca ggagagcgca cgagggagct tccaggggga aacgcctggt atctttatag   9480
tcctgtcggg tttcgccacc tctgacttga gcgtcgattt ttgtgatgct cgtcaggggg   9540
gcggagccta tggaaaaacg ccagcaacgc ggccttttta cggttcctgg ccttttgctg   9600
gccttttgct cacatgttct ttcctgcgtt atcccctgat tctgtggata accgtattac   9660
cgcctttgag tgagctgata ccgctcgccg cagccgaacg accgagcgca gcgagtcagt   9720
gagcgaggaa gcggaagagc gcccaatacg caaaccgcct ctccccgcgc gttggccgat   9780
tcattaatgc agctgtggaa tgtgtgtcag ttagggtgtg gaaagtcccc aggctcccca   9840
gcaggcagaa gtatgcaaag catgcatctc aattagtcag caaccaggtg tggaaagtcc   9900
ccaggctccc cagcaggcag aagtatgcaa agcatgcatc tcaattagtc agcaaccata   9960
gtcccgcccc taactccgcc catcccgccc ctaactccgc ccagttccgc ccattctccg  10020
ccccatggct gactaatttt ttttatttat gcagaggccg aggccgcctc ggcctctgag  10080
ctattccaga agtagtgagg aggcttttt ggaggcctag gcttttgcaa aaagcttgga  10140
cacaagacag gcttgcgaga tatgtttgag aataccactt tatcccgcgt cagggagagg  10200
cagtgcgtaa aaagacgcgg actcatgtga atactggtt tttagtgcgc cagatctcta  10260
taatctcgcg caacctattt tcccctcgaa cacttttaa gccgtagata aacaggctgg  10320
gacacttcac atgagcgaaa aatacatcgt cacctgggac atgttgcaga tccatgcacg  10380
taaactcgca agccgactga tgccttctga acaatggaaa ggcattattg ccgtaagccg  10440
tggcggtctg taccgggtgc gttactggcg cgtgaactgg gtattcgtca tgtcgatacc  10500
gtttgtattt ccagctacga tcacgacaac cagcgcgagc ttaaagtgct gaaacgcgca  10560
gaaggcgatg gcgaaggctt catcgttatt gatgacctgg tggataccgg tggtactgcg  10620
gttgcgattc gtgaaatgta tccaaaagcg cactttgtca ccatcttcgc aaaaccggct  10680
ggtcgtccgc tggttgatga ctatgttgtt gatatcccgc aagatacctg gattgaacag  10740
ccgtgggata tggcgtcgt attcgtcccg ccaatctccg tcgctaatc ttttcaacgc  10800
ctggcactgc cgggcgttgt tctttttaac ttcaggcggg ttacaatagt ttccagtaag  10860
```

```
tattctggag gctgcatcca tgacacaggc aaacctgagc gaaaccctgt tcaaaccccg 10920
ctttaaacat cctgaaacct cgacgctagt ccgccgcttt aatcacggcg cacaaccgcc 10980
tgtgcagtcg gcccttgatg gtaaaaccat ccctcactgg tatcgcatga ttaaccgtct 11040
gatgtggatc tggcgcggca ttgacccacg cgaaatcctc gacgtccagg cacgtattgt 11100
gatgagcgat gccgaacgta ccgacgatga tttatacgat acggtgattg gctaccgtgg 11160
cggcaactgg atttatgagt gggccccgga tctttgtgaa ggaaccttac ttctgtggtg 11220
tgacataatt ggacaaacta cctacagaga tttaaagctc taaggtaaat ataaaatttt 11280
taagtgtata atgtgttaaa ctactgattc taattgtttg tgtattttag attccaacct 11340
atggaactga tgaatgggag cagtggtgga atgcctttaa tgaggaaaac ctgttttgct 11400
cagaagaaat gccatctagt gatgatgagg ctactgctga ctctcaacat tctactcctc 11460
caaaaaagaa gagaaaggta gaagacccca aggactttcc ttcagaattg ctaagttttt 11520
tgagtcatgc tgtgtttagt aatagaactc ttgcttgctt tgctatttac accacaaagg 11580
aaaaagctgc actgctatac aagaaaatta tggaaaaata ttctgtaacc tttataagta 11640
ggcataacag ttataatcat aacatactgt tttttcttac tccacacagg catagagtgt 11700
ctgctattaa taactatgct caaaaattgt gtacctttag ctttttaatt tgtaaagggg 11760
ttaataagga atatttgatg tatagtgcct tgactagaga tcataatcag ccataccaca 11820
tttgtagagg ttttacttgc tttaaaaaac ctcccacacc tcccccctgaa cctgaaacat 11880
aaaatgaatg caattgttgt tgtt 11904
```

<210> SEQ ID NO 4
<211> LENGTH: 5140
<212> TYPE: DNA
<213> ORGANISM: Artificial Sequence
<220> FEATURE:
<223> OTHER INFORMATION: pCMV-VSV-INDco

<400> SEQUENCE: 4

```
ctggatggct ttctcgccgc caaggatctg atggcgcagg ggatcaagct ctgatcaaga 60
gacaggatga ggatcgtttc gcatgattga acaagatgga ttgcacgcag gttctccggc 120
cgcttgggtg gagaggctat tcggctatga ctgggcacaa cagacaatcg gctgctctga 180
tgccgccgtg ttccggctgt cagcgcaggg gcgcccggtt ctttttgtca agaccgacct 240
gtccggtgcc ctgaatgaac tgcaagacga ggcagcgcgg ctatcgtggc tggccacgac 300
gggcgttcct tgcgcagctg tgctcgacgt tgtcactgaa gcgggaaggg actggctgct 360
attgggcgaa gtgccggggc aggatctcct gtcatctcac cttgctcctg ccgagaaagt 420
atccatcatg gctgatgcaa tgcggcggct gcatacgctt gatccggcta cctgcccatt 480
cgaccaccaa gcgaaacatc gcatcgagcg agcacgtact cggatggaag ccggtcttgt 540
cgatcaggat gatctggacg aagagcatca ggggctcgcg ccagccgaac tgttcgccag 600
gctcaaggcg agcatgcccg acggcgagga tctcgtcgtg acccatggcg atgcctgctt 660
gccgaatatc atggtggaaa atggccgctt ttctggattc atcgactgtg gccggctggg 720
tgtggcggac cgctatcagg acatagcgtt ggctacccgt gatattgctg aagagcttgg 780
cggcgaatgg gctgaccgct tcctcgtgct ttacggtatc gccgctcccg attcgcagcg 840
catcgccttc tatcgccttc ttgacgagtt cttctgaatt attaacgctt acaatttcct 900
gatgcggtat tttctcctta cgcatctgtg cggtatttca caccgcatac aggtggcact 960
```

-continued

```
tttcggggaa atgtgcgcgg aacccctatt tgtttatttt tctaaataca ttcaaatatg   1020
tatccgctca tgagacaata accctgataa atgcttcaat aatagcacgt gctaaaactt   1080
cattttaat ttaaaaggat ctaggtgaag atcctttttg ataatctcat gaccaaaatc   1140
ccttaacgtg agttttcgtt ccactgagcg tcagacaccg tagaaaagat caaaggatct   1200
tcttgagatc ctttttttct gcgcgtaatc tgctgcttgc aaacaaaaaa accaccgcta   1260
ccagcggtgg tttgtttgcc ggatcaagag ctaccaactc tttttccgaa ggtaactggc   1320
ttcagcagag cgcagatacc aaatactgtc cttctagtgt agccgtagtt aggccaccac   1380
ttcaagaact ctgtagcacc gcctacatac ctcgctctgc taatcctgtt accagtggct   1440
gctgccagtg gcgataagtc gtgtcttacc gggttggact caagacgata gttaccggat   1500
aaggcgcagc ggtcgggctg aacggggggt tcgtgcacac agcccagctt ggagcgaacg   1560
acctacaccg aactgagata cctacagcgt gagctatgag aaagcgccac gcttcccgaa   1620
gggagaaagg cggacaggta tccggtaagc ggcagggtcg gaacaggaga gcgcacgagg   1680
gagcttccag ggggaaacgc ctggtatctt tatagtcctg tcgggtttcg ccacctctga   1740
cttgagcgtc gatttttgtg atgctcgtca gggggggcgga gcctatggaa aaacgccagc   1800
aacgcggcct ttttacggtt cctgggcttt tgctggcctt ttgctcacat gttcttgact   1860
cttcgcgatg tacgggccag atatacgcgt tgacattgat tattgactag ttattaatag   1920
taatcaatta cggggtcatt agttcatagc ccatatatgg agttccgcgt tacataactt   1980
acggtaaatg gcccgcctgg ctgaccgccc aacgaccccc gcccattgac gtcaataatg   2040
acgtatgttc ccatagtaac gccaataggg actttccatt gacgtcaatg ggtggactat   2100
ttacggtaaa ctgcccactt ggcagtacat caagtgtatc atatgccaag tacgcccct   2160
attgacgtca atgacggtaa atggcccgcc tggcattatg cccagtacat gaccttatgg   2220
gactttccta cttggcagta catctacgta ttagtcatcg ctattaccat ggtgatgcgg   2280
ttttggcagt acatcaatgg gcgtggatag cggtttgact cacggggatt tccaagtctc   2340
caccccattg acgtcaatgg gagtttgttt tggcaccaaa atcaacggga ctttccaaaa   2400
tgtcgtaaca actccgcccc attgacgcaa atgggcggta ggcgtgtacg gtgggaggtc   2460
tatataagca gagctctctg gctaactaga gaacccactg cttactggct tatcgaaatt   2520
aatacgactc actataggga gacccaagct ggctagcgtt taaacttaag cttggtaccg   2580
agctcggatc ctgatcagcc accatgaaat gcctgctcta tctggccttc ctgttcatcg   2640
gcgtgaactg caagttcacc atcgtgttcc cccacaacca aagggcaac tggaagaacg   2700
tgcccagcaa ctaccactac tgccccagca gcagcgacct gaactggcac aacgacctga   2760
tcggcaccgc cctgcaggtg aagatgccca agagccacaa ggccattcag gctgatggct   2820
ggatgtgtca tgccagcaag tgggtgacca cctgcgactt ccggtggtac ggccccaagt   2880
acatcaccca cagcatccgc agcttcaccc ccagcgtgga gcagtgcaaa gagagcatcg   2940
agcagaccaa gcagggcacc tggctgaacc ccggcttccc cccccagtcc tgcggctacg   3000
ccaccgtgac cgacgccgag gccgtgatcg tgcaggtgac ccccaccac gtgctggtcg   3060
acgagtacac cggcgagtgg gtggacagcc agttcatcaa cggcaagtgc agcaactaca   3120
tctgccctac cgtgcacaac agcaccacct ggcacagcga ctacaaggtg aaaggcctgt   3180
gcgacagcaa cctgatcagc atggacatca ccttttttcag cgaggacggc gagctgtcca   3240
gcctgggcaa agagggcacc ggcttcagaa gcaactactt cgcctacgag acaggcggca   3300
aggcctgcaa gatgcagtac tgcaagcact ggggcgtgcg gctgcctagc ggcgtgtggt   3360
```

```
tcgagatggc cgacaaggac ctgttcgccg ctgcccggtt ccctgagtgc cccgagggca   3420
gcagcatcag cgcccccagc cagaccagcg tggacgtgag cctgatccag gacgtggaga   3480
gaatcctgga ctacagcctg tgccaggaaa cctggtccaa gatcagagcc ggcctgccca   3540
tcagccccgt ggacctgagc tacctggccc ccaagaaccc cggcaccggc ccagccttca   3600
ccatcatcaa tggcaccctg aagtacttcg agacacggta catcagagtg gacattgccg   3660
cccctatcct gagccggatg gtgggcatga tcagcggcac caccaccgag cgggagctgt   3720
gggacgactg ggcccctac gaggatgtgg agatcggccc caacggcgtg ctgcggacca   3780
gcagcggcta caagttcccc ctgtacatga tcggccacgg catgctggac agcgacctgc   3840
acctgagcag caaggcccag gtgttcgagc acccccacat ccaggacgcc gccagccagc   3900
tgcccgacga cgagagcctg ttcttcggcg acaccggcct gagcaagaac cccatcgaac   3960
tggtggaggg ctggttcagc agctggaaga gcagcattgc cagctttttc ttcatcatcg   4020
gcctgatcat cgggctgttt ctggtgctga gagtgggcat ccacctgtgc atcaagctga   4080
agcacaccaa gaagcggcag atctacaccg acatcgagat gaatcgcctg ggaagtaag   4140
aattctgcag atatccagca cagtggcggc cgctcgagtg tacaaattcc cgataatcaa   4200
cctctggatt acaaaatttg tgaaagattg actggtattc ttaactatgt tgctcctttt   4260
acgctatgtg gatacgctgc tttaatgcct ttgtatcatg ctattgcttc ccgtatggct   4320
ttcattttct cctccttgta taaatcctgg ttgctgtctc tttatgagga gttgtggccc   4380
gttgtcaggc aacgtggcgt ggtgtgcact gtgtttgctg acgcaacccc cactggttgg   4440
ggcattgcca ccacctgtca gctcctttcc gggactttcg ctttccccct ccctattgcc   4500
acggcggaac tcatcgccgc ctgccttgcc cgctgctgga caggggctcg gctgttgggc   4560
actgacaatt ccgtggtgtt gtcggggaag ctgacgtcct ttccatcgct gctcgcctgt   4620
gttgccacct ggattctgcg cgggacgtcc ttctgctacg tcccttcggc cctcaatcca   4680
gcggaccttc cttcccgcgg cctgctgccg gctctgcggc ctcttccgcg tcttcgcctt   4740
cgccctcaga cgagtcggat ctccctttgg gccgcctccc cgctcgagtc tagagggccc   4800
gtttaaaccc gctgatcagc ctcgactgtg ccttctagtt gccagccatc tgttgtttgc   4860
ccctcccccg tgccttcctt gaccctggaa ggtgccactc ccactgtcct ttcctaataa   4920
aatgaggaaa ttgcatcgca ttgtctgagt aggtgtcatt ctattctggg gggtggggtg   4980
gggcaggaca gcaaggggga ggattgggaa gacaatagca ggcatgctgg ggatgcggtg   5040
ggctctatgg cttctactgg gcggttttat ggacagcaag cgaaccggaa ttgccagctg   5100
gggcgccctc tggtaaggtt gggaagccct gcaaagtaaa                         5140
```

<210> SEQ ID NO 5
<211> LENGTH: 5158
<212> TYPE: DNA
<213> ORGANISM: Artificial Sequence
<220> FEATURE:
<223> OTHER INFORMATION: pCMV-VSV-Njco

<400> SEQUENCE: 5

```
ctggatggct ttctcgccgc caaggatctg atggcgcagg ggatcaagct ctgatcaaga     60
gacaggatga ggatcgtttc gcatgattga acaagatgga ttgcacgcag gttctccggc    120
cgcttgggtg gagaggctat tcggctatga ctgggcacaa cagacaatcg gctgctctga    180
tgccgccgtg ttccggctgt cagcgcaggg gcgcccggtt ctttttgtca agaccgacct    240
```

-continued

```
gtccggtgcc ctgaatgaac tgcaagacga ggcagcgcgg ctatcgtggc tggccacgac      300
gggcgttcct tgcgcagctg tgctcgacgt tgtcactgaa gcgggaaggg actggctgct      360
attgggcgaa gtgccggggc aggatctcct gtcatctcac cttgctcctg ccgagaaagt      420
atccatcatg gctgatgcaa tgcggcggct gcatacgctt gatccggcta cctgcccatt      480
cgaccaccaa gcgaaacatc gcatcgagcg agcacgtact cggatggaag ccggtcttgt      540
cgatcaggat gatctggacg aagagcatca ggggctcgcg ccagccgaac tgttcgccag      600
gctcaaggcg agcatgcccg acggcgagga tctcgtcgtg acccatggcg atgcctgctt      660
gccgaatatc atggtggaaa atggccgctt ttctggattc atcgactgtg gccggctggg      720
tgtggcggac cgctatcagg acatagcgtt ggctacccgt gatattgctg aagagcttgg      780
cggcgaatgg gctgaccgct tcctcgtgct ttacggtatc gccgctcccg attcgcagcg      840
catcgccttc tatcgccttc ttgacgagtt cttctgaatt attaacgctt acaatttcct      900
gatgcggtat tttctcctta cgcatctgtg cggtatttca caccgcatac aggtggcact      960
tttcggggaa atgtgcgcgg aacccctatt tgtttatttt tctaaataca ttcaaatatg     1020
tatccgctca tgagacaata accctgataa atgcttcaat aatagcacgt gctaaaactt     1080
catttttaat ttaaaaggat ctaggtgaag atcctttttg ataatctcat gaccaaaatc     1140
ccttaacgtg agttttcgtt ccactgagcg tcagaccccg tagaaaagat caaaggatct     1200
tcttgagatc ctttttttct gcgcgtaatc tgctgcttgc aaacaaaaaa accaccgcta     1260
ccagcggtgg tttgtttgcc ggatcaagag ctaccaactc tttttccgaa ggtaactggc     1320
ttcagcagag cgcagatacc aaatactgtc cttctagtgt agccgtagtt aggccaccac     1380
ttcaagaact ctgtagcacc gcctacatac ctcgctctgc taatcctgtt accagtggct     1440
gctgccagtg gcgataagtc gtgtcttacc gggttggact caagacgata gttaccggat     1500
aaggcgcagc ggtcgggctg aacggggggt tcgtgcacac agcccagctt ggagcgaacg     1560
acctacaccg aactgagata cctacagcgt gagctatgag aaagcgccac gcttcccgaa     1620
gggagaaagg cggacaggta tccggtaagc ggcagggtcg aacaggaga gcgcacgagg     1680 gagcttccag ggggaaacgc ctggtatctt tatagtcctg tcgggtttcg ccacctctga     1740
cttgagcgtc gatttttgtg atgctcgtca gggggcgga gcctatggaa aaacgccagc     1800
aacgcggcct ttttacggtt cctgggcttt tgctggcctt ttgctcacat gttcttgact     1860
cttcgcgatg tacgggccag atatacgcgt tgacattgat tattgactag ttattaatag     1920
taatcaatta cggggtcatt agttcatagc ccatatatgg agttccgcgt tacataactt     1980
acggtaaatg gcccgcctgg ctgaccgccc aacgaccccc gcccattgac gtcaataatg     2040
acgtatgttc ccatagtaac gccaataggg actttccatt gacgtcaatg ggtggactat     2100
ttacggtaaa ctgcccactt ggcagtacat caagtgtatc atatgccaag tacgccccct     2160
attgacgtca atgacggtaa atggcccgcc tggcattatg cccagtacat gaccttatgg     2220
gactttccta cttggcagta catctacgta ttagtcatcg ctattaccat ggtgatgcgg     2280
ttttggcagt acatcaatgg gcgtggatag cggtttgact cacggggatt tccaagtctc     2340
caccccattg acgtcaatgg gagtttgttt tggcaccaaa atcaacggga ctttccaaaa     2400
tgtcgtaaca actccgcccc attgacgcaa atgggcggta ggcgtgtacg gtgggaggtc     2460
tatataagca gagctctctg gctaactaga acccactg cttactgct tatcgaaatt      2520 aatacgactc actataggga gacccaagct ggctagcgtt taaacttaag cttggtaccg     2580
agctcggatc ctgatcagcc accatgctgt catatctgat cttgcccctg ctgtgagcc     2640
```

```
caatcctcgg aaagatcgaa atcgtgttcc cacaacacac cacagggac tggaagcgcg    2700
tgccccacga gtacaactac tgcccgacct cagccgacaa gaatagccac ggcacgcaga    2760
ccggcatccc tgtggagctg accatgccca aggggctcac aacgcaccaa gtcgaaggct    2820
tcatgtgcca cagcgctctc tggatgacaa cctgcgattt tcgctggtat ggccccaagt    2880
acatcacgca cagcatccac aatgaggaac caaccgacta ccagtgcctc gaagccatca    2940
agtcatacaa ggatggggtg agcttcaacc ccggcttccc gccccaatca tgtggctacg    3000
gcaccgtgac cgacgccgag gcccacatcg tgaccgtgac accccactca gtcaaggtgg    3060
acgagtacac aggcgaatgg atcgacccc acttcatcgg gggccgctgt aagggccaaa    3120
tctgcgagac cgtgcacaac agcaccaagt ggtttacgtc atcagacggc gaaagcgtgt    3180
gcagccaact gtttacgctc gtgggcggca tcttctttag cgacagcgag gagatcacca    3240
gcatgggcct cccggagaca ggaatccgca gcaactactt tccgtacatc agcaccgagg    3300
gaatctgtaa gatgccttt tgccgcaagc agggatataa gctgaagaat gacctgtggt    3360
tccagatcat ggacccggac ctggacaaga ccgtccgcga tctgccccac atcaaggact    3420
gtgatctgtc atcaagcatc atcaccccg gagaacacgc cacggacatc agcctcatca    3480
gcgatgtgga gcgcatcctc gactacgctc tctgccagaa cacatggagc aagatcgaaa    3540
gcggcgaacc catcaccca gtggacctga gctatctcgg cccaaagaac cccggcgtgg    3600
ggcccgtgtt caccatcatc aacgggagcc tgcactactt tacaagcaag tatctgcgcg    3660
tggagctcga aagcccagtc atccccgca tggagggga ggtggccggg acccgcatcg    3720
tgcgccagct gtgggaccag tggttcctt ttggcgaggt ggaaatcggc cccaacggcg    3780
tgctgaagac caagcaagga tataagttcc cgctgcacat catcgggacg ggcgaagtgg    3840
acagcgatat caagatggag cgcgtggtca agcactggga gcacccacac atcgaggctg    3900
ctcagacctt tctcaagaag gacgatacc gcgaagtcct gtattacggg gatacgggag    3960
tgagcaagaa ccctgtggag ctggtggaag gctggttcag cggatggcgc tcaagcctga    4020
tgggcgtgct ggccgtcatc atcggatttg tgatcctgat gttcctcatc aagctgatcg    4080
gcgtgctgtc aagcctgttc cgccctaagc gccgcccaat ctacaagagc gacgtcgaga    4140
tggcccactt tcgctaagaa ttctgcagat atccagcaca gtggcggccg ctcgagtgta    4200
caaattcccg ataatcaacc tctggattac aaaatttgtg aaagattgac tggtattctt    4260
aactatgttg ctccttttac gctatgtgga tacgctgctt taatgccttt gtatcatgct    4320
attgcttccc gtatggcttt cattttctcc tccttgtata aatcctggtt gctgtctctt    4380
tatgaggagt tgtggcccgt tgtcaggcaa cgtggcgtgg tgtgcactgt gtttgctgac    4440
gcaaccccca ctggttgggg cattgccacc acctgtcagc tcctttccgg gactttcgct    4500
ttccccctcc ctattgccac ggcggaactc atcgccgcct gccttgcccg ctgctggaca    4560
ggggctcggc tgttgggcac tgacaattcc gtggtgttgt cggggaagct gacgtccttt    4620
ccatcgctgc tcgcctgtgt tgccacctgg attctgcgcg gacgtccttt ctgctacgtc    4680
ccttcggccc tcaatccagc ggaccttcct tcccgcggcc tgctgccggc tctgcggcct    4740
cttccgcgtc ttcgccttcg ccctcagacg agtcggatct ccctttgggc cgcctccccg    4800
ctcgagtcta gagggcccgt ttaaacccgc tgatcagcct cgactgtgcc ttctagttgc    4860
cagccatctg ttgtttgccc ctcccccgtg ccttccttga ccctggaagg tgccactccc    4920
actgtccttt cctaataaaa tgaggaaatt gcatcgcatt gtctgagtag gtgtcattct    4980
```

```
attctgggggg gtggggtggg gcaggacagc aaggggagg attgggaaga caatagcagg    5040
catgctgggg atgcggtggg ctctatggct tctactgggc ggttttatgg acagcaagcg    5100
aaccggaatt gccagctggg gcgccctctg gtaaggttgg aagccctgc aaagtaaa      5158

<210> SEQ ID NO 6
<211> LENGTH: 720
<212> TYPE: DNA
<213> ORGANISM: Artificial Sequence
<220> FEATURE:
<223> OTHER INFORMATION: eGFP

<400> SEQUENCE: 6
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 7
<211> LENGTH: 239
<212> TYPE: PRT
<213> ORGANISM: Artificial Sequence
<220> FEATURE:
<223> OTHER INFORMATION: eGFP protein

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 8
<211> LENGTH: 1725
<212> TYPE: DNA
<213> ORGANISM: Artificial Sequence
<220> FEATURE:
<223> OTHER INFORMATION: A111-Luciferase

<400> SEQUENCE: 8
ggatccgcca ccatggccgc agccgcagcc gtgaagaact ggatgactca aacgctcgcc     60
gctgcaatgg aagatgccaa aaacattaag aagggcccag cgccattcta cccactcgaa    120
gacgggaccg ccggcgagca gctgcacaaa gccatgaagc gctacgccct ggtgcccggc    180
accatcgcct ttaccgacgc acatatcgag gtggacatta cctacgccga gtacttcgag    240
atgagcgttc ggctggcaga agctatgaag cgctatgggc tgaatacaaa ccatcggatc    300
gtggtgtgca gcgagaatag cttgcagttc ttcatgcccg tgttgggtgc cctgttcatc    360
ggtgtggctg tggccccagc taacgacatc tacaacgagc gcgagctgct gaacagcatg    420
ggcatcagcc agcccaccgt cgtattcgtg agcaagaaag gctgcaaaa gatcctcaac    480 gtgcaaaaga agctaccgat catacaaaag atcatcatca tggatagcaa gaccgactac    540
cagggcttcc aaagcatgta caccttcgtg acttcccatt gccaccggg cttcaacgag    600 tacgacttcg tgcccgagag cttcgaccgg acaaaaccag tcgccctgat catgaacagt    660
agtggcagta ccggattgcc caagggcgta gccctaccgc accgcaccgc ttgtgtccga    720
ttcagtcatg cccgcgaccc catcttcggc aaccagatca tccccgacac cgctatcctc    780
agcgtggtgc catttcacca cggcttcggc atgttcacca cgctgggcta cttgatctgc    840
ggctttcggg tcgtgctcat gtaccgcttc gaggaggagc tattcttgcg cagcttgcaa    900
gactataaga ttcaatctgc cctgctggtg cccacactat ttagcttctt cgctaagagc    960
actctcatcg acaagtacga cctaagcaac ttgcacgaga tcgccagcgg cggggcgccg   1020
ctcagcaagg aggtaggtga ggccgtggcc aaacgcttcc acctaccagg catccgccag   1080
ggctacggcc tgacagaaac aaccagcgcc attctgatca ccccgaagg ggacgacaag   1140 cctggcgcag taggcaaggt ggtgcccttc ttcgaggcta aggtggtgga cttggacacc   1200
ggtaagacac tgggtgtgaa ccagcgcggc gagctgtgcg tccgtggccc catgatcatg   1260
agcggctacg ttaacaaccc cgaggctaca aacgctctca tcgacaagga cggctggctg   1320
cacagcggcg acatcgccta ctgggacgag gacgagcact tcttcatcgt ggaccggctg   1380
aagagcctga tcaaatacaa gggctaccag gtagcccag ccgaactgga gagcatcctg   1440
ctgcaacacc ccaacatctt cgacgccggg gtcgccggcc tgcccgacga cgatgccggc   1500
gagctgcccg ccgcagtcgt cgtgctggaa cacggtaaaa ccatgaccga aggagatc    1560 gtggactatg tggccagcca ggttacaacc gccaagaagc tgcgcggtgg tgttgtgttc   1620
```
gtggacgagg tgcctaaagg actgaccggc aagttggacg cccgcaagat ccgcgagatt   1680
ctcattaagg ccaagaaggg cggcaagatc gccgtgtaac tcgag                   1725

<210> SEQ ID NO 9
<211> LENGTH: 568
<212> TYPE: PRT
<213> ORGANISM: Artificial Sequence
<220> FEATURE:
<223> OTHER INFORMATION: A111-Luciferase

<400> SEQUENCE: 9

Met Ala Ala Ala Ala Val Lys Asn Trp Met Thr Gln Thr Leu Ala
1               5                   10                  15

Ala Ala Met Glu Asp Ala Lys Asn Ile Lys Lys Gly Pro Ala Pro Phe
                20                  25                  30

Tyr Pro Leu Glu Asp Gly Thr Ala Gly Glu Gln Leu His Lys Ala Met
            35                  40                  45

Lys Arg Tyr Ala Leu Val Pro Gly Thr Ile Ala Phe Thr Asp Ala His
50                  55                  60

Ile Glu Val Asp Ile Thr Tyr Ala Glu Tyr Phe Glu Met Ser Val Arg
65                  70                  75                  80

Leu Ala Glu Ala Met Lys Arg Tyr Gly Leu Asn Thr Asn His Arg Ile
                85                  90                  95

Val Val Cys Ser Glu Asn Ser Leu Gln Phe Phe Met Pro Val Leu Gly
            100                 105                 110

Ala Leu Phe Ile Gly Val Ala Val Ala Pro Ala Asn Asp Ile Tyr Asn
        115                 120                 125

Glu Arg Glu Leu Leu Asn Ser Met Gly Ile Ser Gln Pro Thr Val Val
    130                 135                 140

Phe Val Ser Lys Lys Gly Leu Gln Lys Ile Leu Asn Val Gln Lys Lys
145                 150                 155                 160

Leu Pro Ile Ile Gln Lys Ile Ile Met Asp Ser Lys Thr Asp Tyr
                165                 170                 175

Gln Gly Phe Gln Ser Met Tyr Thr Phe Val Thr Ser His Leu Pro Pro
            180                 185                 190

Gly Phe Asn Glu Tyr Asp Phe Val Pro Glu Ser Phe Asp Arg Asp Lys
        195                 200                 205

Thr Ile Ala Leu Ile Met Asn Ser Ser Gly Ser Thr Gly Leu Pro Lys
    210                 215                 220

Gly Val Ala Leu Pro His Arg Thr Ala Cys Val Arg Phe Ser His Ala
225                 230                 235                 240

Arg Asp Pro Ile Phe Gly Asn Gln Ile Ile Pro Asp Thr Ala Ile Leu
                245                 250                 255

Ser Val Val Pro Phe His His Gly Phe Gly Met Phe Thr Thr Leu Gly
            260                 265                 270

Tyr Leu Ile Cys Gly Phe Arg Val Val Leu Met Tyr Arg Phe Glu Glu
        275                 280                 285

Glu Leu Phe Leu Arg Ser Leu Gln Asp Tyr Lys Ile Gln Ser Ala Leu
    290                 295                 300

Leu Val Pro Thr Leu Phe Ser Phe Phe Ala Lys Ser Thr Leu Ile Asp
305                 310                 315                 320

Lys Tyr Asp Leu Ser Asn Leu His Glu Ile Ala Ser Gly Gly Ala Pro
                325                 330                 335

Leu Ser Lys Glu Val Gly Glu Ala Val Ala Lys Arg Phe His Leu Pro

```
                        340                 345                 350
Gly Ile Arg Gln Gly Tyr Gly Leu Thr Glu Thr Thr Ser Ala Ile Leu
            355                 360                 365

Ile Thr Pro Glu Gly Asp Asp Lys Pro Gly Ala Val Gly Lys Val Val
370                 375                 380

Pro Phe Phe Glu Ala Lys Val Val Asp Leu Asp Thr Gly Lys Thr Leu
385                 390                 395                 400

Gly Val Asn Gln Arg Gly Glu Leu Cys Val Arg Gly Pro Met Ile Met
                405                 410                 415

Ser Gly Tyr Val Asn Asn Pro Glu Ala Thr Asn Ala Leu Ile Asp Lys
            420                 425                 430

Asp Gly Trp Leu His Ser Gly Asp Ile Ala Tyr Trp Asp Glu Asp Glu
        435                 440                 445

His Phe Phe Ile Val Asp Arg Leu Lys Ser Leu Ile Lys Tyr Lys Gly
    450                 455                 460

Tyr Gln Val Ala Pro Ala Glu Leu Glu Ser Ile Leu Leu Gln His Pro
465                 470                 475                 480

Asn Ile Phe Asp Ala Gly Val Ala Gly Leu Pro Asp Asp Ala Gly
                485                 490                 495

Glu Leu Pro Ala Ala Val Val Leu Glu His Gly Lys Thr Met Thr
            500                 505                 510

Glu Lys Glu Ile Val Asp Tyr Val Ala Ser Gln Val Thr Thr Ala Lys
        515                 520                 525

Lys Leu Arg Gly Gly Val Val Phe Val Asp Glu Val Pro Lys Gly Leu
    530                 535                 540

Thr Gly Lys Leu Asp Ala Arg Lys Ile Arg Glu Ile Leu Ile Lys Ala
545                 550                 555                 560

Lys Lys Gly Gly Lys Ile Ala Val
                565
```

<210> SEQ ID NO 10
<211> LENGTH: 1026
<212> TYPE: DNA
<213> ORGANISM: Plasmodium berghei
<220> FEATURE:
<221> NAME/KEY: misc_feature
<223> OTHER INFORMATION: circumsporozoite (CS) protein (CSP)

<400> SEQUENCE: 10

```
atggccaaga agtgtaccat actggtcgtt gcgtcacttc tgttggtcaa ttctctgctc      60
ccaggctatg gacagaacaa atccattcag gcacagagga acctcaacga actctgctac     120
aatgaaggga atgacaataa gctgtatcac gtgctgaatt ccaagaacgg caaaatctac     180
aatcgcaaca cagtaaatcg gttgcttgcc gatgcacccg agggtaagaa gaatgaaaag     240
aagaatgaga aaatcgagcg caacaacaag cttaaacagc caccgcctcc tcctaaccca     300
aatgacccac cgccacccaa tccaaacgac caccgcctc  ccaaccctaa cgatcctcca     360
ccgcccaacc ctaatgaccc accacctccc aatgcaaacg atccacccc  tcctaacgct     420
aacgaccctg ctccacccaa cgctaacgat cccgcgcccc caatgccaa  cgaccccgca     480
ccacctaatg ccaacgatcc cgccccgccc aatgctaatg atcctccacc acccaaccca     540
aacgaccctg cccctcctaa tgctaacgat ccaccacctc caatccgaa  tgatcccgct     600
ccacctcagg ggaacaacaa ccctcagccc aacctagac  acagccgca  gcccaacccc     660
caaccccagc ccagcctca  accccagccc agccacgtc  cgcagcctca gcctcaacct     720
```

-continued

```
ggaggcaaca ataacaacaa gaataacaac aacgacgaca gctacattcc aagtgccgag    780
aaaattctgg agtttgttaa gcagatccga gacagcataa ccgaagaatg gtcacagtgt    840
aacgtgacgt gtggatctgg catcagagtg aggaaacgga agggttccaa taagaaagca    900
gaggatctga ctctggagga cattgataca gagatctgca aaatggacaa atgcagctct    960
atcttcaaca tcgtgagtaa tagcctcggg tttgtgattc tgctggtcct ggtgttcttc   1020
aattga                                                             1026
```

<210> SEQ ID NO 11
<211> LENGTH: 341
<212> TYPE: PRT
<213> ORGANISM: Plasmodium berghei
<220> FEATURE:
<221> NAME/KEY: misc_feature
<223> OTHER INFORMATION: CSP

<400> SEQUENCE: 11

```
Met Ala Lys Lys Cys Thr Ile Leu Val Val Ala Ser Leu Leu Leu Val
1               5                   10                  15

Asn Ser Leu Leu Pro Gly Tyr Gly Gln Asn Lys Ser Ile Gln Ala Gln
            20                  25                  30

Arg Asn Leu Asn Glu Leu Cys Tyr Asn Glu Gly Asn Asp Asn Lys Leu
        35                  40                  45

Tyr His Val Leu Asn Ser Lys Asn Gly Lys Ile Tyr Asn Arg Asn Thr
    50                  55                  60

Val Asn Arg Leu Leu Ala Asp Ala Pro Glu Gly Lys Lys Asn Glu Lys
65                  70                  75                  80

Lys Asn Glu Lys Ile Glu Arg Asn Asn Lys Leu Lys Gln Pro Pro Pro
                85                  90                  95

Pro Pro Asn Pro Asn Asp Pro Pro Pro Asn Pro Asn Asp Pro Pro
            100                 105                 110

Pro Pro Asn Pro Asn Asp Pro Pro Pro Asn Pro Asn Asp Pro Pro
            115                 120                 125

Pro Pro Asn Ala Asn Asp Pro Pro Pro Asn Ala Asn Asp Pro Ala
            130                 135                 140

Pro Pro Asn Ala Asn Asp Pro Ala Pro Pro Asn Ala Asn Asp Pro Ala
145                 150                 155                 160

Pro Pro Asn Ala Asn Asp Pro Ala Pro Pro Asn Ala Asn Asp Pro Pro
                165                 170                 175

Pro Pro Asn Pro Asn Asp Pro Ala Pro Pro Asn Ala Asn Asp Pro Pro
            180                 185                 190

Pro Pro Asn Pro Asn Asp Pro Ala Pro Pro Gln Gly Asn Asn Asn Pro
            195                 200                 205

Gln Pro Gln Pro Arg Pro Gln Pro Gln Pro Gln Pro Gln Pro Gln Pro
            210                 215                 220

Gln Pro Gln Pro Gln Pro Gln Pro Arg Pro Gln Pro Gln Pro Gln Pro
225                 230                 235                 240

Gly Gly Asn Asn Asn Asn Lys Asn Asn Asn Asn Asp Asp Ser Tyr Ile
                245                 250                 255

Pro Ser Ala Glu Lys Ile Leu Glu Phe Val Lys Gln Ile Arg Asp Ser
            260                 265                 270

Ile Thr Glu Glu Trp Ser Gln Cys Asn Val Thr Cys Gly Ser Gly Ile
        275                 280                 285

Arg Val Arg Lys Arg Lys Gly Ser Asn Lys Lys Ala Glu Asp Leu Thr
    290                 295                 300
```

```
Leu Glu Asp Ile Asp Thr Glu Ile Cys Lys Met Asp Lys Cys Ser Ser
305                 310                 315                 320

Ile Phe Asn Ile Val Ser Asn Ser Leu Gly Phe Val Ile Leu Leu Val
            325                 330                 335

Leu Val Phe Phe Asn
            340

<210> SEQ ID NO 12
<211> LENGTH: 340
<212> TYPE: PRT
<213> ORGANISM: Plasmodium berghei
<220> FEATURE:
<221> NAME/KEY: misc_feature
<223> OTHER INFORMATION: CSP

<400> SEQUENCE: 12

Met Lys Lys Cys Thr Ile Leu Val Val Ala Ser Leu Leu Leu Val Asn
1               5                   10                  15

Ser Leu Leu Pro Gly Tyr Gly Gln Asn Lys Ser Ile Gln Ala Gln Arg
            20                  25                  30

Asn Leu Asn Glu Leu Cys Tyr Asn Glu Gly Asn Asp Asn Lys Leu Tyr
        35                  40                  45

His Val Leu Asn Ser Lys Asn Gly Lys Ile Tyr Asn Arg Asn Thr Val
    50                  55                  60

Asn Arg Leu Leu Ala Asp Ala Pro Glu Gly Lys Lys Asn Glu Lys Lys
65                  70                  75                  80

Asn Glu Lys Ile Glu Arg Asn Asn Lys Leu Lys Gln Pro Pro Pro Pro
                85                  90                  95

Pro Asn Pro Asn Asp Pro Pro Pro Asn Pro Asn Asp Pro Pro Pro
            100                 105                 110

Pro Asn Pro Asn Asp Pro Pro Pro Asn Pro Asn Asp Pro Pro Pro
            115                 120                 125

Pro Asn Ala Asn Asp Pro Pro Pro Asn Ala Asn Asp Pro Ala Pro
            130                 135                 140

Pro Asn Ala Asn Asp Pro Ala Pro Pro Asn Ala Asn Asp Pro Ala Pro
145                 150                 155                 160

Pro Asn Ala Asn Asp Pro Ala Pro Pro Asn Ala Asn Asp Pro Pro Pro
            165                 170                 175

Pro Asn Pro Asn Asp Pro Ala Pro Pro Asn Ala Asn Asp Pro Pro Pro
            180                 185                 190

Pro Asn Pro Asn Asp Pro Ala Pro Pro Gln Gly Asn Asn Asn Pro Gln
            195                 200                 205

Pro Gln Pro Arg Pro Gln Pro Gln Pro Gln Pro Gln Pro Gln Pro Gln
            210                 215                 220

Pro Gln Pro Gln Pro Gln Pro Arg Pro Gln Pro Gln Pro Gln Pro Gly
225                 230                 235                 240

Gly Asn Asn Asn Asn Lys Asn Asn Asn Asp Asp Ser Tyr Ile Pro
            245                 250                 255

Ser Ala Glu Lys Ile Leu Glu Phe Val Lys Gln Ile Arg Asp Ser Ile
            260                 265                 270

Thr Glu Glu Trp Ser Gln Cys Asn Val Thr Cys Gly Ser Gly Ile Arg
            275                 280                 285

Val Arg Lys Arg Lys Gly Ser Asn Lys Lys Ala Glu Asp Leu Thr Leu
            290                 295                 300

Glu Asp Ile Asp Thr Glu Ile Cys Lys Met Asp Lys Cys Ser Ser Ile
```

```
                305                 310                 315                 320
            Phe Asn Ile Val Ser Asn Ser Leu Gly Phe Val Ile Leu Leu Val Leu
                            325                 330                 335
            Val Phe Phe Asn
                        340

<210> SEQ ID NO 13
<211> LENGTH: 1203
<212> TYPE: DNA
<213> ORGANISM: Artificial Sequence
<220> FEATURE:
<223> OTHER INFORMATION: PfCSPhumanCO

<400> SEQUENCE: 13
gccaccatgg ctatgagaaa gctcgcgatc ctttccgtga gctcattcct gtttgtcgaa      60
gccttgttcc aggagtatca gtgctatgga tcatcctcca acacaagagt gctcaacgaa     120
ctgaactatg acaatgccgg tactaacctc tacaatgaac tggagatgaa ctactacggc     180
aaacaggaga actggtattc cctgaagaag aattccagat cactgggcga aaacgacgat     240
gggaataatg aggataacga gaagttgcgg aaaccaaagc acaagaagtt gaaacaaccc     300
gccgacggaa accctgatcc taacgccaac ccaaatgtag atcccaacgc caacccaaac     360
gtcgatccca atgccaatcc caatgttgac cccaatgcaa accctaatgc aaatcccaat     420
gccaatccca atgcaaatcc taatgctaat ccaaacgcca accctaacgc gaaccccaac     480
gccaatccta acgcaaatcc taacgcaaat cctaatgcca accctaatgc gaacccgaac     540
gctaatccta acgctaatcc gaatgcaaat ccaaatgcaa atccgaacgc caatcccaac     600
gtagacccaa atgcaaaccc gaacgctaac ccgaacgcaa acccaaacgc caatccgaac     660
gctaatccca atgctaatcc aacgctaacc ccaatgcca accggaatgc caaccccaat     720
gcgaatccaa atgcgaaccc aaacgccaat ccgaatgcga atcctaacgc taacccaaat     780
gctaatccaa acgctaatcc aaatgcgaac cccaatgcga atccaaataa gaacaatcag     840
gggaatggtc agggccataa catgcctaac gaccccaacc gaaatgtgga cgagaacgct     900
aacgcaaaca cgctgtaaa gaacaacaac aatgaggagc ttctgacaa gcacatcaaa     960 gagtacctga ataaaatcca gaacagtctt tctacggaat ggtccccatg tagtgttact    1020
tgtggcaatg ggattcaagt caggatcaaa ccaggctctg cgaataagcc taaggatgaa    1080
ctggattatg ccaatgacat cgagaagaaa atatgcaaga tggagaagtg cagtagcgtg    1140
ttcaatgtcg taaactcaag cataggtctg ataatggtac tgagctttct gttcctcaac    1200
taa                                                                   1203

<210> SEQ ID NO 14
<211> LENGTH: 398
<212> TYPE: PRT
<213> ORGANISM: Artificial Sequence
<220> FEATURE:
<223> OTHER INFORMATION: PfCSP

<400> SEQUENCE: 14

Met Ala Met Arg Lys Leu Ala Ile Leu Ser Val Ser Ser Phe Leu Phe
1               5                   10                  15

Val Glu Ala Leu Phe Gln Glu Tyr Gln Cys Tyr Gly Ser Ser Ser Asn
            20                  25                  30

Thr Arg Val Leu Asn Glu Leu Asn Tyr Asp Asn Ala Gly Thr Asn Leu
        35                  40                  45
```

Tyr Asn Glu Leu Glu Met Asn Tyr Tyr Gly Lys Gln Glu Asn Trp Tyr
    50              55              60

Ser Leu Lys Lys Asn Ser Arg Ser Leu Gly Glu Asn Asp Asp Gly Asn
65              70              75              80

Asn Glu Asp Asn Glu Lys Leu Arg Lys Pro Lys His Lys Lys Leu Lys
                85              90              95

Gln Pro Ala Asp Gly Asn Pro Asp Pro Asn Ala Asn Pro Asn Val Asp
            100             105             110

Pro Asn Ala Asn Pro Asn Val Asp Pro Asn Ala Asn Pro Asn Val Asp
        115             120             125

Pro Asn Ala Asn Pro Asn Ala Asn Pro Asn Ala Asn Pro Asn Ala Asn
130             135             140

Pro Asn Ala Asn Pro Asn Ala Asn Pro Asn Ala Asn Pro Asn Ala Asn
145             150             155             160

Pro Asn Ala Asn Pro Asn Ala Asn Pro Asn Ala Asn Pro Asn Ala Asn
            165             170             175

Pro Asn Ala Asn Pro Asn Ala Asn Pro Asn Ala Asn Pro Asn Ala Asn
        180             185             190

Pro Asn Ala Asn Pro Asn Val Asp Pro Asn Ala Asn Pro Asn Ala Asn
    195             200             205

Pro Asn Ala Asn Pro Asn Ala Asn Pro Asn Ala Asn Pro Asn Ala Asn
210             215             220

Pro Asn Ala Asn Pro Asn Ala Asn Pro Asn Ala Asn Pro Asn Ala Asn
225             230             235             240

Pro Asn Ala Asn Pro Asn Ala Asn Pro Asn Ala Asn Pro Asn Ala Asn
            245             250             255

Pro Asn Ala Asn Pro Asn Ala Asn Pro Asn Ala Asn Pro Asn Ala Asn
        260             265             270

Pro Asn Lys Asn Asn Gln Gly Asn Gly Gln Gly His Asn Met Pro Asn
    275             280             285

Asp Pro Asn Arg Asn Val Asp Glu Asn Ala Asn Ala Asn Ser Ala Val
    290             295             300

Lys Asn Asn Asn Glu Glu Pro Ser Asp Lys His Ile Lys Glu Tyr
305             310             315             320

Leu Asn Lys Ile Gln Asn Ser Leu Ser Thr Glu Trp Ser Pro Cys Ser
            325             330             335

Val Thr Cys Gly Asn Gly Ile Gln Val Arg Ile Lys Pro Gly Ser Ala
        340             345             350

Asn Lys Pro Lys Asp Glu Leu Asp Tyr Ala Asn Asp Ile Glu Lys Lys
    355             360             365

Ile Cys Lys Met Glu Lys Cys Ser Ser Val Phe Asn Val Val Asn Ser
370             375             380

Ser Ile Gly Leu Ile Met Val Leu Ser Phe Leu Phe Leu Asn
385             390             395

<210> SEQ ID NO 15
<211> LENGTH: 423
<212> TYPE: PRT
<213> ORGANISM: Artificial Sequence
<220> FEATURE:
<223> OTHER INFORMATION: CSP

<400> SEQUENCE: 15

Met Arg Lys Leu Ala Ile Leu Ser Val Ser Ser Phe Leu Phe Val Glu
1               5               10              15

```
Ala Leu Phe Gln Glu Tyr Gln Cys Tyr Gly Ser Ser Ser Asn Thr Arg
             20                  25                  30

Val Leu Asn Glu Leu Asn Tyr Asp Asn Ala Gly Thr Asn Leu Tyr Asn
             35                  40                  45

Glu Leu Glu Met Asn Tyr Tyr Gly Lys Gln Glu Asn Trp Tyr Ser Leu
             50                  55                  60

Lys Lys Asn Ser Arg Ser Leu Gly Glu Asn Asp Asp Gly Asn Asn Asn
 65                  70                  75                  80

Asn Gly Asp Asn Gly Arg Glu Gly Lys Asp Glu Asp Lys Arg Asp Gly
                 85                  90                  95

Asn Asn Glu Asp Asn Glu Lys Leu Arg Lys Pro Lys His Lys Lys Leu
            100                 105                 110

Lys Gln Pro Gly Asp Gly Asn Pro Asp Pro Asn Ala Asn Pro Asn Val
            115                 120                 125

Asp Pro Asn Ala Asn Pro Asn Val Asp Pro Asn Ala Asn Pro Asn Val
            130                 135                 140

Asp Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
            165                 170                 175

Asn Pro Asn Ala Asn Pro Asn Ala Asn Pro Asn Ala Asn Pro Asn Val
            180                 185                 190

Asp Pro Asn Ala Asn Pro Asn Ala Asn Pro Asn Ala Asn Pro Asn Ala
            195                 200                 205

Asn Pro Asn Ala Asn Pro Asn Ala Asn Pro Asn Ala Asn Pro Asn Ala
            210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
            245                 250                 255

Asn Pro Asn Ala Asn Pro Asn Ala Asn Pro Asn Ala Asn Pro Asn Ala
            260                 265                 270

Asn Pro Asn Ala Asn Pro Asn Ala Asn Pro Asn Ala Asn Pro Asn Ala
            275                 280                 285

Asn Pro Asn Ala Asn Pro Asn Ala Asn Pro Asn Lys Asn Asn Gln Gly
            290                 295                 300

Asn Gly Gln Gly His Asn Met Pro Asn Asp Pro Asn Arg Asn Val Asp
305                 310                 315                 320

Glu Asn Ala Asn Ala Asn Asn Ala Val Lys Asn Asn Asn Asn Glu Glu
            325                 330                 335

Pro Ser Asp Lys His Ile Thr Glu Tyr Leu Lys Lys Ile Gln Asn Ser
            340                 345                 350

Leu Ser Thr Glu Trp Ser Pro Cys Ser Val Thr Cys Gly Asn Gly Ile
            355                 360                 365

Gln Val Arg Ile Lys Pro Gly Ser Ala Gly Lys Ser Lys Asp Glu Leu
            370                 375                 380

Asp Tyr Glu Asn Asp Ile Glu Lys Lys Ile Cys Lys Met Glu Lys Cys
385                 390                 395                 400

Ser Ser Val Phe Asn Val Asn Ser Ser Ile Gly Leu Ile Met Val
                405                 410                 415

Leu Ser Phe Leu Phe Leu Asn
            420
```

<210> SEQ ID NO 16
<211> LENGTH: 1143
<212> TYPE: DNA
<213> ORGANISM: Artificial Sequence
<220> FEATURE:
<223> OTHER INFORMATION: PfCSPhumanCO

<400> SEQUENCE: 16

```
gccaccatgg ctaagaactt cattctgctt gccgtaagct ctattctctt ggtagacttg     60
tttccaacac actgtggaca taatgtagat ctcagtaaag caattaacct caatggtgtt    120
aattttaata atgtagacgc atcctctctc ggcgcggcac acgtgggtca agtgccagt     180
aggggggcgcg gactcggcga gaacccggac gacgaagaag gggatgcgaa aaagaagaag    240
gatgggaaga aggcagaacc caagaatcca agggagaata agctgaagca gccaggagat    300
agagctgacg gccagcctgc cggcgatagg gccgacggaa acccgcgggg agaccgcgcg    360
gatggccaac ctgcgggtga ccgcgctgac gggcagcccg caggagacag agccgccgga    420
caacccgccg cgaccgagc ggatggtcag cccgcgggcg atcgagcgga cggtcagcca    480
gctggagatc gcgcggacgg acaacctgcg ggggacaggg ctgacggtca accagccggt    540
gatagagcag cgggccaacc ggcaggggac cgagccgcag ggcagcccgc cggggacagg    600
gctgacgggc agccagcggg ggataggcc gccggtcaac ctgcaggcga tcgagctgac    660
ggccaacccg cgggtgaccg gcagccggcc caacctgctg gggatcgagc agacggacag    720
ccggccggag atcgggccgc tggccaaccg gctggagaca gagccgctgg tcaacctgcc    780
ggagatcggg ccgctgggca ggccgcgggt gacaggcag ccggacaagc agcaggggg    840
aacgccggtg gacaaggaca gaacaatgag ggtgcgaatg ccccgaatga aaagagcgtt    900
aaagagtacc tggataaggt tagagcaacc gtaggcaccg aatggacccc ctgctccgtg    960
acttgcgggg taggtgttcg ggtcaggcgg agggtcaatg cggcgaacaa gaaaccggaa   1020
gatctgactt tgaacgatct tgaaacagat gtatgcacga tggacaagtg tgctggcata   1080
tttaacgtag tcagtaactc tctcggcctt gtgatcctct ggtcttggc gctgtttaac    1140
tag                                                                 1143
```

<210> SEQ ID NO 17
<211> LENGTH: 378
<212> TYPE: PRT
<213> ORGANISM: Plasmodium vivax
<220> FEATURE:
<221> NAME/KEY: misc_feature
<223> OTHER INFORMATION: PvCSP

<400> SEQUENCE: 17

```
Met Ala Lys Asn Phe Ile Leu Leu Ala Val Ser Ser Ile Leu Leu Val
1               5                   10                  15

Asp Leu Phe Pro Thr His Cys Gly His Asn Val Asp Leu Ser Lys Ala
            20                  25                  30

Ile Asn Leu Asn Gly Val Asn Phe Asn Asn Val Asp Ala Ser Ser Leu
        35                  40                  45

Gly Ala Ala His Val Gly Gln Ser Ala Ser Arg Gly Arg Gly Leu Gly
    50                  55                  60

Glu Asn Pro Asp Asp Glu Gly Asp Ala Lys Lys Lys Asp Gly
65                  70                  75                  80

Lys Lys Ala Glu Pro Lys Asn Pro Arg Glu Asn Lys Leu Lys Gln Pro
                85                  90                  95

Gly Asp Arg Ala Asp Gly Gln Pro Ala Gly Asp Arg Ala Asp Gly Gln
```

```
                    100                 105                 110
Pro Ala Gly Asp Arg Ala Asp Gly Gln Pro Ala Gly Asp Arg Ala Asp
                115                 120                 125

Gly Gln Pro Ala Gly Asp Arg Ala Ala Gly Gln Pro Ala Gly Asp Arg
            130                 135                 140

Ala Asp Gly Gln Pro Ala Gly Asp Arg Ala Asp Gly Gln Pro Ala Gly
145                 150                 155                 160

Asp Arg Ala Asp Gly Gln Pro Ala Gly Asp Arg Ala Asp Gly Gln Pro
                165                 170                 175

Ala Gly Asp Arg Ala Ala Gly Gln Pro Ala Gly Asp Arg Ala Ala Gly
            180                 185                 190

Gln Pro Ala Gly Asp Arg Ala Asp Gly Gln Pro Ala Gly Asp Arg Ala
        195                 200                 205

Ala Gly Gln Pro Ala Gly Asp Arg Ala Asp Gly Gln Pro Ala Gly Asp
    210                 215                 220

Arg Ala Ala Gly Gln Pro Ala Gly Asp Arg Ala Asp Gly Gln Pro Ala
225                 230                 235                 240

Gly Asp Arg Ala Ala Gly Gln Pro Ala Gly Asp Arg Ala Ala Gly Gln
                245                 250                 255

Pro Ala Gly Asp Arg Ala Ala Gly Gln Ala Ala Gly Asp Arg Ala Ala
            260                 265                 270

Gly Gln Ala Ala Gly Gly Asn Ala Gly Gly Gln Gly Gln Asn Asn Glu
        275                 280                 285

Gly Ala Asn Ala Pro Asn Glu Lys Ser Val Lys Glu Tyr Leu Asp Lys
    290                 295                 300

Val Arg Ala Thr Val Gly Thr Glu Trp Thr Pro Cys Ser Val Thr Cys
305                 310                 315                 320

Gly Val Gly Val Arg Val Arg Arg Val Asn Ala Ala Asn Lys Lys
                325                 330                 335

Pro Glu Asp Leu Thr Leu Asn Asp Leu Glu Thr Asp Val Cys Thr Met
            340                 345                 350

Asp Lys Cys Ala Gly Ile Phe Asn Val Val Ser Asn Ser Leu Gly Leu
        355                 360                 365

Val Ile Leu Leu Val Leu Ala Leu Phe Asn
    370                 375

<210> SEQ ID NO 18
<211> LENGTH: 368
<212> TYPE: PRT
<213> ORGANISM: Plasmodium vivax
<220> FEATURE:
<221> NAME/KEY: misc_feature
<223> OTHER INFORMATION: CSP

<400> SEQUENCE: 18

Met Lys Asn Phe Ile Leu Leu Ala Val Ser Ser Ile Leu Leu Val Asp
1               5                   10                  15

Leu Phe Pro Thr His Cys Gly His Asn Val Asp Leu Ser Lys Ala Ile
            20                  25                  30

Asn Leu Asn Gly Val Asn Phe Asn Asn Val Asp Ala Ser Ser Leu Gly
        35                  40                  45

Ala Ala His Val Gly Gln Ser Ala Ser Arg Gly Arg Gly Leu Gly Glu
    50                  55                  60

Asn Pro Asp Asp Glu Glu Gly Asp Ala Lys Lys Lys Asp Gly Lys
65                  70                  75                  80
```

Lys Ala Glu Pro Lys Asn Pro Arg Glu Asn Lys Leu Lys Gln Pro Gly
                85                  90                  95
Asp Arg Ala Asp Gly Gln Pro Ala Gly Asp Arg Ala Asp Gly Gln Pro
            100                 105                 110
Ala Gly Asp Arg Ala Asp Gly Gln Pro Ala Gly Asp Arg Ala Gly Gln
        115                 120                 125
Pro Ala Gly Asp Arg Ala Asp Gly Gln Pro Ala Gly Asp Arg Ala Asp
    130                 135                 140
Gly Gln Pro Ala Gly Asp Arg Ala Asp Gly Gln Pro Ala Gly Asp Arg
145                 150                 155                 160
Ala Asp Gly Gln Pro Ala Gly Asp Arg Ala Gly Gln Pro Ala Gly Asp
                165                 170                 175
Arg Ala Gly Gln Pro Ala Gly Asp Arg Ala Asp Gly Gln Pro Ala Gly
            180                 185                 190
Asp Arg Ala Gly Gln Pro Ala Gly Asp Arg Ala Asp Gly Gln Pro Ala
        195                 200                 205
Gly Asp Arg Ala Gly Gln Pro Ala Gly Asp Arg Ala Asp Gly Gln Pro
    210                 215                 220
Ala Gly Asp Arg Ala Gly Gln Pro Ala Gly Asp Arg Ala Gly Gln Pro
225                 230                 235                 240
Ala Gly Asp Arg Ala Gly Gln Pro Ala Gly Asp Arg Ala Gly Gln Pro
                245                 250                 255
Ala Gly Asn Gly Ala Gly Gly Gln Ala Ala Gly Gly Asn Ala Gly Gly
            260                 265                 270
Gln Gly Gln Asn Asn Glu Gly Ala Asn Ala Pro Asn Glu Lys Ser Val
        275                 280                 285
Lys Glu Tyr Leu Asp Lys Val Arg Ala Thr Val Gly Thr Glu Trp Thr
    290                 295                 300
Pro Cys Ser Val Thr Cys Gly Val Gly Val Arg Val Arg Arg Arg Val
305                 310                 315                 320
Asn Ala Ala Asn Lys Lys Pro Glu Asp Leu Thr Leu Asn Asp Leu Glu
                325                 330                 335
Thr Asp Val Cys Thr Met Asp Lys Cys Ala Gly Ile Phe Asn Val Val
            340                 345                 350
Ser Asn Ser Leu Gly Leu Val Ile Leu Leu Val Leu Ala Leu Phe Asn
        355                 360                 365

<210> SEQ ID NO 19
<211> LENGTH: 1842
<212> TYPE: DNA
<213> ORGANISM: Plasmodium berghei
<220> FEATURE:
<221> NAME/KEY: misc_feature
<223> OTHER INFORMATION: thrombospondin-related anonymous protein (TRAP)

<400> SEQUENCE: 19
ggatccgcca ccatggctaa gcttctgggg aacagtaaat acttctttgt ggtcctgctg      60
ctgtgcatta gcgttttcct caacggtcag gagattctgg acgaaatcaa gtactctgag     120
gaggtctgca cgaacaaat cgatctccac attctgctgg atgggagtgg cagcataggt      180
cactctaact ggatcagtca cgtgataccc atgctgacaa cccttgtgga caatttgaac     240
atcagccgcg atgagatcaa tatctccatg accttgttct ccacttatgc cagggaactt     300
gtgagactta agagatatgg gtctacaagc aaagccagtc tgaggttcat catcgcgcaa     360
ctccagaata actattctcc tcatggaacg acaaatctga ctagcgccct gttgaatgtg     420

```
gacaatctca ttcagaagaa aatgaatcgc cctaatgcca ttcagctcgt gattatcctt    480
actgacggca tccctaacaa tctgaagaag tccactactg ttgtcaacca gctgaagaag    540
aaggacgtca atgtcgctat tattggtgtt ggcgccggag taaacaatat gtttaaccgt    600
atattggtag gatgtggaaa acttgggcct tgtccctact actcttatgg ctcttgggat    660
caagcacaaa ccatgatcaa accatttctc tcaaaggtct gtcaggaagt ggagaaagtg    720
gcactgtgcg gtaagtggga ggagtggagt gagtgttcaa ccacttgcga caacggaacg    780
aaaataagga agcgaaaggt tctccatccc aactgtgccg gggaaatgac agccccatgt    840
aaagtgcggg actgtcctcc caaacctgta gcccctccgg tcattcccat caaagtccct    900
gacgtgcctg tgaaaccagt cgaacctatt gagcccgccg agccagcaga gccagcagaa    960
ccagcagagc ctgcagaacc cgccgaaccc gctgagcccg cggagcccgc cgaacccgct   1020
gaaccggcag aacccgcgga accagcggag cctgcagagc cagctgagcc tgctgaaccg   1080
gcggagcccg ctgaaccagc cgagcctgct aaaccggccg aaccggcaga gcccgctgag   1140
cctgccgagc cagcggaacc agttaacccc gataatccta tcctgccgat caagcccgag   1200
gagccatctg gtggagccga gccattgaat ccagaggtcg agaatccctt tatcatcccc   1260
gacgaaccca tcgaacccat tattgcgcca ggagctgtac cggataagcc catcattcct   1320
gaggaatcaa atgagctgcc aaacaatctt ccagagtctc cctccgatag tcaggtggag   1380
tatcctcggc caaacgacaa tggggataac agcaacaaca caatcaattc caacaagaac   1440
ataccaaata gcatgtgcc tcctacagac gacacccct acaagggcca ggaagaacga   1500
atccctaagc cgcatcggag caacgacgaa tacatttact acaataatgc taacaataac   1560
gacaagctgg agcccgagat accctctaag gattacgagg aaaacaagag caagaaacag   1620
agcaaaagca acaatggcta taagatcgcc ggcggcataa ttggcgggct ggctattatc   1680
ggctgcattg gagtgggcta taacttcata gccgggtcct ccgccgccgc tatggctgga   1740
gaggcggcac cttttgagga cgtgatggct gatgatgaga aggggatcgt ggaaaacgaa   1800
cagttcaaac tgccagagga caatgattgg aattgactcg ag                      1842
```

<210> SEQ ID NO 20
<211> LENGTH: 607
<212> TYPE: PRT
<213> ORGANISM: Plasmodium berghei
<220> FEATURE:
<221> NAME/KEY: misc_feature
<223> OTHER INFORMATION: TRAP

<400> SEQUENCE: 20

```
Met Ala Lys Leu Leu Gly Asn Ser Lys Tyr Phe Phe Val Val Leu Leu
1               5                   10                  15

Leu Cys Ile Ser Val Phe Leu Asn Gly Gln Glu Ile Leu Asp Glu Ile
            20                  25                  30

Lys Tyr Ser Glu Glu Val Cys Asn Glu Gln Ile Asp Leu His Ile Leu
        35                  40                  45

Leu Asp Gly Ser Gly Ser Ile Gly His Ser Asn Trp Ile Ser His Val
    50                  55                  60

Ile Pro Met Leu Thr Thr Leu Val Asp Asn Leu Asn Ile Ser Arg Asp
65                  70                  75                  80

Glu Ile Asn Ile Ser Met Thr Leu Phe Ser Thr Tyr Ala Arg Glu Leu
                85                  90                  95

Val Arg Leu Lys Arg Tyr Gly Ser Thr Ser Lys Ala Ser Leu Arg Phe
            100                 105                 110
```

```
Ile Ile Ala Gln Leu Gln Asn Asn Tyr Ser Pro His Gly Thr Thr Asn
            115                 120                 125
Leu Thr Ser Ala Leu Leu Asn Val Asp Asn Leu Ile Gln Lys Lys Met
        130                 135                 140
Asn Arg Pro Asn Ala Ile Gln Leu Val Ile Ile Leu Thr Asp Gly Ile
145                 150                 155                 160
Pro Asn Asn Leu Lys Lys Ser Thr Thr Val Val Asn Gln Leu Lys Lys
                165                 170                 175
Lys Asp Val Asn Val Ala Ile Ile Gly Val Gly Ala Gly Val Asn Asn
            180                 185                 190
Met Phe Asn Arg Ile Leu Val Gly Cys Gly Lys Leu Gly Pro Cys Pro
        195                 200                 205
Tyr Tyr Ser Tyr Gly Ser Trp Asp Gln Ala Gln Thr Met Ile Lys Pro
    210                 215                 220
Phe Leu Ser Lys Val Cys Gln Glu Val Glu Lys Val Ala Leu Cys Gly
225                 230                 235                 240
Lys Trp Glu Glu Trp Ser Glu Cys Ser Thr Thr Cys Asp Asn Gly Thr
                245                 250                 255
Lys Ile Arg Lys Arg Lys Val Leu His Pro Asn Cys Ala Gly Glu Met
            260                 265                 270
Thr Ala Pro Cys Lys Val Arg Asp Cys Pro Pro Lys Pro Val Ala Pro
        275                 280                 285
Pro Val Ile Pro Ile Lys Val Pro Asp Val Pro Val Lys Pro Val Glu
    290                 295                 300
Pro Ile Glu Pro Ala Glu Pro Ala Glu Pro Ala Glu Pro Ala Glu Pro
305                 310                 315                 320
Ala Glu Pro Ala Glu Pro Ala Glu Pro Ala Glu Pro Ala Glu Pro Ala
                325                 330                 335
Glu Pro Ala Glu Pro Ala Glu Pro Ala Glu Pro Ala Glu Pro Ala Glu
            340                 345                 350
Pro Ala Glu Pro Ala Glu Pro Ala Glu Pro Ala Glu Pro Ala Lys Pro
        355                 360                 365
Ala Glu Pro Ala Glu Pro Ala Glu Pro Ala Glu Pro Ala Glu Pro Val
    370                 375                 380
Asn Pro Asp Asn Pro Ile Leu Pro Ile Lys Pro Glu Glu Pro Ser Gly
385                 390                 395                 400
Gly Ala Glu Pro Leu Asn Pro Glu Val Glu Asn Pro Phe Ile Ile Pro
                405                 410                 415
Asp Glu Pro Ile Glu Pro Ile Ile Ala Pro Gly Ala Val Pro Asp Lys
            420                 425                 430
Pro Ile Ile Pro Glu Glu Ser Asn Glu Leu Pro Asn Asn Leu Pro Glu
        435                 440                 445
Ser Pro Ser Asp Ser Gln Val Glu Tyr Pro Arg Pro Asn Asp Asn Gly
    450                 455                 460
Asp Asn Ser Asn Asn Thr Ile Asn Ser Asn Lys Asn Ile Pro Asn Lys
465                 470                 475                 480
His Val Pro Pro Thr Asp Asp Asn Pro Tyr Lys Gly Gln Glu Glu Arg
                485                 490                 495
Ile Pro Lys Pro His Arg Ser Asn Asp Glu Tyr Ile Tyr Tyr Asn Asn
            500                 505                 510
Ala Asn Asn Asn Asp Lys Leu Glu Pro Glu Ile Pro Ser Lys Asp Tyr
        515                 520                 525
```

```
Glu Glu Asn Lys Ser Lys Lys Gln Ser Lys Ser Asn Asn Gly Tyr Lys
            530                 535                 540

Ile Ala Gly Gly Ile Ile Gly Gly Leu Ala Ile Ile Gly Cys Ile Gly
545                 550                 555                 560

Val Gly Tyr Asn Phe Ile Ala Gly Ser Ser Ala Ala Met Ala Gly
                565                 570                 575

Glu Ala Ala Pro Phe Glu Asp Val Met Ala Asp Asp Glu Lys Gly Ile
            580                 585                 590

Val Glu Asn Glu Gln Phe Lys Leu Pro Glu Asp Asn Asp Trp Asn
            595                 600                 605
```

<210> SEQ ID NO 21
<211> LENGTH: 606
<212> TYPE: PRT
<213> ORGANISM: Plasmodium berghei
<220> FEATURE:
<221> NAME/KEY: misc_feature
<223> OTHER INFORMATION: TRAP

<400> SEQUENCE: 21

```
Met Lys Leu Leu Gly Asn Ser Lys Tyr Phe Phe Val Val Leu Leu Leu
1               5                   10                  15

Cys Ile Ser Val Phe Leu Asn Gly Gln Glu Ile Leu Asp Glu Ile Lys
                20                  25                  30

Tyr Ser Glu Glu Val Cys Asn Glu Gln Ile Asp Leu His Ile Leu Leu
            35                  40                  45

Asp Gly Ser Gly Ser Ile Gly His Ser Asn Trp Ile Ser His Val Ile
    50                  55                  60

Pro Met Leu Thr Thr Leu Val Asp Asn Leu Asn Ile Ser Arg Asp Glu
65                  70                  75                  80

Ile Asn Ile Ser Met Thr Leu Phe Ser Thr Tyr Ala Arg Glu Leu Val
                85                  90                  95

Arg Leu Lys Arg Tyr Gly Ser Thr Ser Lys Ala Ser Leu Arg Phe Ile
            100                 105                 110

Ile Ala Gln Leu Gln Asn Asn Tyr Ser Pro His Gly Thr Thr Asn Leu
        115                 120                 125

Thr Ser Ala Leu Leu Asn Val Asp Asn Leu Ile Gln Lys Lys Met Asn
130                 135                 140

Arg Pro Asn Ala Ile Gln Leu Val Ile Leu Thr Asp Gly Ile Pro
145                 150                 155                 160

Asn Asn Leu Lys Lys Ser Thr Thr Val Val Asn Gln Leu Lys Lys Lys
                165                 170                 175

Asp Val Asn Val Ala Ile Ile Gly Val Gly Ala Gly Val Asn Asn Met
            180                 185                 190

Phe Asn Arg Ile Leu Val Gly Cys Gly Lys Leu Gly Pro Cys Pro Tyr
        195                 200                 205

Tyr Ser Tyr Gly Ser Trp Asp Gln Ala Gln Thr Met Ile Lys Pro Phe
    210                 215                 220

Leu Ser Lys Val Cys Gln Glu Val Glu Lys Val Ala Leu Cys Gly Lys
225                 230                 235                 240

Trp Glu Glu Trp Ser Glu Cys Ser Thr Thr Cys Asp Asn Gly Thr Lys
                245                 250                 255

Ile Arg Lys Arg Lys Val Leu His Pro Asn Cys Ala Gly Glu Met Thr
            260                 265                 270

Ala Pro Cys Lys Val Arg Asp Cys Pro Pro Lys Pro Val Ala Pro Pro
        275                 280                 285
```

| | | | | | | | | | | |
|---|---|---|---|---|---|---|---|---|---|---|
|Val|Ile|Pro|Ile|Lys|Val|Pro|Asp|Val|Pro|Val|Lys|Pro|Val|Glu|Pro|
| | |290| | | |295| | | |300| | | | | |

Ile Glu Pro Ala Glu Pro Ala Glu Pro Ala Glu Pro Ala Glu Pro Ala
305             310             315                 320

Glu Pro Ala Glu Pro Ala Glu Pro Ala Glu Pro Ala Glu Pro Ala Glu
                325             330             335

Pro Ala Glu Pro Ala Glu Pro Ala Glu Pro Ala Glu Pro Ala Glu Pro
            340             345             350

Ala Glu Pro Ala Glu Pro Ala Glu Pro Ala Glu Pro Ala Lys Pro Ala
            355             360             365

Glu Pro Ala Glu Pro Ala Glu Pro Ala Glu Pro Ala Glu Pro Val Asn
            370             375             380

Pro Asp Asn Pro Ile Leu Pro Ile Lys Pro Glu Glu Pro Ser Gly Gly
385             390             395                 400

Ala Glu Pro Leu Asn Pro Glu Val Glu Asn Pro Phe Ile Ile Pro Asp
            405             410             415

Glu Pro Ile Glu Pro Ile Ile Ala Pro Gly Ala Val Pro Asp Lys Pro
            420             425             430

Ile Ile Pro Glu Glu Ser Asn Glu Leu Pro Asn Asn Leu Pro Glu Ser
            435             440             445

Pro Ser Asp Ser Gln Val Glu Tyr Pro Arg Pro Asn Asp Asn Gly Asp
450             455             460

Asn Ser Asn Asn Thr Ile Asn Ser Asn Lys Asn Ile Pro Asn Lys His
465             470             475                 480

Val Pro Pro Thr Asp Asp Asn Pro Tyr Lys Gly Gln Glu Glu Arg Ile
            485             490             495

Pro Lys Pro His Arg Ser Asn Asp Glu Tyr Ile Tyr Tyr Asn Asn Ala
            500             505             510

Asn Asn Asn Asp Lys Leu Glu Pro Glu Ile Pro Ser Lys Asp Tyr Glu
            515             520             525

Glu Asn Lys Ser Lys Lys Gln Ser Lys Ser Asn Asn Gly Tyr Lys Ile
            530             535             540

Ala Gly Gly Ile Ile Gly Gly Leu Ala Ile Ile Gly Cys Ile Gly Val
545             550             555                 560

Gly Tyr Asn Phe Ile Ala Gly Ser Ser Ala Ala Ala Met Ala Gly Glu
            565             570             575

Ala Ala Pro Phe Glu Asp Val Met Ala Asp Asp Glu Lys Gly Ile Val
            580             585             590

Glu Asn Glu Gln Phe Lys Leu Pro Glu Asp Asn Asp Trp Asn
            595             600             605

<210> SEQ ID NO 22
<211> LENGTH: 1734
<212> TYPE: DNA
<213> ORGANISM: Artificial Sequence
<220> FEATURE:
<223> OTHER INFORMATION: thrombospondin-related anonymous protein (TRAP)

<400> SEQUENCE: 22
gccaccatgg ctaatcactt gggcaacgtg aagtacctgg tgatagtgtt cctgatcttc     60
ttcgacctgt ttctggtcaa cggcagagat gtgcagaaca acatagtcga cgagattaag    120
tacagagagg aggtgtgcaa tgacgaggtg gatctctacc tgctgatgga ctgtagcggg    180
tcaatacgac ggcacaattg ggttaatcat gctgtcccct ggctatgaa gctgatccag    240

-continued

| | |
|---|---|
| cagctcaatc tgaacgataa tgccattcac ctgtatgctt ccgtgttcag caataatgca | 300 |
| agggagatca ttcgcctcca cagtgacgct agtaagaata aggagaaagc cctgatcatc | 360 |
| atcaaatccc tgcttagcac caaccttccc tatggcaaga ccaatctcac agacgcgctt | 420 |
| ctgcaggtaa ggaagcatct gaacgatcgc atcaacagag agaatgcgaa tcagctggta | 480 |
| gtaatcctga ctgatgggat tcccgattcc atccaggaca gcctgaagga atcaaggaag | 540 |
| ctcagcgata gaggggtgaa aatcgcagtt ttcggaatcg gtcaggggat taacgtggcc | 600 |
| tttaatcgct ttctggtggg atgtcatcca tctgatggga aatgcaatct gtatgccgat | 660 |
| tctgcgtggg agaatgtgaa gaacgtgatt ggccccttta tgaaagccgt gtgcgtagag | 720 |
| gtggagaaaa ccgcctcctg tggagtttgg gacgaatgga gcccctgttc cgttacttgc | 780 |
| gggaaaggga cccgaagtcg caagagagaa atccttcacg agggttgcac ttctgaactc | 840 |
| caagagcaat gcgaggagga aggtgtctc cctaaacgag aaccccttga tgtgcctgac | 900 |
| gaacctgagg acgatcaacc aagaccaagg ggagacaact tcgccgtcga gaaacccaat | 960 |
| gagaatatca ttgacaacaa tccacaggag ccatcaccta atccgaggag aggcaaaggc | 1020 |
| gaaaacccta acggttttga cttggacgag aatccggaaa atccacccaa cccgcctaac | 1080 |
| cctccaaatc caccaaaccc tccgaatcct cctaaccctg atatcccga gcaagagcct | 1140 |
| aatattccag aggatagcga aaaggaggtc ccctctgacg tccctaagaa ccctgaagat | 1200 |
| gatcgcgaag agaactttga catacccaag aaacccgaga taaacacga taatcagaac | 1260 |
| aatctcccga acgataaatc tgaccgctac attccataca gtccattgag cccaaaggtc | 1320 |
| ttggataatg aacggaaaca gtccgaccct caatcacagg acaataacgg taatcgtcat | 1380 |
| gttccgaact ccgaagatcg ggaaacaagg ccccatgggc gtaacaacga aaaccggagc | 1440 |
| tataaccgga agcacaacaa cacacccaag cacccggaac gggaagaaca tgagaagccc | 1500 |
| gataacaaca gaagaaggc aggctctgac aacaaataca aaatagccgg aggtattgcc | 1560 |
| ggaggattgg cactgctggc ctgcgctggc cttgcttaca agttcgtcgt tccaggcgcc | 1620 |
| gcaacgccct atgcaggcga accagctccc tttgacgaga cactgggaga gaggacaaa | 1680 |
| gacctggacg agcctgaaca gttcagactg cccgaggaaa acgagtggaa ttaa | 1734 |

<210> SEQ ID NO 23
<211> LENGTH: 575
<212> TYPE: PRT
<213> ORGANISM: Artificial Sequence
<220> FEATURE:
<223> OTHER INFORMATION: PfTRAP

<400> SEQUENCE: 23

Met Ala Asn His Leu Gly Asn Val Lys Tyr Leu Val Ile Val Phe Leu
1               5                   10                  15

Ile Phe Phe Asp Leu Phe Leu Val Asn Gly Arg Asp Val Gln Asn Asn
                20                  25                  30

Ile Val Asp Glu Ile Lys Tyr Arg Glu Val Cys Asn Asp Glu Val
        35                  40                  45

Asp Leu Tyr Leu Leu Met Asp Cys Ser Gly Ser Ile Arg Arg His Asn
    50                  55                  60

Trp Val Asn His Ala Val Pro Leu Ala Met Lys Leu Ile Gln Gln Leu
65                  70                  75                  80

Asn Leu Asn Asp Asn Ala Ile His Leu Tyr Ala Ser Val Phe Ser Asn
                85                  90                  95

Asn Ala Arg Glu Ile Ile Arg Leu His Ser Asp Ala Ser Lys Asn Lys

```
              100                 105                 110
Glu Lys Ala Leu Ile Ile Lys Ser Leu Leu Ser Thr Asn Leu Pro
            115                 120                 125

Tyr Gly Lys Thr Asn Leu Thr Asp Ala Leu Leu Gln Val Arg Lys His
            130                 135                 140

Leu Asn Asp Arg Ile Asn Arg Glu Asn Ala Asn Gln Leu Val Val Ile
145                 150                 155                 160

Leu Thr Asp Gly Ile Pro Asp Ser Ile Gln Asp Ser Leu Lys Glu Ser
                165                 170                 175

Arg Lys Leu Ser Asp Arg Gly Val Lys Ile Ala Val Phe Gly Ile Gly
            180                 185                 190

Gln Gly Ile Asn Val Ala Phe Asn Arg Phe Leu Val Gly Cys His Pro
            195                 200                 205

Ser Asp Gly Lys Cys Asn Leu Tyr Ala Asp Ser Ala Trp Glu Asn Val
        210                 215                 220

Lys Asn Val Ile Gly Pro Phe Met Lys Ala Val Cys Val Glu Val Glu
225                 230                 235                 240

Lys Thr Ala Ser Cys Gly Val Trp Asp Glu Trp Ser Pro Cys Ser Val
                245                 250                 255

Thr Cys Gly Lys Gly Thr Arg Ser Arg Lys Arg Glu Ile Leu His Glu
            260                 265                 270

Gly Cys Thr Ser Glu Leu Gln Glu Gln Cys Glu Glu Arg Cys Leu
            275                 280                 285

Pro Lys Arg Glu Pro Leu Asp Val Pro Asp Glu Pro Glu Asp Asp Gln
        290                 295                 300

Pro Arg Pro Arg Gly Asp Asn Phe Ala Val Glu Lys Pro Asn Glu Asn
305                 310                 315                 320

Ile Ile Asp Asn Asn Pro Gln Glu Pro Ser Pro Asn Pro Glu Glu Gly
                325                 330                 335

Lys Gly Glu Asn Pro Asn Gly Phe Asp Leu Asp Glu Asn Pro Glu Asn
            340                 345                 350

Pro Pro Asn Pro Pro Asn Pro Pro Asn Pro Pro Asn Pro Pro Asn Pro
        355                 360                 365

Pro Asn Pro Asp Ile Pro Glu Gln Glu Pro Asn Ile Pro Glu Asp Ser
370                 375                 380

Glu Lys Glu Val Pro Ser Asp Val Pro Lys Asn Pro Glu Asp Asp Arg
385                 390                 395                 400

Glu Glu Asn Phe Asp Ile Pro Lys Lys Pro Glu Asn Lys His Asp Asn
                405                 410                 415

Gln Asn Asn Leu Pro Asn Asp Lys Ser Asp Arg Tyr Ile Pro Tyr Ser
            420                 425                 430

Pro Leu Ser Pro Lys Val Leu Asp Asn Glu Arg Lys Gln Ser Asp Pro
        435                 440                 445

Gln Ser Gln Asp Asn Asn Gly Asn Arg His Val Pro Asn Ser Glu Asp
        450                 455                 460

Arg Glu Thr Arg Pro His Gly Arg Asn Asn Glu Asn Arg Ser Tyr Asn
465                 470                 475                 480

Arg Lys His Asn Asn Thr Pro Lys His Pro Glu Arg Glu Glu His Glu
                485                 490                 495

Lys Pro Asp Asn Asn Lys Lys Lys Ala Gly Ser Asp Asn Lys Tyr Lys
            500                 505                 510

Ile Ala Gly Gly Ile Ala Gly Gly Leu Ala Leu Leu Ala Cys Ala Gly
            515                 520                 525
```

-continued

```
Leu Ala Tyr Lys Phe Val Val Pro Gly Ala Ala Thr Pro Tyr Ala Gly
            530                 535                 540

Glu Pro Ala Pro Phe Asp Glu Thr Leu Gly Glu Asp Lys Asp Leu
545                 550                 555                 560

Asp Glu Pro Glu Gln Phe Arg Leu Pro Glu Glu Asn Glu Trp Asn
                565                 570                 575

<210> SEQ ID NO 24
<211> LENGTH: 560
<212> TYPE: PRT
<213> ORGANISM: Artificial Sequence
<220> FEATURE:
<223> OTHER INFORMATION: TRAP

<400> SEQUENCE: 24

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
                20                  25                  30

Val Asp Glu Ile Lys Tyr Arg Glu Glu Val Cys Asn Asp Glu Val Asp
            35                  40                  45

Leu Tyr Leu Leu Met Asp Cys Ser Gly Ser Ile Arg Arg His Asn Trp
50                  55                  60

Val Asn His Ala Val Pro Leu Ala Met Lys Leu Ile Gln Gln Leu Asn
65                  70                  75                  80

Leu Asn Glu Asn Ala Ile His Leu Tyr Ala Asn Val Phe Ser Asn Asn
                85                  90                  95

Ala Arg Glu Ile Ile Arg Leu His Ser Asp Ala Ser Lys Asn Lys Glu
            100                 105                 110

Lys Ala Leu Ser Ile Ile Lys Ser Leu Leu Ser Thr Asn Leu Pro Phe
        115                 120                 125

Gly Arg Thr Asn Leu Thr Asp Ala Leu Leu Gln Val Arg Lys His Leu
130                 135                 140

Asn Asp Arg Ile Asn Arg Glu Asn Ala Asn Gln Leu Val Val Ile Leu
145                 150                 155                 160

Thr Asp Gly Ile Pro Asn Ser Ile Gln Asp Ser Leu Lys Glu Ser Arg
                165                 170                 175

Lys Leu Ser Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270

Cys Thr Ser Glu Leu Gln Glu Gln Cys Glu Glu Arg Cys Pro Pro
        275                 280                 285

Lys Trp Glu Pro Leu Asp Val Pro Asp Pro Glu Asp Asp Gln Pro
    290                 295                 300

Arg Pro Arg Gly Asp Asn Ser Ser Val Gln Lys Pro Glu Glu Asn Ile
305                 310                 315                 320
```

```
Ile Asp Asn Asn Pro Gln Glu Pro Ser Pro Asn Pro Glu Glu Gly Lys
                325                 330                 335
Gly Glu Asn Pro Asn Gly Phe Asp Leu Asp Glu Asn Pro Glu Asn Pro
            340                 345                 350
Pro Asn Pro Asp Ile Pro Gln Gln Glu Pro Asn Ile Pro Glu Asp Ser
        355                 360                 365
Glu Lys Glu Val Pro Ser Asp Val Pro Lys Asn Pro Glu Asp Asp Arg
    370                 375                 380
Glu Glu Asn Phe Asp Ile Pro Lys Lys Pro Glu Asn Lys His Asp Asn
385                 390                 395                 400
Gln Asn Asn Leu Pro Asn Asp Lys Ser Asp Arg Tyr Ile Pro Tyr Ser
                405                 410                 415
Pro Leu Pro Pro Asn Val Leu Asp Asn Glu Arg Lys Gln Ser Asp Pro
            420                 425                 430
Gln Ser Gln Asp Asn Asn Gly Asn Arg His Val Pro Asn Ser Glu Asp
        435                 440                 445
Arg Glu Thr Arg Pro His Gly Arg Asn Asn Glu Asn Arg Ser Tyr Asn
    450                 455                 460
Arg Lys His Asn Asp Thr Pro Lys His Pro Glu Arg Glu Glu His Glu
465                 470                 475                 480
Lys Pro Asp Asn Asn Lys Lys Lys Gly Gly Ser Ser Asp Asn Lys Tyr
                485                 490                 495
Lys Ile Ala Gly Gly Ile Ala Gly Gly Leu Ala Leu Leu Ala Cys Ala
            500                 505                 510
Gly Leu Ala Tyr Lys Phe Val Val Pro Gly Ala Ala Thr Pro Tyr Ala
        515                 520                 525
Gly Glu Pro Ala Pro Phe Asp Glu Thr Leu Gly Glu Glu Asp Lys Asp
    530                 535                 540
Leu Asp Glu Pro Glu Gln Phe Arg Leu Pro Glu Glu Asn Glu Trp Asn
545                 550                 555                 560

<210> SEQ ID NO 25
<211> LENGTH: 1680
<212> TYPE: DNA
<213> ORGANISM: Artificial Sequence
<220> FEATURE:
<223> OTHER INFORMATION: PvTRAPhumanCO

<400> SEQUENCE: 25
gccaccatgg ctaagctgct gcagaacaag tcttatctcc tggtcgtgtt cctgctttac    60
gtatccatat ttgcacgggg agatgaaaaa gttgtagatg aggtaaagta cagcgaggag   120
gtatgcaacg aatctgtcga tctctatctt ctcgtagatg gctctggtag tattgggtat   180
ccgaactgga taactaaggt aattcctatg ctgaacggtc ttattaatag tttgagcctc   240
agtcgagaca cgatcaatct ctatatgaat ctcttcggaa attacactac agaactcata   300
cggctgggct ctgggcagag tatagataaa cgacaggctc tgtcaaaggt gactgaactt   360
agaaagacct acacgccata tggcactact aacatgacag ccgcgcttga tgaagtccaa   420
aagcacctta tgatagagt gaaccgagag aaagcgatac aacttgtcat attgatgacc   480
gacggggtgc ccaactcaaa atacagggcg ctggaggtcg caaataaact gaagcaacgc   540
aatgtttcct ggccgttat tggtgtcgga caaggaatca accatcagtt caatcggctg   600
atcgcgggct gccgacctcg ggagccgaac tgcaaatttt actcttatgc tgattggaat   660
gaggccgtag cacttataaa gcccttatt gctaaggtat gcacagaagt tgagcgcgtt   720
```

```
gccaactgtg gaccctggga cccctggacc gcgtgtagcg ttacgtgcgg caggggaacg    780
cactccaggt ctcgcccttc attgcatgaa aagtgcacta cccatatggt gtctgaatgt    840
gaagaggggg aatgcccagt ggagcctgag ccactgccag tacctgcgcc actcccaacg    900
gttccagaag atgtaaatcc gcgagacacg gacgacgaaa atgagaaccc gaacttcaac    960
aagggactgg acgtgccgga tgaagatgat gacgaagtac cgcccgcgaa tgaaggtgcg   1020
gatggcaacc cagtcgagga aaatgttttc ccgcctgctg acgatagcgt tcctgatgag   1080
agtaacgtgc tgcctctccc tccggcagtc ccaggcgggt cctctgagga gttcccggcg   1140
gacgttcaga acaatcccga ctctcctgaa gagctgccga tggagcaaga agtgcctcaa   1200
gataataacg tgaatgaacc agagagatcc gatagcaacg ttatggcgt aaatgagaag    1260 gtgataccta atcccctcga caatgagcga gacatggcca ataagaataa gaccgttcac    1320
ccaggccgga aggacagcgc gagagatcga tatgcccgcc ccatggttc cactcatgtc     1380 aataataata gagccaatga gaactcagac ataccaaaca acccagtacc ttctgattac    1440
gaacagccgg aggacaaggc taaaaagtcc tccaataacg gctataaaat cgctggtgga    1500
gtgatcgctg ggctcgcgtt ggttgggtgc gtcggtttcg cgtataactt cgtagcgggt    1560
ggaggcgctg ctggtatggc aggcgaaccg gctcccttg acgaagctat ggccgaagac    1620
gaaaaagacg tagccgaagc ggaccagttc aaattgcctg aggacaacga ttggaattaa   1680

<210> SEQ ID NO 26
<211> LENGTH: 557
<212> TYPE: PRT
<213> ORGANISM: Plasmodium vivax
<220> FEATURE:
<221> NAME/KEY: misc_feature
<223> OTHER INFORMATION: PvTRAP

<400> SEQUENCE: 26

Met Ala Lys Leu Leu Gln Asn Lys Ser Tyr Leu Leu Val Val Phe Leu
1               5                   10                  15

Leu Tyr Val Ser Ile Phe Ala Arg Gly Asp Glu Lys Val Val Asp Glu
            20                  25                  30

Val Lys Tyr Ser Glu Glu Val Cys Asn Glu Ser Val Asp Leu Tyr Leu
        35                  40                  45

Leu Val Asp Gly Ser Gly Ser Ile Gly Tyr Pro Asn Trp Ile Thr Lys
    50                  55                  60

Val Ile Pro Met Leu Asn Gly Leu Ile Asn Ser Leu Ser Leu Ser Arg
65                  70                  75                  80

Asp Thr Ile Asn Leu Tyr Met Asn Leu Phe Gly Asn Tyr Thr Thr Glu
                85                  90                  95

Leu Ile Arg Leu Gly Ser Gly Gln Ser Ile Asp Lys Arg Gln Ala Leu
            100                 105                 110

Ser Lys Val Thr Glu Leu Arg Lys Thr Tyr Thr Pro Tyr Gly Thr Thr
        115                 120                 125

Asn Met Thr Ala Ala Leu Asp Glu Val Gln Lys His Leu Asn Asp Arg
    130                 135                 140

Val Asn Arg Glu Lys Ala Ile Gln Leu Val Ile Leu Met Thr Asp Gly
145                 150                 155                 160

Val Pro Asn Ser Lys Tyr Arg Ala Leu Glu Val Ala Asn Lys Leu Lys
                165                 170                 175

Gln Arg Asn Val Ser Leu Ala Val Ile Gly Val Gly Gln Gly Ile Asn
            180                 185                 190
```

```
His Gln Phe Asn Arg Leu Ile Ala Gly Cys Arg Pro Arg Glu Pro Asn
            195                 200                 205

Cys Lys Phe Tyr Ser Tyr Ala Asp Trp Asn Glu Ala Val Ala Leu Ile
    210                 215                 220

Lys Pro Phe Ile Ala Lys Val Cys Thr Glu Val Glu Arg Val Ala Asn
225                 230                 235                 240

Cys Gly Pro Trp Asp Pro Trp Thr Ala Cys Ser Val Thr Cys Gly Arg
                245                 250                 255

Gly Thr His Ser Arg Ser Arg Pro Ser Leu His Glu Lys Cys Thr Thr
                260                 265                 270

His Met Val Ser Glu Cys Glu Gly Glu Cys Pro Val Glu Pro Glu
            275                 280                 285

Pro Leu Pro Val Pro Ala Pro Leu Pro Thr Val Pro Glu Asp Val Asn
        290                 295                 300

Pro Arg Asp Thr Asp Glu Asn Glu Asn Pro Asn Phe Asn Lys Gly
305                 310                 315                 320

Leu Asp Val Pro Asp Glu Asp Asp Glu Val Pro Pro Ala Asn Glu
                325                 330                 335

Gly Ala Asp Gly Asn Pro Val Glu Glu Asn Val Phe Pro Pro Ala Asp
                340                 345                 350

Asp Ser Val Pro Asp Glu Ser Asn Val Leu Pro Leu Pro Pro Ala Val
                355                 360                 365

Pro Gly Gly Ser Ser Glu Glu Phe Pro Ala Asp Val Gln Asn Asn Pro
        370                 375                 380

Asp Ser Pro Glu Glu Leu Pro Met Glu Gln Glu Val Pro Gln Asp Asn
385                 390                 395                 400

Asn Val Asn Glu Pro Glu Arg Ser Asp Ser Asn Gly Tyr Gly Val Asn
                405                 410                 415

Glu Lys Val Ile Pro Asn Pro Leu Asp Asn Glu Arg Asp Met Ala Asn
                420                 425                 430

Lys Asn Lys Thr Val His Pro Gly Arg Lys Asp Ser Ala Arg Asp Arg
            435                 440                 445

Tyr Ala Arg Pro His Gly Ser Thr His Val Asn Asn Arg Ala Asn
    450                 455                 460

Glu Asn Ser Asp Ile Pro Asn Asn Pro Val Pro Ser Asp Tyr Glu Gln
465                 470                 475                 480

Pro Glu Asp Lys Ala Lys Lys Ser Ser Asn Asn Gly Tyr Lys Ile Ala
                485                 490                 495

Gly Gly Val Ile Ala Gly Leu Ala Leu Val Gly Cys Val Gly Phe Ala
                500                 505                 510

Tyr Asn Phe Val Ala Gly Gly Ala Ala Gly Met Ala Gly Glu Pro
            515                 520                 525

Ala Pro Phe Asp Glu Ala Met Ala Glu Asp Glu Lys Asp Val Ala Glu
            530                 535                 540

Ala Asp Gln Phe Lys Leu Pro Glu Asp Asn Asp Trp Asn
545                 550                 555
```

<210> SEQ ID NO 27
<211> LENGTH: 556
<212> TYPE: PRT
<213> ORGANISM: Plasmodium vivax
<220> FEATURE:
<221> NAME/KEY: misc_feature
<223> OTHER INFORMATION: TRAP -continued

```
<400> SEQUENCE: 27

Met Lys Leu Leu Gln Asn Lys Ser Tyr Leu Val Val Phe Leu Leu
1               5                   10                  15

Tyr Val Ser Ile Phe Ala Arg Gly Asp Glu Lys Val Val Asp Glu Val
            20                  25                  30

Lys Tyr Ser Glu Glu Val Cys Asn Glu Ser Val Asp Leu Tyr Leu Leu
        35                  40                  45

Val Asp Gly Ser Gly Ser Ile Gly Tyr Pro Asn Trp Ile Thr Lys Val
    50                  55                  60

Ile Pro Met Leu Asn Gly Leu Ile Asn Ser Leu Ser Leu Ser Arg Asp
65              70                  75                  80

Thr Ile Asn Leu Tyr Met Asn Leu Phe Gly Asn Tyr Thr Thr Glu Leu
                85                  90                  95

Ile Arg Leu Gly Ser Gly Gln Ser Ile Asp Lys Arg Gln Ala Leu Ser
            100                 105                 110

Lys Val Thr Glu Leu Arg Lys Ser Tyr Ser Pro Tyr Gly Thr Thr Asn
        115                 120                 125

Met Thr Ala Ala Leu Asp Glu Val Gln Lys His Leu Asn Asp Arg Val
    130                 135                 140

Asn Arg Glu Lys Ala Ile Gln Leu Val Ile Leu Met Thr Asp Gly Ile
145                 150                 155                 160

Pro Asn Ser Lys Tyr Thr Ala Leu Glu Val Ala Lys Lys Leu Lys Gln
                165                 170                 175

Arg Asn Val Ser Leu Ala Val Ile Gly Ile Gly Gln Gly Ile Asn His
            180                 185                 190

Gln Phe Asn Arg Leu Ile Ala Gly Cys Arg Pro Arg Glu Ser Asn Cys
        195                 200                 205

Lys Phe Tyr Ser Tyr Ala Asp Trp Asn Glu Ala Val Ala Leu Ile Lys
    210                 215                 220

Pro Phe Ile Ala Lys Val Cys Thr Glu Val Glu Arg Val Ala Asn Cys
225                 230                 235                 240

Gly Pro Trp Asp Pro Trp Thr Ala Cys Ser Val Thr Cys Gly Arg Gly
                245                 250                 255

Thr His Ser Arg Ser Arg Pro Ser Leu His Glu Gly Cys Thr Thr His
            260                 265                 270

Met Val Ser Glu Cys Glu Gly Glu Cys Pro Val Glu Pro Glu Pro
    275                 280                 285

Leu Pro Val Pro Ala Pro Leu Pro Thr Val Pro Glu Asp Val Asn Pro
    290                 295                 300

Arg Asp Thr Asp Asp Glu Asn Glu Asn Pro Asn Phe Asn Lys Gly Leu
305                 310                 315                 320

Asp Val Pro Glu Glu Asp Asp Glu Val Pro Ala Asn Glu Arg
                325                 330                 335

Ala Asp Gly Asn Pro Val Glu Glu Asn Val Phe Pro Ala Asp Asp
            340                 345                 350

Ser Val Pro Asp Glu Ser Asn Val Leu Pro Leu Pro Ala Val Pro
        355                 360                 365

Gly Gly Ser Ser Glu Glu Phe Pro Ala Asp Val Gln Asn Asn Pro Asp
    370                 375                 380

Ser Pro Glu Glu Leu Pro Met Glu Gln Glu Val Pro Gln Asp Asn Asn
385                 390                 395                 400

Val Asn Glu Pro Glu Arg Ser Asp Ser Asn Gly Tyr Gly Val Asn Glu
                405                 410                 415
```

Lys Val Ile Pro Asn Pro Leu Asp Asn Glu Arg Asp Met Ala Asn Lys
            420                 425                 430

Asn Lys Thr Val His Pro Asp Arg Lys Asp Ser Ala Arg Asp Arg Tyr
        435                 440                 445

Ala Arg Pro His Gly Ser Thr His Val Asn Asn Asn Arg Ala Asn Glu
450                 455                 460

Asn Ser Asp Ile Pro Asn Asn Pro Val Pro Ser Asp Tyr Glu Gln Pro
465                 470                 475                 480

Glu Asp Lys Ala Lys Lys Ser Ser Asn Asn Gly Tyr Lys Ile Ala Gly
                485                 490                 495

Gly Val Ile Ala Gly Leu Ala Leu Val Gly Cys Val Gly Phe Ala Tyr
            500                 505                 510

Asn Phe Val Ala Gly Gly Gly Ala Ala Gly Met Ala Gly Glu Pro Ala
            515                 520                 525

Pro Phe Asp Glu Ala Met Ala Glu Asp Glu Lys Asp Val Ala Glu Ala
            530                 535                 540

Asp Gln Phe Lys Leu Pro Glu Asp Asn Asp Trp Asn
545                 550                 555

<210> SEQ ID NO 28
<211> LENGTH: 1086
<212> TYPE: DNA
<213> ORGANISM: Artificial Sequence
<220> FEATURE:
<223> OTHER INFORMATION: inhibitor of cysteine proteases (ICP)

<400> SEQUENCE: 28
ggatccgcca ccatggctaa atccattacc ttctttgtgt tcaacatttg cagcattttg      60
gctctgctga gtcactgtga ggacaatgac atctacagct tcgacattgt caatgagaca     120
aattggctga agatcgccaa gaacatcttc aaaggcaagt ctcctagcaa tttcacgatc     180
ataccgttta caataccgg tagttctaac gataacgagt caaacaagga ggaatcagta     240
ctgctgatca gaaagaagat caaaagcaac aagaatcacg atagttccat cattagtggt     300
gacactgtta acggggacat tagtgacctg aattatacgg ctagcaactt ttccgataac     360
tctgaggaca tagaagataa ccagaaatat cccacaacca gctacaatag tttcaaccat     420
ctcaattcca atatcgcctt taacgaagag tccgaataca ttgagattaa tagcgagtct     480
gacttggaga acaagatcaa ggacatcaac atcaaatcca atcttgagga aaacaatacc     540
atgaacgaat ccggcaaagt ggatagcaag tatgagctca ctggggacga gaaatgtggt     600
aaaagcctga agctcggcaa catcagcaat cagacaaacc aggaaaccat aacccaaagc     660
ctgtcagttg gagagattct gtgcattgac ctcgaaggga atgcaggaac aggctatctg     720
tgggtgttgc tgggcataca caaggatgag ccaatcataa ccccgagaa cttcccaacc      780
aaactgacaa agaagtcttt cttttccgag gaaataagtg tgactcagcc aaagaagtac      840
aagatcgatg agcatgattc ttcaaagaat gtgaatcgcg aaatcgaaag ccctgaacag     900
aaggagtccg actcaaagcc caagaaacct cagatgcaac ttcttggagg accagatcgg     960
atgaggtcag tcatcaaagg acacaaacct ggcaaatatt acattgtgta ctcttactat    1020
cgaccgtttt ctcccacttc tggggcgaac actaaaatca tttacgtcac agtacagtga    1080
ctcgag                                                             1086

<210> SEQ ID NO 29
<211> LENGTH: 355

```
<212> TYPE: PRT
<213> ORGANISM: Plasmodium berghei
<220> FEATURE:
<221> NAME/KEY: misc_feature
<223> OTHER INFORMATION: ICP

<400> SEQUENCE: 29
```

Met Ala Lys Ser Ile Thr Phe Phe Val Phe Asn Ile Cys Ser Ile Leu
1               5                   10                  15

Ala Leu Leu Ser His Cys Glu Asp Asn Asp Ile Tyr Ser Phe Asp Ile
            20                  25                  30

Val Asn Glu Thr Asn Trp Leu Lys Ile Ala Lys Asn Ile Phe Lys Gly
        35                  40                  45

Lys Ser Pro Ser Asn Phe Thr Ile Ile Pro Phe Asn Asn Thr Gly Ser
    50                  55                  60

Ser Asn Asp Asn Glu Ser Asn Lys Glu Glu Ser Val Leu Leu Ile Arg
65                  70                  75                  80

Lys Lys Ile Lys Ser Asn Lys Asn His Asp Ser Ser Ile Ile Ser Gly
                85                  90                  95

Asp Thr Val Asn Gly Asp Ile Ser Asp Leu Asn Tyr Thr Ala Ser Asn
            100                 105                 110

Phe Ser Asp Asn Ser Glu Asp Ile Glu Asp Asn Gln Lys Tyr Pro Thr
        115                 120                 125

Thr Ser Tyr Asn Ser Phe Asn His Leu Asn Ser Asn Ile Ala Phe Asn
    130                 135                 140

Glu Glu Ser Glu Tyr Ile Glu Ile Asn Ser Glu Ser Asp Leu Glu Asn
145                 150                 155                 160

Lys Ile Lys Asp Ile Asn Ile Lys Ser Asn Leu Glu Glu Asn Asn Thr
                165                 170                 175

Met Asn Glu Ser Gly Lys Val Asp Ser Lys Tyr Glu Leu Thr Gly Asp
            180                 185                 190

Glu Lys Cys Gly Lys Ser Leu Lys Leu Gly Asn Ile Ser Asn Gln Thr
        195                 200                 205

Asn Gln Glu Thr Ile Thr Gln Ser Leu Ser Val Gly Glu Ile Leu Cys
    210                 215                 220

Ile Asp Leu Glu Gly Asn Ala Gly Thr Gly Tyr Leu Trp Val Leu Leu
225                 230                 235                 240

Gly Ile His Lys Asp Glu Pro Ile Ile Asn Pro Glu Asn Phe Pro Thr
                245                 250                 255

Lys Leu Thr Lys Lys Ser Phe Phe Ser Glu Glu Ile Ser Val Thr Gln
            260                 265                 270

Pro Lys Lys Tyr Lys Ile Asp Glu His Asp Ser Ser Lys Asn Val Asn
        275                 280                 285

Arg Glu Ile Glu Ser Pro Glu Gln Lys Glu Ser Asp Ser Lys Pro Lys
    290                 295                 300

Lys Pro Gln Met Gln Leu Leu Gly Gly Pro Asp Arg Met Arg Ser Val
305                 310                 315                 320

Ile Lys Gly His Lys Pro Gly Lys Tyr Tyr Ile Val Tyr Ser Tyr Tyr
                325                 330                 335

Arg Pro Phe Ser Pro Thr Ser Gly Ala Asn Thr Lys Ile Ile Tyr Val
            340                 345                 350

Thr Val Gln
        355

```
<210> SEQ ID NO 30
```

```
<211> LENGTH: 354
<212> TYPE: PRT
<213> ORGANISM: Plasmodium berghei
<220> FEATURE:
<221> NAME/KEY: misc_feature
<223> OTHER INFORMATION: ICP

<400> SEQUENCE: 30
```

| Met | Lys | Ser | Ile | Thr | Phe | Phe | Val | Phe | Asn | Ile | Cys | Ser | Ile | Leu | Ala |
|---|---|---|---|---|---|---|---|---|---|---|---|---|---|---|---|
| 1 | | | | 5 | | | | | 10 | | | | | 15 | |

| Leu | Leu | Ser | His | Cys | Glu | Asp | Asn | Asp | Ile | Tyr | Ser | Phe | Asp | Ile | Val |
|---|---|---|---|---|---|---|---|---|---|---|---|---|---|---|---|
| | | | 20 | | | | | 25 | | | | | 30 | | |

| Asn | Glu | Thr | Asn | Trp | Leu | Lys | Ile | Ala | Lys | Asn | Ile | Phe | Lys | Gly | Lys |
|---|---|---|---|---|---|---|---|---|---|---|---|---|---|---|---|
| | | 35 | | | | | 40 | | | | | 45 | | | |

| Ser | Pro | Ser | Asn | Phe | Thr | Ile | Ile | Pro | Phe | Asn | Asn | Thr | Gly | Ser | Ser |
|---|---|---|---|---|---|---|---|---|---|---|---|---|---|---|---|
| 50 | | | | | 55 | | | | | 60 | | | | | |

| Asn | Asp | Asn | Glu | Ser | Asn | Lys | Glu | Glu | Ser | Val | Leu | Leu | Ile | Arg | Lys |
|---|---|---|---|---|---|---|---|---|---|---|---|---|---|---|---|
| 65 | | | | | 70 | | | | | 75 | | | | | 80 |

| Lys | Ile | Lys | Ser | Asn | Lys | Asn | His | Asp | Ser | Ser | Ile | Ile | Ser | Gly | Asp |
|---|---|---|---|---|---|---|---|---|---|---|---|---|---|---|---|
| | | | | 85 | | | | | 90 | | | | | 95 | |

| Thr | Val | Asn | Gly | Asp | Ile | Ser | Asp | Leu | Asn | Tyr | Thr | Ala | Ser | Asn | Phe |
|---|---|---|---|---|---|---|---|---|---|---|---|---|---|---|---|
| | | | 100 | | | | | 105 | | | | | 110 | | |

| Ser | Asp | Asn | Ser | Glu | Asp | Ile | Glu | Asp | Asn | Gln | Lys | Tyr | Pro | Thr | Thr |
|---|---|---|---|---|---|---|---|---|---|---|---|---|---|---|---|
| | | 115 | | | | | 120 | | | | | 125 | | | |

| Ser | Tyr | Asn | Ser | Phe | Asn | His | Leu | Asn | Ser | Asn | Ile | Ala | Phe | Asn | Glu |
|---|---|---|---|---|---|---|---|---|---|---|---|---|---|---|---|
| | 130 | | | | | 135 | | | | | 140 | | | | |

| Glu | Ser | Glu | Tyr | Ile | Glu | Ile | Asn | Ser | Glu | Ser | Asp | Leu | Glu | Asn | Lys |
|---|---|---|---|---|---|---|---|---|---|---|---|---|---|---|---|
| 145 | | | | | 150 | | | | | 155 | | | | | 160 |

| Ile | Lys | Asp | Ile | Asn | Ile | Lys | Ser | Asn | Leu | Glu | Glu | Asn | Asn | Thr | Met |
|---|---|---|---|---|---|---|---|---|---|---|---|---|---|---|---|
| | | | | 165 | | | | | 170 | | | | | 175 | |

| Asn | Glu | Ser | Gly | Lys | Val | Asp | Ser | Lys | Tyr | Glu | Leu | Thr | Gly | Asp | Glu |
|---|---|---|---|---|---|---|---|---|---|---|---|---|---|---|---|
| | | | 180 | | | | | 185 | | | | | 190 | | |

| Lys | Cys | Gly | Lys | Ser | Leu | Lys | Leu | Gly | Asn | Ile | Ser | Asn | Gln | Thr | Asn |
|---|---|---|---|---|---|---|---|---|---|---|---|---|---|---|---|
| | | 195 | | | | | 200 | | | | | 205 | | | |

| Gln | Glu | Thr | Ile | Thr | Gln | Ser | Leu | Ser | Val | Gly | Glu | Ile | Leu | Cys | Ile |
|---|---|---|---|---|---|---|---|---|---|---|---|---|---|---|---|
| | 210 | | | | | 215 | | | | | 220 | | | | |

| Asp | Leu | Glu | Gly | Asn | Ala | Gly | Thr | Gly | Tyr | Leu | Trp | Val | Leu | Leu | Gly |
|---|---|---|---|---|---|---|---|---|---|---|---|---|---|---|---|
| 225 | | | | | 230 | | | | | 235 | | | | | 240 |

| Ile | His | Lys | Asp | Glu | Pro | Ile | Ile | Asn | Pro | Glu | Asn | Phe | Pro | Thr | Lys |
|---|---|---|---|---|---|---|---|---|---|---|---|---|---|---|---|
| | | | | 245 | | | | | 250 | | | | | 255 | |

| Leu | Thr | Lys | Lys | Ser | Phe | Phe | Ser | Glu | Glu | Ile | Ser | Val | Thr | Gln | Pro |
|---|---|---|---|---|---|---|---|---|---|---|---|---|---|---|---|
| | | | 260 | | | | | 265 | | | | | 270 | | |

| Lys | Lys | Tyr | Lys | Ile | Asp | Glu | His | Asp | Ser | Ser | Lys | Asn | Val | Asn | Arg |
|---|---|---|---|---|---|---|---|---|---|---|---|---|---|---|---|
| | | 275 | | | | | 280 | | | | | 285 | | | |

| Glu | Ile | Glu | Ser | Pro | Glu | Gln | Lys | Glu | Ser | Asp | Ser | Lys | Pro | Lys | Lys |
|---|---|---|---|---|---|---|---|---|---|---|---|---|---|---|---|
| | 290 | | | | | 295 | | | | | 300 | | | | |

| Pro | Gln | Met | Gln | Leu | Leu | Gly | Gly | Pro | Asp | Arg | Met | Arg | Ser | Val | Ile |
|---|---|---|---|---|---|---|---|---|---|---|---|---|---|---|---|
| 305 | | | | | 310 | | | | | 315 | | | | | 320 |

| Lys | Gly | His | Lys | Pro | Gly | Lys | Tyr | Tyr | Ile | Val | Tyr | Ser | Tyr | Arg |
|---|---|---|---|---|---|---|---|---|---|---|---|---|---|---|
| | | | | 325 | | | | | 330 | | | | | 335 |

| Pro | Phe | Ser | Pro | Thr | Ser | Gly | Ala | Asn | Thr | Lys | Ile | Ile | Tyr | Val | Thr |
|---|---|---|---|---|---|---|---|---|---|---|---|---|---|---|---|
| | | | 340 | | | | | 345 | | | | | 350 | | |

| Val | Gln |
|---|---|

```
<210> SEQ ID NO 31
```

<211> LENGTH: 1251
<212> TYPE: DNA
<213> ORGANISM: Artificial Sequence
<220> FEATURE:
<223> OTHER INFORMATION: PfICPhumanCO

<400> SEQUENCE: 31

```
gccaccatgg ctaatctgtt ggtgttcttt tgcttctttc tgttgtcttg catcgtacac        60
ctctctcgtt gttctgacaa caattcatat agctttgaga tcgtgaatcg gagcacatgg       120
ctcaacattg ctgaacggat attcaaaggc aatgcaccat caactttac tattataccg        180
tacaactatg tgaacaatag tactgaagag aataataaca aagactctgt ccttctgata       240
agcaagaatc tgaagaattc ctcaaaccca gtggacgaaa ataaccacat cattgactca       300
accaagaaga acacgtccaa taacaacaat aataacagca atatcgtcgg aatatacgaa       360
agtcaggtac atgaggagaa gattaaagag gacaatacaa gacaggataa tatcaacaag       420
aaggaaaacg agataatcaa caataaccat cagatccctg tgtccaacat cttttcagag       480
aacattgaca acaacaagaa ctacattgag gcaactaca agagcaccta taacaataat        540
cccgagttga ttcatagcac agatttcatt ggcagtaata acaaccacac tttcaatttc       600
ctgtctcgct ataacaactc agtgctgaac aacatgcaag ggaataccaa agttccaggg       660
aatgttcccg aactgaaagc ccgcattttc tccgaggaag aaaacaccga agtcgaaagc       720
gccgaaaaca atcacactaa cagtctgaat cctaacgagt cttgtgatca aatcatcaaa       780
ctgggcgata tcattaacag cgtcaatgag aagatcatca gcatcaatag tacggtgaat       840
aacgtgctct gcataaatct ggattccgtc aatggcaatg cttcgtttg gacccttctt        900
ggggtacaca agaagaaacc cctgattgac ccctccaatt ttcccactaa agggtgact        960
cagtcctacg tttcacctga catttccgtt acaaaccctg tgccaattcc aaagaacagc      1020
aacaccaaca agatgacag catcaataat aaacaggatg gttcccagaa taacacaaca       1080
acgaatcact ttccgaagcc tagagagcaa ctcgtgggtg gatcttctat gctgatcagt      1140
aagatcaaac cccataaacc cggaaagtat ttcatcgtgt atagctacta cagaccattt      1200
gaccctacaa gggataccaa cacccgaatt gtggagctga atgtccagta a              1251
```

<210> SEQ ID NO 32
<211> LENGTH: 414
<212> TYPE: PRT
<213> ORGANISM: Plasmodium falciparum
<220> FEATURE:
<221> NAME/KEY: misc_feature
<223> OTHER INFORMATION: PfICP

<400> SEQUENCE: 32

```
Met Ala Asn Leu Leu Val Phe Phe Cys Phe Phe Leu Leu Ser Cys Ile
1               5                   10                  15

Val His Leu Ser Arg Cys Ser Asp Asn Asn Ser Tyr Ser Phe Glu Ile
            20                  25                  30

Val Asn Arg Ser Thr Trp Leu Asn Ile Ala Glu Arg Ile Phe Lys Gly
        35                  40                  45

Asn Ala Pro Phe Asn Phe Thr Ile Ile Pro Tyr Asn Tyr Val Asn Asn
    50                  55                  60

Ser Thr Glu Glu Asn Asn Asn Lys Asp Ser Val Leu Leu Ile Ser Lys
65                  70                  75                  80

Asn Leu Lys Asn Ser Ser Asn Pro Val Asp Glu Asn Asn His Ile Ile
                85                  90                  95
```

```
Asp Ser Thr Lys Lys Asn Thr Ser Asn Asn Asn Asn Asn Ser Asn
            100                 105                 110

Ile Val Gly Ile Tyr Glu Ser Gln Val His Glu Lys Ile Lys Glu
            115                 120                 125

Asp Asn Thr Arg Gln Asp Asn Ile Asn Lys Lys Glu Asn Glu Ile Ile
            130                 135                 140

Asn Asn Asn His Gln Ile Pro Val Ser Asn Ile Phe Ser Glu Asn Ile
145                 150                 155                 160

Asp Asn Asn Lys Asn Tyr Ile Glu Ser Asn Tyr Lys Ser Thr Tyr Asn
            165                 170                 175

Asn Asn Pro Glu Leu Ile His Ser Thr Asp Phe Ile Gly Ser Asn Asn
            180                 185                 190

Asn His Thr Phe Asn Phe Leu Ser Arg Tyr Asn Asn Ser Val Leu Asn
            195                 200                 205

Asn Met Gln Gly Asn Thr Lys Val Pro Gly Asn Val Pro Glu Leu Lys
            210                 215                 220

Ala Arg Ile Phe Ser Glu Glu Asn Thr Glu Val Glu Ser Ala Glu
225                 230                 235                 240

Asn Asn His Thr Asn Ser Leu Asn Pro Asn Glu Ser Cys Asp Gln Ile
            245                 250                 255

Ile Lys Leu Gly Asp Ile Ile Asn Ser Val Asn Glu Lys Ile Ile Ser
            260                 265                 270

Ile Asn Ser Thr Val Asn Asn Val Leu Cys Ile Asn Leu Asp Ser Val
            275                 280                 285

Asn Gly Asn Gly Phe Val Trp Thr Leu Leu Gly Val His Lys Lys Lys
            290                 295                 300

Pro Leu Ile Asp Pro Ser Asn Phe Pro Thr Lys Arg Val Thr Gln Ser
305                 310                 315                 320

Tyr Val Ser Pro Asp Ile Ser Val Thr Asn Pro Val Pro Ile Pro Lys
            325                 330                 335

Asn Ser Asn Thr Asn Lys Asp Asp Ser Ile Asn Asn Lys Gln Asp Gly
            340                 345                 350

Ser Gln Asn Asn Thr Thr Thr Asn His Phe Pro Lys Pro Arg Glu Gln
            355                 360                 365

Leu Val Gly Gly Ser Ser Met Leu Ile Ser Lys Ile Lys Pro His Lys
            370                 375                 380

Pro Gly Lys Tyr Phe Ile Val Tyr Ser Tyr Tyr Arg Pro Phe Asp Pro
385                 390                 395                 400

Thr Arg Asp Thr Asn Thr Arg Ile Val Glu Leu Asn Val Gln
            405                 410

<210> SEQ ID NO 33
<211> LENGTH: 413
<212> TYPE: PRT
<213> ORGANISM: Plasmodium falciparum
<220> FEATURE:
<221> NAME/KEY: misc_feature
<223> OTHER INFORMATION: ICP

<400> SEQUENCE: 33

Met Asn Leu Leu Val Phe Phe Cys Phe Phe Leu Leu Ser Cys Ile Val
1               5                   10                  15

His Leu Ser Arg Cys Ser Asp Asn Asn Ser Tyr Ser Phe Glu Ile Val
            20                  25                  30

Asn Arg Ser Thr Trp Leu Asn Ile Ala Glu Arg Ile Phe Lys Gly Asn
            35                  40                  45
```

Ala Pro Phe Asn Phe Thr Ile Ile Pro Tyr Asn Tyr Val Asn Asn Ser
 50                  55                  60

Thr Glu Glu Asn Asn Asn Lys Asp Ser Val Leu Leu Ile Ser Lys Asn
 65                  70                  75                  80

Leu Lys Asn Ser Ser Asn Pro Val Asp Glu Asn Asn His Ile Ile Asp
                 85                  90                  95

Ser Thr Lys Lys Asn Thr Ser Asn Asn Asn Asn Asn Ser Asn Ile
             100                 105                 110

Val Gly Ile Tyr Glu Ser Gln Val His Glu Glu Lys Ile Lys Glu Asp
             115                 120                 125

Asn Thr Arg Gln Asp Asn Ile Asn Lys Lys Glu Asn Glu Ile Ile Asn
             130                 135                 140

Asn Asn His Gln Ile Pro Val Ser Asn Ile Phe Ser Glu Asn Ile Asp
145                 150                 155                 160

Asn Asn Lys Asn Tyr Ile Glu Ser Asn Tyr Lys Ser Thr Tyr Asn Asn
                 165                 170                 175

Asn Pro Glu Leu Ile His Ser Thr Asp Phe Ile Gly Ser Asn Asn Asn
             180                 185                 190

His Thr Phe Asn Phe Leu Ser Arg Tyr Asn Asn Ser Val Leu Asn Asn
             195                 200                 205

Met Gln Gly Asn Thr Lys Val Pro Gly Asn Val Pro Glu Leu Lys Ala
             210                 215                 220

Arg Ile Phe Ser Glu Glu Glu Asn Thr Glu Val Glu Ser Ala Glu Asn
225                 230                 235                 240

Asn His Thr Asn Ser Leu Asn Pro Asn Glu Ser Cys Asp Gln Ile Ile
                 245                 250                 255

Lys Leu Gly Asp Ile Ile Asn Ser Val Asn Glu Lys Ile Ile Ser Ile
             260                 265                 270

Asn Ser Thr Val Asn Asn Val Leu Cys Ile Asn Leu Asp Ser Val Asn
             275                 280                 285

Gly Asn Gly Phe Val Trp Thr Leu Leu Gly Val His Lys Lys Lys Pro
             290                 295                 300

Leu Ile Asp Pro Ser Asn Phe Pro Thr Lys Arg Val Thr Gln Ser Tyr
305                 310                 315                 320

Val Ser Pro Asp Ile Ser Val Thr Asn Pro Val Pro Ile Pro Lys Asn
                 325                 330                 335

Ser Asn Thr Asn Lys Asp Asp Ser Ile Asn Asn Lys Gln Asp Gly Ser
             340                 345                 350

Gln Asn Asn Thr Thr Thr Asn His Phe Pro Lys Pro Arg Glu Gln Leu
             355                 360                 365

Val Gly Gly Ser Ser Met Leu Ile Ser Lys Ile Lys Pro His Lys Pro
             370                 375                 380

Gly Lys Tyr Phe Ile Val Tyr Ser Tyr Arg Pro Phe Asp Pro Thr
385                 390                 395                 400

Arg Asp Thr Asn Thr Arg Ile Val Glu Leu Asn Val Gln
                 405                 410

<210> SEQ ID NO 34
<211> LENGTH: 1104
<212> TYPE: DNA
<213> ORGANISM: Artificial Sequence
<220> FEATURE:
<223> OTHER INFORMATION: PvICPhumanCO

<400> SEQUENCE: 34

-continued

```
gccaccatgg ctaagttgtc tagcctgttc tgcctggttg tgtgttctag tgttgcccac      60
ctctcttcct gtagtgatca aaacacttat agttttgata ttgttaatcg aaacacttgg     120
tacagcatag ccaagaaaat ctttcaaggc acgaccccct gtaatttcac tgtaatccct     180
agttcctatg tcaacaactc tgacggagtg tctacgagtg atgattccgt actgctcatc     240
cgcaaaaagc tcaaggatcc gagtgaagct ggccttgacg gatcttcagt ttctggttca     300
tccagttctg gaaacagtca ctccggttct gcaccttgtt gtgataaggg tacccccgct     360
aaagaggcag agctgaaatt ttctacaaag tttgagggcg atgactatgc taagctgaga     420
gattctctga gccttataga caagtcactc cgagaagagt caagctcaga ggaggacagt     480
aagatggaag atagtcaggt cggtgaagta actcatgaag agactatcac ctacaacatg     540
cccgaagaat atatgcccca gaacatttcc gaggtattga tcggtgccgc tgaagaggat     600
aggacatacg cgttgaaggg ggacgagccg tgtgatgtgt acttgaaact tggcgagata     660
atcaatggaa ctaatgaaaa gactatcgag tattctctcc aaaaaaataa gatactgtgc     720
gttcaactcg aagcaattgg gggaaatgga tacctctggg ctctcctcgg cgtacacaaa     780
gaaaaacccc aaatcaaccc agaggagttt ccacgaaaaa agatcacaaa atctttttc     840
accaatgaga tatccgtcac gcagcctaaa gcagtgcaaa agaacaaatc taataatgga     900
ggtgagagca gttcaaactc acctggctat gggaaacccc ccgcaagcga acagctcggg     960
ggatttgtgg gtggcacatc catgcttcag agtatagtaa aggctcataa agagggcacc    1020
tttttcgtag tttatagcta ctaccgcccc ttcgacccta ccgccaacgc caacacgaag    1080
atactcaaac ttacggtttc atag                                            1104
```

<210> SEQ ID NO 35
<211> LENGTH: 365
<212> TYPE: PRT
<213> ORGANISM: Artificial Sequence
<220> FEATURE:
<223> OTHER INFORMATION: PVICP humanco + kozac
<220> FEATURE:
<221> NAME/KEY: misc_feature
<223> OTHER INFORMATION: PvICP

<400> SEQUENCE: 35

```
Met Ala Lys Leu Ser Ser Leu Phe Cys Leu Val Val Cys Ser Val
1               5                   10                  15

Ala His Leu Ser Ser Cys Ser Asp Gln Asn Thr Tyr Ser Phe Asp Ile
            20                  25                  30

Val Asn Arg Asn Thr Trp Tyr Ser Ile Ala Lys Lys Ile Phe Gln Gly
        35                  40                  45

Thr Thr Pro Cys Asn Phe Thr Val Ile Pro Ser Ser Tyr Val Asn Asn
    50                  55                  60

Ser Asp Gly Val Ser Thr Ser Asp Ser Val Leu Leu Ile Arg Lys
65                  70                  75                  80

Lys Leu Lys Asp Pro Ser Glu Ala Gly Leu Asp Gly Ser Ser Val Ser
                85                  90                  95

Gly Ser Ser Ser Gly Asn Ser His Ser Gly Ser Ala Pro Cys Cys
            100                 105                 110

Asp Lys Gly Thr Pro Ala Lys Glu Ala Glu Leu Lys Phe Ser Thr Lys
        115                 120                 125

Phe Glu Gly Asp Asp Tyr Ala Lys Leu Arg Asp Ser Leu Ser Leu Ile
    130                 135                 140
```

-continued

```
Asp Lys Ser Leu Arg Glu Glu Ser Ser Ser Glu Glu Asp Ser Lys Met
145                 150                 155                 160

Glu Asp Ser Gln Val Gly Glu Val Thr His Glu Glu Thr Ile Thr Tyr
                165                 170                 175

Asn Met Pro Glu Glu Tyr Met Pro Gln Asn Ile Ser Glu Val Leu Ile
            180                 185                 190

Gly Ala Ala Glu Glu Asp Arg Thr Tyr Ala Leu Lys Gly Asp Glu Pro
        195                 200                 205

Cys Asp Val Tyr Leu Lys Leu Gly Glu Ile Ile Asn Gly Thr Asn Glu
    210                 215                 220

Lys Thr Ile Glu Tyr Ser Leu Gln Lys Asn Lys Ile Leu Cys Val Gln
225                 230                 235                 240

Leu Glu Ala Ile Gly Gly Asn Gly Tyr Leu Trp Ala Leu Leu Gly Val
                245                 250                 255

His Lys Glu Lys Pro Gln Ile Asn Pro Glu Glu Phe Pro Arg Lys Lys
            260                 265                 270

Ile Thr Lys Ser Phe Phe Thr Asn Glu Ile Ser Val Thr Gln Pro Lys
        275                 280                 285

Ala Val Gln Lys Asn Lys Ser Asn Asn Gly Gly Glu Ser Ser Ser Asn
    290                 295                 300

Ser Pro Gly Tyr Gly Lys Pro Pro Ala Ser Glu Gln Leu Gly Gly Phe
305                 310                 315                 320

Val Gly Gly Thr Ser Met Leu Gln Ser Ile Val Lys Ala His Lys Glu
                325                 330                 335

Gly Thr Phe Phe Val Val Tyr Ser Tyr Tyr Arg Pro Phe Asp Pro Thr
            340                 345                 350

Ala Asn Ala Asn Thr Lys Ile Leu Lys Leu Thr Val Ser
        355                 360                 365

<210> SEQ ID NO 36
<211> LENGTH: 359
<212> TYPE: PRT
<213> ORGANISM: Plasmodium vivax
<220> FEATURE:
<221> NAME/KEY: misc_feature
<223> OTHER INFORMATION: ICP

<400> SEQUENCE: 36

Met Lys Leu Ser Ser Leu Phe Cys Leu Val Val Cys Ser Ser Val Ala
1               5                   10                  15

His Leu Ser Ser Cys Ser Asp Gln Asn Thr Tyr Ser Phe Asp Ile Val
            20                  25                  30

Asn Arg Asn Thr Trp Tyr Ser Ile Ala Lys Lys Ile Phe Gln Gly Thr
        35                  40                  45

Thr Pro Cys Asn Phe Thr Val Ile Pro Ser Ser Tyr Val Asn Asn Ser
    50                  55                  60

Asp Gly Val Ser Thr Ser Asp Asp Ser Val Leu Leu Ile Arg Lys Lys
65                  70                  75                  80

Leu Lys Asp Pro Ser Glu Ala Gly Leu Asp Gly Ser Ser Val Ser Gly
                85                  90                  95

Asn Ser His Ser Gly Ser Ala Pro Cys Cys Asp Lys Gly Thr Pro Ala
            100                 105                 110

Lys Glu Ala Glu Leu Asn Phe Ser Thr Lys Phe Glu Gly Asp Asp Tyr
        115                 120                 125

Ala Lys Leu Arg Asp Ser Leu Ser Leu Ile Asp Lys Ser Leu Arg Glu
    130                 135                 140
```

```
Glu Ser Ser Glu Glu Asp Ser Lys Met Glu Asp Ser Gln Val Gly
145                 150                 155                 160

Glu Val Thr His Glu Thr Ile Thr Tyr Asn Met Pro Glu Glu Tyr
            165                 170                 175

Met Pro Gln Asn Ile Ser Glu Val Leu Ile Gly Ala Ala Glu Asp
        180                 185                 190

Arg Thr Tyr Ala Leu Lys Gly Asp Glu Pro Cys Asp Val Tyr Leu Lys
        195                 200                 205

Leu Gly Glu Ile Ile Asn Gly Thr Asn Glu Lys Thr Ile Glu Tyr Ser
210                 215                 220

Leu Gln Lys Asn Lys Ile Leu Cys Val Gln Leu Glu Ala Ile Gly Gly
225                 230                 235                 240

Asn Gly Tyr Leu Trp Ala Leu Leu Gly Val His Lys Glu Lys Pro Gln
            245                 250                 255

Ile Asn Pro Glu Glu Phe Pro Arg Lys Lys Ile Thr Lys Ser Phe Phe
        260                 265                 270

Thr Asn Glu Ile Ser Val Thr Gln Pro Lys Ala Val Gln Lys Asn Lys
        275                 280                 285

Ser Asn Asn Gly Gly Glu Ser Ser Asn Ser Pro Gly Tyr Gly Lys
290                 295                 300

Pro Pro Ala Ser Glu Gln Leu Gly Gly Phe Val Gly Gly Thr Ser Met
305                 310                 315                 320

Leu Gln Ser Ile Val Lys Ala His Lys Glu Gly Thr Phe Phe Val Val
            325                 330                 335

Tyr Ser Tyr Tyr Arg Pro Phe Asp Pro Thr Ala Asn Ala Asn Thr Lys
            340                 345                 350

Ile Leu Lys Leu Thr Val Ser
        355

<210> SEQ ID NO 37
<211> LENGTH: 2355
<212> TYPE: DNA
<213> ORGANISM: Artificial Sequence
<220> FEATURE:
<223> OTHER INFORMATION: Falcilysin, Bergheilysin-A-CO

<400> SEQUENCE: 37
ggatccgcca ccatggctaa attgatgaag gttttgggtt acatcaacat tattaccaac      60
tgcgtgaatg gaatcctctg caaggtgac aagaaaaggt actccatctt caccaataat     120
tacatctaca gcatatcaac cctcaataat tatagctttg ctgcaacaat gaacaaaatg     180
cccgcttggg ttaacgagaa atgtccagaa cacaaaagct acgacatcgt tgagaagcgc     240
tacaatgaga acctcaatct cacgtacaca gtctatgagc acaagaaggc caagactcag     300
gtcatagcac tggggtctaa cgatcctctc gacgctgagc aagcatttgg cttctacgtg     360
aaaaccctga cgcattcaga taaaggcatt ccgcacatac tggaacacac tgtcctgagt     420
ggctctaaga atttcaacta caaggactca atggggcttt tggagaaagg caccctgaac     480
acacacctga atgcctacac cttcaatgac aggaccatct acatggccgg agtatgaac     540 aatagggatt tctttaacat tatggccgtc tacatggata gcgtgttcca gcctaacgta     600
ctggaaaaca aattcatctt ccagacagag ggatggacct atgaggtaga aagctgaag     660 gaggaggaga gaaccctcga cattcccaag attaaggact acaaggtgtc ttttaacgga     720
atcgtgtata atgagatgaa gggtgcgttt agcaatcctc tgcaggacct gtattatgaa     780
```

| | |
|---|---|
| gtgatgagaa acatgttccc cgacaacgta cacagtaaca tctccggagg agatcctaaa | 840 |
| gaaataccaa atctgtcata tgaagagttt aaggagtttt actacaagaa ttacaatccg | 900 |
| aagaaaatca aagtgttctt tttctccaaa ataatccga cagagctgct caactttgtg | 960 |
| gacaactatc tctgtcagct ggacttcacg aaatatcggg atgatgctgt ggaacatgtc | 1020 |
| aattaccaag aataccgcaa aggcccattc tatattaaga agaaattcgc tgatcactca | 1080 |
| gaagagaaag aaaatcttgc ctccgtgagt tggcttctga atcccaagaa acacaagaat | 1140 |
| tccgatactg atctctctct ggagtctcct acagactatt tcgccttgct catcatcaat | 1200 |
| aatctgctta ctcataccag tgagagcgtc ctgtacaaag ccctgataga atccggattg | 1260 |
| gggaatagta ttgtagatcg agggctgaat gattccctgg ttcagtatgt gttcagcatc | 1320 |
| ggcctgaaag gcataaaaga gaagaacgag aagaacatct ccctggacaa ggtccactac | 1380 |
| gaggtggaaa agatcgttct tgaggcactg aaaaaagtgg tcaagaagg tttcaataag | 1440 |
| tcagcagttg aggcagccat taacaatatt gagttcgtcc tgaaagaagc caatctcaag | 1500 |
| atctccaaat ctatagactt tgtgtttgaa atggccagca gactgaacta tggcaaagat | 1560 |
| ccactgctga tctttgagtt tgaaaagcat ctcaacgtag tgaaggacaa gatcaagaac | 1620 |
| gagcctaaat acctggagaa gtatgtggag aaacatcttc tgaacaatga tcatcgagtc | 1680 |
| gttattctgc tggaagggga tgaaaactat ggcaccgaac aggagaaact ggaaaaggac | 1740 |
| atgctgaaga agcggattga aagcttcact gagaaagaaa aggagaatat tatcacagac | 1800 |
| ttcgaaaatc ttacgaagta caagaacact gaggaatctc ccgaacatct ggacaagttt | 1860 |
| cccatcatta gcattagcga cctcaatgga aagactttgg agatcccgt gaaccctttc | 1920 |
| tttaccaacc tgaacaacga gaacaacatg cagcactata atgagacaaa gaacaaccaa | 1980 |
| accctggtca agaaaaacat ggaccgtttc attaacaaat acattctcaa caaggatgga | 2040 |
| aacgataaga acgacagcaa gaacgcggat gtgccaatgc tgatttatga atcccaaca | 2100 |
| tctggcatat tgtatctgca gtttatcttc tctctggata accttacact ggaagaattg | 2160 |
| tcctacctga atctgtttaa aagcttgata ctggagaaca agactaacaa gagatcaagt | 2220 |
| gaagagtttg tgatcttgcg ggagaagaat attgggaata tgatgaccaa tgttgctctt | 2280 |
| cttagcacat ccgatcgcct caatgtgact gacaaatata atgcgaaagg tttcttttaac | 2340 |
| tttgagtaac tcgag | 2355 |

<210> SEQ ID NO 38
<211> LENGTH: 778
<212> TYPE: PRT
<213> ORGANISM: Plasmodium berghei
<220> FEATURE:
<221> NAME/KEY: misc_feature
<223> OTHER INFORMATION: Falcilysin, Bergheilysin-A

<400> SEQUENCE: 38

Met Ala Lys Leu Met Lys Val Leu Gly Tyr Ile Asn Ile Ile Thr Asn
1               5                   10                  15

Cys Val Asn Gly Ile Leu Cys Lys Gly Asp Lys Lys Arg Tyr Ser Ile
                20                  25                  30

Phe Thr Asn Asn Tyr Ile Tyr Ser Ile Ser Thr Leu Asn Asn Tyr Ser
            35                  40                  45

Phe Ala Ala Thr Met Asn Lys Met Pro Ala Trp Val Asn Glu Lys Cys
        50                  55                  60

Pro Glu His Lys Ser Tyr Asp Ile Val Glu Lys Arg Tyr Asn Glu Asn
65                  70                  75                  80

```
Leu Asn Leu Thr Tyr Thr Val Tyr Glu His Lys Lys Ala Lys Thr Gln
                85                  90                  95

Val Ile Ala Leu Gly Ser Asn Asp Pro Leu Asp Ala Glu Gln Ala Phe
            100                 105                 110

Gly Phe Tyr Val Lys Thr Leu Thr His Ser Asp Lys Gly Ile Pro His
        115                 120                 125

Ile Leu Glu His Thr Val Leu Ser Gly Ser Lys Asn Phe Asn Tyr Lys
    130                 135                 140

Asp Ser Met Gly Leu Leu Glu Lys Gly Thr Leu Asn Thr His Leu Asn
145                 150                 155                 160

Ala Tyr Thr Phe Asn Asp Arg Thr Ile Tyr Met Ala Gly Ser Met Asn
                165                 170                 175

Asn Arg Asp Phe Phe Asn Ile Met Ala Val Tyr Met Asp Ser Val Phe
            180                 185                 190

Gln Pro Asn Val Leu Glu Asn Lys Phe Ile Phe Gln Thr Glu Gly Trp
        195                 200                 205

Thr Tyr Glu Val Glu Lys Leu Lys Glu Glu Lys Asn Leu Asp Ile
    210                 215                 220

Pro Lys Ile Lys Asp Tyr Lys Val Ser Phe Asn Gly Ile Val Tyr Asn
225                 230                 235                 240

Glu Met Lys Gly Ala Phe Ser Asn Pro Leu Gln Asp Leu Tyr Tyr Glu
                245                 250                 255

Val Met Arg Asn Met Phe Pro Asp Asn Val His Ser Asn Ile Ser Gly
            260                 265                 270

Gly Asp Pro Lys Glu Ile Pro Asn Leu Ser Tyr Glu Gly Phe Lys Glu
        275                 280                 285

Phe Tyr Tyr Lys Asn Tyr Asn Pro Lys Lys Ile Lys Val Phe Phe Phe
    290                 295                 300

Ser Lys Asn Asn Pro Thr Glu Leu Leu Asn Phe Val Asp Asn Tyr Leu
305                 310                 315                 320

Cys Gln Leu Asp Phe Thr Lys Tyr Arg Asp Asp Ala Val Glu His Val
                325                 330                 335

Asn Tyr Gln Glu Tyr Arg Lys Gly Pro Phe Tyr Ile Lys Lys Lys Phe
            340                 345                 350

Ala Asp His Ser Glu Glu Lys Glu Asn Leu Ala Ser Val Ser Trp Leu
        355                 360                 365

Leu Asn Pro Lys Lys His Lys Asn Ser Asp Thr Asp Leu Ser Leu Glu
    370                 375                 380

Ser Pro Thr Asp Tyr Phe Ala Leu Leu Ile Ile Asn Asn Leu Leu Thr
385                 390                 395                 400

His Thr Ser Glu Ser Val Leu Tyr Lys Ala Leu Ile Glu Ser Gly Leu
                405                 410                 415

Gly Asn Ser Ile Val Asp Arg Gly Leu Asn Asp Ser Leu Val Gln Tyr
            420                 425                 430

Val Phe Ser Ile Gly Leu Lys Gly Ile Lys Glu Lys Asn Glu Lys Asn
        435                 440                 445

Ile Ser Leu Asp Lys Val His Tyr Glu Val Glu Lys Ile Val Leu Glu
    450                 455                 460

Ala Leu Lys Lys Val Val Lys Glu Gly Phe Asn Lys Ser Ala Val Glu
465                 470                 475                 480

Ala Ala Ile Asn Asn Ile Glu Phe Val Leu Lys Glu Ala Asn Leu Lys
                485                 490                 495
```

```
Ile Ser Lys Ser Ile Asp Phe Val Phe Glu Met Ala Ser Arg Leu Asn
            500                 505                 510

Tyr Gly Lys Asp Pro Leu Leu Ile Phe Glu Phe Glu Lys His Leu Asn
            515                 520                 525

Val Val Lys Asp Lys Ile Lys Asn Glu Pro Lys Tyr Leu Glu Lys Tyr
            530                 535                 540

Val Glu Lys His Leu Leu Asn Asn Asp His Arg Val Val Ile Leu Leu
545                 550                 555                 560

Glu Gly Asp Glu Asn Tyr Gly Thr Glu Gln Glu Lys Leu Glu Lys Asp
            565                 570                 575

Met Leu Lys Lys Arg Ile Glu Ser Phe Thr Glu Lys Lys Glu Asn
            580                 585                 590

Ile Ile Thr Asp Phe Glu Asn Leu Thr Lys Tyr Lys Asn Thr Glu Glu
            595                 600                 605

Ser Pro Glu His Leu Asp Lys Phe Pro Ile Ile Ser Ile Ser Asp Leu
            610                 615                 620

Asn Gly Lys Thr Leu Glu Ile Pro Val Asn Pro Phe Phe Thr Asn Leu
625                 630                 635                 640

Asn Asn Glu Asn Asn Met Gln His Tyr Asn Glu Thr Lys Asn Asn Gln
            645                 650                 655

Thr Leu Val Lys Glu Asn Met Asp Arg Phe Ile Asn Lys Tyr Ile Leu
            660                 665                 670

Asn Lys Asp Gly Asn Asp Lys Asn Asp Ser Lys Asn Ala Asp Val Pro
            675                 680                 685

Met Leu Ile Tyr Glu Ile Pro Thr Ser Gly Ile Leu Tyr Leu Gln Phe
            690                 695                 700

Ile Phe Ser Leu Asp Asn Leu Thr Leu Glu Glu Leu Ser Tyr Leu Asn
705                 710                 715                 720

Leu Phe Lys Ser Leu Ile Leu Glu Asn Lys Thr Asn Lys Arg Ser Ser
            725                 730                 735

Glu Glu Phe Val Ile Leu Arg Glu Lys Asn Ile Gly Asn Met Met Thr
            740                 745                 750

Asn Val Ala Leu Leu Ser Thr Ser Asp Arg Leu Asn Val Thr Asp Lys
            755                 760                 765

Tyr Asn Ala Lys Gly Phe Phe Asn Phe Glu
            770                 775

<210> SEQ ID NO 39
<211> LENGTH: 1149
<212> TYPE: PRT
<213> ORGANISM: Plasmodium berghei
<220> FEATURE:
<221> NAME/KEY: misc_feature
<223> OTHER INFORMATION: Falcilysin, Bergheilysin-A

<400> SEQUENCE: 39

Met Lys Leu Met Lys Val Leu Gly Tyr Ile Asn Ile Ile Thr Asn Cys
1               5                   10                  15

Val Asn Gly Ile Leu Cys Lys Gly Asp Lys Lys Arg Tyr Ser Ile Phe
            20                  25                  30

Thr Asn Asn Tyr Ile Tyr Ser Ile Ser Thr Leu Asn Asn Tyr Ser Phe
        35                  40                  45

Ala Ala Thr Met Asn Lys Met Pro Ala Trp Val Asn Glu Lys Cys Pro
    50                  55                  60

Glu His Lys Ser Tyr Asp Ile Val Glu Lys Arg Tyr Asn Glu Asn Leu
65                  70                  75                  80
```

```
Asn Leu Thr Tyr Thr Val Tyr Glu His Lys Lys Ala Lys Thr Gln Val
                85                  90                  95
Ile Ala Leu Gly Ser Asn Asp Pro Leu Asp Ala Glu Gln Ala Phe Gly
            100                 105                 110
Phe Tyr Val Lys Thr Leu Thr His Ser Asp Lys Gly Ile Pro His Ile
        115                 120                 125
Leu Glu His Thr Val Leu Ser Gly Ser Lys Asn Phe Asn Tyr Lys Asp
    130                 135                 140
Ser Met Gly Leu Leu Glu Lys Gly Thr Leu Asn Thr His Leu Asn Ala
145                 150                 155                 160
Tyr Thr Phe Asn Asp Arg Thr Ile Tyr Met Ala Gly Ser Met Asn Asn
                165                 170                 175
Arg Asp Phe Phe Asn Ile Met Ala Val Tyr Met Asp Ser Val Phe Gln
            180                 185                 190
Pro Asn Val Leu Glu Asn Lys Phe Ile Phe Gln Thr Glu Gly Trp Thr
        195                 200                 205
Tyr Glu Val Glu Lys Leu Lys Glu Glu Lys Asn Leu Asp Ile Pro
    210                 215                 220
Lys Ile Lys Asp Tyr Lys Val Ser Phe Asn Gly Ile Val Tyr Asn Glu
225                 230                 235                 240
Met Lys Gly Ala Phe Ser Asn Pro Leu Gln Asp Leu Tyr Tyr Glu Val
                245                 250                 255
Met Arg Asn Met Phe Pro Asp Asn Val His Ser Asn Ile Ser Gly Gly
            260                 265                 270
Asp Pro Lys Glu Ile Pro Asn Leu Ser Tyr Glu Glu Phe Lys Glu Phe
        275                 280                 285
Tyr Tyr Lys Asn Tyr Asn Pro Lys Lys Ile Lys Val Phe Phe Phe Ser
    290                 295                 300
Lys Asn Asn Pro Thr Glu Leu Leu Asn Phe Val Asp Asn Tyr Leu Cys
305                 310                 315                 320
Gln Leu Asp Phe Thr Lys Tyr Arg Asp Asp Ala Val Glu His Val Asn
                325                 330                 335
Tyr Gln Glu Tyr Arg Lys Gly Pro Phe Tyr Ile Lys Lys Lys Phe Ala
            340                 345                 350
Asp His Ser Glu Glu Lys Glu Asn Leu Ala Ser Val Ser Trp Leu Leu
        355                 360                 365
Asn Pro Lys Lys His Lys Asn Ser Asp Thr Asp Leu Ser Leu Glu Ser
    370                 375                 380
Pro Thr Asp Tyr Phe Ala Leu Leu Ile Ile Asn Asn Leu Leu Thr His
385                 390                 395                 400
Thr Ser Glu Ser Val Leu Tyr Lys Ala Leu Ile Glu Ser Gly Leu Gly
                405                 410                 415
Asn Ser Ile Val Asp Arg Gly Leu Asn Asp Ser Leu Val Gln Tyr Val
            420                 425                 430
Phe Ser Ile Gly Leu Lys Gly Ile Lys Glu Lys Asn Glu Lys Asn Ile
        435                 440                 445
Ser Leu Asp Lys Val His Tyr Glu Val Glu Lys Ile Val Leu Glu Ala
    450                 455                 460
Leu Lys Lys Val Val Lys Glu Gly Phe Asn Lys Ser Ala Val Glu Ala
465                 470                 475                 480
Ala Ile Asn Asn Ile Glu Phe Val Leu Lys Glu Ala Asn Leu Lys Ile
                485                 490                 495
```

```
Ser Lys Ser Ile Asp Phe Val Phe Glu Met Ala Ser Arg Leu Asn Tyr
            500                 505                 510

Gly Lys Asp Pro Leu Leu Ile Phe Glu Phe Glu Lys His Leu Asn Val
            515                 520                 525

Val Lys Asp Lys Ile Lys Asn Glu Pro Lys Tyr Leu Glu Lys Tyr Val
            530                 535                 540

Glu Lys His Leu Leu Asn Asn Asp His Arg Val Val Ile Leu Leu Glu
545                 550                 555                 560

Gly Asp Glu Asn Tyr Gly Thr Glu Gln Lys Leu Glu Lys Asp Met
            565                 570                 575

Leu Lys Lys Arg Ile Glu Ser Phe Thr Glu Lys Glu Lys Glu Asn Ile
            580                 585                 590

Ile Thr Asp Phe Glu Asn Leu Thr Lys Tyr Lys Asn Thr Glu Glu Ser
            595                 600                 605

Pro Glu His Leu Asp Lys Phe Pro Ile Ile Ser Ile Ser Asp Leu Asn
            610                 615                 620

Gly Lys Thr Leu Glu Ile Pro Val Asn Pro Phe Phe Thr Asn Leu Asn
625                 630                 635                 640

Asn Glu Asn Asn Met Gln His Tyr Asn Glu Thr Lys Asn Asn Gln Thr
            645                 650                 655

Leu Val Lys Glu Asn Met Asp Arg Phe Ile Asn Lys Tyr Ile Leu Asn
            660                 665                 670

Lys Asp Gly Asn Asp Lys Asn Asp Ser Lys Asn Ala Asp Val Pro Met
            675                 680                 685

Leu Ile Tyr Glu Ile Pro Thr Ser Gly Ile Leu Tyr Leu Gln Phe Ile
            690                 695                 700

Phe Ser Leu Asp Asn Leu Thr Leu Glu Glu Leu Ser Tyr Leu Asn Leu
705                 710                 715                 720

Phe Lys Ser Leu Ile Leu Glu Asn Lys Thr Asn Lys Arg Ser Ser Glu
            725                 730                 735

Glu Phe Val Ile Leu Arg Glu Lys Asn Ile Gly Asn Met Met Thr Asn
            740                 745                 750

Val Ala Leu Leu Ser Thr Ser Asp Arg Leu Asn Val Thr Asp Lys Tyr
            755                 760                 765

Asn Ala Lys Gly Phe Phe Asn Phe Glu Met His Met Leu Ser His Lys
            770                 775                 780

Cys Asn Asp Ala Leu Glu Ile Ala Leu Glu Ala Leu Lys Glu Ser Asp
785                 790                 795                 800

Phe Ser Asn Lys Lys Val Ile Glu Ile Leu Lys Arg Lys Ile Asn
            805                 810                 815

Gly Met Lys Thr Thr Phe Ala Ser Lys Gly His Ser Ile Leu Ile Lys
            820                 825                 830

Tyr Val Lys Ser Arg Ile Asn Ser Lys Tyr Tyr Ala Tyr Asp Leu Ile
            835                 840                 845

His Gly Tyr Asp Asn Tyr Leu Lys Leu Gln Gln Leu Lys Leu Ala
            850                 855                 860

Glu Thr Asn Tyr Glu Ser Leu Glu Ala Ile Leu Asn Arg Ile Arg Lys
865                 870                 875                 880

Lys Ile Phe Lys Arg Asn Asn Leu Ile Met Asn Val Thr Val Asp Pro
            885                 890                 895

Gly Thr Ile Asp Gln Leu Phe Ala Lys Ser Lys Asn Ser Phe Asn Asn
            900                 905                 910

Leu Leu Ser Tyr Phe Asp Glu Asn Glu Ser Tyr Cys Ser Lys Asn Asp
```

| | | | | | | | | | | |
|---|---|---|---|---|---|---|---|---|---|---|
| | | 915 | | | 920 | | | 925 | | |
| Ser | Phe | Asn | Lys | Val | Val | Gly | Trp | Asn | Lys | Glu | Ile | Gln | Glu | Lys | Lys |
| 930 | | | | | 935 | | | | 940 | | |

Ser Phe Asn Lys Val Val Gly Trp Asn Lys Glu Ile Gln Glu Lys Lys
930                     935                     940

Leu Leu Glu Gly Glu Glu Val Lys Lys Glu Leu Leu Val Val Pro Thr
945                     950                     955                 960

Phe Val Asn Ser Val Ser Met Ser Gly Val Leu Phe Asn Lys Gly Glu
            965                     970                     975

Tyr Leu Asp Pro Ser Phe Thr Val Ile Val Ala Ala Leu Lys Asn Ser
                980                     985                 990

Tyr Leu Trp Glu Thr Val Arg Gly Leu Asn Gly Ala Tyr Gly Val Phe
            995                     1000                    1005

Ala Asp Ile Glu Tyr Asp Gly Thr Val Val Phe Leu Ser Ala Arg
    1010                    1015                    1020

Asp Pro Asn Leu Glu Lys Thr Leu Gln Thr Phe Arg Glu Ala Ala
    1025                    1030                    1035

Gln Gly Leu Arg Lys Met Ala Asp Val Met Thr Lys Asn Asp Leu
    1040                    1045                    1050

Leu Arg Tyr Ile Ile Asn Ala Ile Gly Thr Ile Asp Arg Pro Arg
    1055                    1060                    1065

Arg Gly Val Glu Leu Ser Lys Leu Ser Phe Ser Arg Ile Ile Ser
    1070                    1075                    1080

Asn Glu Thr Glu Gln Asp Arg Ile Glu Phe Arg Asn Arg Val Met
    1085                    1090                    1095

Asn Thr Lys Lys Glu Asp Phe Tyr Lys Phe Ala Asp Leu Leu Glu
    1100                    1105                    1110

Lys Lys Val Lys Glu Phe Glu Lys Asn Val Val Ile Ile Thr Ser
    1115                    1120                    1125

Lys Glu Lys Ala Asn Glu Tyr Ile Asn Asn Val Asp Asn Asp Phe
    1130                    1135                    1140

Lys Lys Ile Leu Ile Glu
    1145

<210> SEQ ID NO 40
<211> LENGTH: 3591
<212> TYPE: DNA
<213> ORGANISM: Artificial Sequence
<220> FEATURE:
<223> OTHER INFORMATION: PfFalcilysin Human CO

<400> SEQUENCE: 40

| | |
|---|---|
| gccaccatgg ctaatcttac caaacttatg aaagtaatag atatataaa cattataact | 60 |
| aattgtgtac aatcttttac taacagagcg gacaagaaga ggtacaatgt ttttgcaaag | 120 |
| tctttcatca atacgataaa cacgaacctg tacaccttca agcggtgat gtcaaaaacg | 180 |
| cctgaatgga tccatgagaa atctcccaaa cacaacagtt atgacataat tgagaaacgc | 240 |
| tataatgaag agttcaaaat gacatacacg gtttatcaac ataaaaaagc aaagacgcag | 300 |
| gtaatttcac tcggtacgaa cgacccactt gatgtcgaac aggcctttgc cttctatgta | 360 |
| aagactctga cccactctgg aaggggatt ccccacatcc tcgaacacag tgtcctctca | 420 |
| gggagtaaaa attacaacta caaaaattcc attggactcc ttgagaaggg aactctgcac | 480 |
| acccaccta acgcatacac cttcaatgac cgaactgtgt acatggccgg ttctatgaat | 540 |
| aacaaagact tcttcaatat aatgggcgtc tatatggaca gtgtcttcca acctaatgta | 600 |
| ctggaaaaca atacatatt cgagacggag ggatggactt acgaggtgga aaagctgaaa | 660 |

```
gaggatgaga agggaaaagc tgagattcca cagatgaaag attataaagt atctttcaac    720
ggaattgttt ataatgaaat gaagggtgcc ttgtcttccc cgttggaaga tctttaccat    780
gaagagatga agtatatgtt cccagacaac gtccactcta ataacagtgg cggagaccca    840
aaagagatca caaacttgac ctatgaggag ttcaaggagt tctattacaa aaactataat    900
ccaaaaaaag ttaaagtgtt cttcttttca agaacaacc caacggagct tctcaatttc    960
gtagaccagt acctcggaca gctggactac agcaaatacc gcgacgatgc tgttgaaagt   1020
gttgaatacc aaacgtataa aaaggacct ttctacatta aaaaaagta tggggaccat    1080 agcgaagaga aggagaatct tgtttccgta gcgtggcttc tgaaccccaa ggttgacaag   1140
actaacaatc ataataataa ccatagtaat aaccaatcta gcgaaaataa tggttactcc   1200
aacggctccc actctagcga tttgtccttg gagaatccca cggactattt cgtgctcttg   1260
attatcaata acctccttat acatacccca gaaagcgtcc tgtacaaggc cctcacagat   1320
tgcgggctgg gaataatgt aattgatagg ggtttgaatg attcacttgt ccaatacatt   1380
ttcagtattg ggctgaaggg aatcaaacgc aacaatgaaa aaattaaaaa cttcgataaa   1440
gtgcactatg aagtagaaga cgtaattatg aatgctctca aaaagtggt caaggaggga    1500 ttcaataaat ccgccgtaga agccagcata ataatatcg agtttatcct gaaagaagcc   1560
aatttgaaaa cttcaaaatc tatagatttc gttttgaga tgacttccaa gctcaattat   1620
aatagggatc cactgctgat cttcgagttt gagaaatatc ttaatattgt gaagaataag   1680
attaagaacg aacctatgta tttggagaag tttgttgaaa acacttcat caacaacgca   1740 catcggtcag tgatccttct tgaggggac gagaactatg cacaggaaca ggaaaacctt   1800
gagaaacaag aactgaagaa acgcatagag aacttcaatg agcaggagaa agagcaagtc   1860
attaagaact tcgaggagct gtccaagtac aagaacgcgg aagagagccc ggaacacttg   1920
aacaagtttc caataatctc catttccgac ctcaataaga aaacactgga agtcccagtt   1980
aacgtctact tcacgaacat caacgaaaac aacaatataa tggagacata taacaagctg   2040
aagacaaatg agcacatgct taaggacaac atggacgtgt ttctcaaaaa atacgttctc   2100
aaaaacgata agcacaacac caacaataat aacaacaata ataataatat ggactactct   2160
ttcaccgaaa ctaaatatga aggaaatgtg ccaatccttg tgtacgaaat gccgacgact   2220
ggaatagtct atttgcagtt cgttttctcc ctcgatcacc tgaccgtaga cgagctcgcc   2280
tatttgaatt tgttcaagac acttatcttg gagaacaaga caaacaaacg ctccagtgag   2340
gatttcgtca ttttgagaga aaaaatatt gggtcaatgt cagcgaatgt ggcgctctac   2400
agcaaggacg accacctgaa cgtaaccgac aagtataacg cgcaagcact cttcaatctg   2460
gaaatgcacg tactttctca taatgcaac gatgcgctga acattgccct tgaagctgtt   2520
aaagaatctg acttcagtaa taaaaaaag gtcatagata tccttaagag gaagattaat   2580
ggaatgaaaa ctacgttctc agaaaaagga tatgctatac tgatgaaata cgttaaagcc   2640
catcttaata gcaagcatta cgcccataac ataatttatg ggtacgaaaa ctatttgaag   2700
ctgcaagagc aattggagct tgcagaaaac gattttaaaa cattggagaa tattttggtg   2760
agaataagaa acaaaatctt taacaaaaaa aacttgatgg tcagcgtgac gtccgactat   2820
ggtgctctca acacctgtt tgtgaatagc aacgaatcct gaaaaacct tgtaagttac    2880 ttcgaggaaa acgataagta tatcaacgat atgcagaata aagtgaatga ccctaccgtc   2940
atggggtgga atgaagaaat caagtctaaa aagctgttcg acgaggagaa ggtgaaaaag   3000
gagttctttg tcttgccgac ctttgtcaac agcgtctcaa tgagtggtat cctgttcaag   3060
```

-continued

```
ccgggcgaat atctcgaccc gagtttcact gtcatcgttg cggccctgaa aaatagctat   3120
ttgtgggaca cagttcgagg acttaacggg gcttacggtg tattcgctga tatcgaatac   3180
gatggctctg tagtatttct ttcagctcga gaccccaatc tcgaaaagac cctcgccact   3240
ttccgagaat ctgctaaagg attgcgcaaa atggctgaca ccatgacaga gaacgatttg   3300
cttcggtata ttattaacac aattggcacg atcgacaagc ctcgacgagg gatagaactt   3360
tctaagctgt cattccttag acttatttcc aacgagtcag agcaagatcg ggtggagttc   3420
cggaaacgga taatgaacac aaaaaaggaa gatttctata aattcgcaga tcttcttgag   3480
agcaaagtaa atgaattcga aaaaatatc gttatcataa caacaaaaga aaaggccaac     3540
gaatatatag caaacgtaga tggcgagttt aagaaagtct tgatcgagtg a            3591
```

<210> SEQ ID NO 41
<211> LENGTH: 1194
<212> TYPE: PRT
<213> ORGANISM: Plasmodium falciparum
<220> FEATURE:
<221> NAME/KEY: misc_feature
<223> OTHER INFORMATION: PfFalcilysin

<400> SEQUENCE: 41

```
Met Ala Asn Leu Thr Lys Leu Met Lys Val Ile Gly Tyr Ile Asn Ile
1               5                   10                  15

Ile Thr Asn Cys Val Gln Ser Phe Thr Asn Arg Ala Asp Lys Lys Arg
            20                  25                  30

Tyr Asn Val Phe Ala Lys Ser Phe Ile Asn Thr Ile Asn Thr Asn Leu
        35                  40                  45

Tyr Thr Phe Lys Ala Val Met Ser Lys Thr Pro Glu Trp Ile His Glu
    50                  55                  60

Lys Ser Pro Lys His Asn Ser Tyr Asp Ile Ile Glu Lys Arg Tyr Asn
65                  70                  75                  80

Glu Glu Phe Lys Met Thr Tyr Thr Val Tyr Gln His Lys Lys Ala Lys
                85                  90                  95

Thr Gln Val Ile Ser Leu Gly Thr Asn Asp Pro Leu Asp Val Glu Gln
            100                 105                 110

Ala Phe Ala Phe Tyr Val Lys Thr Leu Thr His Ser Gly Lys Gly Ile
        115                 120                 125

Pro His Ile Leu Glu His Ser Val Leu Ser Gly Ser Lys Asn Tyr Asn
    130                 135                 140

Tyr Lys Asn Ser Ile Gly Leu Leu Glu Lys Gly Thr Leu His Thr His
145                 150                 155                 160

Leu Asn Ala Tyr Thr Phe Asn Asp Arg Thr Val Tyr Met Ala Gly Ser
                165                 170                 175

Met Asn Asn Lys Asp Phe Phe Asn Ile Met Gly Val Tyr Met Asp Ser
            180                 185                 190

Val Phe Gln Pro Asn Val Leu Glu Asn Lys Tyr Ile Phe Glu Thr Glu
        195                 200                 205

Gly Trp Thr Tyr Glu Val Glu Lys Leu Lys Glu Asp Glu Lys Gly Lys
    210                 215                 220

Ala Glu Ile Pro Gln Met Lys Asp Tyr Lys Val Ser Phe Asn Gly Ile
225                 230                 235                 240

Val Tyr Asn Glu Met Lys Gly Ala Leu Ser Ser Pro Leu Glu Asp Leu
                245                 250                 255

Tyr His Glu Glu Met Lys Tyr Met Phe Pro Asp Asn Val His Ser Asn
```

-continued

```
                260                 265                 270
Asn Ser Gly Gly Asp Pro Lys Glu Ile Thr Asn Leu Thr Tyr Glu Glu
            275                 280                 285
Phe Lys Glu Phe Tyr Tyr Lys Asn Tyr Asn Pro Lys Lys Val Lys Val
            290                 295                 300
Phe Phe Phe Ser Lys Asn Asn Pro Thr Glu Leu Leu Asn Phe Val Asp
305                 310                 315                 320
Gln Tyr Leu Gly Gln Leu Asp Tyr Ser Lys Tyr Arg Asp Asp Ala Val
                325                 330                 335
Glu Ser Val Glu Tyr Gln Thr Tyr Lys Lys Gly Pro Phe Tyr Ile Lys
                340                 345                 350
Lys Lys Tyr Gly Asp His Ser Glu Glu Lys Glu Asn Leu Val Ser Val
                355                 360                 365
Ala Trp Leu Leu Asn Pro Lys Val Asp Lys Thr Asn Asn His Asn Asn
            370                 375                 380
Asn His Ser Asn Asn Gln Ser Ser Glu Asn Asn Gly Tyr Ser Asn Gly
385                 390                 395                 400
Ser His Ser Ser Asp Leu Ser Leu Glu Asn Pro Thr Asp Tyr Phe Val
                405                 410                 415
Leu Leu Ile Ile Asn Asn Leu Leu Ile His Thr Pro Glu Ser Val Leu
                420                 425                 430
Tyr Lys Ala Leu Thr Asp Cys Gly Leu Gly Asn Asn Val Ile Asp Arg
                435                 440                 445
Gly Leu Asn Asp Ser Leu Val Gln Tyr Ile Phe Ser Ile Gly Leu Lys
            450                 455                 460
Gly Ile Lys Arg Asn Asn Glu Lys Ile Lys Asn Phe Asp Lys Val His
465                 470                 475                 480
Tyr Glu Val Glu Asp Val Ile Met Asn Ala Leu Lys Lys Val Val Lys
                485                 490                 495
Glu Gly Phe Asn Lys Ser Ala Val Glu Ala Ser Ile Asn Asn Ile Glu
            500                 505                 510
Phe Ile Leu Lys Glu Ala Asn Leu Lys Thr Ser Lys Ser Ile Asp Phe
            515                 520                 525
Val Phe Glu Met Thr Ser Lys Leu Asn Tyr Asn Arg Asp Pro Leu Leu
            530                 535                 540
Ile Phe Glu Phe Glu Lys Tyr Leu Asn Ile Val Lys Asn Lys Ile Lys
545                 550                 555                 560
Asn Glu Pro Met Tyr Leu Glu Lys Phe Val Glu Lys His Phe Ile Asn
                565                 570                 575
Asn Ala His Arg Ser Val Ile Leu Leu Glu Gly Asp Glu Asn Tyr Ala
            580                 585                 590
Gln Glu Gln Glu Asn Leu Glu Lys Gln Glu Leu Lys Lys Arg Ile Glu
            595                 600                 605
Asn Phe Asn Glu Gln Glu Lys Glu Gln Val Ile Lys Asn Phe Glu Glu
            610                 615                 620
Leu Ser Lys Tyr Lys Asn Ala Glu Glu Ser Pro Glu His Leu Asn Lys
625                 630                 635                 640
Phe Pro Ile Ile Ser Ile Ser Asp Leu Asn Lys Lys Thr Leu Glu Val
                645                 650                 655
Pro Val Asn Val Tyr Phe Thr Asn Ile Asn Glu Asn Asn Asn Ile Met
            660                 665                 670
Glu Thr Tyr Asn Lys Leu Lys Thr Asn Glu His Met Leu Lys Asp Asn
                675                 680                 685
```

```
Met Asp Val Phe Leu Lys Lys Tyr Val Leu Lys Asn Asp Lys His Asn
    690                 695                 700

Thr Asn Asn Asn Asn Asn Asn Asn Asn Met Asp Tyr Ser Phe Thr
705                 710                 715                 720

Glu Thr Lys Tyr Glu Gly Asn Val Pro Ile Leu Val Tyr Glu Met Pro
                725                 730                 735

Thr Thr Gly Ile Val Tyr Leu Gln Phe Val Phe Ser Leu Asp His Leu
            740                 745                 750

Thr Val Asp Glu Leu Ala Tyr Leu Asn Leu Phe Lys Thr Leu Ile Leu
        755                 760                 765

Glu Asn Lys Thr Asn Lys Arg Ser Ser Glu Asp Phe Val Ile Leu Arg
    770                 775                 780

Glu Lys Asn Ile Gly Ser Met Ser Ala Asn Val Ala Leu Tyr Ser Lys
785                 790                 795                 800

Asp Asp His Leu Asn Val Thr Asp Lys Tyr Asn Ala Gln Ala Leu Phe
                805                 810                 815

Asn Leu Glu Met His Val Leu Ser His Lys Cys Asn Asp Ala Leu Asn
            820                 825                 830

Ile Ala Leu Glu Ala Val Lys Glu Ser Asp Phe Ser Asn Lys Lys Lys
        835                 840                 845

Val Ile Asp Ile Leu Lys Arg Lys Ile Asn Gly Met Lys Thr Thr Phe
    850                 855                 860

Ser Glu Lys Gly Tyr Ala Ile Leu Met Lys Tyr Val Lys Ala His Leu
865                 870                 875                 880

Asn Ser Lys His Tyr Ala His Asn Ile Ile Tyr Gly Tyr Glu Asn Tyr
                885                 890                 895

Leu Lys Leu Gln Glu Gln Leu Glu Leu Ala Glu Asn Asp Phe Lys Thr
            900                 905                 910

Leu Glu Asn Ile Leu Val Arg Ile Arg Asn Lys Ile Phe Asn Lys Lys
        915                 920                 925

Asn Leu Met Val Ser Val Thr Ser Asp Tyr Gly Ala Leu Lys His Leu
    930                 935                 940

Phe Val Asn Ser Asn Glu Ser Leu Lys Asn Leu Val Ser Tyr Phe Glu
945                 950                 955                 960

Glu Asn Asp Lys Tyr Ile Asn Asp Met Gln Asn Lys Val Asn Asp Pro
                965                 970                 975

Thr Val Met Gly Trp Asn Glu Glu Ile Lys Ser Lys Lys Leu Phe Asp
            980                 985                 990

Glu Glu Lys Val Lys Lys Glu Phe  Phe Val Leu Pro Thr  Phe Val Asn
        995                 1000                1005

Ser Val Ser Met Ser Gly Ile Leu Phe Lys Pro Gly Glu Tyr Leu
    1010                1015                1020

Asp Pro Ser Phe Thr Val Ile Val Ala Ala Leu Lys Asn Ser Tyr
    1025                1030                1035

Leu Trp Asp Thr Val Arg Gly Leu Asn Gly Ala Tyr Gly Val Phe
    1040                1045                1050

Ala Asp Ile Glu Tyr Asp Gly Ser Val Val Phe Leu Ser Ala Arg
    1055                1060                1065

Asp Pro Asn Leu Glu Lys Thr Leu Ala Thr Phe Arg Glu Ser Ala
    1070                1075                1080

Lys Gly Leu Arg Lys Met Ala Asp Thr Met Thr Glu Asn Asp Leu
    1085                1090                1095
```

-continued

```
Leu Arg Tyr Ile Ile Asn Thr Ile Gly Thr Ile Asp Lys Pro Arg
    1100                1105                1110

Arg Gly Ile Glu Leu Ser Lys Leu Ser Phe Leu Arg Leu Ile Ser
    1115                1120                1125

Asn Glu Ser Glu Gln Asp Arg Val Glu Phe Arg Lys Arg Ile Met
    1130                1135                1140

Asn Thr Lys Lys Glu Asp Phe Tyr Lys Phe Ala Asp Leu Leu Glu
    1145                1150                1155

Ser Lys Val Asn Glu Phe Glu Lys Asn Ile Val Ile Ile Thr Thr
1160                1165                1170

Lys Glu Lys Ala Asn Glu Tyr Ile Ala Asn Val Asp Gly Glu Phe
    1175                1180                1185

Lys Lys Val Leu Ile Glu
    1190

<210> SEQ ID NO 42
<211> LENGTH: 1193
<212> TYPE: PRT
<213> ORGANISM: Plasmodium falciparum
<220> FEATURE:
<221> NAME/KEY: misc_feature
<223> OTHER INFORMATION: Falcilysin

<400> SEQUENCE: 42

Met Asn Leu Thr Lys Leu Met Lys Val Ile Gly Tyr Ile Asn Ile Ile
1               5                   10                  15

Thr Asn Cys Val Gln Ser Phe Thr Asn Arg Ala Asp Lys Lys Arg Tyr
            20                  25                  30

Asn Val Phe Ala Lys Ser Phe Ile Asn Thr Ile Asn Thr Asn Leu Tyr
        35                  40                  45

Thr Phe Lys Ala Val Met Ser Lys Thr Pro Glu Trp Ile His Glu Lys
    50                  55                  60

Ser Pro Lys His Asn Ser Tyr Asp Ile Ile Glu Lys Arg Tyr Asn Glu
65                  70                  75                  80

Glu Phe Lys Met Thr Tyr Thr Val Tyr Gln His Lys Lys Ala Lys Thr
                85                  90                  95

Gln Val Ile Ser Leu Gly Thr Asn Asp Pro Leu Asp Val Glu Gln Ala
            100                 105                 110

Phe Ala Phe Tyr Val Lys Thr Leu Thr His Ser Gly Lys Gly Ile Pro
        115                 120                 125

His Ile Leu Glu His Ser Val Leu Ser Gly Ser Lys Asn Tyr Asn Tyr
    130                 135                 140

Lys Asn Ser Ile Gly Leu Leu Glu Lys Gly Thr Leu His Thr His Leu
145                 150                 155                 160

Asn Ala Tyr Thr Phe Asn Asp Arg Thr Val Tyr Met Ala Gly Ser Met
                165                 170                 175

Asn Asn Lys Asp Phe Phe Asn Ile Met Gly Val Tyr Met Asp Ser Val
            180                 185                 190

Phe Gln Pro Asn Val Leu Glu Asn Lys Tyr Ile Phe Glu Thr Glu Gly
        195                 200                 205

Trp Thr Tyr Glu Val Glu Lys Leu Lys Glu Asp Glu Lys Gly Lys Ala
    210                 215                 220

Glu Ile Pro Gln Met Lys Asp Tyr Lys Val Ser Phe Asn Gly Ile Val
225                 230                 235                 240

Tyr Asn Glu Met Lys Gly Ala Leu Ser Ser Pro Leu Glu Asp Leu Tyr
                245                 250                 255
```

His Glu Glu Met Lys Tyr Met Phe Pro Asp Asn Val His Ser Asn Asn
                260                 265                 270

Ser Gly Gly Asp Pro Lys Glu Ile Thr Asn Leu Thr Tyr Glu Glu Phe
                275                 280                 285

Lys Glu Phe Tyr Tyr Lys Asn Tyr Asn Pro Lys Lys Val Lys Val Phe
290                 295                 300

Phe Phe Ser Lys Asn Asn Pro Thr Glu Leu Leu Asn Phe Val Asp Gln
305                 310                 315                 320

Tyr Leu Gly Gln Leu Asp Tyr Ser Lys Tyr Arg Asp Asp Ala Val Glu
                325                 330                 335

Ser Val Glu Tyr Gln Thr Tyr Lys Lys Gly Pro Phe Tyr Ile Lys Lys
                340                 345                 350

Lys Tyr Gly Asp His Ser Glu Glu Lys Glu Asn Leu Val Ser Val Ala
                355                 360                 365

Trp Leu Leu Asn Pro Lys Val Asp Lys Thr Asn Asn His Asn Asn Asn
                370                 375                 380

His Ser Asn Asn Gln Ser Ser Glu Asn Asn Gly Tyr Ser Asn Gly Ser
385                 390                 395                 400

His Ser Ser Asp Leu Ser Leu Glu Asn Pro Thr Asp Tyr Phe Val Leu
                405                 410                 415

Leu Ile Ile Asn Asn Leu Leu Ile His Thr Pro Glu Ser Val Leu Tyr
                420                 425                 430

Lys Ala Leu Thr Asp Cys Gly Leu Gly Asn Asn Val Ile Asp Arg Gly
                435                 440                 445

Leu Asn Asp Ser Leu Val Gln Tyr Ile Phe Ser Ile Gly Leu Lys Gly
                450                 455                 460

Ile Lys Arg Asn Asn Glu Lys Ile Lys Asn Phe Asp Lys Val His Tyr
465                 470                 475                 480

Glu Val Glu Asp Val Ile Met Asn Ala Leu Lys Lys Val Val Lys Glu
                485                 490                 495

Gly Phe Asn Lys Ser Ala Val Glu Ala Ser Ile Asn Asn Ile Glu Phe
                500                 505                 510

Ile Leu Lys Glu Ala Asn Leu Lys Thr Ser Lys Ser Ile Asp Phe Val
                515                 520                 525

Phe Glu Met Thr Ser Lys Leu Asn Tyr Asn Arg Asp Pro Leu Leu Ile
                530                 535                 540

Phe Glu Phe Glu Lys Tyr Leu Asn Ile Val Lys Asn Lys Ile Lys Asn
545                 550                 555                 560

Glu Pro Met Tyr Leu Glu Lys Phe Val Glu Lys His Phe Ile Asn Asn
                565                 570                 575

Ala His Arg Ser Val Ile Leu Leu Glu Gly Asp Glu Asn Tyr Ala Gln
                580                 585                 590

Glu Gln Glu Asn Leu Glu Lys Gln Glu Leu Lys Lys Arg Ile Glu Asn
                595                 600                 605

Phe Asn Glu Gln Glu Lys Glu Gln Val Ile Lys Asn Phe Glu Glu Leu
                610                 615                 620

Ser Lys Tyr Lys Asn Ala Glu Glu Ser Pro Glu His Leu Asn Lys Phe
625                 630                 635                 640

Pro Ile Ile Ser Ile Ser Asp Leu Asn Lys Lys Thr Leu Glu Val Pro
                645                 650                 655

Val Asn Val Tyr Phe Thr Asn Ile Asn Glu Asn Asn Ile Met Glu
                660                 665                 670

```
Thr Tyr Asn Lys Leu Lys Thr Asn Glu His Met Leu Lys Asp Asn Met
            675                 680                 685

Asp Val Phe Leu Lys Lys Tyr Val Leu Lys Asn Asp Lys His Asn Thr
690                 695                 700

Asn Asn Asn Asn Asn Asn Asn Asn Met Asp Tyr Ser Phe Thr Glu
705                 710                 715                 720

Thr Lys Tyr Glu Gly Asn Val Pro Ile Leu Val Tyr Glu Met Pro Thr
                725                 730                 735

Thr Gly Ile Val Tyr Leu Gln Phe Phe Ser Leu Asp His Leu Thr
                740                 745                 750

Val Asp Glu Leu Ala Tyr Leu Asn Leu Phe Lys Thr Leu Ile Leu Glu
            755                 760                 765

Asn Lys Thr Asn Lys Arg Ser Ser Glu Asp Phe Val Ile Leu Arg Glu
            770                 775                 780

Lys Asn Ile Gly Ser Met Ser Ala Asn Val Ala Leu Tyr Ser Lys Asp
785                 790                 795                 800

Asp His Leu Asn Val Thr Asp Lys Tyr Asn Ala Gln Ala Leu Phe Asn
                805                 810                 815

Leu Glu Met His Val Leu Ser His Lys Cys Asn Asp Ala Leu Asn Ile
                820                 825                 830

Ala Leu Glu Ala Val Lys Glu Ser Asp Phe Ser Asn Lys Lys Lys Val
                835                 840                 845

Ile Asp Ile Leu Lys Arg Lys Ile Asn Gly Met Lys Thr Thr Phe Ser
            850                 855                 860

Glu Lys Gly Tyr Ala Ile Leu Met Lys Tyr Val Lys Ala His Leu Asn
865                 870                 875                 880

Ser Lys His Tyr Ala His Asn Ile Ile Tyr Gly Tyr Glu Asn Tyr Leu
                885                 890                 895

Lys Leu Gln Glu Gln Leu Glu Leu Ala Glu Asn Asp Phe Lys Thr Leu
                900                 905                 910

Glu Asn Ile Leu Val Arg Ile Arg Asn Lys Ile Phe Asn Lys Lys Asn
            915                 920                 925

Leu Met Val Ser Val Thr Ser Asp Tyr Gly Ala Leu Lys His Leu Phe
930                 935                 940

Val Asn Ser Asn Glu Ser Leu Lys Asn Leu Val Ser Tyr Phe Glu Glu
945                 950                 955                 960

Asn Asp Lys Tyr Ile Asn Asp Met Gln Asn Lys Val Asn Asp Pro Thr
                965                 970                 975

Val Met Gly Trp Asn Glu Glu Ile Lys Ser Lys Lys Leu Phe Asp Glu
            980                 985                 990

Glu Lys Val Lys Lys Glu Phe Phe  Val Leu Pro Thr Phe  Val Asn Ser
            995                 1000                1005

Val Ser  Met Ser Gly Ile Leu  Phe Lys Pro Gly Glu  Tyr Leu Asp
    1010                1015                1020

Pro Ser  Phe Thr Val Ile Val  Ala Ala Leu Lys Asn  Ser Tyr Leu
    1025                1030                1035

Trp Asp  Thr Val Arg Gly Leu  Asn Gly Ala Tyr Gly  Val Phe Ala
    1040                1045                1050

Asp Ile  Glu Tyr Asp Gly Ser  Val Val Phe Leu Ser  Ala Arg Asp
    1055                1060                1065

Pro Asn  Leu Glu Lys Thr Leu  Ala Thr Phe Arg Glu  Ser Ala Lys
    1070                1075                1080

Gly Leu  Arg Lys Met Ala Asp  Thr Met Thr Glu Asn  Asp Leu Leu
```

Arg Tyr Ile Ile Asn Thr Ile Gly Thr Ile Asp Lys Pro Arg Arg
1100                1105                1110

Gly Ile Glu Leu Ser Lys Leu Ser Phe Leu Arg Leu Ile Ser Asn
1115                1120                1125

Glu Ser Glu Gln Asp Arg Val Glu Phe Arg Lys Arg Ile Met Asn
1130                1135                1140

Thr Lys Lys Glu Asp Phe Tyr Lys Phe Ala Asp Leu Leu Glu Ser
1145                1150                1155

Lys Val Asn Glu Phe Glu Lys Asn Ile Val Ile Ile Thr Thr Lys
1160                1165                1170

Glu Lys Ala Asn Glu Tyr Ile Ala Asn Val Asp Gly Glu Phe Lys
1175                1180                1185

Lys Val Leu Ile Glu
1190

<210> SEQ ID NO 43
<211> LENGTH: 3471
<212> TYPE: DNA
<213> ORGANISM: Artificial Sequence
<220> FEATURE:
<223> OTHER INFORMATION: PvFalcilysin Human CO

<400> SEQUENCE: 43

```
gccaccatgg ctaaactgat gagggtcttt ggttatctta acataattac taactgcgtt      60
aacggacttc tctgtaaagc ggagaaacgc aaatataacg tctttacgaa cagctttatc     120
tattctatct ctacaacaaa tctgtactcc ttcacggcca tgatgaacaa atcacccgag     180
tgggtgcagg aaaagtgtcc cgagcacaag tcttataaca tccttgaaaa gcggttttct     240
gataaattcc aaatgacgta tacagtgtac gagcacaaaa aagcgaaaac ccaagtcatt     300
gccctcggca gcaatgaccc tctggacgtt gagcagactt tgcctttta cgtaaagacc     360
ctgacgaact caggtaaggg tattcctcac atactcgagc acacagtttt gagcgggagc     420
aaaaatttca attacaaaga tagcatggga ctccctggaaa agggaacact taacacccat     480
ttgaatgcgt atactttcaa cgacaggact gtgtatatgg cggggtctat gaataataga     540
gacttttttca acataatggc ggtgtatatg gatagcgtgt ttcaaccgaa tgttcttgaa     600
aataagttta tcttccaaac ggaaggatgg acctacgaag tggaaaagtt gaaagatgag     660
gagaagaacg ctgatgtacc gaaaattaaa gattataagg tttcctacaa tggtatagtc     720
tattccgaaa tgaagggag cttctcctct cccctgcaat atctttatta tttgatcatg     780
aaaaacatct ccctgacaa cgtccattct aacataagtg gagggaccc taaggagatt     840
ccaacgctca cgtatgagga attcaaagag ttctactata agaattacaa tcctaaaaaa     900
attaaagtca ttttcttcag caaaaacaat cctacagagt tgttgaattt cgtcgacgat     960
tatttgaacc agctcgactt tactaaatac agagacgatg cagtagaaaa cgttaattat    1020
caggagtaca agaagggggcc attctatgtt aagaagaaat ttgcggatca cagtgaggaa    1080
aaggaaaatc ttgtttccat ttcatggctt ctcaacccga aaaaaaatga cctcctggat    1140
gttgatctta gccttgaaag cccccaagac tacttcgctt tgttgattat taacaacctt    1200
ctgacgcaca ccaccgaatc tgtgctttac aaggcgctta ttgactgcgg tttgggtaac    1260
accgttatcg atacaggcct tgacgacagc ctggtacagt tcatattttc tataggtctg    1320
aagggtatca aggaaaagaa tgaaaagaac gtatcattgg acgttgtcca ttatgaagtg    1380
```

```
gaaaaggtgg ttctcaaagc gctccaaaaa gtagtggatg aaggcttcaa caaatcagcg    1440
gtcgaggcca gcattaacaa catagaattc gttttgaaag aagccaatct taaaacgtcc    1500
aaaagcgtgg actacatatt tgaaatggct tccaggctga attataatag agaccctctg    1560
ctgatctttg aattcgagaa gcacttgaac gtcgttaaag ataagatcaa gaatgaacca    1620
aagtatttgg agaaattcat tgagaaacac tttataaaca ataaccatcg ggctgtcatc    1680
ttgatggagg gtgatgaaaa ctatgggaaa gaacaggagg atttggaaaa ggagactttg    1740
aaaaagaaga tcgaatcact cacggaaaaa gaacgggacg acataatagt tgatttcgag    1800
aacctgacaa agtataagaa catggtcgag agccccgaac atttggataa tttttcccatc    1860 atctctatca gcgatctgaa caaagaaacg ctggaaatcc ctgctaatgc atatttcacg    1920
tccacggcag aggaaaataa tatggaaaag tacaataaag tgaaggcaag cgaggatgtt    1980
atgaagaaaa acatggacca cctcatcgac aaatatgttc tgaaaggagc gcaaggaggc    2040
gctgctaccg acggtgcagc caaacagggt gattccagcg atggtgaaat ccccatgctc    2100
gtttacgaga tgcctaccag tggaatcttg tatctgcaat ttatctttaa cctcgatcat    2160
ctgagcctgg aggaaatgtc atatctcaat ctctttaaga tgctcatcct tgagaacaaa    2220
actatgaaac gctcctctga ggagtttgtc attttgaggg aaaagaatat cggcaacata    2280
atggctaacg tcgccttgta tagtatcagc gatcacctca aggtcacttc taaatacaac    2340
gctcacggtc tgttcaattt tgaaatgcat gtattgagtc acaagtgcaa tgagtctttg    2400
gaaattgcct tggaagctct caaggactct gattttagca acaagaagaa aatagtggag    2460
atcctgaaac ggaagatcaa cggcatgaag acggtcttct cttctaaagg ctactcactt    2520
ctcctcaagt atgtaaagtc acaaatgaat gcaaaatact acgctcatga tttggttttt    2580
ggatacggca actatttgaa gttgcaagaa cagctcaagc tcgccgaaag tgactttcca    2640
cagttcgagc agattctcaa cagaatccga ataagatttt tcactaagaa gaatctgctg    2700
atcagcgtga ccagtgacgc tgcagcgttg atcaactgt ttgtgcatag caaggaatcc    2760
ctgaagaacc ttcttgggta tttcgaagag aatgatgcca agtctggaga ggctgagacc    2820
atagggtgga atgaggagat taaacaatca aaagtgatcg aaaaggaaca aaagaagaag    2880
gaattctttg taataccaac atttgtcaat gcagtatcaa tggctggaat gttgtttaat    2940
gagaaggagt tcctggatcc gtctttcata gttatcgtgg ccgcattgaa aaactcatac    3000
ctttgggaga ccgtgagggg actcaacggg gcatatggag ttttttgctga tatagaatac    3060 gatggtgccg tcgtgttctt gtcagcccgc gatccgaatc tggaaaagac gctgcaaacg    3120
ttcaaggagt ctgctcaagg gttgagaaag atggcggata caatgaccaa aaatgaccttt    3180 cggcgctaca taatcaatgc gatcggcaat attgataagc cgagacgggg tgttgagctc    3240
tcaaagctct cacttttgag aattatatct aatgaaacca acaggaccg aatcgactt    3300 cgcaagagga ttatggagac gacgaaggaa gacttctata aattcgctga cttgcttgaa    3360
aagaagattg cagaatttga aaagaatatt gttattatca catctaagga aaaagcctca    3420
gaatacagca ctaacgtaga ccaggatttt aagcagattc atatcgagta g            3471
```

<210> SEQ ID NO 44
<211> LENGTH: 1154
<212> TYPE: PRT
<213> ORGANISM: Plasmodium vivax
<220> FEATURE:
<221> NAME/KEY: misc_feature
<223> OTHER INFORMATION: PvFalcilysin

<400> SEQUENCE: 44

```
Met Ala Lys Leu Met Arg Val Phe Gly Tyr Leu Asn Ile Ile Thr Asn
1               5                   10                  15

Cys Val Asn Gly Leu Leu Cys Lys Ala Glu Lys Arg Lys Tyr Asn Val
            20                  25                  30

Phe Thr Asn Ser Phe Ile Tyr Ser Ile Ser Thr Thr Asn Leu Tyr Ser
        35                  40                  45

Phe Thr Ala Met Met Asn Lys Ser Pro Glu Trp Val Gln Glu Lys Cys
    50                  55                  60

Pro Glu His Lys Ser Tyr Asn Ile Leu Glu Lys Arg Phe Ser Asp Lys
65                  70                  75                  80

Phe Gln Met Thr Tyr Thr Val Tyr Glu His Lys Lys Ala Lys Thr Gln
                85                  90                  95

Val Ile Ala Leu Gly Ser Asn Asp Pro Leu Asp Val Glu Gln Thr Phe
            100                 105                 110

Ala Phe Tyr Val Lys Thr Leu Thr Asn Ser Gly Lys Gly Ile Pro His
        115                 120                 125

Ile Leu Glu His Thr Val Leu Ser Gly Ser Lys Asn Phe Asn Tyr Lys
    130                 135                 140

Asp Ser Met Gly Leu Leu Glu Lys Gly Thr Leu Asn Thr His Leu Asn
145                 150                 155                 160

Ala Tyr Thr Phe Asn Asp Arg Thr Val Tyr Met Ala Gly Ser Met Asn
                165                 170                 175

Asn Arg Asp Phe Phe Asn Ile Met Ala Val Tyr Met Asp Ser Val Phe
            180                 185                 190

Gln Pro Asn Val Leu Glu Asn Lys Phe Ile Phe Gln Thr Glu Gly Trp
        195                 200                 205

Thr Tyr Glu Val Glu Lys Leu Lys Asp Glu Lys Asn Ala Asp Val
    210                 215                 220

Pro Lys Ile Lys Asp Tyr Lys Val Ser Tyr Asn Gly Ile Val Tyr Ser
225                 230                 235                 240

Glu Met Lys Gly Ser Phe Ser Ser Pro Leu Gln Tyr Leu Tyr Tyr Leu
                245                 250                 255

Ile Met Lys Asn Ile Phe Pro Asp Asn Val His Ser Asn Ile Ser Gly
            260                 265                 270

Gly Asp Pro Lys Glu Ile Pro Thr Leu Thr Tyr Glu Glu Phe Lys Glu
        275                 280                 285

Phe Tyr Tyr Lys Asn Tyr Asn Pro Lys Lys Ile Lys Val Ile Phe Phe
    290                 295                 300

Ser Lys Asn Asn Pro Thr Glu Leu Leu Asn Phe Val Asp Asp Tyr Leu
305                 310                 315                 320

Asn Gln Leu Asp Phe Thr Lys Tyr Arg Asp Asp Ala Val Glu Asn Val
                325                 330                 335

Asn Tyr Gln Glu Tyr Lys Lys Gly Pro Phe Tyr Val Lys Lys Lys Phe
            340                 345                 350

Ala Asp His Ser Glu Glu Lys Glu Asn Leu Val Ser Ile Ser Trp Leu
        355                 360                 365

Leu Asn Pro Lys Lys Asn Asp Leu Leu Asp Val Asp Leu Ser Leu Glu
370                 375                 380

Ser Pro Gln Asp Tyr Phe Ala Leu Leu Ile Ile Asn Asn Leu Leu Thr
385                 390                 395                 400

His Thr Thr Glu Ser Val Leu Tyr Lys Ala Leu Ile Asp Cys Gly Leu
                405                 410                 415
```

```
Gly Asn Thr Val Ile Asp Thr Gly Leu Asp Asp Ser Leu Val Gln Phe
                420                 425                 430

Ile Phe Ser Ile Gly Leu Lys Gly Ile Lys Glu Lys Asn Glu Lys Asn
                435                 440                 445

Val Ser Leu Asp Val Val His Tyr Glu Val Lys Val Val Leu Lys
                450                 455                 460

Ala Leu Gln Lys Val Val Asp Glu Gly Phe Asn Lys Ser Ala Val Glu
465                 470                 475                 480

Ala Ser Ile Asn Asn Ile Glu Phe Val Leu Lys Glu Ala Asn Leu Lys
                485                 490                 495

Thr Ser Lys Ser Val Asp Tyr Ile Phe Glu Met Ala Ser Arg Leu Asn
                500                 505                 510

Tyr Asn Arg Asp Pro Leu Leu Ile Phe Glu Phe Glu Lys His Leu Asn
                515                 520                 525

Val Val Lys Asp Lys Ile Lys Asn Glu Pro Lys Tyr Leu Glu Lys Phe
                530                 535                 540

Ile Glu Lys His Phe Ile Asn Asn Asn His Arg Ala Val Ile Leu Met
545                 550                 555                 560

Glu Gly Asp Glu Asn Tyr Gly Lys Glu Gln Glu Asp Leu Glu Lys Glu
                565                 570                 575

Thr Leu Lys Lys Lys Ile Glu Ser Leu Thr Glu Lys Glu Arg Asp Asp
                580                 585                 590

Ile Ile Val Asp Phe Glu Asn Leu Thr Lys Tyr Lys Asn Met Val Glu
                595                 600                 605

Ser Pro Glu His Leu Asp Asn Phe Pro Ile Ile Ser Ile Ser Asp Leu
                610                 615                 620

Asn Lys Glu Thr Leu Glu Ile Pro Ala Asn Ala Tyr Phe Thr Ser Thr
625                 630                 635                 640

Ala Glu Glu Asn Asn Met Glu Lys Tyr Asn Lys Val Lys Ala Ser Glu
                645                 650                 655

Asp Val Met Lys Lys Asn Met Asp His Leu Ile Asp Lys Tyr Val Leu
                660                 665                 670

Lys Gly Ala Gln Gly Gly Ala Ala Thr Asp Gly Ala Ala Lys Gln Gly
                675                 680                 685

Asp Ser Ser Asp Gly Glu Ile Pro Met Leu Val Tyr Glu Met Pro Thr
                690                 695                 700

Ser Gly Ile Leu Tyr Leu Gln Phe Ile Phe Asn Leu Asp His Leu Ser
705                 710                 715                 720

Leu Glu Glu Met Ser Tyr Leu Asn Leu Phe Lys Met Leu Ile Leu Glu
                725                 730                 735

Asn Lys Thr Met Lys Arg Ser Ser Glu Glu Phe Val Ile Leu Arg Glu
                740                 745                 750

Lys Asn Ile Gly Asn Ile Met Ala Asn Val Ala Leu Tyr Ser Ile Ser
                755                 760                 765

Asp His Leu Lys Val Thr Ser Lys Tyr Asn Ala His Gly Leu Phe Asn
                770                 775                 780

Phe Glu Met His Val Leu Ser His Lys Cys Asn Glu Ser Leu Glu Ile
785                 790                 795                 800

Ala Leu Glu Ala Leu Lys Asp Ser Asp Phe Ser Asn Lys Lys Ile
                805                 810                 815

Val Glu Ile Leu Lys Arg Lys Ile Asn Gly Met Lys Thr Val Phe Ser
                820                 825                 830
```

```
Ser Lys Gly Tyr Ser Leu Leu Lys Tyr Val Lys Ser Gln Met Asn
        835                 840                 845

Ala Lys Tyr Tyr Ala His Asp Leu Val Phe Gly Tyr Gly Asn Tyr Leu
850                 855                 860

Lys Leu Gln Glu Gln Leu Lys Leu Ala Glu Ser Asp Phe Pro Gln Phe
865                 870                 875                 880

Glu Gln Ile Leu Asn Arg Ile Arg Asn Lys Ile Phe Thr Lys Lys Asn
                885                 890                 895

Leu Leu Ile Ser Val Thr Ser Asp Ala Ala Leu Asp Gln Leu Phe
            900                 905                 910

Val His Ser Lys Glu Ser Leu Lys Asn Leu Gly Tyr Phe Glu Glu
            915                 920                 925

Asn Asp Ala Lys Ser Gly Glu Ala Glu Thr Ile Gly Trp Asn Glu Glu
        930                 935                 940

Ile Lys Gln Ser Lys Val Ile Glu Lys Glu Gln Lys Lys Lys Glu Phe
945                 950                 955                 960

Phe Val Ile Pro Thr Phe Val Asn Ala Val Ser Met Ala Gly Met Leu
                965                 970                 975

Phe Asn Glu Lys Glu Phe Leu Asp Pro Ser Phe Ile Val Ile Val Ala
            980                 985                 990

Ala Leu Lys Asn Ser Tyr Leu Trp Glu Thr Val Arg Gly Leu Asn Gly
        995                 1000                1005

Ala Tyr Gly Val Phe Ala Asp Ile Glu Tyr Asp Gly Ala Val Val
        1010                1015                1020

Phe Leu Ser Ala Arg Asp Pro Asn Leu Glu Lys Thr Leu Gln Thr
        1025                1030                1035

Phe Lys Glu Ser Ala Gln Gly Leu Arg Lys Met Ala Asp Thr Met
        1040                1045                1050

Thr Lys Asn Asp Leu Arg Arg Tyr Ile Ile Asn Ala Ile Gly Asn
        1055                1060                1065

Ile Asp Lys Pro Arg Arg Gly Val Glu Leu Ser Lys Leu Ser Leu
        1070                1075                1080

Leu Arg Ile Ile Ser Asn Glu Thr Lys Gln Asp Arg Ile Asp Phe
        1085                1090                1095

Arg Lys Arg Ile Met Glu Thr Thr Lys Glu Asp Phe Tyr Lys Phe
        1100                1105                1110

Ala Asp Leu Leu Glu Lys Lys Ile Ala Glu Phe Glu Lys Asn Ile
        1115                1120                1125

Val Ile Ile Thr Ser Lys Glu Lys Ala Ser Glu Tyr Ser Thr Asn
        1130                1135                1140

Val Asp Gln Asp Phe Lys Gln Ile His Ile Glu
        1145                1150

<210> SEQ ID NO 45
<211> LENGTH: 1153
<212> TYPE: PRT
<213> ORGANISM: Plasmodium vivax
<220> FEATURE:
<221> NAME/KEY: misc_feature
<223> OTHER INFORMATION: Falcilysin

<400> SEQUENCE: 45

Met Lys Leu Met Arg Val Phe Gly Tyr Leu Asn Ile Ile Thr Asn Cys
1               5                   10                  15

Val Asn Gly Leu Leu Cys Lys Ala Glu Lys Arg Lys Tyr Asn Val Phe
                20                  25                  30
```

-continued

```
Thr Asn Ser Phe Ile Tyr Ser Ile Ser Thr Asn Leu Tyr Ser Phe
        35                  40                  45

Thr Ala Met Met Asn Lys Ser Pro Glu Trp Val Gln Glu Lys Cys Pro
 50                  55                  60

Glu His Lys Ser Tyr Asn Ile Leu Glu Lys Arg Phe Ser Asp Lys Phe
 65                  70                  75                  80

Gln Met Thr Tyr Thr Val Tyr Glu His Lys Lys Ala Lys Thr Gln Val
                 85                  90                  95

Ile Ala Leu Gly Ser Asn Asp Pro Leu Asp Val Glu Gln Thr Phe Ala
                100                 105                 110

Phe Tyr Val Lys Thr Leu Thr Asn Ser Gly Lys Gly Ile Pro His Ile
                115                 120                 125

Leu Glu His Thr Val Leu Ser Gly Ser Lys Asn Phe Asn Tyr Lys Asp
                130                 135                 140

Ser Met Gly Leu Leu Glu Lys Gly Thr Leu Asn Thr His Leu Asn Ala
145                 150                 155                 160

Tyr Thr Phe Asn Asp Arg Thr Val Tyr Met Ala Gly Ser Met Asn Asn
                    165                 170                 175

Arg Asp Phe Phe Asn Ile Met Ala Val Tyr Met Asp Ser Val Phe Gln
                180                 185                 190

Pro Asn Val Leu Glu Asn Lys Phe Ile Phe Gln Thr Glu Gly Trp Thr
                195                 200                 205

Tyr Glu Val Glu Lys Leu Lys Asp Glu Glu Lys Asn Ala Asp Val Pro
210                 215                 220

Lys Ile Lys Asp Tyr Lys Val Ser Tyr Asn Gly Ile Val Tyr Ser Glu
225                 230                 235                 240

Met Lys Gly Ser Phe Ser Ser Pro Leu Gln Tyr Leu Tyr Tyr Leu Ile
                245                 250                 255

Met Lys Asn Ile Phe Pro Asp Asn Val His Ser Asn Ile Ser Gly Gly
                260                 265                 270

Asp Pro Lys Glu Ile Pro Thr Leu Thr Tyr Glu Glu Phe Lys Glu Phe
                275                 280                 285

Tyr Tyr Lys Asn Tyr Asn Pro Lys Lys Ile Lys Val Ile Phe Phe Ser
                290                 295                 300

Lys Asn Asn Pro Thr Glu Leu Leu Asn Phe Val Asp Asp Tyr Leu Asn
305                 310                 315                 320

Gln Leu Asp Phe Thr Lys Tyr Arg Asp Asp Ala Val Glu Asn Val Asn
                325                 330                 335

Tyr Gln Glu Tyr Lys Lys Gly Pro Phe Tyr Val Lys Lys Lys Phe Ala
                340                 345                 350

Asp His Ser Glu Glu Lys Glu Asn Leu Val Ser Ile Ser Trp Leu Leu
                355                 360                 365

Asn Pro Lys Lys Asn Asp Leu Leu Asp Val Asp Leu Ser Leu Glu Ser
370                 375                 380

Pro Gln Asp Tyr Phe Ala Leu Leu Ile Ile Asn Asn Leu Leu Thr His
385                 390                 395                 400

Thr Thr Glu Ser Val Leu Tyr Lys Ala Leu Ile Asp Cys Gly Leu Gly
                405                 410                 415

Asn Thr Val Ile Asp Thr Gly Leu Asp Asp Ser Leu Val Gln Phe Ile
                420                 425                 430

Phe Ser Ile Gly Leu Lys Gly Ile Lys Glu Lys Asn Glu Lys Asn Val
                435                 440                 445
```

```
Ser Leu Asp Val Val His Tyr Glu Val Glu Lys Val Leu Lys Ala
450                 455                 460

Leu Gln Lys Val Val Asp Glu Gly Phe Asn Lys Ser Ala Val Glu Ala
465                 470                 475                 480

Ser Ile Asn Asn Ile Glu Phe Val Leu Lys Glu Ala Asn Leu Lys Thr
                485                 490                 495

Ser Lys Ser Val Asp Tyr Ile Phe Glu Met Ala Ser Arg Leu Asn Tyr
            500                 505                 510

Asn Arg Asp Pro Leu Leu Ile Phe Glu Phe Lys His Leu Asn Val
        515                 520                 525

Val Lys Asp Lys Ile Lys Asn Glu Pro Lys Tyr Leu Glu Lys Phe Ile
530                 535                 540

Glu Lys His Phe Ile Asn Asn Asn His Arg Ala Val Ile Leu Met Glu
545                 550                 555                 560

Gly Asp Glu Asn Tyr Gly Lys Glu Gln Glu Asp Leu Glu Lys Glu Thr
                565                 570                 575

Leu Lys Lys Lys Ile Glu Ser Leu Thr Glu Lys Glu Arg Asp Asp Ile
            580                 585                 590

Ile Val Asp Phe Glu Asn Leu Thr Lys Tyr Lys Asn Met Val Glu Ser
        595                 600                 605

Pro Glu His Leu Asp Asn Phe Pro Ile Ile Ser Ile Ser Asp Leu Asn
    610                 615                 620

Lys Glu Thr Leu Glu Ile Pro Ala Asn Ala Tyr Phe Thr Ser Thr Ala
625                 630                 635                 640

Glu Glu Asn Asn Met Glu Lys Tyr Asn Lys Val Lys Ala Ser Glu Asp
                645                 650                 655

Val Met Lys Lys Asn Met Asp His Leu Ile Asp Lys Tyr Val Leu Lys
            660                 665                 670

Gly Ala Gln Gly Gly Ala Ala Thr Asp Gly Ala Ala Lys Gln Gly Asp
        675                 680                 685

Ser Ser Asp Gly Glu Ile Pro Met Leu Val Tyr Glu Met Pro Thr Ser
    690                 695                 700

Gly Ile Leu Tyr Leu Gln Phe Ile Phe Asn Leu Asp His Leu Ser Leu
705                 710                 715                 720

Glu Glu Met Ser Tyr Leu Asn Leu Phe Lys Met Leu Ile Leu Glu Asn
                725                 730                 735

Lys Thr Met Lys Arg Ser Ser Glu Glu Phe Val Ile Leu Arg Glu Lys
            740                 745                 750

Asn Ile Gly Asn Ile Met Ala Asn Val Ala Leu Tyr Ser Ile Ser Asp
        755                 760                 765

His Leu Lys Val Thr Ser Lys Tyr Asn Ala His Gly Leu Phe Asn Phe
    770                 775                 780

Glu Met His Val Leu Ser His Lys Cys Asn Glu Ser Leu Glu Ile Ala
785                 790                 795                 800

Leu Glu Ala Leu Lys Asp Ser Asp Phe Ser Asn Lys Lys Ile Val
                805                 810                 815

Glu Ile Leu Lys Arg Lys Ile Asn Gly Met Lys Thr Val Phe Ser Ser
            820                 825                 830

Lys Gly Tyr Ser Leu Leu Lys Tyr Val Lys Ser Gln Met Asn Ala
        835                 840                 845

Lys Tyr Tyr Ala His Asp Leu Val Phe Gly Tyr Gly Asn Tyr Leu Lys
    850                 855                 860

Leu Gln Glu Gln Leu Lys Leu Ala Glu Ser Asp Phe Pro Gln Phe Glu
```

```
           865              870              875              880
       Gln Ile Leu Asn Arg Ile Arg Asn Lys Ile Phe Thr Lys Lys Asn Leu
                         885              890              895
       Leu Ile Ser Val Thr Ser Asp Ala Ala Ala Leu Asp Gln Leu Phe Val
                     900              905              910
       His Ser Lys Glu Ser Leu Lys Asn Leu Leu Gly Tyr Phe Glu Glu Asn
                     915              920              925
       Asp Ala Lys Ser Gly Glu Ala Glu Thr Ile Gly Trp Asn Glu Ile
                     930              935              940
       Lys Gln Ser Lys Val Ile Glu Lys Glu Gln Lys Lys Glu Phe Phe
       945              950              955              960
       Val Ile Pro Thr Phe Val Asn Ala Val Ser Met Ala Gly Met Leu Phe
                         965              970              975
       Asn Glu Lys Glu Phe Leu Asp Pro Ser Phe Ile Val Ile Val Ala Ala
                     980              985              990
       Leu Lys Asn Ser Tyr Leu Trp Glu Thr Val Arg Gly Leu Asn Gly Ala
                     995             1000             1005
       Tyr Gly Val Phe Ala Asp Ile Glu Tyr Asp Gly Ala Val Val Phe
                    1010             1015             1020
       Leu Ser Ala Arg Asp Pro Asn Leu Glu Lys Thr Leu Gln Thr Phe
                    1025             1030             1035
       Lys Glu Ser Ala Gln Gly Leu Arg Lys Met Ala Asp Thr Met Thr
                    1040             1045             1050
       Lys Asn Asp Leu Arg Arg Tyr Ile Ile Asn Ala Ile Gly Asn Ile
                    1055             1060             1065
       Asp Lys Pro Arg Arg Gly Val Glu Leu Ser Lys Leu Ser Leu Leu
                    1070             1075             1080
       Arg Ile Ile Ser Asn Glu Thr Lys Gln Asp Arg Ile Asp Phe Arg
                    1085             1090             1095
       Lys Arg Ile Met Glu Thr Thr Lys Glu Asp Phe Tyr Lys Phe Ala
                    1100             1105             1110
       Asp Leu Leu Glu Lys Lys Ile Ala Glu Phe Glu Lys Asn Ile Val
                    1115             1120             1125
       Ile Ile Thr Ser Lys Glu Lys Ala Ser Glu Tyr Ser Thr Asn Val
                    1130             1135             1140
       Asp Gln Asp Phe Lys Gln Ile His Ile Glu
                    1145             1150

<210> SEQ ID NO 46
<211> LENGTH: 1227
<212> TYPE: DNA
<213> ORGANISM: Artificial Sequence
<220> FEATURE:
<223> OTHER INFORMATION: Falcilysin, Bergheilysin-B-CO

<400> SEQUENCE: 46
ggatccgcca ccatggctaa actcatgaag gtcttggggt atatcaacat catcacgaat      60
tgcgtgaatg gcatactgtg taaaggcgat aagaagcgat acatgcacat gctctcccat     120
aagtgtaacg acgctctgga gattgcgctg gaagccctga agaaagcga tttcagcaat     180 aagaagaaag tgattgaaat cctgaagagg aaaatcaatg gcatgaaaac cacgtttgcc     240
agcaaaggtc actcaatact gattaagtac gtgaagtctc ggattaatag caaatattac     300
gcttatgacc tgattcatgg gtatgacaac tatctgaagc tccaggaaca gcttaaactg     360
gcggagacaa actacgagag tctggaagcc atacttaatc gcatcaggaa gagatctttt     420
```

-continued

```
aagcggaaca atctgatcat gaacgtgact gtcgatccag gaactattga tcagctgttt    480
gccaaatcca agaatagctt caacaacctt ctgtcatact ttgacgagaa cgagagctac    540
tgctctaaga atgactcctt caacaaagtg gtaggctgga acaaggagat tcaggagaag    600
aagctgcttg aaggagagga ggtcaagaaa gagctcttgg tcgtacccac atttgtgaac    660
agtgtctcta tgagtggagt gctgttcaac aaaggcgaat atcttgaccc ctcattcacc    720
gtaatcgttg cagccttgaa aaactcatac ctttgggaga cagttcgagg actgaatgga    780
gcttatgggg tgtttgccga catagagtat gacggtactg tcgttttcct gagtgcaaga    840
gatccgaatc tggaaaagac tctccaaacc tttcgtgaag cagcacaagg tctgcgtaaa    900
atggctgatg tgatgacaaa gaatgatctt ctgcggtata tcattaacgc tattgggacc    960
atcgatagac ctcgcagagg cgttgagttg tccaagctgt ccttctctcg cataataagc   1020
aacgaaaccg aacaggacag gattgaattc aggaaccggg tgatgaatac caagaaagag   1080
gatttctaca aatttgcgga tttgctcgaa aagaaagtca aggaatttga gaagaatgtg   1140
gtgatcatca catctaagga gaaagccaac gagtacatca acaatgttga caatgacttc   1200
aagaagatcc tcattgagta actcgag                                       1227
```

<210> SEQ ID NO 47
<211> LENGTH: 402
<212> TYPE: PRT
<213> ORGANISM: Plasmodium Berghei
<220> FEATURE:
<221> NAME/KEY: misc_feature
<223> OTHER INFORMATION: Falcilysin, Bergheilysin-B

<400> SEQUENCE: 47

```
Met Ala Lys Leu Met Lys Val Leu Gly Tyr Ile Asn Ile Ile Thr Asn
1               5                   10                  15

Cys Val Asn Gly Ile Leu Cys Lys Gly Asp Lys Lys Arg Tyr Met His
            20                  25                  30

Met Leu Ser His Lys Cys Asn Asp Ala Leu Glu Ile Ala Leu Glu Ala
        35                  40                  45

Leu Lys Glu Ser Asp Phe Ser Asn Lys Lys Val Ile Glu Ile Leu
    50                  55                  60

Lys Arg Lys Ile Asn Gly Met Lys Thr Thr Phe Ala Ser Lys Gly His
65                  70                  75                  80

Ser Ile Leu Ile Lys Tyr Val Lys Ser Arg Ile Asn Ser Lys Tyr Tyr
                85                  90                  95

Ala Tyr Asp Leu Ile His Gly Tyr Asp Asn Tyr Leu Lys Leu Gln Glu
            100                 105                 110

Gln Leu Lys Leu Ala Glu Thr Asn Tyr Glu Ser Leu Glu Ala Ile Leu
        115                 120                 125

Asn Arg Ile Arg Lys Lys Ile Phe Lys Arg Asn Asn Leu Ile Met Asn
    130                 135                 140

Val Thr Val Asp Pro Gly Thr Ile Asp Gln Leu Phe Ala Lys Ser Lys
145                 150                 155                 160

Asn Ser Phe Asn Asn Leu Leu Ser Tyr Phe Asp Glu Asn Glu Ser Tyr
                165                 170                 175

Cys Ser Lys Asn Asp Ser Phe Asn Lys Val Val Gly Trp Asn Lys Glu
            180                 185                 190

Ile Gln Glu Lys Lys Leu Leu Glu Gly Glu Val Lys Lys Glu Leu
        195                 200                 205
```

```
Leu Val Val Pro Thr Phe Val Asn Ser Val Ser Met Ser Gly Val Leu
210                 215                 220

Phe Asn Lys Gly Glu Tyr Leu Asp Pro Ser Phe Thr Val Ile Val Ala
225                 230                 235                 240

Ala Leu Lys Asn Ser Tyr Leu Trp Glu Thr Val Arg Gly Leu Asn Gly
                245                 250                 255

Ala Tyr Gly Val Phe Ala Asp Ile Glu Tyr Asp Gly Thr Val Val Phe
                260                 265                 270

Leu Ser Ala Arg Asp Pro Asn Leu Glu Lys Thr Leu Gln Thr Phe Arg
                275                 280                 285

Glu Ala Ala Gln Gly Leu Arg Lys Met Ala Asp Val Met Thr Lys Asn
290                 295                 300

Asp Leu Leu Arg Tyr Ile Ile Asn Ala Ile Gly Thr Ile Asp Arg Pro
305                 310                 315                 320

Arg Arg Gly Val Glu Leu Ser Lys Leu Ser Phe Ser Arg Ile Ile Ser
                325                 330                 335

Asn Glu Thr Glu Gln Asp Arg Ile Glu Phe Arg Asn Arg Val Met Asn
                340                 345                 350

Thr Lys Lys Glu Asp Phe Tyr Lys Phe Ala Asp Leu Leu Glu Lys Lys
                355                 360                 365

Val Lys Glu Phe Glu Lys Asn Val Val Ile Ile Thr Ser Lys Glu Lys
370                 375                 380

Ala Asn Glu Tyr Ile Asn Asn Val Asp Asn Asp Phe Lys Lys Ile Leu
385                 390                 395                 400

Ile Glu

<210> SEQ ID NO 48
<211> LENGTH: 2454
<212> TYPE: DNA
<213> ORGANISM: Plasmodium Berghei
<220> FEATURE:
<221> NAME/KEY: misc_feature
<223> OTHER INFORMATION: perforin like protein 1 (SPECT2)

<400> SEQUENCE: 48
ggatccgcca ccatggctaa gatgcggaac attaagaaat cacttccggt gctcttcatt     60
ctcttgtgca tttatcagca gtactttata aactctctcc gtatttccgt ccgcaacaat    120
aagaaccaca gggatgaaaa caaattcaac aagaatatgg agcttggtac gatggagaaa    180
cccatcaaca ttctttgcaa tgacgtcagc tgtaacacag agaataacat ttctttcgta    240
aaccagaaga aaaaggaaat agatagtgac agcgaccctc tataacatgtt cgatgacgac    300 gcctctacct ccgctggtga tgacgaagat gactatgacg actacacaga tgataagaac    360
gctgagatca agatgaaga gcaaaatgag cacatcgaca agatcgacca agaagaggat    420
aagaaacgca cattctctat caataagcag gaggaagaaa tcaacgaaaa taaaaacaaa    480
acggagaaat tcttcaagaa atacaagttt aacgacgcca actcagaagg ggacgacgat    540
gagtcagaca ccgatgacga gaatttggac aactccacgg agaacagcta cgaggaaaac    600
aagaatcccg agaacgttat cgacaagcat atggccgtat tcctgggct ctattttgtg    660 gggatcggct acgatattct gttcgggaat cctctcggag aaaccgattc tctgagcgac    720
cctggttata gagcacagat ttacctgttg aattgggaat tctcaaacca tggcatcgcc    780
aacgatctgc acacgctcca accaattaat gcctggattc ggaaagagaa tgcatgctca    840
cgagttgaat ccatcaacga atgttcctct gttagtgagt atacaaagaa tctgtcagtg    900
```

| | |
|---|---|
| gacgtaagtg tatcaggcag ctatatgggc ttcggcagtt tctccgctag cactgggtac | 960 |
| aagaaattca ttaacgagat aagcaagaga acatccaaga cctactttat aaagagcaac | 1020 |
| tgcatcaagt ataccatcgg acttccacct tatgtgccat gggagcatac cactgcttac | 1080 |
| atgaatgcgg tgaatattct gccaaaggaa tttaccggcc tggatggaga cagcgaatgc | 1140 |
| acaccggatg tttacgagca gaagaagatg actaaacagt gtaagaacgt gcaactgtgg | 1200 |
| attcagttct ttaagaccta tggtacacac ataatcgtgg aggctcaatt gggagggaaa | 1260 |
| ataaccaaaa tcatcaatgt ctctaacaca agcgtgaacc agatgaagaa ggatggcgtc | 1320 |
| agtgtgaaag cccagatcca ggctcagttt ggttttgcaa gtgtgggcgg tagtacaagc | 1380 |
| gtgtcaagtg acaatagcac taagaacgac aatagcagct acgacatgtc tgagaaactc | 1440 |
| gtggttatcg gagggaatcc tataaaagac gtcaccaaag aggagaatct gtacgaatgg | 1500 |
| agcaaaacag tgtcctctaa ccccatgcct atccacatca agctgctgcc aatctataag | 1560 |
| tccttcgata gtgaggaact gaaagagtct tacgagaaag cggttctcta ctacaccagg | 1620 |
| ctttatggca gctctcccca cggaactatt cagaaagatg agaacgacat catcaaaatc | 1680 |
| ttgacggcca gtaccaccat cactaaaatt ggtgctccac ccataacagc ggaatgtcca | 1740 |
| cataatcaag tggtgctgtt tgggtatgtc ctgaagcaga acttctggga caacacctcc | 1800 |
| aacctgaagg gatacgacat tgagatctgt gaggctggac tgaatagttg cacgtccaaa | 1860 |
| cagggaagta caaacaagta cgatgtgagc tatctgtaca ttgaatgtgg cacacaggca | 1920 |
| atgtcattct ccgatcaagt cataaccgca tccaacacta cttacaatac catcaagtgt | 1980 |
| cccaatgact acactattat ctttggattc gggttttcct ctagctccgg taagggagtt | 2040 |
| tctgccatgc acacccacat tacatcctgt agacccggca tgaaaagctg ctccctgaat | 2100 |
| atgggcaaca gcaatgacaa gaactacatg tacctggtgt gcgtcgatgc cacaatctgg | 2160 |
| tctggcatta atgagctgac tattgtggcc aaagatgatt tcacggcgc agtgaatagg | 2220 |
| tctaagcagt tcaatgatgg cgaattggta ctgtcctgtc aggaaaatgg cactatcctg | 2280 |
| acagggttca ctggggagac tcataccct agcccgtatg tcaagagccc ttttagcaag | 2340 |
| tgtcttaaat cactgaagag ctgctcagtc catgggagtg acaatctat cggatatacc | 2400 |
| aactataagt cactgttttc catcatactg tgcaagaacg gtgagtgact cgag | 2454 |

<210> SEQ ID NO 49
<211> LENGTH: 811
<212> TYPE: PRT
<213> ORGANISM: Plasmodium Berghei
<220> FEATURE:
<221> NAME/KEY: misc_feature
<223> OTHER INFORMATION: perforin like protein 1 (SPECT2)

<400> SEQUENCE: 49

```
Met Ala Lys Met Arg Asn Ile Lys Lys Ser Leu Pro Val Leu Phe Ile
1               5                   10                  15

Leu Leu Cys Ile Tyr Gln Gln Tyr Phe Ile Asn Ser Leu Arg Ile Ser
            20                  25                  30

Val Arg Asn Asn Lys Asn His Arg Asp Glu Asn Lys Phe Asn Lys Asn
        35                  40                  45

Met Glu Leu Gly Thr Met Glu Lys Pro Ile Asn Ile Leu Cys Asn Asp
    50                  55                  60

Val Ser Cys Asn Thr Glu Asn Asn Ile Ser Phe Val Asn Gln Lys Lys
65                  70                  75                  80

Lys Glu Ile Asp Ser Asp Ser Asp Leu Tyr Asn Met Phe Asp Asp Asp
```

```
                85                  90                  95
Ala Ser Thr Ser Ala Gly Asp Asp Glu Asp Asp Tyr Asp Asp Tyr Thr
                100                 105                 110
Asp Asp Lys Asn Ala Glu Ile Lys Asp Glu Glu Gln Asn Glu His Ile
                115                 120                 125
Asp Lys Ile Asp Gln Lys Lys Asp Lys Lys Arg Thr Phe Ser Ile Asn
                130                 135                 140
Lys Gln Glu Glu Glu Ile Asn Glu Asn Lys Asn Lys Thr Glu Lys Phe
145                 150                 155                 160
Phe Lys Lys Tyr Lys Phe Asn Asp Ala Asn Ser Glu Gly Asp Asp Asp
                165                 170                 175
Glu Ser Asp Thr Asp Asp Glu Asn Leu Asp Asn Ser Thr Glu Asn Ser
                180                 185                 190
Tyr Glu Glu Asn Lys Asn Pro Glu Asn Val Ile Asp Lys His Met Ala
                195                 200                 205
Val Phe Pro Gly Leu Tyr Phe Val Gly Ile Gly Tyr Asp Ile Leu Phe
                210                 215                 220
Gly Asn Pro Leu Gly Glu Thr Asp Ser Leu Ser Asp Pro Gly Tyr Arg
225                 230                 235                 240
Ala Gln Ile Tyr Leu Leu Asn Trp Glu Phe Ser Asn His Gly Ile Ala
                245                 250                 255
Asn Asp Leu His Thr Leu Gln Pro Ile Asn Ala Trp Ile Arg Lys Glu
                260                 265                 270
Asn Ala Cys Ser Arg Val Glu Ser Ile Asn Glu Cys Ser Ser Val Ser
                275                 280                 285
Glu Tyr Thr Lys Asn Leu Ser Val Asp Val Ser Val Ser Gly Ser Tyr
                290                 295                 300
Met Gly Phe Gly Ser Phe Ser Ala Ser Thr Gly Tyr Lys Lys Phe Ile
305                 310                 315                 320
Asn Glu Ile Ser Lys Arg Thr Ser Lys Thr Tyr Phe Ile Lys Ser Asn
                325                 330                 335
Cys Ile Lys Tyr Thr Ile Gly Leu Pro Pro Tyr Val Pro Trp Glu His
                340                 345                 350
Thr Thr Ala Tyr Met Asn Ala Val Asn Ile Leu Pro Lys Glu Phe Thr
                355                 360                 365
Gly Leu Asp Gly Asp Ser Glu Cys Thr Pro Asp Val Tyr Glu Gln Lys
                370                 375                 380
Lys Met Thr Lys Gln Cys Lys Asn Val Gln Leu Trp Ile Gln Phe Phe
385                 390                 395                 400
Lys Thr Tyr Gly Thr His Ile Ile Val Glu Ala Gln Leu Gly Gly Lys
                405                 410                 415
Ile Thr Lys Ile Ile Asn Val Ser Thr Ser Val Asn Gln Met Lys
                420                 425                 430
Lys Asp Gly Val Ser Val Lys Ala Gln Ile Gln Ala Gln Phe Gly Phe
                435                 440                 445
Ala Ser Val Gly Gly Ser Thr Ser Val Ser Ser Asp Asn Ser Thr Lys
                450                 455                 460
Asn Asp Asn Ser Ser Tyr Asp Met Ser Glu Lys Leu Val Val Ile Gly
465                 470                 475                 480
Gly Asn Pro Ile Lys Asp Val Thr Lys Glu Glu Asn Leu Tyr Glu Trp
                485                 490                 495
Ser Lys Thr Val Ser Ser Asn Pro Met Pro Ile His Ile Lys Leu Leu
                500                 505                 510
```

```
Pro Ile Tyr Lys Ser Phe Asp Ser Glu Glu Leu Lys Glu Ser Tyr Glu
            515                 520                 525

Lys Ala Val Leu Tyr Tyr Thr Arg Leu Tyr Gly Ser Ser Pro His Gly
    530                 535                 540

Thr Ile Gln Lys Asp Glu Asn Asp Ile Ile Lys Ile Leu Thr Ala Ser
545                 550                 555                 560

Thr Thr Ile Thr Lys Ile Gly Ala Pro Pro Ile Thr Ala Glu Cys Pro
                565                 570                 575

His Asn Gln Val Val Leu Phe Gly Tyr Val Leu Lys Gln Asn Phe Trp
            580                 585                 590

Asp Asn Thr Ser Asn Leu Lys Gly Tyr Asp Ile Glu Ile Cys Glu Ala
            595                 600                 605

Gly Leu Asn Ser Cys Thr Ser Lys Gln Gly Ser Thr Asn Lys Tyr Asp
        610                 615                 620

Val Ser Tyr Leu Tyr Ile Glu Cys Gly Thr Gln Ala Met Ser Phe Ser
625                 630                 635                 640

Asp Gln Val Ile Thr Ala Ser Asn Thr Thr Tyr Asn Thr Ile Lys Cys
                645                 650                 655

Pro Asn Asp Tyr Thr Ile Ile Phe Gly Phe Gly Phe Ser Ser Ser Ser
            660                 665                 670

Gly Lys Gly Val Ser Ala Met His Thr His Ile Thr Ser Cys Arg Pro
        675                 680                 685

Gly Met Lys Ser Cys Ser Leu Asn Met Gly Asn Ser Asn Asp Lys Asn
    690                 695                 700

Tyr Met Tyr Leu Val Cys Val Asp Ala Thr Ile Trp Ser Gly Ile Asn
705                 710                 715                 720

Glu Leu Thr Ile Val Ala Lys Asp Asp Phe His Gly Ala Val Asn Arg
                725                 730                 735

Ser Lys Gln Phe Asn Asp Gly Glu Leu Val Leu Ser Cys Gln Glu Asn
            740                 745                 750

Gly Thr Ile Leu Thr Gly Phe Thr Gly Glu Thr His Thr Ser Ser Pro
        755                 760                 765

Tyr Val Lys Ser Pro Phe Ser Lys Cys Leu Lys Ser Leu Lys Ser Cys
    770                 775                 780

Ser Val His Gly Ser Gly Gln Ser Ile Gly Tyr Thr Asn Tyr Lys Ser
785                 790                 795                 800

Leu Phe Ser Ile Ile Leu Cys Lys Asn Gly Glu
                805                 810

<210> SEQ ID NO 50
<211> LENGTH: 810
<212> TYPE: PRT
<213> ORGANISM: Plasmodium berghei
<220> FEATURE:
<221> NAME/KEY: misc_feature
<223> OTHER INFORMATION: SPECT2

<400> SEQUENCE: 50

Met Lys Met Arg Asn Ile Lys Lys Ser Leu Pro Val Leu Phe Ile Leu
1               5                   10                  15

Leu Cys Ile Tyr Gln Gln Tyr Phe Ile Asn Ser Leu Arg Ile Ser Val
                20                  25                  30

Arg Asn Asn Lys Asn His Arg Asp Glu Asn Lys Phe Asn Lys Asn Met
            35                  40                  45

Glu Leu Gly Thr Met Glu Lys Pro Ile Asn Ile Leu Cys Asn Asp Val
```

```
           50                  55                  60
Ser Cys Asn Thr Glu Asn Asn Ile Ser Phe Val Asn Gln Lys Lys Lys
 65                  70                  75                  80

Glu Ile Asp Ser Asp Ser Asp Leu Tyr Asn Met Phe Asp Asp Asp Ala
                 85                  90                  95

Ser Thr Ser Ala Gly Asp Asp Glu Asp Tyr Asp Asp Tyr Thr Asp
                100                 105                 110

Asp Lys Asn Ala Glu Ile Lys Asp Glu Glu Gln Asn Glu His Ile Asp
                115                 120                 125

Lys Ile Asp Gln Lys Lys Asp Lys Lys Arg Thr Phe Ser Ile Asn Lys
            130                 135                 140

Gln Glu Glu Glu Ile Asn Glu Asn Lys Asn Lys Thr Glu Lys Phe Phe
145                 150                 155                 160

Lys Lys Tyr Lys Phe Asn Asp Ala Asn Ser Glu Gly Asp Asp Asp Glu
                165                 170                 175

Ser Asp Thr Asp Asp Glu Asn Leu Asp Asn Ser Thr Glu Asn Ser Tyr
                180                 185                 190

Glu Glu Asn Lys Asn Pro Glu Asn Val Ile Asp Lys His Met Ala Val
            195                 200                 205

Phe Pro Gly Leu Tyr Phe Val Gly Ile Gly Tyr Asp Ile Leu Phe Gly
210                 215                 220

Asn Pro Leu Gly Glu Thr Asp Ser Leu Ser Asp Pro Gly Tyr Arg Ala
225                 230                 235                 240

Gln Ile Tyr Leu Leu Asn Trp Glu Phe Ser Asn His Gly Ile Ala Asn
                245                 250                 255

Asp Leu His Thr Leu Gln Pro Ile Asn Ala Trp Ile Arg Lys Glu Asn
                260                 265                 270

Ala Cys Ser Arg Val Glu Ser Ile Asn Glu Cys Ser Ser Val Ser Glu
            275                 280                 285

Tyr Thr Lys Asn Leu Ser Val Asp Val Ser Val Ser Gly Ser Tyr Met
            290                 295                 300

Gly Phe Gly Ser Phe Ser Ala Ser Thr Gly Tyr Lys Lys Phe Ile Asn
305                 310                 315                 320

Glu Ile Ser Lys Arg Thr Ser Lys Thr Tyr Phe Ile Lys Ser Asn Cys
                325                 330                 335

Ile Lys Tyr Thr Ile Gly Leu Pro Pro Tyr Val Pro Trp Glu His Thr
            340                 345                 350

Thr Ala Tyr Met Asn Ala Val Asn Ile Leu Pro Lys Glu Phe Thr Gly
            355                 360                 365

Leu Asp Gly Asp Ser Glu Cys Thr Pro Asp Val Tyr Glu Gln Lys Lys
            370                 375                 380

Met Thr Lys Gln Cys Lys Asn Val Gln Leu Trp Ile Gln Phe Phe Lys
385                 390                 395                 400

Thr Tyr Gly Thr His Ile Ile Val Glu Ala Gln Leu Gly Gly Lys Ile
                405                 410                 415

Thr Lys Ile Ile Asn Val Ser Asn Thr Ser Val Asn Gln Met Lys Lys
            420                 425                 430

Asp Gly Val Ser Val Lys Ala Gln Ile Gln Ala Gln Phe Gly Phe Ala
            435                 440                 445

Ser Val Gly Gly Ser Thr Ser Val Ser Ser Asp Asn Ser Thr Lys Asn
            450                 455                 460

Asp Asn Ser Ser Tyr Asp Met Ser Glu Lys Leu Val Val Ile Gly Gly
465                 470                 475                 480
```

Asn Pro Ile Lys Asp Val Thr Lys Glu Glu Asn Leu Tyr Glu Trp Ser
            485                 490                 495

Lys Thr Val Ser Ser Asn Pro Met Pro Ile His Ile Lys Leu Leu Pro
        500                 505                 510

Ile Tyr Lys Ser Phe Asp Ser Glu Glu Leu Lys Glu Ser Tyr Glu Lys
            515                 520                 525

Ala Val Leu Tyr Tyr Thr Arg Leu Tyr Gly Ser Ser Pro His Gly Thr
    530                 535                 540

Ile Gln Lys Asp Glu Asn Asp Ile Ile Lys Ile Leu Thr Ala Ser Thr
545                 550                 555                 560

Thr Ile Thr Lys Ile Gly Ala Pro Pro Ile Thr Ala Glu Cys Pro His
            565                 570                 575

Asn Gln Val Val Leu Phe Gly Tyr Val Leu Lys Gln Asn Phe Trp Asp
        580                 585                 590

Asn Thr Ser Asn Leu Lys Gly Tyr Asp Ile Glu Ile Cys Glu Ala Gly
            595                 600                 605

Leu Asn Ser Cys Thr Ser Lys Gln Gly Ser Thr Asn Lys Tyr Asp Val
    610                 615                 620

Ser Tyr Leu Tyr Ile Glu Cys Gly Thr Gln Ala Met Ser Phe Ser Asp
625                 630                 635                 640

Gln Val Ile Thr Ala Ser Asn Thr Thr Tyr Asn Thr Ile Lys Cys Pro
            645                 650                 655

Asn Asp Tyr Thr Ile Ile Phe Gly Phe Gly Phe Ser Ser Ser Ser Gly
        660                 665                 670

Lys Gly Val Ser Ala Met His Thr His Ile Thr Ser Cys Arg Pro Gly
            675                 680                 685

Met Lys Ser Cys Ser Leu Asn Met Gly Asn Ser Asn Asp Lys Asn Tyr
    690                 695                 700

Met Tyr Leu Val Cys Val Asp Ala Thr Ile Trp Ser Gly Ile Asn Glu
705                 710                 715                 720

Leu Thr Ile Val Ala Lys Asp Asp Phe His Gly Ala Val Asn Arg Ser
            725                 730                 735

Lys Gln Phe Asn Asp Gly Glu Leu Val Leu Ser Cys Gln Glu Asn Gly
        740                 745                 750

Thr Ile Leu Thr Gly Phe Thr Gly Glu Thr His Thr Ser Ser Pro Tyr
    755                 760                 765

Val Lys Ser Pro Phe Ser Lys Cys Leu Lys Ser Leu Lys Ser Cys Ser
770                 775                 780

Val His Gly Ser Gly Gln Ser Ile Gly Tyr Thr Asn Tyr Lys Ser Leu
785                 790                 795                 800

Phe Ser Ile Ile Leu Cys Lys Asn Gly Glu
            805                 810

<210> SEQ ID NO 51
<211> LENGTH: 2538
<212> TYPE: DNA
<213> ORGANISM: Artificial Sequence
<220> FEATURE:
<223> OTHER INFORMATION: PfSPECT2 human CO

<400> SEQUENCE: 51
gccaccatgg ctaagctgag aatcctcaag aagcactatt atgtcgtgtt tatccttctg      60
tatctgtatg acatcagctg cttcaagtgc attcggctga acaaccgttc catctacaag     120
aacaagtaca agaataacgt gcacatagga accaatgaga atatcaggag tattgagaag     180

-continued

```
tatagcaacg tgctgtgtaa cagcatcttg tgtaagaacg ataaaatctc tagcttcatt      240
aaccagagga agaatgtgga tgacgacgat gagtctgaga acgatgacat gtacgagagc      300
accacagctg gctcttctag tgaaacggac aacgagagcg atgaagaaga gaatgacagc      360
agtgacaaca ataatagcga tgaggaacag atagagaact ccaacaacaa taattctgac      420
gaggaacaga atgactcctc ttccaacgac aataatgatg aggagaatga ggaacaggac      480
gacgtcatgg acaatgacca aaacgataag aagatcaagc atagcttcaa tctcgccaac      540
gagagtaaac acactaaaga ggaacgagtg aaagaagaga aaagctgaa gatctatgac       600 ttcataaacg acaaggagaa aagacttaac tttaatggcg atcagaaaga tgaagataac      660
gaggagaacg atgataaaga tgagaacacg cttgagaatc ggaatatcat ctccaaacac      720
acttcagtgt ttcctggcct gtacttcatc gggattgggt ataacctcct cttcgggaac      780
cccttgggtg aagctgattc ccttatcgat ccaggttatc gggcgcaaat ttacctgatg      840
gaatgggctc tcagcaagga aggcattgcc aacgacctga gcactctgca acccgtgaat      900
ggatggatac gaaaggagaa tgcctgctcc agagttgaat ctattacaga atgcagctct      960
atatctgact acaccaaatc cctgtcagcg gaggcaaagg ttagtggctc ttattgggga      1020
atcgcctcct tctcagcatc caccgggtat agctcttttc tccacgaggt gacaaaacgc      1080
agcaagaaaa ccttcctcgt gaaatccaac tgtgtgaaat acactatcgg gcttcctccc      1140
tatattccct gggacaagac cacggcctac aagaatgccg taaatgaact gccagctgta      1200
tttaccggtt tggataaaga atccgaatgt ccctctgatg tgtacgaaga gaacaagaca      1260
aaatcaaact gcgagaacgt gagtctgtgg atgaagttct tcgacattta tggcactcac      1320
atcatttatg aaagtcaatt gggaggaaag ataacaaaga ttatcaatgt ttccacctca      1380
agtattgagc agatgaagaa aaatggagtc tcagtcaaag cgaaaattca agcacagttt      1440
gggtttggtt cagccggtgg ctcaaccgac gtgaatagca gtaactcctc cgcaaatgat      1500
gagcagtctt acgacatgaa tgaacagctg atcgtcatag gagggaatcc gatcaaagac      1560
gtcaccaagg aggagaatct gtttgagtgg tctaaaactg tgacaaacca tcctatgccg      1620
atcaacatta aactgactcc cattagcgac agttttgact cagacgacct gaaagaatcc      1680
tatgataaag ccatcatcta ctattctcgc ctgtacggac tgtcccctca tgacacaatg      1740
cagaaggatg acaaggatat tatcaagatc ctgaccaacg ctgatacggt taccaagaac      1800
tcagctcctc caatcaacgc tcagtgtcct catgggaaag tcgttatgtt cggattcagc      1860
ctgaagcaga atttctggga caacaccaac gcactcaaag gatacaacat cgaagtctgc      1920
gaagcaggga gcaattcttg cactagcaaa caagggagca gcaataaata cgatacatct      1980
tacctttaca tggaatgtgg cgatcagcca ttgccctta gcgagcaggt gattagcgag      2040
agtacaagta cctataatac cgtgaaatgt ccgaatgatt actccattct cctgggcttc      2100
ggaatatcaa gtagctcagg gaggataaat agcgctgaat atgtctacag cacaccatgt      2160
attcccggca tgaagtcctg cagcctcaat atgaataatg acaaccagaa gtcatacatc      2220
tacgtgctgt gtgtagatac tacgatctgg agtggcgtga acaacctgag cctggttgcc      2280
cttgatggcg cacatggtaa ggtaaaccgc agtaagaagt actccgacgg tgaactggtt      2340
ggcacctgtc cactggacgg cacagtcctg actggattta aggttgagtt tcacacttca      2400
tctccatatg tgcagacacc tttcgagaaa tgcgccaaaa gcttgaaagc ctgctccgta      2460
catggctccg gtcacgccat tggcattcag aactttaagt cactgttcat atacatgttg      2520
```
tgcaagaaca ataagtaa                                           2538

<210> SEQ ID NO 52
<211> LENGTH: 843
<212> TYPE: PRT
<213> ORGANISM: Plasmodium falciparum
<220> FEATURE:
<221> NAME/KEY: misc_feature
<223> OTHER INFORMATION: PfSPECT2

<400> SEQUENCE: 52

```
Met Ala Lys Leu Arg Ile Leu Lys Lys His Tyr Tyr Val Val Phe Ile
1               5                   10                  15

Leu Leu Tyr Leu Tyr Asp Ile Ser Cys Phe Lys Cys Ile Arg Leu Asn
            20                  25                  30

Asn Arg Ser Ile Tyr Lys Asn Lys Tyr Lys Asn Val His Ile Gly
        35                  40                  45

Thr Asn Glu Asn Ile Arg Ser Ile Glu Lys Tyr Ser Asn Val Leu Cys
    50                  55                  60

Asn Ser Ile Leu Cys Lys Asn Asp Lys Ile Ser Ser Phe Ile Asn Gln
65                  70                  75                  80

Arg Lys Asn Val Asp Asp Asp Glu Ser Glu Asn Asp Asp Met Tyr
                85                  90                  95

Glu Ser Thr Thr Ala Gly Ser Ser Ser Glu Thr Asp Asn Glu Ser Asp
            100                 105                 110

Glu Glu Glu Asn Asp Ser Ser Asp Asn Asn Asn Ser Asp Glu Glu Gln
        115                 120                 125

Ile Glu Asn Ser Asn Asn Asn Ser Asp Glu Glu Gln Asn Asp Ser
    130                 135                 140

Ser Ser Asn Asp Asn Asn Asp Glu Glu Asn Glu Glu Gln Asp Asp Val
145                 150                 155                 160

Met Asp Asn Asp Gln Asn Asp Lys Lys Ile Lys His Ser Phe Asn Leu
                165                 170                 175

Ala Asn Glu Ser Lys His Thr Lys Glu Glu Arg Val Lys Glu Lys
            180                 185                 190

Lys Leu Lys Ile Tyr Asp Phe Ile Asn Asp Lys Glu Lys Arg Leu Asn
        195                 200                 205

Phe Asn Gly Asp Gln Lys Asp Glu Asp Asn Glu Glu Asn Asp Asp Lys
    210                 215                 220

Asp Glu Asn Thr Leu Glu Asn Arg Asn Ile Ile Ser Lys His Thr Ser
225                 230                 235                 240

Val Phe Pro Gly Leu Tyr Phe Ile Gly Ile Gly Tyr Asn Leu Leu Phe
                245                 250                 255

Gly Asn Pro Leu Gly Glu Ala Asp Ser Leu Ile Asp Pro Gly Tyr Arg
            260                 265                 270

Ala Gln Ile Tyr Leu Met Glu Trp Ala Leu Ser Lys Glu Gly Ile Ala
        275                 280                 285

Asn Asp Leu Ser Thr Leu Gln Pro Val Asn Gly Trp Ile Arg Lys Glu
    290                 295                 300

Asn Ala Cys Ser Arg Val Glu Ser Ile Thr Glu Cys Ser Ser Ile Ser
305                 310                 315                 320

Asp Tyr Thr Lys Ser Leu Ser Ala Glu Ala Lys Val Ser Gly Ser Tyr
                325                 330                 335

Trp Gly Ile Ala Ser Phe Ser Ala Ser Thr Gly Tyr Ser Ser Phe Leu
            340                 345                 350
```

```
His Glu Val Thr Lys Arg Ser Lys Lys Thr Phe Leu Val Lys Ser Asn
            355                 360                 365

Cys Val Lys Tyr Thr Ile Gly Leu Pro Pro Tyr Ile Pro Trp Asp Lys
    370                 375                 380

Thr Thr Ala Tyr Lys Asn Ala Val Asn Glu Leu Pro Ala Val Phe Thr
385                 390                 395                 400

Gly Leu Asp Lys Glu Ser Glu Cys Pro Ser Asp Val Tyr Glu Glu Asn
                405                 410                 415

Lys Thr Lys Ser Asn Cys Glu Asn Val Ser Leu Trp Met Lys Phe Phe
                420                 425                 430

Asp Ile Tyr Gly Thr His Ile Ile Tyr Glu Ser Gln Leu Gly Gly Lys
            435                 440                 445

Ile Thr Lys Ile Ile Asn Val Ser Thr Ser Ser Ile Glu Gln Met Lys
        450                 455                 460

Lys Asn Gly Val Ser Val Lys Ala Lys Ile Gln Ala Gln Phe Gly Phe
465                 470                 475                 480

Gly Ser Ala Gly Gly Ser Thr Asp Val Asn Ser Ser Asn Ser Ser Ala
                485                 490                 495

Asn Asp Glu Gln Ser Tyr Asp Met Asn Glu Gln Leu Ile Val Ile Gly
                500                 505                 510

Gly Asn Pro Ile Lys Asp Val Thr Lys Glu Glu Asn Leu Phe Glu Trp
            515                 520                 525

Ser Lys Thr Val Thr Asn His Pro Met Pro Ile Asn Ile Lys Leu Thr
        530                 535                 540

Pro Ile Ser Asp Ser Phe Asp Ser Asp Asp Leu Lys Glu Ser Tyr Asp
545                 550                 555                 560

Lys Ala Ile Ile Tyr Tyr Ser Arg Leu Tyr Gly Leu Ser Pro His Asp
                565                 570                 575

Thr Met Gln Lys Asp Asp Lys Asp Ile Ile Lys Ile Leu Thr Asn Ala
                580                 585                 590

Asp Thr Val Thr Lys Asn Ser Ala Pro Pro Ile Asn Ala Gln Cys Pro
            595                 600                 605

His Gly Lys Val Val Met Phe Gly Phe Ser Leu Lys Gln Asn Phe Trp
        610                 615                 620

Asp Asn Thr Asn Ala Leu Lys Gly Tyr Asn Ile Glu Val Cys Glu Ala
625                 630                 635                 640

Gly Ser Asn Ser Cys Thr Ser Lys Gln Gly Ser Ser Asn Lys Tyr Asp
                645                 650                 655

Thr Ser Tyr Leu Tyr Met Glu Cys Gly Asp Gln Pro Leu Pro Phe Ser
                660                 665                 670

Glu Gln Val Ile Ser Glu Ser Thr Ser Thr Tyr Asn Thr Val Lys Cys
            675                 680                 685

Pro Asn Asp Tyr Ser Ile Leu Leu Gly Phe Gly Ile Ser Ser Ser Ser
        690                 695                 700

Gly Arg Ile Asn Ser Ala Glu Tyr Val Tyr Ser Thr Pro Cys Ile Pro
705                 710                 715                 720

Gly Met Lys Ser Cys Ser Leu Asn Met Asn Asn Asp Asn Gln Lys Ser
                725                 730                 735

Tyr Ile Tyr Val Leu Cys Val Asp Thr Thr Ile Trp Ser Gly Val Asn
                740                 745                 750

Asn Leu Ser Leu Val Ala Leu Asp Gly Ala His Gly Lys Val Asn Arg
            755                 760                 765

Ser Lys Lys Tyr Ser Asp Gly Glu Leu Val Gly Thr Cys Pro Leu Asp
```

```
                            770                 775                 780
Gly Thr Val Leu Thr Gly Phe Lys Val Glu Phe His Thr Ser Ser Pro
785                 790                 795                 800

Tyr Val Gln Thr Pro Phe Glu Lys Cys Ala Lys Ser Leu Lys Ala Cys
                805                 810                 815

Ser Val His Gly Ser Gly His Ala Ile Gly Ile Gln Asn Phe Lys Ser
                820                 825                 830

Leu Phe Ile Tyr Met Leu Cys Lys Asn Asn Lys
            835                 840

<210> SEQ ID NO 53
<211> LENGTH: 842
<212> TYPE: PRT
<213> ORGANISM: Plasmodium falciparum
<220> FEATURE:
<221> NAME/KEY: misc_feature
<223> OTHER INFORMATION: SPECT2

<400> SEQUENCE: 53

Met Lys Leu Arg Ile Leu Lys Lys His Tyr Tyr Val Val Phe Ile Leu
1               5                   10                  15

Leu Tyr Leu Tyr Asp Ile Ser Cys Phe Lys Cys Ile Arg Leu Asn Asn
            20                  25                  30

Arg Ser Ile Tyr Lys Asn Lys Tyr Lys Asn Asn Val His Ile Gly Thr
        35                  40                  45

Asn Glu Asn Ile Arg Ser Ile Glu Lys Tyr Ser Asn Val Leu Cys Asn
    50                  55                  60

Ser Ile Leu Cys Lys Asn Asp Lys Ile Ser Ser Phe Ile Asn Gln Arg
65                  70                  75                  80

Lys Asn Val Asp Asp Asp Asp Glu Ser Glu Asn Asp Asp Met Tyr Glu
                85                  90                  95

Ser Thr Thr Ala Gly Ser Ser Ser Glu Thr Asp Asn Glu Ser Asp Glu
            100                 105                 110

Glu Glu Asn Asp Ser Ser Asp Asn Asn Asn Ser Asp Glu Glu Gln Ile
        115                 120                 125

Glu Asn Ser Asn Asn Asn Ser Asp Glu Glu Gln Asn Asp Ser Ser
    130                 135                 140

Ser Asn Asp Asn Asn Asp Glu Glu Asn Glu Glu Gln Asp Asp Val Met
145                 150                 155                 160

Asp Asn Asp Gln Asn Asp Lys Lys Ile Lys His Ser Phe Asn Leu Ala
                165                 170                 175

Asn Glu Ser Lys His Thr Lys Glu Glu Arg Val Lys Glu Glu Lys Lys
            180                 185                 190

Leu Lys Ile Tyr Asp Phe Ile Asn Asp Lys Lys Arg Leu Asn Phe
        195                 200                 205

Asn Gly Asp Gln Lys Asp Glu Asp Asn Glu Asn Asp Asp Lys Asp
    210                 215                 220

Glu Asn Thr Leu Glu Asn Arg Asn Ile Ile Ser Lys His Thr Ser Val
225                 230                 235                 240

Phe Pro Gly Leu Tyr Phe Ile Gly Ile Gly Tyr Asn Leu Leu Phe Gly
                245                 250                 255

Asn Pro Leu Gly Glu Ala Asp Ser Leu Ile Asp Pro Gly Tyr Arg Ala
            260                 265                 270

Gln Ile Tyr Leu Met Glu Trp Ala Leu Ser Lys Glu Gly Ile Ala Asn
        275                 280                 285
```

-continued

```
Asp Leu Ser Thr Leu Gln Pro Val Asn Gly Trp Ile Arg Lys Glu Asn
    290                 295                 300
Ala Cys Ser Arg Val Glu Ser Ile Thr Glu Cys Ser Ser Ile Ser Asp
305                 310                 315                 320
Tyr Thr Lys Ser Leu Ser Ala Glu Ala Lys Val Ser Gly Ser Tyr Trp
                325                 330                 335
Gly Ile Ala Ser Phe Ser Ala Ser Thr Gly Tyr Ser Ser Phe Leu His
                340                 345                 350
Glu Val Thr Lys Arg Ser Lys Lys Thr Phe Leu Val Lys Ser Asn Cys
            355                 360                 365
Val Lys Tyr Thr Ile Gly Leu Pro Pro Tyr Ile Pro Trp Asp Lys Thr
    370                 375                 380
Thr Ala Tyr Lys Asn Ala Val Asn Glu Leu Pro Ala Val Phe Thr Gly
385                 390                 395                 400
Leu Asp Lys Glu Ser Glu Cys Pro Ser Asp Val Tyr Glu Glu Asn Lys
                405                 410                 415
Thr Lys Ser Asn Cys Glu Asn Val Ser Leu Trp Met Lys Phe Phe Asp
                420                 425                 430
Ile Tyr Gly Thr His Ile Ile Tyr Glu Ser Gln Leu Gly Gly Lys Ile
            435                 440                 445
Thr Lys Ile Ile Asn Val Ser Thr Ser Ser Ile Glu Gln Met Lys Lys
    450                 455                 460
Asn Gly Val Ser Val Lys Ala Lys Ile Gln Ala Gln Phe Gly Phe Gly
465                 470                 475                 480
Ser Ala Gly Gly Ser Thr Asp Val Asn Ser Ser Asn Ser Ser Ala Asn
                485                 490                 495
Asp Glu Gln Ser Tyr Asp Met Asn Glu Gln Leu Ile Val Ile Gly Gly
            500                 505                 510
Asn Pro Ile Lys Asp Val Thr Lys Glu Glu Asn Leu Phe Glu Trp Ser
    515                 520                 525
Lys Thr Val Thr Asn His Pro Met Pro Ile Asn Ile Lys Leu Thr Pro
530                 535                 540
Ile Ser Asp Ser Phe Asp Ser Asp Leu Lys Glu Ser Tyr Asp Lys
545                 550                 555                 560
Ala Ile Ile Tyr Tyr Ser Arg Leu Tyr Gly Leu Ser Pro His Asp Thr
                565                 570                 575
Met Gln Lys Asp Asp Lys Asp Ile Ile Lys Ile Leu Thr Asn Ala Asp
            580                 585                 590
Thr Val Thr Lys Asn Ser Ala Pro Pro Ile Asn Ala Gln Cys Pro His
    595                 600                 605
Gly Lys Val Val Met Phe Gly Phe Ser Leu Lys Gln Asn Phe Trp Asp
610                 615                 620
Asn Thr Asn Ala Leu Lys Gly Tyr Asn Ile Glu Val Cys Glu Ala Gly
625                 630                 635                 640
Ser Asn Ser Cys Thr Ser Lys Gln Gly Ser Asn Lys Tyr Asp Thr
                645                 650                 655
Ser Tyr Leu Tyr Met Glu Cys Gly Asp Gln Pro Leu Pro Phe Ser Glu
                660                 665                 670
Gln Val Ile Ser Glu Ser Thr Thr Tyr Asn Thr Val Lys Cys Pro
            675                 680                 685
Asn Asp Tyr Ser Ile Leu Leu Gly Phe Gly Ile Ser Ser Ser Ser Gly
    690                 695                 700
Arg Ile Asn Ser Ala Glu Tyr Val Tyr Ser Thr Pro Cys Ile Pro Gly
```

```
                705                  710                 715                 720
Met Lys Ser Cys Ser Leu Asn Met Asn Asp Asn Gln Lys Ser Tyr
                     725                 730                 735

Ile Tyr Val Leu Cys Val Asp Thr Thr Ile Trp Ser Gly Val Asn Asn
                 740                 745                 750

Leu Ser Leu Val Ala Leu Asp Gly Ala His Gly Lys Val Asn Arg Ser
             755                 760                 765

Lys Lys Tyr Ser Asp Gly Glu Leu Val Gly Thr Cys Pro Leu Asp Gly
         770                 775                 780

Thr Val Leu Thr Gly Phe Lys Val Glu Phe His Thr Ser Ser Pro Tyr
785                 790                 795                 800

Val Gln Thr Pro Phe Glu Lys Cys Ala Lys Ser Leu Lys Ala Cys Ser
                     805                 810                 815

Val His Gly Ser Gly His Ala Ile Gly Ile Gln Asn Phe Lys Ser Leu
                 820                 825                 830

Phe Ile Tyr Met Leu Cys Lys Asn Asn Lys
             835                 840
```

<210> SEQ ID NO 54
<211> LENGTH: 2541
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<223> OTHER INFORMATION: PvSPECT2 human CO

<400> SEQUENCE: 54

```
gccaccatgg ctaagccaag aaatataaac tctctgttgg ccatatggtg tattctcttc    60
tcaatctgtg agtacggcta tgtgggatct ttgagaatag gtcttcggag aaactatagt   120 caagggggact cctctgatcg gctcgggggt agtgacgtgg acgtgagacg gtccggcgag   180
cttatggacc tcggtaagaa cgcaaacatc ctctgcaata acatcagctg taacagtaaa   240
aaagaggctt cttttctgag tcagaaaaaa caacttgagg atgacgatga cgacgagctg   300
gccgcgctgt acaatgatga tgatgacgat gctagcacaa ccactggggg gggttcagaa   360
actagcgatg acgacgagct tgaactccct gatcaggacg aaggtgcgga cgagggtgaa   420
gcagaggacc aactcgcgac acaggaggat tccgacaact cagggaccga ccaaggtctg   480
aaaaaaaaag taaaccttag ccgccacgaa agttgatag aagacaaaaa acaacagaca   540
gagaatactt ttaagaagta caggtttggg gatgaggagg aagagtcaga ggagaaatcc   600
ccggggaaat ctaagtcact cgatccaagc agcctcgatg atgacgacgg cgaaggtgat   660
gatgatgatg atggcgacga gagagaaaag aagcaaagta atacaaggaa agccatgaag   720
aaggacttgg atgttttccc agggctttac tttgcaggca tcggatacga tagcctcttc   780
ggaaaccccc tggcgaggc tgacagcttg accgatcccg ggtaccgggg ccaaatcata   840
ctcatgaact gggaactctc aaataaggga gttgcgaatg atcttgcgac attgcaacct   900
ctgaatggat ggatccgcaa ggaaaatgcg tgcagtcgag cagaatctat aaaagagtgt   960
tcttcagtat cagactacac gaaaaatttg accgcagagg catctgtatc tggctcctac  1020
atgggctttg gagcttttag tgctagtact ggttataaga aattttttgca agaagccagt  1080 aaacgcacgt ccaaaactta tctggtaaaa agcaattgcg tgaaatacac ggtcgggctc  1140
cctccttatg tgcgctggga gcagacgacc gcctttaaga acgctgtgaa cgggttgcca  1200
```

| | | |
|---|---|---|
| ccgcatttca ccggactgga ggccgactct gaatgcgcct ctgatgtcta cgaacaaaag | 1260 | |
| aagacatctg aagaatgcga accgtacat gcctggatac gcttttttaa gacttatgga | 1320 | |
| acacacgtga tcatggaagc acagcttggc ggcaaaataa caaagattat ccgggtcgag | 1380 | |
| aatagctccg tcaatcaaat gaagaaagac ggagtcagcg tgaaagccca gatcaaagcc | 1440 | |
| caattcggct ttgcatctgt gggggggaagc acaaacgtct ctagtgacca tagttcaaaa | 1500 | |
| aagaacgagg ataattatga gatgtctgag cagctggtag tgattggagg caacccaatc | 1560 | |
| aaggatgtga cgaaagaaga aaatctctat gagtggtcta aaacggtctc aacaaatccg | 1620 | |
| atgcctatca atatcaagct cctgccgatt agcactatct ttgactccga cgatctgaaa | 1680 | |
| aatagttacg aaaaggcatt gatctactac actcgcttgt atggctttc accccatgat | 1740 | |
| acaatgcaaa aagatgaaaa ggatattgtt aagatcctga cggccagcac cacagtcaca | 1800 | |
| aagacaggcc cgccgcctat atctgcagag tgtccgcata atatggtggt cttgttcggt | 1860 | |
| ttcgtagtca aacagaattt ttgggatcat acgaacaaac tccagagtta tgaaatggag | 1920 | |
| atttgtgaaa gcggtgccag ctcatgcacg tctaagcagg aaatacaaa taagtatgac | 1980 | |
| gtatcctata cgtatattga gtgcggacca caggcattgc cgttcactga gcaggttgta | 2040 | |
| tctgtatccg gtacaacata taactctgtt aaatgcccga atgactacag cgtgttgttt | 2100 | |
| ggctttggaa tggctacgag ttctggcagg caccaaagtg cgctttatag ctatttcaca | 2160 | |
| ccatgtcgac cagggctcaa aagctgtagc ttgaatatga cgaacatga tgataagtct | 2220 | |
| tacatttacc tggtctgcgt cgacgcgact atctggacgg gacttaacgc gttgagcatg | 2280 | |
| atcgcgaaag acgatttgca cagtgccgtg aaccggtacc aacaattcaa tgatggagag | 2340 | |
| ctggttgtga cgtgtcctag cgagggcact atactgactg gattctatgg ggagacccat | 2400 | |
| acctccagtc catatgttac tgtaccttt gggaaatgcg caaagtcatt gaaagcctgt | 2460 | |
| tctgttcatg ggtccggcca agccataggc attacaatt atagaacttt gttcacagtc | 2520 | |
| gcactgtgta agaataatta g | 2541 | |

<210> SEQ ID NO 55
<211> LENGTH: 844
<212> TYPE: PRT
<213> ORGANISM: Plasmodium vivax
<220> FEATURE:
<221> NAME/KEY: misc_feature
<223> OTHER INFORMATION: PvSPECT2

<400> SEQUENCE: 55

Met Ala Lys Pro Arg Asn Ile Asn Ser Leu Leu Ala Ile Trp Cys Ile
1               5                   10                  15

Leu Phe Ser Ile Cys Glu Tyr Gly Tyr Val Gly Ser Leu Arg Ile Gly
            20                  25                  30

Leu Arg Arg Asn Tyr Ser Gln Gly Asp Ser Ser Asp Arg Leu Gly Gly
        35                  40                  45

Ser Asp Val Asp Val Arg Arg Ser Gly Glu Leu Met Asp Leu Gly Lys
    50                  55                  60

Asn Ala Asn Ile Leu Cys Asn Asn Ile Ser Cys Asn Ser Lys Lys Glu
65                  70                  75                  80

Ala Ser Phe Leu Ser Gln Lys Lys Gln Leu Glu Asp Asp Asp Asp
            85                  90                  95

Glu Leu Ala Ala Leu Tyr Asn Asp Asp Asp Asp Ala Ser Thr Thr
            100                 105                 110

Thr Gly Gly Gly Ser Glu Thr Ser Asp Asp Asp Glu Leu Glu Leu Pro

```
            115                 120                 125
Asp Gln Asp Glu Gly Ala Asp Glu Gly Glu Ala Glu Asp Gln Leu Ala
            130                 135                 140
Thr Gln Glu Asp Ser Asp Asn Ser Gly Thr Asp Gln Gly Leu Lys Lys
145                 150                 155                 160
Lys Val Asn Leu Ser Arg His Glu Lys Leu Ile Glu Asp Lys Lys Gln
                165                 170                 175
Gln Thr Glu Asn Thr Phe Lys Lys Tyr Arg Phe Gly Asp Glu Glu Glu
                180                 185                 190
Glu Ser Glu Glu Lys Ser Pro Gly Lys Ser Lys Ser Leu Asp Pro Ser
                195                 200                 205
Ser Leu Asp Asp Asp Asp Gly Glu Gly Asp Asp Asp Asp Asp Gly Asp
            210                 215                 220
Glu Arg Glu Lys Lys Gln Ser Asn Thr Arg Lys Ala Met Lys Lys Asp
225                 230                 235                 240
Leu Asp Val Phe Pro Gly Leu Tyr Phe Ala Gly Ile Gly Tyr Asp Ser
                245                 250                 255
Leu Phe Gly Asn Pro Leu Gly Glu Ala Asp Ser Leu Thr Asp Pro Gly
                260                 265                 270
Tyr Arg Gly Gln Ile Ile Leu Met Asn Trp Glu Leu Ser Asn Lys Gly
                275                 280                 285
Val Ala Asn Asp Leu Ala Thr Leu Gln Pro Leu Asn Gly Trp Ile Arg
            290                 295                 300
Lys Glu Asn Ala Cys Ser Arg Ala Glu Ser Ile Lys Glu Cys Ser Ser
305                 310                 315                 320
Val Ser Asp Tyr Thr Lys Asn Leu Thr Ala Glu Ala Ser Val Ser Gly
                325                 330                 335
Ser Tyr Met Gly Phe Gly Ala Phe Ser Ala Ser Thr Gly Tyr Lys Lys
                340                 345                 350
Phe Leu Gln Glu Ala Ser Lys Arg Thr Ser Lys Thr Tyr Leu Val Lys
                355                 360                 365
Ser Asn Cys Val Lys Tyr Thr Val Gly Leu Pro Pro Tyr Val Arg Trp
            370                 375                 380
Glu Gln Thr Thr Ala Phe Lys Asn Ala Val Asn Gly Leu Pro Pro His
385                 390                 395                 400
Phe Thr Gly Leu Glu Ala Asp Ser Glu Cys Ala Ser Asp Val Tyr Glu
                405                 410                 415
Gln Lys Lys Thr Ser Glu Glu Cys Glu Thr Val His Ala Trp Ile Arg
                420                 425                 430
Phe Phe Lys Thr Tyr Gly Thr His Val Ile Met Glu Ala Gln Leu Gly
                435                 440                 445
Gly Lys Ile Thr Lys Ile Ile Arg Val Glu Asn Ser Ser Val Asn Gln
            450                 455                 460
Met Lys Lys Asp Gly Val Ser Val Lys Ala Gln Ile Lys Ala Gln Phe
465                 470                 475                 480
Gly Phe Ala Ser Val Gly Gly Ser Thr Asn Val Ser Ser Asp His Ser
                485                 490                 495
Ser Lys Lys Asn Glu Asp Asn Tyr Glu Met Ser Glu Gln Leu Val Val
                500                 505                 510
Ile Gly Gly Asn Pro Ile Lys Asp Val Thr Lys Glu Glu Asn Leu Tyr
                515                 520                 525
Glu Trp Ser Lys Thr Val Ser Thr Asn Pro Met Pro Ile Asn Ile Lys
            530                 535                 540
```

```
Leu Leu Pro Ile Ser Thr Ile Phe Asp Ser Asp Leu Lys Asn Ser
545                 550                 555                 560

Tyr Glu Lys Ala Leu Ile Tyr Tyr Thr Arg Leu Tyr Gly Phe Ser Pro
            565                 570                 575

His Asp Thr Met Gln Lys Asp Glu Lys Asp Ile Val Lys Ile Leu Thr
                580                 585                 590

Ala Ser Thr Thr Val Thr Lys Thr Gly Pro Pro Ile Ser Ala Glu
            595                 600                 605

Cys Pro His Asn Met Val Val Leu Phe Gly Phe Val Val Lys Gln Asn
        610                 615                 620

Phe Trp Asp His Thr Asn Lys Leu Gln Ser Tyr Glu Met Glu Ile Cys
625                 630                 635                 640

Glu Ser Gly Ala Ser Ser Cys Thr Ser Lys Gln Gly Asn Thr Asn Lys
                645                 650                 655

Tyr Asp Val Ser Tyr Thr Tyr Ile Glu Cys Gly Pro Gln Ala Leu Pro
            660                 665                 670

Phe Thr Glu Gln Val Val Ser Val Ser Gly Thr Thr Tyr Asn Ser Val
        675                 680                 685

Lys Cys Pro Asn Asp Tyr Ser Val Leu Phe Gly Phe Gly Met Ala Thr
690                 695                 700

Ser Ser Gly Arg His Gln Ser Ala Leu Tyr Ser Tyr Phe Thr Pro Cys
705                 710                 715                 720

Arg Pro Gly Leu Lys Ser Cys Ser Leu Asn Met Asn Glu His Asp Asp
                725                 730                 735

Lys Ser Tyr Ile Tyr Leu Val Cys Val Asp Ala Thr Ile Trp Thr Gly
            740                 745                 750

Leu Asn Ala Leu Ser Met Ile Ala Lys Asp Asp Leu His Ser Ala Val
        755                 760                 765

Asn Arg Tyr Gln Gln Phe Asn Asp Gly Glu Leu Val Val Thr Cys Pro
770                 775                 780

Ser Glu Gly Thr Ile Leu Thr Gly Phe Tyr Gly Glu Thr His Thr Ser
785                 790                 795                 800

Ser Pro Tyr Val Thr Val Pro Phe Gly Lys Cys Ala Lys Ser Leu Lys
                805                 810                 815

Ala Cys Ser Val His Gly Ser Gly Gln Ala Ile Gly Ile His Asn Tyr
            820                 825                 830

Arg Thr Leu Phe Thr Val Ala Leu Cys Lys Asn Asn
        835                 840

<210> SEQ ID NO 56
<211> LENGTH: 843
<212> TYPE: PRT
<213> ORGANISM: Plasmodium vivax
<220> FEATURE:
<221> NAME/KEY: misc_feature
<223> OTHER INFORMATION: SPECT2

<400> SEQUENCE: 56

Met Lys Pro Arg Asn Ile Asn Ser Leu Leu Ala Ile Trp Cys Ile Leu
1               5                   10                  15

Phe Ser Ile Cys Glu Tyr Gly Tyr Val Gly Ser Leu Arg Ile Gly Leu
            20                  25                  30

Arg Arg Asn Tyr Ser Gln Gly Asp Ser Ser Asp Arg Leu Gly Gly Ser
        35                  40                  45

Asp Val Asp Val Arg Arg Ser Gly Glu Leu Met Asp Phe Gly Lys Asn
```

-continued

```
              50                  55                  60
Ala Asn Ile Leu Cys Asn Asn Ile Ser Cys Asn Ser Lys Lys Glu Ala
 65                  70                  75                  80

Ser Phe Leu Ser Gln Lys Lys Gln Leu Glu Asp Asp Asp Asp Asp Glu
                     85                  90                  95

Leu Ala Ala Leu Tyr Asn Asp Asp Asp Asp Ala Ser Thr Thr Thr
                100                 105                 110

Gly Gly Gly Ser Glu Thr Ser Asp Asp Asp Glu Leu Glu Leu Pro Asp
                115                 120                 125

Gln Asp Glu Gly Ala Asp Glu Gly Ala Glu Asp Gln Leu Ala Thr
130                 135                 140

Gln Glu Asp Ser Asp Asn Ser Gly Thr Asp Gln Gly Leu Lys Lys Lys
145                 150                 155                 160

Val Ser Leu Ser Arg His Glu Lys Leu Ile Glu Asp Lys Lys Gln Gln
                165                 170                 175

Thr Glu Asn Thr Phe Lys Lys Tyr Arg Phe Gly Asp Glu Glu Glu Glu
                180                 185                 190

Ser Glu Glu Lys Ser Pro Gly Lys Ser Lys Ser Leu Asp Pro Ser Ser
                195                 200                 205

Leu Asp Asp Asp Asp Gly Glu Gly Asp Asp Asp Asp Gly Asp Glu
    210                 215                 220

Arg Glu Lys Lys Gln Ser Asn Thr Arg Lys Ala Met Lys Lys Asp Leu
225                 230                 235                 240

Asp Val Phe Pro Gly Leu Tyr Phe Ala Gly Ile Gly Tyr Asp Ser Leu
                245                 250                 255

Phe Gly Asn Pro Leu Gly Glu Ala Asp Ser Leu Thr Asp Pro Gly Tyr
                260                 265                 270

Arg Gly Gln Ile Ile Leu Met Asn Trp Glu Leu Ser Asn Lys Gly Val
                275                 280                 285

Ala Asn Asp Leu Ala Thr Leu Gln Pro Leu Asn Gly Trp Ile Arg Lys
                290                 295                 300

Glu Asn Ala Cys Ser Arg Ala Glu Ser Ile Lys Glu Cys Ser Ser Val
305                 310                 315                 320

Ser Asp Tyr Thr Lys Asn Leu Thr Ala Glu Ala Ser Val Ser Gly Ser
                325                 330                 335

Tyr Met Gly Phe Gly Ala Phe Ser Ala Ser Thr Gly Tyr Lys Lys Phe
                340                 345                 350

Leu Gln Glu Ala Ser Lys Arg Thr Ser Lys Thr Tyr Leu Val Lys Ser
                355                 360                 365

Asn Cys Val Lys Tyr Thr Val Gly Leu Pro Pro Tyr Val Arg Trp Glu
370                 375                 380

Gln Thr Thr Ala Phe Lys Asn Ala Val Asn Gly Leu Pro Pro His Phe
385                 390                 395                 400

Thr Gly Leu Glu Ala Asp Ser Glu Cys Ala Ser Asp Val Tyr Glu Gln
                405                 410                 415

Lys Lys Thr Ser Glu Glu Cys Glu Thr Val His Ala Trp Ile Arg Phe
                420                 425                 430

Phe Lys Tyr Gly Thr His Val Ile Met Glu Ala Gln Leu Gly Gly
                435                 440                 445

Lys Ile Thr Lys Ile Ile Arg Val Glu Asn Ser Ser Val Asn Gln Met
                450                 455                 460

Lys Lys Asp Gly Val Ser Val Lys Ala Gln Ile Lys Ala Gln Phe Gly
465                 470                 475                 480
```

Phe Ala Ser Val Gly Gly Ser Thr Asn Val Ser Ser Asp His Ser Ser
                485                 490                 495

Lys Lys Asn Glu Asp Asn Tyr Glu Met Ser Glu Gln Leu Val Val Ile
                500                 505                 510

Gly Gly Asn Pro Ile Lys Asp Val Thr Lys Glu Glu Asn Leu Tyr Glu
                515                 520                 525

Trp Ser Lys Thr Val Ser Thr Asn Pro Met Pro Ile Asn Ile Lys Leu
            530                 535                 540

Leu Pro Ile Ser Thr Ile Phe Asp Ser Asp Asp Leu Lys Asn Ser Tyr
545                 550                 555                 560

Glu Lys Ala Leu Ile Tyr Tyr Thr Arg Leu Tyr Gly Phe Ser Pro His
                565                 570                 575

Asp Thr Met Gln Lys Asp Glu Lys Asp Ile Val Lys Ile Leu Thr Ala
                580                 585                 590

Ser Thr Thr Val Thr Lys Thr Gly Pro Pro Ile Ser Ala Glu Cys
                595                 600                 605

Pro His Asn Met Val Val Leu Phe Gly Phe Val Val Lys Gln Asn Phe
            610                 615                 620

Trp Asp His Thr Asn Lys Leu Gln Ser Tyr Glu Met Glu Ile Cys Glu
625                 630                 635                 640

Ser Gly Ala Ser Ser Cys Thr Ser Lys Gln Gly Asn Thr Asn Lys Tyr
                645                 650                 655

Asp Val Ser Tyr Thr Tyr Ile Glu Cys Gly Pro Gln Ala Leu Pro Phe
                660                 665                 670

Thr Glu Gln Val Val Ser Val Ser Gly Thr Thr Tyr Asn Ser Val Lys
                675                 680                 685

Cys Pro Asn Asp Tyr Ser Val Leu Phe Gly Phe Gly Met Ala Thr Ser
            690                 695                 700

Ser Gly Arg His Gln Ser Ala Leu Tyr Ser Tyr Phe Thr Pro Cys Arg
705                 710                 715                 720

Pro Gly Leu Lys Ser Cys Ser Leu Asn Met Asn Glu His Asp Asp Lys
                725                 730                 735

Ser Tyr Ile Tyr Leu Val Cys Val Asp Ala Thr Ile Trp Thr Gly Leu
                740                 745                 750

Asn Ala Leu Ser Met Ile Ala Lys Asp Asp Leu His Ser Ala Val Asn
            755                 760                 765

Arg Tyr Gln Gln Phe Asn Asp Gly Glu Leu Val Val Thr Cys Pro Ser
770                 775                 780

Glu Gly Thr Ile Leu Thr Gly Phe Tyr Gly Glu Thr His Thr Ser Ser
785                 790                 795                 800

Pro Tyr Val Thr Val Pro Phe Gly Lys Cys Ala Lys Ser Leu Lys Ala
                805                 810                 815

Cys Ser Val His Gly Ser Gly Gln Ala Ile Gly Ile His Asn Tyr Arg
            820                 825                 830

Thr Leu Phe Thr Val Ala Leu Cys Lys Asn Asn
            835                 840

<210> SEQ ID NO 57
<211> LENGTH: 2478
<212> TYPE: DNA
<213> ORGANISM: Plasmodium berghei
<220> FEATURE:
<221> NAME/KEY: misc_feature
<223> OTHER INFORMATION: GPI_P113

```
<400> SEQUENCE: 57
ggatccgcca ccatggctaa gatcttcctg tttagtttct tcttcgtatg gttccagtat      60
tgctattcta agaacccctc agactacgct catagcattg tctctaattt tgagtccgag     120
aatacgttga agtgtttgaa aggcaacgtg tatatacttc aatgtcagat caagtgcatg     180
aactcaaaca acgagatcat atacaaggag tgtctcaacg atatcgaaaa gatttgcaaa     240
gataagaaaa catgcagtta ttacttcgac tacatcttca aaaccaagaa tcacaagctt     300
agaaacaaca acaataacaa catctacatc gacaattgca tcgattccga caagaatgag     360
atcaaatcta ccttcacctg tgtcctcaat ccattgctgg aatttgacaa taacaaccac     420
gtcatttata acttcctgct gaacaacaag aacaatgaca agatcgtctg taaaaatagc     480
aacatatata ttaacaacgc tactattcac tataccttct ccgacattaa gtttaaagac     540
gtgactagct acataaaaga gaaatgtaac gagaaaacta attgcgtgat aaaccctat      600
tctatccaaa ccgatatcct gaatgagaag aacgacgcat atctgctgaa ctcatacatc     660
agcatatcct tcgcatgtgt gaaaattaac ctggaaagct atctgtacgg aggtgatatc     720
gatgaatttg atcagataaa cgatgaagaa aatgaggaca ataagtacct ggatcacaat     780
gatctcgatg aaaaaaatga ggaaattatt tccctgaaga acgaaatcaa cgacatcctg     840
aatgacgaga agatcgataa catcgccgag aagctgaaga ttgcgaaatt tacaataagc     900
aagaaaatca acgaggagat caagaagaag aacgacatct taacaaccct ggccaacgac     960
atctaccagt tcatcggtaa cgagtactac tttacttccg acatcaaaga catgattgaa    1020
gataggtaca atgaactgaa caaaacatct cagtctgact tgtattacat ttaccttctg    1080
aatgtgtttg acattgaaaa gatttacggg atctacctgt ctagttatca ggagcgactg    1140
cagcagatcc tgcaaaccaa catgacaaat ctggactatg ttgagaagaa gattggaagc    1200
ttgcggaaca tttacatgtt cctgtataaa aagagtaaga agtataacgc gctggatatc    1260
ttcgacgaat actacgatta tgtgctcaat tacaatgact tcgctaaaga caatgagata    1320
atcagcgccg acattttcat taagtcaaaa cctgatatcc ctcaactcaa tttcgagatc    1380
aacaatgaga acaagaacgt gaagtataaa gacgttaccg atcttgacga gctggataac    1440
ctcaacagga taaatagaat tatcaatatc cggaatgtgc tggtcaagca gctcaagatc    1500
ctttacaacc agagaaataa catatttatc aaacaggcca tgctggtgaa atcatactgc    1560
tacaaaaatc cactggatat tacggatttc agcagcatct tcaagaataa ctacaataag    1620
ttgaaatacg acgcctataa ggagggcaat ggacacatta acgtggccga caaaatcaat    1680
ccaaactttg tcgtgaaata cctgaacaat ctttataaac agcatgttaa caagaattat    1740
atcctgaaca gctgggaccc taaatacaat cgcatgaata agaagattaa gatcattctc    1800
attttggggt atggccaggt aatccagatc gagaaacaga ttaaccgtca tataggcaag    1860
tacaacgccc tgcttgaaaa ggcaacccct cataacgtgg aaatctctt tacacagact    1920
acgaatattt tgaacgacat ctcaggctca ctgaacgatg gcttgaccc gaacatccat    1980
gatcaggagg atgtcactgt cgttgaatcc tctgaaagta acaagctcgc agaacctgag    2040
gaacccattg agaaggtaga ggttgatagg gtagagaaat ccgatgatgc caataatgcc    2100
actcaacaag tgacaggaac agacgaggcc aattacgata cagctagcgg gaatagtacc    2160
aacatcaaca ttgacaacat agactatggt gtggacgaat ctatccgaat tattaagtac    2220
tccaaggctg aggaggatga atataatgag agcggcaata acgaaaatga aaacaacgag    2280
aataacgaga acgagaacaa tgaaaatgag aacaacgaga atgagaataa tgagaatgaa    2340
```

```
aataacgaga acgaaaatat agaactgaag aatatagaac acgaaaacaa atccaacgca    2400
tctagcgctt ccctcagtaa catttctctt acctttatca ttgcagctct gtttatccgc    2460 cccttctgt gactcgag                                                   2478
```

<210> SEQ ID NO 58
<211> LENGTH: 819
<212> TYPE: PRT
<213> ORGANISM: Plasmodium berghei
<220> FEATURE:
<221> NAME/KEY: misc_feature
<223> OTHER INFORMATION: GPI_P113

<400> SEQUENCE: 58

```
Met Ala Lys Ile Phe Leu Phe Ser Phe Phe Val Trp Phe Gln Tyr
1               5                   10                  15

Cys Tyr Ser Lys Asn Pro Ser Asp Tyr Ala His Ser Ile Val Ser Asn
                20                  25                  30

Phe Glu Ser Glu Asn Thr Leu Lys Cys Leu Lys Gly Asn Val Tyr Ile
            35                  40                  45

Leu Gln Cys Gln Ile Lys Cys Met Asn Ser Asn Asn Glu Ile Ile Tyr
        50                  55                  60

Lys Glu Cys Leu Asn Asp Ile Glu Lys Ile Cys Lys Asp Lys Lys Thr
65                  70                  75                  80

Cys Ser Tyr Tyr Phe Asp Tyr Ile Phe Lys Thr Lys Asn His Lys Leu
                85                  90                  95

Arg Asn Asn Asn Asn Asn Ile Tyr Ile Asp Asn Cys Ile Asp Ser
            100                 105                 110

Asp Lys Asn Glu Ile Lys Ser Thr Phe Thr Cys Val Leu Asn Pro Leu
        115                 120                 125

Leu Glu Phe Asp Asn Asn Asn His Val Ile Tyr Asn Phe Leu Leu Asn
    130                 135                 140

Asn Lys Asn Asn Asp Lys Ile Val Cys Lys Asn Ser Asn Ile Tyr Ile
145                 150                 155                 160

Asn Asn Ala Thr Ile His Tyr Thr Phe Ser Asp Ile Lys Phe Lys Asp
                165                 170                 175

Val Thr Ser Tyr Ile Lys Glu Lys Cys Asn Glu Lys Thr Asn Cys Val
            180                 185                 190

Ile Asn Pro Tyr Ser Ile Gln Thr Asp Ile Leu Asn Glu Lys Asn Asp
        195                 200                 205

Ala Tyr Leu Leu Asn Ser Tyr Ile Ser Ile Ser Phe Ala Cys Val Lys
    210                 215                 220

Ile Asn Leu Glu Ser Tyr Leu Tyr Gly Gly Asp Ile Asp Glu Phe Asp
225                 230                 235                 240

Gln Ile Asn Asp Glu Glu Asn Glu Asp Asn Lys Tyr Leu Asp His Asn
                245                 250                 255

Asp Leu Asp Glu Lys Asn Glu Glu Ile Ile Ser Leu Asn Glu Ile
            260                 265                 270

Asn Asp Ile Leu Asn Asp Glu Lys Ile Asp Asn Ile Ala Glu Lys Leu
        275                 280                 285

Lys Ile Ala Lys Phe Thr Ile Ser Lys Lys Ile Asn Glu Glu Ile Lys
    290                 295                 300

Lys Lys Asn Asp Ile Phe Asn Asn Leu Ala Asn Asp Ile Tyr Gln Phe
305                 310                 315                 320

Ile Gly Asn Glu Tyr Tyr Phe Thr Ser Asp Ile Lys Asp Met Ile Glu
```

```
            325                 330                 335
Asp Arg Tyr Asn Glu Leu Asn Lys Thr Ser Gln Ser Asp Leu Tyr Tyr
            340                 345                 350
Ile Tyr Leu Leu Asn Val Phe Asp Ile Glu Lys Ile Tyr Gly Ile Tyr
            355                 360                 365
Leu Ser Ser Tyr Gln Glu Arg Leu Gln Gln Ile Leu Gln Thr Asn Met
            370                 375                 380
Thr Asn Leu Asp Tyr Val Glu Lys Lys Ile Gly Ser Leu Arg Asn Ile
385                 390                 395                 400
Tyr Met Phe Leu Tyr Lys Lys Ser Lys Lys Tyr Asn Ala Leu Asp Ile
                    405                 410                 415
Phe Asp Glu Tyr Tyr Asp Tyr Val Leu Asn Tyr Asn Asp Phe Ala Lys
                    420                 425                 430
Asp Asn Glu Ile Ile Ser Ala Asp Ile Phe Ile Lys Ser Lys Pro Asp
            435                 440                 445
Ile Pro Gln Leu Asn Phe Glu Ile Asn Asn Glu Asn Lys Asn Val Lys
            450                 455                 460
Tyr Lys Asp Val Thr Asp Leu Asp Glu Leu Asp Asn Leu Asn Arg Ile
465                 470                 475                 480
Asn Arg Ile Ile Asn Ile Arg Asn Val Leu Val Lys Gln Leu Lys Ile
                    485                 490                 495
Leu Tyr Asn Gln Arg Asn Asn Ile Phe Ile Lys Gln Ala Met Leu Val
                    500                 505                 510
Lys Ser Tyr Cys Tyr Lys Asn Pro Leu Asp Ile Thr Asp Phe Ser Ser
                    515                 520                 525
Ile Phe Lys Asn Asn Tyr Asn Lys Leu Lys Tyr Asp Ala Tyr Lys Glu
            530                 535                 540
Gly Asn Gly His Ile Asn Val Ala Asp Lys Ile Asn Pro Asn Phe Val
545                 550                 555                 560
Val Lys Tyr Leu Asn Asn Leu Tyr Lys Gln His Val Asn Lys Asn Tyr
                    565                 570                 575
Ile Leu Asn Ser Trp Asp Pro Lys Tyr Asn Arg Met Asn Lys Lys Ile
            580                 585                 590
Lys Ile Ile Leu Ile Leu Gly Tyr Gly Gln Val Ile Gln Ile Glu Lys
            595                 600                 605
Gln Ile Asn Arg His Ile Gly Lys Tyr Asn Ala Leu Leu Glu Lys Ala
            610                 615                 620
Thr Leu Tyr Asn Val Gly Asn Leu Phe Thr Gln Thr Asn Ile Leu
625                 630                 635                 640
Asn Asp Ile Ser Gly Ser Leu Asn Asp Gly Leu Asp Pro Asn Ile His
                    645                 650                 655
Asp Gln Glu Asp Val Thr Val Val Glu Ser Ser Glu Ser Asn Lys Leu
                    660                 665                 670
Ala Glu Pro Glu Glu Pro Ile Glu Lys Val Glu Val Asp Arg Val Glu
                    675                 680                 685
Lys Ser Asp Asp Ala Asn Asn Ala Thr Gln Gln Val Thr Gly Thr Asp
            690                 695                 700
Glu Ala Asn Tyr Asp Thr Ala Ser Gly Asn Ser Thr Asn Ile Asn Ile
705                 710                 715                 720
Asp Asn Ile Asp Tyr Gly Val Asp Glu Ser Ile Arg Ile Ile Lys Tyr
                    725                 730                 735
Ser Lys Ala Glu Glu Asp Glu Tyr Asn Glu Ser Gly Asn Asn Glu Asn
            740                 745                 750
```

Glu Asn Asn Glu Asn Glu Asn Glu Asn Glu Asn Glu Asn Asn
          755                 760                 765

Glu Asn Glu Asn Glu Asn Glu Asn Asn Glu Asn Glu Asn Ile Glu
          770                 775                 780

Leu Lys Asn Ile Glu His Glu Asn Lys Ser Asn Ala Ser Ser Ala Ser
785                 790                 795                 800

Leu Ser Asn Ile Phe Phe Thr Phe Ile Ile Ala Ala Leu Phe Ile Arg
                  805                 810                 815

Pro Phe Leu

<210> SEQ ID NO 59
<211> LENGTH: 818
<212> TYPE: PRT
<213> ORGANISM: Plasmodium berghei
<220> FEATURE:
<221> NAME/KEY: misc_feature
<223> OTHER INFORMATION: P113

<400> SEQUENCE: 59

Met Lys Ile Phe Leu Phe Ser Phe Phe Phe Val Trp Phe Gln Tyr Cys
1               5                   10                  15

Tyr Ser Lys Asn Pro Ser Asp Tyr Ala His Ser Ile Val Ser Asn Phe
              20                  25                  30

Glu Ser Glu Asn Thr Leu Lys Cys Leu Lys Gly Asn Val Tyr Ile Leu
          35                  40                  45

Gln Cys Gln Ile Lys Cys Met Asn Ser Asn Asn Glu Ile Ile Tyr Lys
      50                  55                  60

Glu Cys Leu Asn Asp Ile Glu Lys Ile Cys Lys Asp Lys Lys Thr Cys
65                  70                  75                  80

Ser Tyr Tyr Phe Asp Tyr Ile Phe Lys Thr Lys Asn His Lys Leu Arg
                  85                  90                  95

Asn Asn Asn Asn Asn Asn Ile Tyr Ile Asp Asn Cys Ile Asp Ser Asp
              100                 105                 110

Lys Asn Glu Ile Lys Ser Thr Phe Thr Cys Val Leu Asn Pro Leu Leu
          115                 120                 125

Glu Phe Asp Asn Asn Asn His Val Ile Tyr Asn Phe Leu Leu Asn Asn
      130                 135                 140

Lys Asn Asn Asp Lys Ile Val Cys Lys Asn Ser Asn Ile Tyr Ile Asn
145                 150                 155                 160

Asn Ala Thr Ile His Tyr Thr Phe Ser Asp Ile Lys Phe Lys Asp Val
                  165                 170                 175

Thr Ser Tyr Ile Lys Glu Lys Cys Asn Glu Lys Thr Asn Cys Val Ile
              180                 185                 190

Asn Pro Tyr Ser Ile Gln Thr Asp Ile Leu Asn Glu Lys Asn Asp Ala
          195                 200                 205

Tyr Leu Leu Asn Ser Tyr Ile Ser Ile Ser Phe Ala Cys Val Lys Ile
      210                 215                 220

Asn Leu Glu Ser Tyr Leu Tyr Gly Gly Asp Ile Asp Glu Phe Asp Gln
225                 230                 235                 240

Ile Asn Asp Glu Glu Asn Glu Asp Asn Lys Tyr Leu Asp His Asn Asp
                  245                 250                 255

Leu Asp Glu Lys Asn Glu Glu Ile Ile Ser Leu Lys Asn Glu Ile Asn
              260                 265                 270

Asp Ile Leu Asn Asp Glu Lys Ile Asp Asn Ile Ala Glu Lys Leu Lys
          275                 280                 285

```
Ile Ala Lys Phe Thr Ile Ser Lys Lys Ile Asn Glu Glu Ile Lys Lys
    290                 295                 300
Lys Asn Asp Ile Phe Asn Asn Leu Ala Asn Asp Ile Tyr Gln Phe Ile
305                 310                 315                 320
Gly Asn Glu Tyr Tyr Phe Thr Ser Asp Ile Lys Asp Met Ile Glu Asp
                325                 330                 335
Arg Tyr Asn Glu Leu Asn Lys Thr Ser Gln Ser Asp Leu Tyr Tyr Ile
            340                 345                 350
Tyr Leu Leu Asn Val Phe Asp Ile Glu Lys Ile Tyr Gly Ile Tyr Leu
        355                 360                 365
Ser Ser Tyr Gln Glu Arg Leu Gln Gln Ile Leu Gln Thr Asn Met Thr
370                 375                 380
Asn Leu Asp Tyr Val Glu Lys Lys Ile Gly Ser Leu Arg Asn Ile Tyr
385                 390                 395                 400
Met Phe Leu Tyr Lys Lys Ser Lys Lys Tyr Asn Ala Leu Asp Ile Phe
                405                 410                 415
Asp Glu Tyr Tyr Asp Tyr Val Leu Asn Tyr Asn Asp Phe Ala Lys Asp
            420                 425                 430
Asn Glu Ile Ile Ser Ala Asp Ile Phe Ile Lys Ser Lys Pro Asp Ile
        435                 440                 445
Pro Gln Leu Asn Phe Glu Ile Asn Asn Glu Asn Lys Asn Val Lys Tyr
450                 455                 460
Lys Asp Val Thr Asp Leu Asp Glu Leu Asp Asn Leu Asn Arg Ile Asn
465                 470                 475                 480
Arg Ile Ile Asn Ile Arg Asn Val Leu Val Lys Gln Leu Lys Ile Leu
                485                 490                 495
Tyr Asn Gln Arg Asn Asn Ile Phe Ile Lys Gln Ala Met Leu Val Lys
            500                 505                 510
Ser Tyr Cys Tyr Lys Asn Pro Leu Asp Ile Thr Asp Phe Ser Ser Ile
        515                 520                 525
Phe Lys Asn Asn Tyr Asn Lys Leu Lys Tyr Asp Ala Tyr Lys Glu Gly
530                 535                 540
Asn Gly His Ile Asn Val Ala Asp Lys Ile Asn Pro Asn Phe Val Val
545                 550                 555                 560
Lys Tyr Leu Asn Asn Leu Tyr Lys Gln His Val Asn Lys Asn Tyr Ile
                565                 570                 575
Leu Asn Ser Trp Asp Pro Lys Tyr Asn Arg Met Asn Lys Lys Ile Lys
            580                 585                 590
Ile Ile Leu Ile Leu Gly Tyr Gly Gln Val Ile Gln Ile Glu Lys Gln
        595                 600                 605
Ile Asn Arg His Ile Gly Lys Tyr Asn Ala Leu Leu Glu Lys Ala Thr
610                 615                 620
Leu Tyr Asn Val Gly Asn Leu Phe Thr Gln Thr Asn Ile Leu Asn
625                 630                 635                 640
Asp Ile Ser Gly Ser Leu Asn Asp Gly Leu Asp Pro Asn Ile His Asp
                645                 650                 655
Gln Glu Asp Val Thr Val Val Glu Ser Ser Glu Ser Asn Lys Leu Ala
            660                 665                 670
Glu Pro Glu Glu Pro Ile Glu Lys Val Glu Val Asp Arg Val Glu Lys
        675                 680                 685
Ser Asp Asp Ala Asn Asn Ala Thr Gln Gln Val Thr Gly Thr Asp Glu
    690                 695                 700
```

```
Ala Asn Tyr Asp Thr Ala Ser Gly Asn Ser Thr Asn Ile Asn Ile Asp
705                 710                 715                 720

Asn Ile Asp Tyr Gly Val Asp Glu Ser Ile Arg Ile Ile Lys Tyr Ser
            725                 730                 735

Lys Ala Glu Glu Asp Glu Tyr Asn Glu Ser Gly Asn Asn Glu Asn Glu
        740                 745                 750

Asn Asn Glu Asn Asn Glu Asn Glu Asn Asn Glu Asn Glu Asn Asn Glu
    755                 760                 765

Asn Glu Asn Asn Glu Asn Glu Asn Asn Glu Asn Glu Asn Ile Glu Leu
770                 775                 780

Lys Asn Ile Glu His Glu Asn Lys Ser Asn Ala Ser Ser Ala Ser Leu
785                 790                 795                 800

Ser Asn Ile Phe Phe Thr Phe Ile Ile Ala Ala Leu Phe Ile Arg Pro
            805                 810                 815

Phe Leu

<210> SEQ ID NO 60
<211> LENGTH: 2919
<212> TYPE: DNA
<213> ORGANISM: Artificial Sequence
<220> FEATURE:
<223> OTHER INFORMATION: PfP113 human CO

<400> SEQUENCE: 60
gccaccatgg ctaagatccc gttctttatt ctgcacatcc tcctcctgca gtttctgctt      60
tgtctgatac gctgttatgt gcacaatgat gtgattaagt tcggtgagga gaatagcctg     120
aagtgctctc agggaaactt gtatgtgttg cactgtgagg tgcagtgcct aatggcaat      180 aatgagatta tccacaagag gtgtaatgac gacattgaga aaagtgcaa cggcaataat      240 aaatgcatat acttctttga gtacgaactg cggaagaaaa cacaaagctt tcgaaataag     300
aattctatcg agatttccga gtgtgtcgaa agcgagcaga acgaagtgaa acctcaact      360 acctgtctcc tgagcaattc ctttattctt gacgaggcct ttatacagta tttcttcttc     420
ataaagaaca gaacgaaga gcctgtgatt tgtaaggatg ggaatatcaa cattaagagt      480
gcactcctgc actctccgtt ctgtgaaatc aaactcaagg acatttccga atatatacgc     540
aaaaagtgtg acaacaacaa ggaatgcctt atagatcctc tcgatgttca gaagaatttg     600
ctgaacgaag aagatccctg ctacatcaat aacagttacg tatctgtgaa tgtggtctgc     660
aacaaagagg aggagatagg ggatgagagc actgacagct catcaatgga gatccaggac     720
tcaacatcaa atgagcaaga cgagaatgtt aaaggaatgt caagcagcca agagatgaac     780
tcaaacaacg atgaaaacaa aaaccaagac aacgaaagcg acgatgacgt caataataat      840
aacaacaata caatgatga ccaggacgag caaggaaacg atggcgatgt caccagctct     900
atgaacaaga atgaggacaa caaggatttg gagcatggtt cctccaatga tgtcaataac      960
aacactgaca ccttggttaa caacaaagag aataaggagt cgtccttaa agagaagtct    1020 agccttactt ctaaaattaa caaagagctg gctcatagaa ctgccctgtt taacaaactt    1080
gcagacaaca tatcacttct gcttaacaag aaatacgatt ccttcgaaat taaggatgtg    1140
ctggaagata ggtacaacga gatgaagagg gacgcaaacc ccgatgtcta ctacatatac    1200
ctgatggata tctctggatat tgaaaagatc gaagatatca acctggaaga ggttaagatg    1260
tctctgctgg catcactgaa agaaacgatg aacaaaattg atacgatcga aagaaaatc    1320 gaagaattta agaacaagta catctcccttg tataacaagg tgaaaccac aatgcccgaa    1380
```

```
ctctttgacc tgaatgagga tcttgtactg ctctacaacg attttcccct tgacaacggc   1440
atgatcagct ccgacatctt ctttaagtac aatccttccg agaacatcat ggatcatcag   1500
gaaatggtga agaaagggag tatcaccgaa gatgaactca ggattgttaa cgatcttgag   1560
ccactggata actatagacg tcgtaaacga attacagagc tgagaaagat tctggtggag   1620
aagctgcgga ttctgtacct ggagaagaac aatctcttca atacacaggc gagttgcatc   1680
aagagctatt gctataagaa tcctctgaac ctcaaaacct tggaagtgct cttgaagaag   1740
aactactata gactgaagga gaataaagat tacgatgttg tatccagcat atccagcat    1800 ctcgacaatg tagacgccaa caagaagaag aaatggctga cccatgaacg gatactgaag   1860
aagctccaag ttctgattgc cgaaggctat aagcggatca acgagaaaga aaaggacatc   1920
gaccgaagaa tggctgtcta caatgccctc tatgagaaag cacagtctta caacctgcag   1980
aagcttttca cgactccaa cgattttctg aagaaatatg ccataatggg aaacagtttc     2040
gacgacggcg atgaggtttt cggttcccaa agctcaaact ttaacatctt cgatagcaat   2100
aacaccgacc agaacaatga gcaagagcag ccaaagcaag atgaccagct tttgaacaat   2160
aataacgatg acgtgctctc agagtcaaac aatgagaata agagaaaac aagtgatgac     2220 gctactcata aggagactca ggagaaaagc gaccaggaac cttcccagaa cattcaggag   2280
gacaactccg atgagaaaca tgccgaaaac gaggagaacg tagaacagat cgaaactgat   2340
agtaatgtca gcgaagaagc caatgacgag aataaggata catgcagac aaccactgac    2400 gaaggaaccg aagaacttca gcagaatgac gaagatgcgg agagtctgac caaggagaat   2460
tccaaatctg aggagcagga gaatgaagat tctactgacg ccgaggcgat tgataaagag   2520
gaagttgaaa cggaagagaa gggaaaggac gaacagaaga agatgagca gaaggagcag     2580 gatgaggaag aggatggaga gaaagaaaat aagcacaaga gctccgaaac taccaatgag   2640
actgtgaccg acatcgagga aaataagaac gaggtcaaag gtgaggagca tcttcagggg   2700
tctgagcaga gcattgaggc ttccgaatca tcccagaaag atgagactaa agaaacagag   2760
gacaaggagg aatacgtgaa cgctaatgat gacgaatctt ctgaggagga cacgacgcct   2820
aacgagacaa ataaaaccga caacgggtca agtttcttct tcgcgatgag caatgcactt   2880
ctcgtgatct tgctgttgct tttcatcgaa ttcctgtaa                          2919
```

<210> SEQ ID NO 61
<211> LENGTH: 970
<212> TYPE: PRT
<213> ORGANISM: Plasmodium falciparum
<220> FEATURE:
<221> NAME/KEY: misc_feature
<223> OTHER INFORMATION: PfP113

<400> SEQUENCE: 61

```
Met Ala Lys Ile Pro Phe Phe Ile Leu His Ile Leu Leu Leu Gln Phe
1               5                   10                  15

Leu Leu Cys Leu Ile Arg Cys Tyr Val His Asn Asp Val Ile Lys Phe
            20                  25                  30

Gly Glu Glu Asn Ser Leu Lys Cys Ser Gln Gly Asn Leu Tyr Val Leu
        35                  40                  45

His Cys Glu Val Gln Cys Leu Asn Gly Asn Asn Glu Ile Ile His Lys
    50                  55                  60

Arg Cys Asn Asp Asp Ile Glu Lys Lys Cys Asn Gly Asn Asn Lys Cys
65                  70                  75                  80

Ile Tyr Phe Phe Glu Tyr Glu Leu Arg Lys Lys Thr Gln Ser Phe Arg
```

85                  90                  95
Asn Lys Asn Ser Ile Glu Ile Ser Glu Cys Val Glu Ser Glu Gln Asn
            100                 105                 110

Glu Val Lys Thr Ser Thr Thr Cys Leu Leu Ser Asn Ser Phe Ile Leu
            115                 120                 125

Asp Glu Ala Phe Ile Gln Tyr Phe Phe Ile Lys Asn Lys Asn Glu
        130                 135                 140

Glu Pro Val Ile Cys Lys Asp Gly Asn Ile Asn Ile Lys Ser Ala Leu
145                 150                 155                 160

Leu His Ser Pro Phe Cys Glu Ile Lys Leu Lys Asp Ile Ser Glu Tyr
                165                 170                 175

Ile Arg Lys Lys Cys Asp Asn Asn Lys Glu Cys Leu Ile Asp Pro Leu
                180                 185                 190

Asp Val Gln Lys Asn Leu Leu Asn Glu Glu Asp Pro Cys Tyr Ile Asn
            195                 200                 205

Asn Ser Tyr Val Ser Val Asn Val Cys Asn Lys Glu Glu Glu Ile
        210                 215                 220

Gly Asp Glu Ser Thr Asp Ser Ser Ser Met Glu Ile Gln Asp Ser Thr
225                 230                 235                 240

Ser Asn Glu Gln Asp Glu Asn Val Lys Gly Met Ser Ser Ser Gln Glu
                245                 250                 255

Met Asn Ser Asn Asn Asp Glu Asn Lys Asn Gln Asp Asn Glu Ser Asp
                260                 265                 270

Asp Asp Val Asn Asn Asn Asn Asn Asn Asp Asp Gln Asp Glu
            275                 280                 285

Gln Gly Asn Asp Gly Asp Val Thr Ser Ser Met Asn Lys Asn Glu Asp
            290                 295                 300

Asn Lys Asp Leu Glu His Gly Ser Ser Asn Asp Val Asn Asn Asn Thr
305                 310                 315                 320

Asp Thr Leu Val Asn Asn Lys Glu Asn Lys Glu Phe Val Leu Lys Glu
                325                 330                 335

Lys Ser Ser Leu Thr Ser Lys Ile Asn Lys Glu Leu Ala His Arg Thr
                340                 345                 350

Ala Leu Phe Asn Lys Leu Ala Asp Asn Ile Ser Leu Leu Leu Asn Lys
            355                 360                 365

Lys Tyr Asp Ser Phe Glu Ile Lys Asp Val Leu Glu Asp Arg Tyr Asn
            370                 375                 380

Glu Met Lys Arg Asp Ala Asn Pro Asp Val Tyr Tyr Ile Tyr Leu Met
385                 390                 395                 400

Asp Thr Leu Asp Ile Glu Lys Ile Glu Asp Ile Asn Leu Glu Glu Val
                405                 410                 415

Lys Met Ser Leu Leu Ala Ser Leu Lys Glu Thr Met Asn Lys Ile Asp
            420                 425                 430

Thr Ile Glu Lys Lys Ile Glu Glu Phe Lys Asn Lys Tyr Ile Ser Leu
            435                 440                 445

Tyr Asn Lys Val Lys Thr Thr Met Pro Glu Leu Phe Asp Leu Asn Glu
        450                 455                 460

Asp Leu Val Leu Leu Tyr Asn Asp Phe Pro Phe Asp Asn Gly Met Ile
465                 470                 475                 480

Ser Ser Asp Ile Phe Phe Lys Tyr Asn Pro Ser Glu Asn Ile Met Asp
                485                 490                 495

His Gln Glu Met Val Lys Lys Gly Ser Ile Thr Glu Asp Glu Leu Arg
            500                 505                 510

```
Ile Val Asn Asp Leu Glu Pro Leu Asp Asn Tyr Arg Arg Lys Arg
            515                 520                 525

Ile Thr Glu Leu Arg Lys Ile Leu Val Glu Lys Leu Arg Ile Leu Tyr
        530                 535                 540

Leu Glu Lys Asn Asn Leu Phe Asn Thr Gln Ala Ser Cys Ile Lys Ser
545                 550                 555                 560

Tyr Cys Tyr Lys Asn Pro Leu Asn Leu Lys Thr Leu Glu Val Leu Leu
                565                 570                 575

Lys Lys Asn Tyr Tyr Arg Leu Lys Glu Asn Lys Asp Tyr Asp Val Val
            580                 585                 590

Ser Ser Ile Ile Gln His Leu Asp Asn Val Asp Ala Asn Lys Lys Lys
        595                 600                 605

Lys Trp Leu Thr His Glu Arg Ile Leu Lys Leu Gln Val Leu Ile
    610                 615                 620

Ala Glu Gly Tyr Lys Arg Ile Asn Glu Lys Glu Lys Asp Ile Asp Arg
625                 630                 635                 640

Arg Met Ala Val Tyr Asn Ala Leu Tyr Glu Lys Ala Gln Ser Tyr Asn
                645                 650                 655

Leu Gln Lys Leu Phe Asn Asp Ser Asn Asp Phe Leu Lys Lys Tyr Ala
            660                 665                 670

Ile Met Gly Asn Ser Phe Asp Asp Gly Asp Glu Val Phe Gly Ser Gln
        675                 680                 685

Ser Ser Asn Phe Asn Ile Phe Asp Ser Asn Asn Thr Asp Gln Asn Asn
    690                 695                 700

Glu Gln Glu Gln Pro Lys Gln Asp Gln Leu Asn Asn Asn
705                 710                 715                 720

Asp Asp Val Leu Ser Glu Ser Asn Asn Glu Asn Lys Glu Lys Thr Ser
                725                 730                 735

Asp Asp Ala Thr His Lys Glu Thr Gln Glu Lys Ser Asp Gln Glu Pro
            740                 745                 750

Ser Gln Asn Ile Gln Glu Asp Asn Ser Asp Glu Lys His Ala Glu Asn
        755                 760                 765

Glu Glu Asn Val Glu Gln Ile Glu Thr Asp Ser Asn Val Ser Glu Glu
    770                 775                 780

Ala Asn Asp Glu Asn Lys Asp Asn Met Gln Thr Thr Thr Asp Glu Gly
785                 790                 795                 800

Thr Glu Glu Leu Gln Gln Asn Asp Glu Asp Ala Glu Ser Leu Thr Lys
                805                 810                 815

Glu Asn Ser Lys Ser Glu Gln Glu Asn Glu Asp Ser Thr Asp Ala
            820                 825                 830

Glu Ala Ile Asp Lys Glu Glu Val Glu Thr Glu Lys Gly Lys Asp
        835                 840                 845

Glu Gln Lys Lys Asp Glu Gln Lys Glu Gln Asp Glu Glu Asp Gly
    850                 855                 860

Glu Lys Glu Asn Lys His Lys Ser Ser Glu Thr Thr Asn Glu Thr Val
865                 870                 875                 880

Thr Asp Ile Glu Glu Asn Lys Asn Glu Val Lys Gly Glu Glu His Leu
                885                 890                 895

Gln Gly Ser Glu Gln Ser Ile Glu Ala Ser Glu Ser Ser Gln Lys Asp
            900                 905                 910

Glu Thr Lys Glu Thr Glu Asp Lys Glu Glu Tyr Val Asn Ala Asn Asp
        915                 920                 925
```

```
Asp Glu Ser Ser Glu Glu Asp Thr Thr Pro Asn Glu Thr Asn Lys Thr
            930                 935                 940

Asp Asn Gly Ser Ser Phe Phe Phe Ala Met Ser Asn Ala Leu Leu Val
945                 950                 955                 960

Ile Leu Leu Leu Leu Phe Ile Glu Phe Leu
                965                 970

<210> SEQ ID NO 62
<211> LENGTH: 969
<212> TYPE: PRT
<213> ORGANISM: Plasmodium falciparum
<220> FEATURE:
<221> NAME/KEY: misc_feature
<223> OTHER INFORMATION: PfP113

<400> SEQUENCE: 62

Met Lys Ile Pro Phe Phe Ile Leu His Ile Leu Leu Gln Phe Leu
1               5                   10                  15

Leu Cys Leu Ile Arg Cys Tyr Val His Asn Asp Val Ile Lys Phe Gly
            20                  25                  30

Glu Glu Asn Ser Leu Lys Cys Ser Gln Gly Asn Leu Tyr Val Leu His
            35                  40                  45

Cys Glu Val Gln Cys Leu Asn Gly Asn Asn Glu Ile Ile His Lys Arg
50                  55                  60

Cys Asn Asp Asp Ile Glu Lys Lys Cys Asn Gly Asn Lys Cys Ile
65                  70                  75                  80

Tyr Phe Phe Glu Tyr Glu Leu Arg Lys Lys Thr Gln Ser Phe Arg Asn
                85                  90                  95

Lys Asn Ser Ile Glu Ile Ser Glu Cys Val Glu Ser Glu Gln Asn Glu
            100                 105                 110

Val Lys Thr Ser Thr Thr Cys Leu Leu Ser Asn Ser Phe Ile Leu Asp
            115                 120                 125

Glu Ala Phe Ile Gln Tyr Phe Phe Phe Ile Lys Asn Lys Asn Glu Glu
130                 135                 140

Pro Val Ile Cys Lys Asp Gly Asn Ile Asn Ile Lys Ser Ala Leu Leu
145                 150                 155                 160

His Ser Pro Phe Cys Glu Ile Lys Leu Lys Asp Ile Ser Glu Tyr Ile
                165                 170                 175

Arg Lys Lys Cys Asp Asn Asn Lys Glu Cys Leu Ile Asp Pro Leu Asp
            180                 185                 190

Val Gln Lys Asn Leu Leu Asn Glu Glu Asp Pro Cys Tyr Ile Asn Asn
            195                 200                 205

Ser Tyr Val Ser Val Asn Val Val Cys Asn Lys Glu Glu Ile Gly
210                 215                 220

Asp Glu Ser Thr Asp Ser Ser Ser Met Glu Ile Gln Asp Ser Thr Ser
225                 230                 235                 240

Asn Glu Gln Asp Glu Asn Val Lys Gly Met Ser Ser Ser Gln Glu Met
                245                 250                 255

Asn Ser Asn Asn Asp Glu Asn Lys Asn Gln Asp Asn Glu Ser Asp Asp
            260                 265                 270

Asp Val Asn Asn Asn Asn Asn Asn Asp Asp Gln Asp Glu Gln
            275                 280                 285

Gly Asn Asp Gly Asp Val Thr Ser Ser Met Lys Asn Glu Asp Asn
290                 295                 300

Lys Asp Leu Glu His Gly Ser Ser Asn Asp Val Asn Asn Asn Thr Asp
305                 310                 315                 320
```

```
Thr Leu Val Asn Asn Lys Glu Asn Lys Glu Phe Val Leu Lys Glu Lys
                325                 330                 335

Ser Ser Leu Thr Ser Lys Ile Asn Lys Glu Leu Ala His Arg Thr Ala
                340                 345                 350

Leu Phe Asn Lys Leu Ala Asp Asn Ile Ser Leu Leu Asn Lys Lys
                355                 360                 365

Tyr Asp Ser Phe Glu Ile Lys Asp Val Leu Glu Asp Arg Tyr Asn Glu
                370                 375                 380

Met Lys Arg Asp Ala Asn Pro Asp Val Tyr Tyr Ile Tyr Leu Met Asp
385                 390                 395                 400

Thr Leu Asp Ile Glu Lys Ile Glu Asp Ile Asn Leu Glu Glu Val Lys
                405                 410                 415

Met Ser Leu Leu Ala Ser Leu Lys Glu Thr Met Asn Lys Ile Asp Thr
                420                 425                 430

Ile Glu Lys Lys Ile Glu Glu Phe Lys Asn Lys Tyr Ile Ser Leu Tyr
                435                 440                 445

Asn Lys Val Lys Thr Thr Met Pro Glu Leu Phe Asp Leu Asn Glu Asp
                450                 455                 460

Leu Val Leu Leu Tyr Asn Asp Phe Pro Phe Asp Asn Gly Met Ile Ser
465                 470                 475                 480

Ser Asp Ile Phe Phe Lys Tyr Asn Pro Ser Glu Asn Ile Met Asp His
                485                 490                 495

Gln Glu Met Val Lys Lys Gly Ser Ile Thr Glu Asp Glu Leu Arg Ile
                500                 505                 510

Val Asn Asp Leu Glu Pro Leu Asp Asn Tyr Arg Arg Lys Arg Ile
                515                 520                 525

Thr Glu Leu Arg Lys Ile Leu Val Glu Lys Leu Arg Ile Leu Tyr Leu
                530                 535                 540

Glu Lys Asn Asn Leu Phe Asn Thr Gln Ala Ser Cys Ile Lys Ser Tyr
545                 550                 555                 560

Cys Tyr Lys Asn Pro Leu Asn Leu Lys Thr Leu Glu Val Leu Leu Lys
                565                 570                 575

Lys Asn Tyr Tyr Arg Leu Lys Glu Asn Lys Asp Tyr Asp Val Val Ser
                580                 585                 590

Ser Ile Ile Gln His Leu Asp Asn Val Asp Ala Asn Lys Lys Lys Lys
                595                 600                 605

Trp Leu Thr His Glu Arg Ile Leu Lys Lys Leu Gln Val Leu Ile Ala
                610                 615                 620

Glu Gly Tyr Lys Arg Ile Asn Glu Lys Glu Lys Asp Ile Asp Arg Arg
625                 630                 635                 640

Met Ala Val Tyr Asn Ala Leu Tyr Glu Lys Ala Gln Ser Tyr Asn Leu
                645                 650                 655

Gln Lys Leu Phe Asn Asp Ser Asn Asp Phe Leu Lys Lys Tyr Ala Ile
                660                 665                 670

Met Gly Asn Ser Phe Asp Asp Gly Asp Glu Val Phe Gly Ser Gln Ser
                675                 680                 685

Ser Asn Phe Asn Ile Phe Asp Ser Asn Asn Thr Asp Gln Asn Asn Glu
                690                 695                 700

Gln Glu Gln Pro Lys Gln Asp Asp Gln Leu Leu Asn Asn Asn Asn Asp
705                 710                 715                 720

Asp Val Leu Ser Glu Ser Asn Asn Glu Asn Lys Glu Lys Thr Ser Asp
                725                 730                 735
```

```
Asp Ala Thr His Lys Glu Thr Gln Glu Lys Ser Asp Gln Glu Pro Ser
                740                 745                 750

Gln Asn Ile Gln Glu Asp Asn Ser Asp Glu Lys His Ala Glu Asn Glu
            755                 760                 765

Glu Asn Val Glu Gln Ile Glu Thr Asp Ser Asn Val Ser Glu Ala
        770                 775                 780

Asn Asp Glu Asn Lys Asp Asn Met Gln Thr Thr Asp Glu Gly Thr
785                 790                 795                 800

Glu Glu Leu Gln Gln Asn Asp Glu Asp Ala Glu Ser Leu Thr Lys Glu
                805                 810                 815

Asn Ser Lys Ser Glu Glu Gln Glu Asn Glu Asp Ser Thr Asp Ala Glu
            820                 825                 830

Ala Ile Asp Lys Glu Glu Val Glu Thr Glu Glu Lys Gly Lys Asp Glu
        835                 840                 845

Gln Lys Lys Asp Glu Gln Lys Glu Gln Asp Glu Glu Asp Gly Glu
    850                 855                 860

Lys Glu Asn Lys His Lys Ser Ser Glu Thr Thr Asn Glu Thr Val Thr
865                 870                 875                 880

Asp Ile Glu Glu Asn Lys Asn Glu Val Lys Gly Glu Glu His Leu Gln
                885                 890                 895

Gly Ser Glu Gln Ser Ile Glu Ala Ser Glu Ser Ser Gln Lys Asp Glu
            900                 905                 910

Thr Lys Glu Thr Glu Asp Lys Glu Glu Tyr Val Asn Ala Asn Asp Asp
        915                 920                 925

Glu Ser Ser Glu Asp Thr Thr Pro Asn Glu Thr Asn Lys Thr Asp
    930                 935                 940

Asn Gly Ser Ser Phe Phe Phe Ala Met Ser Asn Ala Leu Leu Val Ile
945                 950                 955                 960

Leu Leu Leu Leu Phe Ile Glu Phe Leu
                965

<210> SEQ ID NO 63
<211> LENGTH: 3141
<212> TYPE: DNA
<213> ORGANISM: Artificial Sequence
<220> FEATURE:
<223> OTHER INFORMATION: PvP113 human CO

<400> SEQUENCE: 63
gccaccatgg ctaagctccc gcccctctgc aggttgccac ttgcgctggt gcttctttgt      60
ctgacatcca gagcgcgctg ttatgtacac aacgacgtga tgaaatttgg tgaagaaaac     120
tctctcaagt gttcacaagg gtctctctac atccttcact gcgaggtcaa gtgtgtgaat     180
gcaaagaaca gaatcatcca ccgaagttgc atcgaccagg ttgaggcgaa gtgcatgggc     240
aacgccaaat gtaagtacta ttttgactat gtcgtgaaat cccgcggaca gagtttgcgg     300
aacaaaaatg aaatcgaaat agaagaatgc gtggaatccg aacggaatga gattaagacg     360
tccacaactt gccttctgtc aaattcattt ttgctggatg agacctacat tcaatatttc     420
tttttcatca aaacaaaaa tgaagaaccc ataacgtgtc gagacggtag actgagcgta     480
aagagtgcga tacttcatag tccctttttgc aaaataaatc ttaaggacat cactgagatt     540
ctcaagagac aatgcgatca cagtaaggag tgcgtcatta atccgtatgt cctccaaaaa     600
gatgcattga atgagagaga ccagtgttac attaacaact catatgtctc actcaatgtc     660
gtttgcacca agaaggggga ggagcaacca gaagagagtg gacataaaca gaagagggat     720
```

```
gacgacgtgg acgaaaccga ggaaggctca tatgacgtct ctgcggatca gaacaaatca    780
gcaatagtcg gcgagggaaa cgatgatccg gaatccctgg gtgaagaaga tgagctttca    840
gagactaacg aggcagttga tctcattatg aactccaagg aaagctttga aaacaaaatt    900
cggaaggcga agtcaatact tctctcacag atgaacgagc aggaggtgaa aaagaatgca    960
atattcaaga aactcgggga agagctttcc aaaatggtcc tccagaaata tgaaccaagt   1020
gatctgaaag acttgatcga ggacaggtat aatgaaatga cggtcccc tgaccaagac     1080 ctttattatc tctaccttat agatacactc gaaataaata aaatggaaga tcttgacgtg   1140
actgcactgc aagaccagct cgctatattg ttggaagagc agatgggcaa gatgaatcgc   1200
attgagaaaa cgattaaccg attgaggaaa aaatacctt ctatttacaa caaagcgaag    1260
aacaagaaag ttaaagacat ttacgatgaa ggagttgatc ctgtactcac gtacgacgac   1320
ttcgcgcacg gcaacggcat tattacggca gatattttct ttaagtataa gcctgccatt   1380
aagccgttga cttttagcaa atctaatgcc tctgaggagc ggggtcatc caaaaaaaaa    1440 gagtacaagg accttcttga gatggacgcg ctggatgagt acaaccggaa gaaacggata   1500
actgacatgc gaaacggtct gatggagact ttgaagaaaa tgtattacgc aaaaaatggg   1560
atattcaata atctggcgag ttgcattaag tcatattgct ataaaaggcc tctcaacctt   1620
aatgcacttt cctccgttct taaaagaaat tttgaaaatc ttcgagagaa aaaatcaacc   1680
gatccagtgg cccccatagt cagatatttg caaaaggtca gtggcgaggt tggcggggaa   1740
gtgggaggcg cggctggcgg tgctgcgggg ggtgctgcaa gtggtgccgc atcaggagct   1800
gtcagtgaag cagtaggagg cgccataggt ggggctgtgg gcgaggcatc tatcgcagta   1860
aatccgcccc gatgggaaaa atcacgacga attcttcaaa agctcaaggc tttgctgcac   1920
ctgggttatc aacaggcact ggacaaagag ttggagatcg acgagaggac tgacaaatac   1980
aacgctctga atgagaaagc aaaagaatat aaccttcagc ggcttttttc cgagtcagac   2040
aagttgctta agaaggtcgc aatgcttacg tcagccagtg aaagtgcaga tgaagtattc   2100
ggtaaccaag cgagcttttt cgatgtttac agaggagagg cagcgtcaca aaaaggagta   2160
gccgccagtg aaaagggcgt agctgcaaga gagaaaggag tcgccgcgag tgagaagggg   2220
gtcgcggcat cagaaaaggg tgtggcggcc agcgagaagg gtgtcgcggc atcagaaaaa   2280
ggtgttgccg caagccaaaa aggcggagaa acgtctgagg aaggggaggc tgccagtcaa   2340
aaggatgttg ctacgtccga ggagggtgga gctagcagcg agaaacgcga tgacgacgag   2400
atgaatccgc ccgacgaagg gtatgagtcc gctaaggaag acgggagaa tgcacaagat    2460 gacgacagcg gcggaaatgc tgaacccgta gagggaaaag caggcgaaag tgaagacgct   2520
gatggggtaa atgccggctc caataaagaa ggtgaggatg gggagagcgt tgaagaagaa   2580
gctgcggaag gggaagcggc acccaaggag gaggctgcag acggagaaga tgctccggag   2640
gaggaagccg agggtgagga tgccccagaa gaagaggccg atggcgaaga cgccccgaag   2700
gaggaggcta ctgacggaga ggacgcccct aaagaggaag aggccgaagg tgaggatgca   2760
agcaaggacg aggaggccga cgaaggctca actgacgagg aagaagccgc cgacggcggg   2820
agtactgatg ctacagcagc cgatgaagct gcaggcggag tcgcggacca aaacgacgtg   2880
cccgttaagg gagaagactc agatggcgcg gaatctgatg gagcagaaga tgccgccact   2940
gaaattaggg gtgaggctga agccggtgaa gaggccgcgg agcaacctac tggagaggcc   3000
gtagtcaaag gggattccga gggcgggct tctgggctgg aaaccgagaa gaagggagac    3060
gacgggggct ccttcttcca aggtctttcc cgagtgttgc ttactgttct tgcaatactt   3120
```

-continued

```
tccttggaat ttctcctttg a                                             3141
```

<210> SEQ ID NO 64
<211> LENGTH: 1044
<212> TYPE: PRT
<213> ORGANISM: Plasmodium vivax
<220> FEATURE:
<221> NAME/KEY: misc_feature
<223> OTHER INFORMATION: PvP113

<400> SEQUENCE: 64

```
Met Ala Lys Leu Pro Pro Leu Cys Arg Leu Pro Leu Ala Leu Val Leu
1               5                   10                  15

Leu Cys Leu Thr Ser Arg Ala Arg Cys Tyr Val His Asn Asp Val Met
            20                  25                  30

Lys Phe Gly Glu Glu Asn Ser Leu Lys Cys Ser Gln Gly Ser Leu Tyr
        35                  40                  45

Ile Leu His Cys Glu Val Lys Cys Val Asn Ala Lys Asn Arg Ile Ile
    50                  55                  60

His Arg Ser Cys Ile Asp Gln Val Glu Ala Lys Cys Met Gly Asn Ala
65                  70                  75                  80

Lys Cys Lys Tyr Tyr Phe Asp Tyr Val Lys Ser Arg Gly Gln Ser
                85                  90                  95

Leu Arg Asn Lys Asn Glu Ile Glu Ile Glu Glu Cys Val Glu Ser Glu
            100                 105                 110

Arg Asn Glu Ile Lys Thr Ser Thr Thr Cys Leu Leu Ser Asn Ser Phe
        115                 120                 125

Leu Leu Asp Glu Thr Tyr Ile Gln Tyr Phe Phe Ile Lys Asn Lys
    130                 135                 140

Asn Glu Glu Pro Ile Thr Cys Arg Asp Gly Arg Leu Ser Val Lys Ser
145                 150                 155                 160

Ala Ile Leu His Ser Pro Phe Cys Lys Ile Asn Leu Lys Asp Ile Thr
                165                 170                 175

Glu Ile Leu Lys Arg Gln Cys Asp His Ser Lys Glu Cys Val Ile Asn
            180                 185                 190

Pro Tyr Val Leu Gln Lys Asp Ala Leu Asn Glu Arg Asp Gln Cys Tyr
        195                 200                 205

Ile Asn Asn Ser Tyr Val Ser Leu Asn Val Val Cys Thr Lys Glu Gly
    210                 215                 220

Glu Glu Gln Pro Glu Glu Ser Gly His Lys Gln Lys Arg Asp Asp Asp
225                 230                 235                 240

Val Asp Glu Thr Glu Glu Gly Ser Tyr Asp Val Ser Ala Asp Gln Asn
                245                 250                 255

Lys Ser Ala Ile Val Gly Glu Gly Asn Asp Pro Glu Ser Leu Gly
            260                 265                 270

Glu Glu Asp Glu Leu Ser Glu Thr Asn Glu Ala Val Asp Leu Ile Met
        275                 280                 285

Asn Ser Lys Glu Ser Phe Glu Asn Lys Ile Arg Lys Ala Lys Ser Ile
    290                 295                 300

Leu Leu Ser Gln Met Asn Glu Gln Glu Val Lys Lys Asn Ala Ile Phe
305                 310                 315                 320

Lys Lys Leu Gly Glu Glu Leu Ser Lys Met Val Leu Gln Lys Tyr Glu
                325                 330                 335

Pro Ser Asp Leu Lys Asp Leu Ile Glu Asp Arg Tyr Asn Glu Met Arg
            340                 345                 350
```

-continued

```
Arg Ser Pro Asp Gln Asp Leu Tyr Tyr Leu Tyr Leu Ile Asp Thr Leu
        355                 360                 365

Glu Ile Asn Lys Met Glu Asp Leu Asp Val Thr Ala Leu Gln Asp Gln
370                 375                 380

Leu Ala Ile Leu Glu Glu Gln Met Gly Lys Met Asn Arg Ile Glu
385                 390                 395                 400

Lys Thr Ile Asn Arg Leu Arg Lys Lys Tyr Leu Ser Ile Tyr Asn Lys
                405                 410                 415

Ala Lys Asn Lys Lys Val Lys Asp Ile Tyr Asp Glu Gly Val Asp Pro
                420                 425                 430

Val Leu Thr Tyr Asp Asp Phe Ala His Gly Asn Gly Ile Ile Thr Ala
                435                 440                 445

Asp Ile Phe Phe Lys Tyr Lys Pro Ala Ile Lys Pro Leu Thr Phe Ser
        450                 455                 460

Lys Ser Asn Ala Ser Glu Glu Arg Gly Ser Ser Lys Lys Lys Glu Tyr
465                 470                 475                 480

Lys Asp Leu Leu Glu Met Asp Ala Leu Asp Glu Tyr Asn Arg Lys Lys
                485                 490                 495

Arg Ile Thr Asp Met Arg Asn Gly Leu Met Glu Thr Leu Lys Lys Met
                500                 505                 510

Tyr Tyr Ala Lys Asn Gly Ile Phe Asn Asn Leu Ala Ser Cys Ile Lys
                515                 520                 525

Ser Tyr Cys Tyr Lys Arg Pro Leu Asn Leu Asn Ala Leu Ser Ser Val
        530                 535                 540

Leu Lys Arg Asn Phe Glu Asn Leu Arg Glu Lys Lys Ser Thr Asp Pro
545                 550                 555                 560

Val Ala Pro Ile Val Arg Tyr Leu Gln Lys Val Ser Gly Glu Val Gly
                565                 570                 575

Gly Glu Val Gly Gly Ala Ala Gly Gly Ala Ala Gly Gly Ala Ala Ser
                580                 585                 590

Gly Ala Ala Ser Gly Ala Val Ser Glu Ala Val Gly Gly Ala Ile Gly
        595                 600                 605

Gly Ala Val Gly Glu Ala Ser Ile Ala Val Asn Pro Pro Arg Trp Glu
610                 615                 620

Lys Ser Arg Arg Ile Leu Gln Lys Leu Lys Ala Leu Leu His Leu Gly
625                 630                 635                 640

Tyr Gln Gln Ala Leu Asp Lys Glu Leu Glu Ile Asp Glu Arg Thr Asp
                645                 650                 655

Lys Tyr Asn Ala Leu Asn Glu Lys Ala Lys Glu Tyr Asn Leu Gln Arg
                660                 665                 670

Leu Phe Ser Glu Ser Asp Lys Leu Leu Lys Lys Val Ala Met Leu Thr
        675                 680                 685

Ser Ala Ser Glu Ser Ala Asp Glu Val Phe Gly Asn Gln Ala Ser Phe
690                 695                 700

Phe Asp Val Tyr Arg Gly Glu Ala Ser Gln Lys Gly Val Ala Ala
705                 710                 715                 720

Ser Glu Lys Gly Val Ala Ala Arg Glu Lys Gly Val Ala Ala Ser Glu
                725                 730                 735

Lys Gly Val Ala Ala Ser Glu Lys Gly Val Ala Ala Ser Glu Lys Gly
                740                 745                 750

Val Ala Ala Ser Glu Lys Gly Val Ala Ala Ser Gln Lys Gly Gly Glu
        755                 760                 765
```

Thr Ser Glu Glu Gly Glu Ala Ala Ser Gln Lys Asp Val Ala Thr Ser
    770             775             780

Glu Glu Gly Gly Ala Ser Ser Glu Lys Arg Asp Asp Glu Met Asn
785             790             795             800

Pro Pro Asp Glu Gly Tyr Glu Ser Ala Lys Glu Asp Gly Glu Asn Ala
                805             810             815

Gln Asp Asp Asp Ser Gly Gly Asn Ala Glu Pro Val Glu Gly Lys Ala
            820             825             830

Gly Glu Ser Glu Asp Ala Asp Gly Val Asn Ala Gly Ser Asn Lys Glu
            835             840             845

Gly Glu Asp Gly Glu Ser Val Glu Glu Glu Ala Ala Glu Gly Glu Ala
            850             855             860

Ala Pro Lys Glu Glu Ala Ala Asp Gly Glu Asp Ala Pro Glu Glu Glu
865             870             875             880

Ala Glu Gly Glu Asp Ala Pro Glu Glu Ala Asp Gly Glu Asp Ala
            885             890             895

Pro Lys Glu Glu Ala Thr Asp Gly Glu Asp Ala Pro Lys Glu Glu Glu
            900             905             910

Ala Glu Gly Glu Asp Ala Ser Lys Asp Glu Glu Ala Asp Glu Gly Ser
            915             920             925

Thr Asp Glu Glu Glu Ala Ala Asp Gly Gly Ser Thr Asp Ala Thr Ala
    930             935             940

Ala Asp Glu Ala Ala Gly Gly Val Ala Asp Gln Asn Asp Val Pro Val
945             950             955             960

Lys Gly Glu Asp Ser Asp Gly Ala Glu Ser Asp Gly Ala Glu Asp Ala
            965             970             975

Ala Thr Glu Ile Arg Gly Glu Ala Glu Ala Gly Glu Ala Ala Glu
            980             985             990

Gln Pro Thr Gly Glu Ala Val Val Lys Gly Asp Ser Glu Gly Gly Ala
    995             1000            1005

Ser Gly Leu Glu Thr Glu Lys Lys Gly Asp Asp Gly Gly Ser Phe
    1010            1015            1020

Phe Gln Gly Leu Ser Arg Val Leu Leu Thr Val Leu Ala Ile Leu
    1025            1030            1035

Ser Leu Glu Phe Leu Leu
    1040

<210> SEQ ID NO 65
<211> LENGTH: 969
<212> TYPE: PRT
<213> ORGANISM: Plasmodium vivax
<220> FEATURE:
<221> NAME/KEY: misc_feature
<223> OTHER INFORMATION: P113

<400> SEQUENCE: 65

Met Lys Leu Pro Pro Leu Cys Arg Leu Pro Ala Leu Val Leu Leu
1               5                   10                  15

Cys Leu Thr Ser Arg Ala Arg Cys Tyr Val His Asn Asp Val Met Lys
            20                  25                  30

Phe Gly Glu Glu Asn Ser Leu Cys Ser Gln Gly Ser Leu Tyr Ile
        35                  40                  45

Leu His Cys Glu Val Lys Cys Val Asn Ala Lys Asn Arg Ile Ile His
    50                  55                  60

Arg Ser Cys Ile Asp Gln Val Glu Ala Lys Cys Met Gly Asn Ala Lys
65                  70                  75                  80

```
Cys Lys Tyr Tyr Phe Asp Tyr Val Lys Ser Arg Gly Gln Ser Leu
                85                  90                  95

Arg Asn Lys Asn Glu Ile Glu Ile Glu Cys Val Glu Ser Glu Arg
            100                 105                 110

Asn Glu Ile Lys Thr Ser Thr Cys Leu Leu Ser Asn Ser Phe Leu
            115                 120                 125

Leu Asp Glu Thr Tyr Ile Gln Tyr Phe Phe Ile Lys Asn Lys Asn
130                 135                 140

Glu Glu Pro Ile Thr Cys Arg Asp Gly Arg Leu Ser Val Lys Ser Ala
145                 150                 155                 160

Ile Leu His Ser Pro Phe Cys Lys Ile Asn Leu Lys Asp Ile Thr Glu
                165                 170                 175

Ile Leu Lys Arg Gln Cys Asp His Ser Lys Glu Cys Val Ile Asn Pro
            180                 185                 190

Tyr Val Leu Gln Lys Asp Ala Leu Asn Glu Arg Asp Gln Cys Tyr Ile
            195                 200                 205

Asn Asn Ser Tyr Val Ser Leu Asn Val Val Cys Thr Lys Glu Gly Glu
            210                 215                 220

Glu Gln Pro Glu Glu Ser Gly His Lys Gln Lys Arg Asp Asp Asp Val
225                 230                 235                 240

Asp Glu Thr Glu Glu Gly Ser Tyr Asp Val Ser Ala Asp Gln Asn Lys
                245                 250                 255

Ser Ala Ile Val Gly Glu Gly Asn Asp Pro Glu Ser Leu Gly Glu
                260                 265                 270

Glu Asp Glu Leu Ser Glu Thr Asn Glu Ala Val Asp Leu Ile Met Asn
            275                 280                 285

Ser Lys Glu Ser Phe Glu Asn Lys Ile Arg Lys Ala Lys Ser Ile Leu
            290                 295                 300

Leu Ser Gln Met Asn Glu Gln Glu Val Lys Lys Asn Ala Ile Phe Lys
305                 310                 315                 320

Lys Leu Gly Glu Glu Leu Ser Lys Met Val Leu Gln Lys Tyr Glu Pro
                325                 330                 335

Ser Asp Leu Lys Asp Leu Ile Glu Asp Arg Tyr Asn Glu Met Arg Arg
            340                 345                 350

Ser Pro Asp Gln Asp Leu Tyr Tyr Leu Tyr Leu Ile Asp Thr Leu Glu
            355                 360                 365

Ile Asn Lys Met Glu Asn Leu Asp Val Thr Ala Leu Gln Asp Gln Leu
            370                 375                 380

Ala Ile Leu Leu Glu Glu Gln Met Gly Lys Met Asn Arg Ile Glu Lys
385                 390                 395                 400

Thr Ile Asn Arg Leu Arg Lys Lys Tyr Leu Ser Ile Tyr Asn Lys Ala
                405                 410                 415

Lys Asn Lys Lys Val Lys Asp Ile Tyr Asp Glu Gly Val Asp Pro Val
            420                 425                 430

Leu Thr Tyr Asp Asp Phe Ala His Gly Asn Gly Ile Ile Thr Ala Asp
            435                 440                 445

Ile Phe Phe Lys Tyr Lys Pro Ala Ile Lys Pro Leu Thr Phe Ser Lys
450                 455                 460

Ser Asn Ala Ser Glu Glu Arg Gly Ser Ser Lys Lys Glu Tyr Lys
465                 470                 475                 480

Asp Leu Leu Glu Met Asp Ala Leu Asp Glu Tyr Asn Arg Lys Lys Arg
                485                 490                 495
```

```
Ile Thr Asp Met Arg Asn Gly Leu Met Glu Thr Leu Lys Lys Met Tyr
            500                 505                 510

Tyr Ala Lys Asn Gly Ile Phe Asn Asn Leu Ala Ser Cys Ile Lys Ser
            515                 520                 525

Tyr Cys Tyr Lys Arg Pro Leu Asn Leu Asn Ala Leu Ser Ser Val Leu
            530                 535                 540

Lys Arg Asn Phe Glu Asn Leu Arg Glu Lys Lys Ser Thr Asp Pro Val
545                 550                 555                 560

Ala Pro Ile Val Arg Tyr Leu Gln Lys Lys Ser Arg Arg Ile Leu Gln
                565                 570                 575

Lys Leu Lys Ala Leu Leu His Leu Gly Tyr Gln Gln Ala Leu Asp Lys
            580                 585                 590

Glu Leu Glu Ile Asp Glu Arg Thr Asp Lys Tyr Asn Ala Leu Asn Glu
            595                 600                 605

Lys Ala Lys Glu Tyr Asn Leu Gln Arg Leu Phe Ser Glu Ser Asp Lys
610                 615                 620

Leu Leu Lys Lys Val Ala Met Leu Thr Ser Ala Ser Glu Ser Ala Asp
625                 630                 635                 640

Glu Val Phe Gly Asn Gln Ala Ser Phe Phe Asp Val Tyr Arg Gly Glu
                645                 650                 655

Ala Ala Ser Glu Lys Gly Val Ala Ala Ser Gln Lys Gly Gly Glu Thr
            660                 665                 670

Ser Glu Glu Gly Glu Ala Ala Ser Gln Lys Asp Val Ala Thr Ser Glu
            675                 680                 685

Glu Gly Gly Ala Ser Ser Glu Lys Arg Asp Asp Glu Met Asn Pro
690                 695                 700

Pro Asp Glu Gly Tyr Glu Ser Ala Lys Glu Asp Gly Glu Asn Ala Gln
705                 710                 715                 720

Asp Asp Asp Ser Gly Gly Asn Ala Glu Pro Val Glu Gly Lys Ala Gly
                725                 730                 735

Glu Ser Glu Asp Ala Asp Gly Val Asn Ala Gly Ser Asn Lys Glu Gly
            740                 745                 750

Glu Asp Gly Glu Ser Val Glu Glu Ala Ala Glu Gly Glu Ala Ala
            755                 760                 765

Pro Lys Glu Glu Ala Ala Asp Gly Glu Asp Ala Pro Glu Glu Glu Ala
770                 775                 780

Glu Gly Glu Asp Ala Pro Lys Glu Glu Ala Ala Asp Gly Glu Ala Ser
785                 790                 795                 800

Ser Lys Glu Glu Glu Thr Asp Gly Glu Val Ala Pro Glu Glu Ala Ala
            805                 810                 815

Asp Gly Glu Asp Ala Pro Lys Glu Glu Ala Thr Asp Gly Glu Asp Ala
            820                 825                 830

Pro Lys Glu Glu Glu Ala Glu Gly Glu Asp Ala Ser Lys Asp Glu Glu
            835                 840                 845

Ala Asp Glu Gly Ser Thr Asp Glu Glu Ala Ala Asp Gly Gly Ser
850                 855                 860

Thr Asp Ala Thr Ala Ala Asp Glu Ala Ala Gly Gly Val Ala Asp Gln
865                 870                 875                 880

Asn Asp Val Pro Val Lys Gly Glu Asp Ser Asp Gly Ala Glu Ser Asp
                885                 890                 895

Gly Ala Glu Asp Ala Ala Thr Glu Ile Arg Gly Glu Ala Glu Ala Gly
            900                 905                 910

Glu Glu Ala Ala Glu Gln Pro Thr Gly Glu Ala Val Val Lys Gly Asp
```

```
                      915                 920                 925
Ser Glu Gly Gly Ala Ser Gly Leu Glu Thr Glu Lys Lys Gly Asp Asp
        930                 935                 940

Gly Gly Ser Phe Phe Gln Gly Leu Ser Arg Val Leu Leu Thr Val Leu
945                 950                 955                 960

Ala Ile Leu Ser Leu Glu Phe Leu Leu
                965

<210> SEQ ID NO 66
<211> LENGTH: 654
<212> TYPE: DNA
<213> ORGANISM: Plasmodium berghei
<220> FEATURE:
<221> NAME/KEY: misc_feature
<223> OTHER INFORMATION: Ag40

<400> SEQUENCE: 66
ggatccgcca ccatggctgg ggcgagtatg agccacttgc agtgtctgac atctgttgct    60
ggtctgtcct ctatcgtcat gtcaatgttc cccaaactca ttgccaataa tccttccctg   120
tttagaccac tgctcaacat ttcctgggga tatctgttcg gaagcactgt atggctgtgc   180
ttcttcagtg agattgggtt ggtcaggaga atcaatgctc ctaaacggaa gaatctgcca   240
gagaatgcag aacaagccaa agaacagctg aaggagatca gaacaacga aggcgatttt    300 aaccgacgca atatcgactt caagtacttc tttagccttt ccacaatctt ctctagcata   360
ctgctgctta gcacagtgaa actcgccaac aacaatctgc agttgaggat ctgttccacc   420
attgtgtcac tgagttgcat actgaacaat atgtactttc agaacaagat acactcactt   480
gcactgaaga agagagtct ctttaaggac atgatcgatc gtccgaaaga taccactatt    540
ctggtgaacc tgaagaagaa caagaccgac tttcacatcc atcatggcct ttctctgctc   600
ttgctctata gcagcttctt tggcctcact ccctacattt tcacgtgact cgag           654

<210> SEQ ID NO 67
<211> LENGTH: 211
<212> TYPE: PRT
<213> ORGANISM: Plasmodium berghei
<220> FEATURE:
<221> NAME/KEY: misc_feature
<223> OTHER INFORMATION: Ag40

<400> SEQUENCE: 67

Met Ala Gly Ala Ser Met Ser His Leu Gln Cys Leu Thr Ser Val Ala
1               5                   10                  15

Gly Leu Ser Ser Ile Val Met Ser Met Phe Pro Lys Leu Ile Ala Asn
            20                  25                  30

Asn Pro Ser Leu Phe Arg Pro Leu Leu Asn Ile Ser Trp Gly Tyr Leu
        35                  40                  45

Phe Gly Ser Thr Val Trp Leu Cys Phe Phe Ser Glu Ile Gly Leu Val
    50                  55                  60

Arg Arg Ile Asn Ala Pro Lys Arg Lys Asn Leu Pro Glu Asn Ala Glu
65                  70                  75                  80

Gln Ala Lys Glu Gln Leu Lys Glu Ile Lys Asn Asn Glu Gly Asp Phe
                85                  90                  95

Asn Arg Arg Asn Ile Asp Phe Lys Tyr Phe Phe Ser Leu Ser Thr Ile
            100                 105                 110

Phe Ser Ser Ile Leu Leu Leu Ser Thr Val Lys Leu Ala Asn Asn Asn
        115                 120                 125
```

-continued

Leu Gln Leu Arg Ile Cys Ser Thr Ile Val Ser Leu Ser Cys Ile Leu
    130                 135                 140

Asn Asn Met Tyr Phe Gln Asn Lys Ile His Ser Leu Ala Leu Lys Lys
145                 150                 155                 160

Glu Ser Leu Phe Lys Asp Met Ile Asp Arg Pro Lys Asp Thr Thr Ile
                165                 170                 175

Leu Val Asn Leu Lys Lys Asn Lys Thr Asp Phe His Ile His His Gly
                180                 185                 190

Leu Ser Leu Leu Leu Tyr Ser Ser Phe Phe Gly Leu Thr Pro Tyr
                195                 200                 205

Ile Phe Thr
    210

<210> SEQ ID NO 68
<211> LENGTH: 210
<212> TYPE: PRT
<213> ORGANISM: Plasmodium berghei
<220> FEATURE:
<221> NAME/KEY: misc_feature
<223> OTHER INFORMATION: Ag40

<400> SEQUENCE: 68

Met Gly Ala Ser Met Ser His Leu Gln Cys Leu Thr Ser Val Ala Gly
1               5                   10                  15

Leu Ser Ser Ile Val Met Ser Met Phe Pro Lys Leu Ile Ala Asn Asn
                20                  25                  30

Pro Ser Leu Phe Arg Pro Leu Leu Asn Ile Ser Trp Gly Tyr Leu Phe
            35                  40                  45

Gly Ser Thr Val Trp Leu Cys Phe Phe Ser Glu Ile Gly Leu Val Arg
    50                  55                  60

Arg Ile Asn Ala Pro Lys Arg Lys Asn Leu Pro Glu Asn Ala Glu Gln
65                  70                  75                  80

Ala Lys Glu Gln Leu Lys Glu Ile Lys Asn Asn Glu Gly Asp Phe Asn
                85                  90                  95

Arg Arg Asn Ile Asp Phe Lys Tyr Phe Phe Ser Leu Ser Thr Ile Phe
            100                 105                 110

Ser Ser Ile Leu Leu Leu Ser Thr Val Lys Leu Ala Asn Asn Asn Leu
        115                 120                 125

Gln Leu Arg Ile Cys Ser Thr Ile Val Ser Leu Ser Cys Ile Leu Asn
    130                 135                 140

Asn Met Tyr Phe Gln Asn Lys Ile His Ser Leu Ala Leu Lys Lys Glu
145                 150                 155                 160

Ser Leu Phe Lys Asp Met Ile Asp Arg Pro Lys Asp Thr Thr Ile Leu
                165                 170                 175

Val Asn Leu Lys Lys Asn Lys Thr Asp Phe His Ile His His Gly Leu
                180                 185                 190

Ser Leu Leu Leu Tyr Ser Ser Phe Phe Gly Leu Thr Pro Tyr Ile
                195                 200                 205

Phe Thr
    210

<210> SEQ ID NO 69
<211> LENGTH: 642
<212> TYPE: DNA
<213> ORGANISM: Artificial Sequence
<220> FEATURE:
<223> OTHER INFORMATION: PfAg40 human CO

<400> SEQUENCE: 69

```
gccaccatgg ctgggtgtac agtctctaat ctcaaatgcg tgaccaatgt ggcaggactg      60
gcaagtctgg ttatcagtct gtttccgaaa ctcatcataa agaacccaca agtgcttcga     120
ccactgctga atgtgtcctg gggttatctg tttggtagca ccttttggct gtgcttcttc     180
tccgaagtag gactgcttcg cagcctgaag aacatgaaag gggtaccttt gcctgaatca     240
gccagtgagg cgaagaagct tctcgaagag atgaagaact ctgagggcga tttcaatcgg     300
agatcactgg acttccagta cttcttttcc ctcgctacgt tgttctcagg cattctgttg     360
ctgagcacag tgaagttggc caaccataac ctgcagctta ggcttagtag ctctgtggtc     420
gtcatcacat cactgctgaa tagcctgtat ctgcacaata aagtgcataa tctgaaaagc     480
aagaaagaaa gcctctataa cgactttatt gccaatccca agaacgagaa aactgtcgct     540
gatctgaaga agaacaagaa agagtttcac atctttcacg gattgtccgt tctctctctc     600
tacgtttcct tcttcggcct gactccctac attttcacct aa                       642
```

<210> SEQ ID NO 70
<211> LENGTH: 211
<212> TYPE: PRT
<213> ORGANISM: Plasmodium falciparum
<220> FEATURE:
<221> NAME/KEY: misc_feature
<223> OTHER INFORMATION: PfAg40

<400> SEQUENCE: 70

```
Met Ala Gly Cys Thr Val Ser Asn Leu Lys Cys Val Thr Asn Val Ala
1               5                   10                  15

Gly Leu Ala Ser Leu Val Ile Ser Leu Phe Pro Lys Leu Ile Ile Lys
            20                  25                  30

Asn Pro Gln Val Leu Arg Pro Leu Asn Val Ser Trp Gly Tyr Leu
        35                  40                  45

Phe Gly Ser Thr Phe Trp Leu Cys Phe Phe Ser Glu Val Gly Leu Leu
    50                  55                  60

Arg Ser Leu Lys Asn Met Lys Gly Val Pro Leu Pro Glu Ser Ala Ser
65                  70                  75                  80

Glu Ala Lys Lys Leu Leu Glu Glu Met Lys Asn Ser Glu Gly Asp Phe
                85                  90                  95

Asn Arg Arg Ser Leu Asp Phe Gln Tyr Phe Phe Ser Leu Ala Thr Leu
            100                 105                 110

Phe Ser Gly Ile Leu Leu Leu Ser Thr Val Lys Leu Ala Asn His Asn
        115                 120                 125

Leu Gln Leu Arg Leu Ser Ser Ser Val Val Val Ile Thr Ser Leu Leu
    130                 135                 140

Asn Ser Leu Tyr Leu His Asn Lys Val His Asn Leu Lys Ser Lys Lys
145                 150                 155                 160

Glu Ser Leu Tyr Asn Asp Phe Ile Ala Asn Pro Lys Asn Glu Lys Thr
                165                 170                 175

Val Ala Asp Leu Lys Lys Asn Lys Lys Glu Phe His Ile Phe His Gly
            180                 185                 190

Leu Ser Val Leu Ser Leu Tyr Val Ser Phe Phe Gly Leu Thr Pro Tyr
        195                 200                 205

Ile Phe Thr
    210
```

<210> SEQ ID NO 71

<211> LENGTH: 210
<212> TYPE: PRT
<213> ORGANISM: Plasmodium falciparum
<220> FEATURE:
<221> NAME/KEY: misc_feature
<223> OTHER INFORMATION: Ag40

<400> SEQUENCE: 71

Met Gly Cys Thr Val Ser Asn Leu Lys Cys Val Thr Asn Val Ala Gly
1               5                   10                  15
Leu Ala Ser Leu Val Ile Ser Leu Phe Pro Lys Leu Ile Ile Lys Asn
            20                  25                  30
Pro Gln Val Leu Arg Pro Leu Leu Asn Val Ser Trp Gly Tyr Leu Phe
        35                  40                  45
Gly Ser Thr Phe Trp Leu Cys Phe Phe Ser Glu Val Gly Leu Leu Arg
    50                  55                  60
Ser Leu Lys Asn Met Lys Gly Val Pro Leu Pro Glu Ser Ala Ser Glu
65                  70                  75                  80
Ala Lys Lys Leu Leu Glu Glu Met Lys Asn Ser Glu Gly Asp Phe Asn
                85                  90                  95
Arg Arg Ser Leu Asp Phe Gln Tyr Phe Phe Ser Leu Ala Thr Leu Phe
            100                 105                 110
Ser Gly Ile Leu Leu Leu Ser Thr Val Lys Leu Ala Asn His Asn Leu
        115                 120                 125
Gln Leu Arg Leu Ser Ser Ser Val Val Ile Thr Ser Leu Leu Asn
    130                 135                 140
Ser Leu Tyr Leu His Asn Lys Val His Asn Leu Lys Ser Lys Lys Glu
145                 150                 155                 160
Ser Leu Tyr Asn Asp Phe Ile Ala Asn Pro Lys Asn Glu Lys Thr Val
                165                 170                 175
Ala Asp Leu Lys Lys Asn Lys Lys Glu Phe His Ile Phe His Gly Leu
            180                 185                 190
Ser Val Leu Ser Leu Tyr Val Ser Phe Phe Gly Leu Thr Pro Tyr Ile
        195                 200                 205
Phe Thr
    210

<210> SEQ ID NO 72
<211> LENGTH: 639
<212> TYPE: DNA
<213> ORGANISM: Artificial Sequence
<220> FEATURE:
<223> OTHER INFORMATION: PvAg40 human CO + kozac

<400> SEQUENCE: 72
gccaccatgg gggcgacggt atcatatctt agatgcgtga ccagtatagc agggctgagc        60
agcctcgtgc tgtctttgtt tcccaagctg attatgaaaa accctcaggt actccgacca       120
ctccttaaca ttagctgggg ttatttgttt ggctcaacct tttggttgtg tttgttctcc       180
gaagtaggac ttttccggtc cctgaaaaat atgaagcgca taccaatccc tgaaaacgca       240
gaagaggcta agaagcaatt ggaggagatg aaaagcatgg aagggatttt accaggcgc        300 agggaagatt ccaatatttt ttttggtttt tccaccttgt tttctggtat tcttcttctc       360
agtacggtaa gacttgcgaa tcacaacatg caactgagga tttccagtac catcgttgcc       420
cttagctgcc tgctcaataa cttgtacctt cagaataagg tacattctct taaaatccaa       480
aaagaaaacc tgtacaacga actcatccgc aatcctaagt cagagacgac tatagcggag       540
attaagaaaa acaaaaaaga tttccatata taccacggct tgtccctgtt gtccctttac    600
ataagcttcc tcggccttac tccatatata tttacctag    639

<210> SEQ ID NO 73
<211> LENGTH: 210
<212> TYPE: PRT
<213> ORGANISM: Plasmodium vivax
<220> FEATURE:
<221> NAME/KEY: misc_feature
<223> OTHER INFORMATION: PvAg40

<400> SEQUENCE: 73

Met Gly Ala Thr Val Ser Tyr Leu Arg Cys Val Thr Ser Ile Ala Gly
1               5                   10                  15

Leu Ser Ser Leu Val Leu Ser Leu Phe Pro Lys Leu Ile Met Lys Asn
            20                  25                  30

Pro Gln Val Leu Arg Pro Leu Leu Asn Ile Ser Trp Gly Tyr Leu Phe
        35                  40                  45

Gly Ser Thr Phe Trp Leu Cys Leu Phe Ser Glu Val Gly Leu Phe Arg
    50                  55                  60

Ser Leu Lys Asn Met Lys Arg Ile Pro Ile Pro Glu Asn Ala Glu Glu
65                  70                  75                  80

Ala Lys Lys Gln Leu Glu Glu Met Lys Ser Met Glu Gly Asp Phe Thr
                85                  90                  95

Arg Arg Arg Glu Asp Phe Gln Tyr Phe Phe Gly Phe Ser Thr Leu Phe
            100                 105                 110

Ser Gly Ile Leu Leu Leu Ser Thr Val Arg Leu Ala Asn His Asn Met
        115                 120                 125

Gln Leu Arg Ile Ser Ser Thr Ile Val Ala Leu Ser Cys Leu Leu Asn
    130                 135                 140

Asn Leu Tyr Leu Gln Asn Lys Val His Ser Leu Lys Ile Gln Lys Glu
145                 150                 155                 160

Asn Leu Tyr Asn Glu Leu Ile Arg Asn Pro Lys Ser Glu Thr Thr Ile
                165                 170                 175

Ala Glu Ile Lys Lys Asn Lys Lys Asp Phe His Ile Tyr His Gly Leu
            180                 185                 190

Ser Leu Leu Ser Leu Tyr Ile Ser Phe Leu Gly Leu Thr Pro Tyr Ile
        195                 200                 205

Phe Thr
    210

<210> SEQ ID NO 74
<211> LENGTH: 210
<212> TYPE: PRT
<213> ORGANISM: Plasmodium vivax
<220> FEATURE:
<221> NAME/KEY: misc_feature
<223> OTHER INFORMATION: Ag40

<400> SEQUENCE: 74

Met Gly Ala Thr Val Ser Tyr Leu Arg Cys Val Thr Ser Ile Ala Gly
1               5                   10                  15

Leu Ser Ser Leu Val Leu Ser Leu Phe Pro Lys Leu Ile Met Lys Asn
            20                  25                  30

Pro Gln Val Leu Arg Pro Leu Leu Asn Ile Ser Trp Gly Tyr Leu Phe
        35                  40                  45

Gly Ser Thr Phe Trp Leu Cys Leu Phe Ser Glu Val Gly Leu Phe Arg
    50                  55                  60

```
Ser Leu Lys Asn Met Lys Arg Ile Pro Ile Pro Glu Asn Ala Glu Glu
 65                  70                  75                  80

Ala Lys Lys Gln Leu Glu Glu Met Lys Ser Met Glu Gly Asp Phe Thr
                 85                  90                  95

Arg Arg Arg Glu Asp Phe Gln Tyr Phe Phe Gly Phe Ser Thr Leu Phe
            100                 105                 110

Ser Gly Ile Leu Leu Leu Ser Thr Val Arg Leu Ala Asn His Asn Met
        115                 120                 125

Gln Leu Arg Ile Ser Ser Thr Ile Val Ala Leu Ser Cys Leu Leu Asn
130                 135                 140

Asn Leu Tyr Leu Gln Asn Lys Val His Ser Leu Lys Ile Gln Lys Glu
145                 150                 155                 160

Asn Leu Tyr Asn Glu Leu Ile Arg Asn Pro Lys Ser Glu Thr Thr Ile
                165                 170                 175

Ala Glu Ile Lys Lys Asn Lys Lys Asp Phe His Ile Tyr His Gly Leu
            180                 185                 190

Ser Leu Leu Ser Leu Tyr Ile Ser Phe Leu Gly Leu Thr Pro Tyr Ile
        195                 200                 205

Phe Thr
    210

<210> SEQ ID NO 75
<211> LENGTH: 1077
<212> TYPE: DNA
<213> ORGANISM: Plasmodium berghei
<220> FEATURE:
<221> NAME/KEY: misc_feature
<223> OTHER INFORMATION: Ag45

<400> SEQUENCE: 75
ggatccgcca ccatggcttc ttactcaaac tcttccatta agcagaaatc cgatagtgtg      60
agtgtctaca atactcggac tggaaatgtc agtaaaactc gcttgatccg tctgcaaaat     120
gggcattacc gtagagtggt cgacattagc aataaggacg agaaggagat tctcttcagg     180
acatgtgctt gcgcttgtcc aacacctcga aatgaggaga cacgcaaaac ctatatgcca     240
cctctgaaca atgtgtctac cgtagcgtat agaaagcgga tctattcttc ctttgggaat     300
aaggacggta acgatacagg caacaacgag agcataacag aacatgagga cccgattagg     360 acctttccg aaacgacaag taggcaggaa agtaccatcg acgacaaaac ggagactagc      420
atcaatagca aggaaacaga tgatggcaac cagtttggaa ggttgtttga agaactggag     480
gagaaagagg atgaactgat tgaggaaaag gaggaggagc tgatagaaga aggaggagag     540
gaacttatag aggagaaaga agaagagctg atcgaagaga aagaggaaat cacccctgag     600
aacaaaaccc tcataatgcc ctctaaaact ctgatgaagg gcattaagac caacatttac     660
ttcctgtcaa acaaggaaaa gatccaagtg cttatgtgct ataactacaa gtgtgatgcc     720
gttgtgttcg agaaagacac ctttctgcgc tatctctaca tcaagagcat caataatatc     780
atcctgaacg aaagaatgat tgaacagttg tgcaagaacg aaaacctgaa gtacatcctt     840
gcctgcaaca gcatagtggt tgaatcaagc gacttcatca acccctgat cattgagttt      900 gagtcatcca cttccaagaa catcttcgta agcacatta agcacaatag ccagaaagaa      960
atggacatca acaagttcaa cgagtatatg cgggatctca aaagcaatga gaagctcaga    1020
ctgaagaaag tcgagcgatt ccactctatt aatctggcag ccaagaaatg actcgag      1077
```

-continued

```
<210> SEQ ID NO 76
<211> LENGTH: 352
<212> TYPE: PRT
<213> ORGANISM: Plasmodium berghei
<220> FEATURE:
<221> NAME/KEY: misc_feature
<223> OTHER INFORMATION: Ag45

<400> SEQUENCE: 76

Met Ala Ser Tyr Ser Asn Ser Ser Ile Lys Gln Lys Ser Asp Ser Val
1               5                   10                  15

Ser Val Tyr Asn Thr Arg Thr Gly Asn Val Ser Lys Thr Arg Leu Ile
            20                  25                  30

Arg Leu Gln Asn Gly His Tyr Arg Arg Val Val Asp Ile Ser Asn Lys
        35                  40                  45

Asp Glu Lys Glu Ile Leu Phe Arg Thr Cys Ala Cys Ala Cys Pro Thr
    50                  55                  60

Pro Arg Asn Glu Glu Thr Arg Lys Thr Tyr Met Pro Pro Leu Asn Asn
65                  70                  75                  80

Val Ser Thr Val Ala Tyr Arg Lys Arg Ile Tyr Ser Ser Phe Gly Asn
                85                  90                  95

Lys Asp Gly Asn Asp Thr Gly Asn Asn Glu Ser Ile Thr Glu His Glu
            100                 105                 110

Asp Pro Ile Arg Thr Phe Ser Glu Thr Ser Arg Gln Glu Ser Thr
        115                 120                 125

Ile Asp Asp Lys Thr Glu Thr Ser Ile Asn Ser Lys Glu Thr Asp Asp
    130                 135                 140

Gly Asn Gln Phe Gly Arg Leu Phe Glu Glu Leu Glu Glu Lys Glu Asp
145                 150                 155                 160

Glu Leu Ile Glu Glu Lys Glu Glu Leu Ile Glu Glu Lys Glu Glu
                165                 170                 175

Glu Leu Ile Glu Glu Lys Glu Glu Leu Ile Glu Glu Lys Glu Glu
            180                 185                 190

Ile Thr Pro Glu Asn Lys Thr Leu Ile Met Pro Ser Lys Thr Leu Met
        195                 200                 205

Lys Gly Ile Lys Thr Asn Ile Tyr Phe Leu Ser Asn Lys Glu Lys Ile
    210                 215                 220

Gln Val Leu Met Cys Tyr Asn Tyr Lys Cys Asp Ala Val Val Phe Glu
225                 230                 235                 240

Lys Asp Thr Phe Leu Arg Tyr Leu Tyr Ile Lys Ser Ile Asn Asn Ile
                245                 250                 255

Ile Leu Asn Glu Arg Met Ile Glu Gln Leu Cys Lys Asn Glu Asn Leu
            260                 265                 270

Lys Tyr Ile Leu Ala Cys Asn Ser Ile Val Val Glu Ser Ser Asp Phe
        275                 280                 285

Ile Lys Pro Leu Ile Ile Glu Phe Glu Ser Ser Thr Ser Lys Asn Ile
    290                 295                 300

Phe Val Lys His Ile Lys His Asn Ser Gln Lys Glu Met Asp Ile Asn
305                 310                 315                 320

Lys Phe Asn Glu Tyr Met Arg Asp Leu Lys Ser Asn Glu Lys Leu Arg
                325                 330                 335

Leu Lys Lys Val Glu Arg Phe His Ser Ile Asn Leu Ala Ala Lys Lys
            340                 345                 350

<210> SEQ ID NO 77
<211> LENGTH: 351
```

```
<212> TYPE: PRT
<213> ORGANISM: Plasmodium berghei
<220> FEATURE:
<221> NAME/KEY: misc_feature
<223> OTHER INFORMATION: Ag45

<400> SEQUENCE: 77

Met Ser Tyr Ser Asn Ser Ser Ile Lys Gln Lys Ser Asp Ser Val Ser
1               5                   10                  15

Val Tyr Asn Thr Arg Thr Gly Asn Val Ser Lys Thr Arg Leu Ile Arg
            20                  25                  30

Leu Gln Asn Gly His Tyr Arg Arg Val Val Asp Ile Ser Asn Lys Asp
        35                  40                  45

Glu Lys Glu Ile Leu Phe Arg Thr Cys Ala Cys Ala Cys Pro Thr Pro
50                  55                  60

Arg Asn Glu Glu Thr Arg Lys Thr Tyr Met Pro Pro Leu Asn Asn Val
65                  70                  75                  80

Ser Thr Val Ala Tyr Arg Lys Arg Ile Tyr Ser Ser Phe Gly Asn Lys
                85                  90                  95

Asp Gly Asn Asp Thr Gly Asn Asn Glu Ser Ile Thr Glu His Glu Asp
            100                 105                 110

Pro Ile Arg Thr Phe Ser Glu Thr Thr Ser Arg Gln Glu Ser Thr Ile
        115                 120                 125

Asp Asp Lys Thr Glu Thr Ser Ile Asn Ser Lys Glu Thr Asp Asp Gly
130                 135                 140

Asn Gln Phe Gly Arg Leu Phe Glu Glu Leu Glu Glu Lys Glu Asp Glu
145                 150                 155                 160

Leu Ile Glu Glu Lys Glu Glu Glu Leu Ile Glu Glu Lys Glu Glu Glu
                165                 170                 175

Leu Ile Glu Glu Lys Glu Glu Glu Leu Ile Glu Glu Lys Glu Glu Ile
            180                 185                 190

Thr Pro Glu Asn Lys Thr Leu Ile Met Pro Ser Lys Thr Leu Met Lys
        195                 200                 205

Gly Ile Lys Thr Asn Ile Tyr Phe Leu Ser Asn Lys Glu Lys Ile Gln
210                 215                 220

Val Leu Met Cys Tyr Asn Tyr Lys Cys Asp Ala Val Val Phe Glu Lys
225                 230                 235                 240

Asp Thr Phe Leu Arg Tyr Leu Tyr Ile Lys Ser Ile Asn Asn Ile Ile
                245                 250                 255

Leu Asn Glu Arg Met Ile Glu Gln Leu Cys Lys Asn Glu Asn Leu Lys
            260                 265                 270

Tyr Ile Leu Ala Cys Asn Ser Ile Val Val Glu Ser Ser Asp Phe Ile
        275                 280                 285

Lys Pro Leu Ile Ile Glu Phe Glu Ser Ser Thr Ser Lys Asn Ile Phe
290                 295                 300

Val Lys His Ile Lys His Asn Ser Gln Lys Glu Met Asp Ile Asn Lys
305                 310                 315                 320

Phe Asn Glu Tyr Met Arg Asp Leu Lys Ser Asn Glu Lys Leu Arg Leu
                325                 330                 335

Lys Lys Val Glu Arg Phe His Ser Ile Asn Leu Ala Ala Lys Lys
            340                 345                 350

<210> SEQ ID NO 78
<211> LENGTH: 1197
<212> TYPE: DNA
<213> ORGANISM: Artificial Sequence
```

<220> FEATURE:
<223> OTHER INFORMATION: PfAg45 human CO

<400> SEQUENCE: 78

```
gccaccatgg cttcagatta ctttacaatt ctgtccaata ttttcacaag cactagcctg      60
aagaagaaat acagttcccg ttgagcaca aatccaaga agaaccaaaa gcgagtcaaa       120
ctgataagac tgcggaatgg acattttcgc cgaattgtgg atatttccaa cattgacgag     180
aagagcatct tccccagaag ctgtactttt gcgtcaatta gcagtgctag caaagaaaac     240
gagaggaaga attcaagcga ggacacaaaa gaacctcagg agaatctgta tggcaaatca     300
aacacttcaa gctctatcac gataaagatc aatttcgacg aaagcgatga gaacaagagt     360
gatcaggata ccactctat cgataccatt agcgacatct cttttaccca gacttcacgc      420
aaatctcttg aaattgaaag taatacctat gagagttatc gcgaagtgga aggaggagac    480
attgaggagg aggaggaaga ggagaaagaa gaagaatatg aggaggaaga agaagaagag   540
gaatacgaag aggaagagga agaagaggag gaagagtatg aggaggaggg tctgaaaacc   600
gaagaggaga aggaagaaga taataaggag gtagagccag aagaggagct aaagaagaa     660
gatgacaagg aggttgagcc tgaggaggag aaggagaatg agcagaagaa agaagaacaa    720
gaggagaata acctcgaagc tcccagcaaa acactgatga aggggttaa gaccaacata      780
tacttcctgt ctaccaaaga gcggatagaa gcactcatgt gctacaacta catatccaac     840
gccattattt tcgaaaaggg caagtttctc cgttatatct tcatgaacaa tgtcaacaat     900
atcatcgtga acgagcacat gatcaatatg ttgtgcaaga aggaaaagat caaatacatc    960
ctgtcatcta actccatcat cattgaaagc aacgacttca tcaaaccgct catcattgag     1020
tttgacagta acatctctaa gaagatcttt gtcaaacact tgaaaatggt ggactccttc     1080
aaactggatg acaagctgta cagggagtac ctgaatgacc tttctgaaca tgagagggat    1140
agactgaaac atgtggagtc cttctattcc aatgccataa aggtgcacaa tacgtaa       1197
```

<210> SEQ ID NO 79
<211> LENGTH: 396
<212> TYPE: PRT
<213> ORGANISM: Plasmodium falciparum
<220> FEATURE:
<221> NAME/KEY: misc_feature
<223> OTHER INFORMATION: PfAg45

<400> SEQUENCE: 79

```
Met Ala Ser Asp Tyr Phe Thr Ile Leu Ser Asn Ile Phe Thr Ser Thr
1               5                   10                  15

Ser Leu Lys Lys Lys Tyr Ser Ser Arg Leu Ser Thr Lys Ser Lys Lys
            20                  25                  30

Asn Gln Lys Arg Val Lys Leu Ile Arg Leu Arg Asn Gly His Phe Arg
        35                  40                  45

Arg Ile Val Asp Ile Ser Asn Ile Asp Glu Lys Ser Ile Phe Pro Arg
    50                  55                  60

Ser Cys Thr Phe Ala Ser Ile Ser Ser Ala Ser Lys Glu Asn Glu Arg
65                  70                  75                  80

Lys Asn Ser Ser Glu Asp Thr Lys Glu Pro Gln Glu Asn Leu Tyr Gly
                85                  90                  95

Lys Ser Asn Thr Ser Ser Ser Ile Thr Ile Lys Ile Asn Phe Asp Glu
            100                 105                 110

Ser Asp Glu Asn Lys Ser Asp Gln Asp Asn His Ser Ile Asp Thr Ile
        115                 120                 125
```

Ser Asp Ile Ser Phe Thr Gln Thr Ser Arg Lys Ser Leu Glu Ile Glu
        130                 135                 140

Ser Asn Thr Tyr Glu Ser Tyr Arg Glu Val Glu Lys Glu Asp Ile Glu
145                 150                 155                 160

Glu Glu Glu Glu Glu Glu Lys Glu Glu Tyr Glu Glu Glu Glu Glu Glu
                165                 170                 175

Glu Glu Glu Tyr Glu Glu Glu Glu Glu Glu Glu Glu Glu Glu Tyr Glu
            180                 185                 190

Glu Glu Gly Leu Lys Thr Glu Glu Lys Glu Glu Asp Asn Lys Glu
        195                 200                 205

Val Glu Pro Glu Glu Leu Lys Glu Glu Asp Asp Lys Glu Val Glu
210                 215                 220

Pro Glu Glu Lys Glu Asn Glu Gln Lys Lys Glu Glu Gln Glu Glu
225                 230                 235                 240

Asn Asn Leu Glu Ala Pro Ser Lys Thr Leu Met Lys Gly Val Lys Thr
            245                 250                 255

Asn Ile Tyr Phe Leu Ser Thr Lys Glu Arg Ile Glu Ala Leu Met Cys
            260                 265                 270

Tyr Asn Tyr Ile Ser Asn Ala Ile Ile Phe Glu Lys Gly Lys Phe Leu
            275                 280                 285

Arg Tyr Ile Phe Met Asn Asn Val Asn Asn Ile Ile Val Asn Glu His
        290                 295                 300

Met Ile Asn Met Leu Cys Lys Lys Glu Lys Ile Lys Tyr Ile Leu Ser
305                 310                 315                 320

Ser Asn Ser Ile Ile Ile Glu Ser Asn Asp Phe Ile Lys Pro Leu Ile
            325                 330                 335

Ile Glu Phe Asp Ser Asn Ile Ser Lys Lys Ile Phe Val Lys His Leu
        340                 345                 350

Lys Met Val Asp Ser Phe Lys Leu Asp Asp Lys Leu Tyr Arg Glu Tyr
            355                 360                 365

Leu Asn Asp Leu Ser Glu His Glu Arg Asp Arg Leu Lys His Val Glu
        370                 375                 380

Ser Phe Tyr Ser Asn Ala Ile Lys Val His Asn Thr
385                 390                 395

<210> SEQ ID NO 80
<211> LENGTH: 395
<212> TYPE: PRT
<213> ORGANISM: Plasmodium falciparum
<220> FEATURE:
<221> NAME/KEY: misc_feature
<223> OTHER INFORMATION: Ag45

<400> SEQUENCE: 80

Met Ser Asp Tyr Phe Thr Ile Leu Ser Asn Ile Phe Thr Ser Thr Ser
1               5                   10                  15

Leu Lys Lys Lys Tyr Ser Ser Arg Leu Ser Thr Lys Ser Lys Lys Asn
            20                  25                  30

Gln Lys Arg Val Lys Leu Ile Arg Leu Arg Asn Gly His Phe Arg Arg
        35                  40                  45

Ile Val Asp Ile Ser Asn Ile Asp Glu Lys Ser Ile Phe Pro Arg Ser
    50                  55                  60

Cys Thr Phe Ala Ser Ile Ser Ser Ala Ser Lys Glu Asn Glu Arg Lys
65                  70                  75                  80

Asn Ser Ser Glu Asp Thr Lys Glu Pro Gln Glu Asn Leu Tyr Gly Lys

|     |     | 85  |     |     |     | 90  |     |     |     | 95  |     |
| --- | --- | --- | --- | --- | --- | --- | --- | --- | --- | --- | --- |

Ser Asn Thr Ser Ser Ser Ile Thr Ile Lys Ile Asn Phe Asp Glu Ser
                100                 105                 110

Asp Glu Asn Lys Ser Asp Gln Asp Asn His Ser Ile Asp Thr Ile Ser
            115                 120                 125

Asp Ile Ser Phe Thr Gln Thr Ser Arg Lys Ser Leu Glu Ile Glu Ser
130                 135                 140

Asn Thr Tyr Glu Ser Tyr Arg Glu Val Glu Lys Glu Asp Ile Glu Glu
145                 150                 155                 160

Glu Glu Glu Glu Glu Lys Glu Glu Tyr Glu Glu Glu Glu Glu Glu Glu
                165                 170                 175

Glu Glu Tyr Glu Glu Glu Glu Glu Glu Glu Glu Glu Glu Tyr Glu Glu
                180                 185                 190

Glu Gly Leu Lys Thr Glu Glu Lys Glu Glu Asp Asn Lys Glu Val
                195                 200                 205

Glu Pro Glu Glu Glu Leu Lys Glu Glu Asp Asp Lys Glu Val Glu Pro
    210                 215                 220

Glu Glu Glu Lys Glu Asn Glu Gln Lys Lys Glu Glu Gln Glu Glu Asn
225                 230                 235                 240

Asn Leu Glu Ala Pro Ser Lys Thr Leu Met Lys Gly Val Lys Thr Asn
                245                 250                 255

Ile Tyr Phe Leu Ser Thr Lys Glu Arg Ile Glu Ala Leu Met Cys Tyr
                260                 265                 270

Asn Tyr Ile Ser Asn Ala Ile Ile Phe Glu Lys Gly Lys Phe Leu Arg
                275                 280                 285

Tyr Ile Phe Met Asn Asn Val Asn Asn Ile Ile Val Asn Glu His Met
                290                 295                 300

Ile Asn Met Leu Cys Lys Lys Glu Lys Ile Lys Tyr Ile Leu Ser Ser
305                 310                 315                 320

Asn Ser Ile Ile Ile Glu Ser Asn Asp Phe Ile Lys Pro Leu Ile Ile
                325                 330                 335

Glu Phe Asp Ser Asn Ile Ser Lys Lys Ile Phe Val Lys His Leu Lys
                340                 345                 350

Met Val Asp Ser Phe Lys Leu Asp Asp Lys Leu Tyr Arg Glu Tyr Leu
                355                 360                 365

Asn Asp Leu Ser Glu His Glu Arg Asp Arg Leu Lys His Val Glu Ser
                370                 375                 380

Phe Tyr Ser Asn Ala Ile Lys Val His Asn Thr
385                 390                 395

<210> SEQ ID NO 81
<211> LENGTH: 1122
<212> TYPE: DNA
<213> ORGANISM: Artificial Sequence
<220> FEATURE:
<223> OTHER INFORMATION: PvAg45 human CO + kozac

<400> SEQUENCE: 81
gccaccatgg ctaatttgag ttctcccctc ctggccttgc ccgaggaggg taagaagcga     60
agaacaaaac tcatccgact gaggaacggt cactataggc ggatagtgga catttcaaat    120
accgacgaac ggaagctcat tccttctatg tgccgctgcg cgtgtgtcac tcccagaaaa    180
gacgaagtgg agaatgaggg taagtgggaa gacgctaaga agcaaaaatc aagccaggaa    240
tatgatgaaa cttctgatta tgttgaatct gaaaagaaag agagctatat gctcgcagtc    300

```
aatgaggagg atcgacggga ggatatgtac tcaaagacga tcagctttac ttctataacc    360
cctacatcta taagatccga agagccagag ccaaggcgga aactctccct tctggatgtt    420
aaagaagaag aggaagagga ggaggaggaa gaagaagagg aagaagagga agaggaggaa    480
gaggaagagg aagaagagga agagaaagaa aaagaaaaag agaaggagga agaggaagaa    540
gaggaggagg aagaggaaga ggaagaggag gaggaagaag aagaggaaga tgaaatagaa    600
tctaccgcag aggaaaagga agaagagaag aagcaagtcc caccggaagg taagaaattg    660
atcgaaccct caaagaccct tatgagaggg actaagacca acatttattt tttgagtaat    720
aaggagatgg ttcaaactct gatgtgttat aattataatt gcaacgcagt ggtattcgaa    780
aaagacactt ttttgaggta tctgtacatg aagagcatca gcaacatcat cctcaacgaa    840
cgaatgatag atgaactgtg caaacaggaa gatcttaaat acgtgcttac aagcaatgct    900
atcgtgttgg aatctactga ctttcttaag cctcttataa ttgagtttga atccagtatt    960
agtaaaagag ttttcgtgcg ccacctgaag cataacgctc gcaaggaaat cgacatgaaa   1020
aaatatcatg attacatggg cgaacttaac gctaacgaga agattaggct gatgaaaatt   1080
gagcgatttc atagtttcaa caagatgatc caatgcaact ag                     1122

<210> SEQ ID NO 82
<211> LENGTH: 371
<212> TYPE: PRT
<213> ORGANISM: Plasmodium vivax
<220> FEATURE:
<221> NAME/KEY: misc_feature
<223> OTHER INFORMATION: PvAg45

<400> SEQUENCE: 82

Met Ala Asn Leu Ser Ser Pro Leu Leu Ala Leu Pro Glu Glu Gly Lys
1               5                   10                  15

Lys Arg Arg Thr Lys Leu Ile Arg Leu Arg Asn Gly His Tyr Arg Arg
            20                  25                  30

Ile Val Asp Ile Ser Asn Thr Asp Glu Arg Lys Leu Ile Pro Ser Met
        35                  40                  45

Cys Arg Cys Ala Cys Val Thr Pro Arg Lys Asp Glu Val Glu Asn Glu
    50                  55                  60

Gly Lys Trp Glu Asp Ala Lys Lys Ala Lys Ser Ser Gln Glu Tyr Asp
65                  70                  75                  80

Glu Thr Ser Asp Tyr Val Glu Ser Glu Lys Glu Ser Tyr Met Leu
                85                  90                  95

Ala Val Asn Glu Glu Asp Gln Thr Glu Asp Met Tyr Ser Lys Thr Ile
            100                 105                 110

Ser Phe Thr Ser Ile Thr Pro Thr Ser Ile Arg Ser Glu Glu Pro Glu
        115                 120                 125

Pro Arg Arg Lys Leu Ser Leu Leu Asp Val Lys Glu Glu Glu Glu Glu
    130                 135                 140

Glu Glu Glu Glu Glu Glu Glu Glu Glu Glu Glu Glu Glu Glu Glu Glu
145                 150                 155                 160

Glu Glu Glu Glu Glu Glu Lys Glu Lys Glu Lys Glu Lys Glu Glu
                165                 170                 175

Glu Glu Glu Glu Glu Glu Glu Glu Glu Glu Glu Glu Glu Glu Glu Glu
            180                 185                 190

Glu Glu Asp Glu Ile Glu Ser Thr Ala Glu Lys Glu Glu Glu Lys
        195                 200                 205

Lys Gln Val Pro Pro Glu Gly Lys Lys Leu Ile Glu Pro Ser Lys Thr
```

```
                210                 215                 220
Leu Met Arg Gly Thr Lys Thr Asn Ile Tyr Phe Leu Ser Asn Lys Glu
225                 230                 235                 240

Met Val Gln Thr Leu Met Cys Tyr Asn Tyr Asn Cys Asn Ala Val Val
                245                 250                 255

Phe Glu Lys Asp Thr Phe Leu Arg Tyr Leu Tyr Met Lys Ser Ile Ser
                260                 265                 270

Asn Ile Ile Leu Asn Glu Arg Met Ile Asp Glu Leu Cys Lys Gln Glu
                275                 280                 285

Asp Leu Lys Tyr Val Leu Thr Ser Asn Ala Ile Val Leu Glu Ser Thr
290                 295                 300

Asp Phe Leu Lys Pro Leu Ile Ile Glu Phe Glu Ser Ser Ile Ser Lys
305                 310                 315                 320

Arg Val Phe Val Arg His Leu Lys His Asn Ala Arg Lys Glu Ile Asp
                325                 330                 335

Met Lys Lys Tyr His Asp Tyr Met Gly Glu Leu Asn Ala Asn Glu Lys
                340                 345                 350

Ile Arg Leu Met Lys Ile Glu Arg Phe His Ser Phe Asn Lys Met Ile
                355                 360                 365

Gln Cys Asn
    370

<210> SEQ ID NO 83
<211> LENGTH: 345
<212> TYPE: PRT
<213> ORGANISM: Plasmodium vivax
<220> FEATURE:
<221> NAME/KEY: misc_feature
<223> OTHER INFORMATION: Ag45

<400> SEQUENCE: 83

Met Asn Leu Ser Ser Pro Leu Leu Ala Leu Pro Glu Glu Gly Lys Lys
1               5                   10                  15

Arg Arg Thr Lys Leu Ile Arg Leu Arg Asn Gly His Tyr Arg Arg Ile
                20                  25                  30

Val Asp Ile Ser Asn Thr Asp Glu Arg Lys Leu Ile Pro Ser Met Cys
                35                  40                  45

Arg Cys Ala Cys Val Thr Pro Arg Lys Asp Glu Val Glu Asn Glu Gly
                50                  55                  60

Lys Trp Glu Asp Ala Lys Lys Ala Lys Ser Ser Gln Glu Tyr Asp Glu
65                  70                  75                  80

Thr Ser Asp Tyr Val Glu Ser Glu Lys Lys Glu Ser Tyr Met Leu Ala
                85                  90                  95

Val Asn Glu Glu Asp Gln Thr Glu Asp Met Tyr Ser Lys Thr Ile Ser
                100                 105                 110

Phe Thr Ser Ile Thr Pro Thr Ser Ile Arg Ser Glu Glu Pro Glu Pro
                115                 120                 125

Arg Arg Lys Leu Ser Leu Leu Asp Val Lys Glu Glu Glu Glu Glu Glu
                130                 135                 140

Glu Glu Glu Glu Glu Glu Glu Glu Glu Glu Glu Glu Glu Glu Glu Glu
145                 150                 155                 160

Glu Lys Glu Glu Glu Glu Glu Asp Glu Ile Glu Ser Thr Ala Glu
                165                 170                 175

Glu Lys Glu Glu Glu Lys Lys Gln Val Pro Pro Glu Gly Lys Lys Leu
                180                 185                 190
```

-continued

```
Ile Glu Pro Ser Lys Thr Leu Met Arg Gly Thr Lys Thr Asn Ile Tyr
            195                 200                 205
Phe Leu Ser Asn Lys Glu Met Val Gln Thr Leu Met Cys Tyr Asn Tyr
        210                 215                 220
Asn Cys Asn Ala Val Val Phe Glu Lys Asp Thr Phe Leu Arg Tyr Leu
225                 230                 235                 240
Tyr Met Lys Ser Ile Ser Asn Ile Ile Leu Asn Glu Arg Met Ile Asp
                245                 250                 255
Glu Leu Cys Lys Gln Glu Asp Leu Lys Tyr Val Leu Thr Ser Asn Ala
            260                 265                 270
Ile Val Leu Glu Ser Thr Asp Phe Leu Lys Pro Leu Ile Glu Phe
        275                 280                 285
Glu Ser Ser Ile Ser Lys Arg Val Phe Val Arg His Leu Lys His Asn
    290                 295                 300
Ala Arg Lys Glu Ile Asp Met Lys Lys Tyr His Asp Tyr Met Gly Glu
305                 310                 315                 320
Leu Asn Ala Asn Glu Lys Ile Arg Leu Met Lys Ile Glu Arg Phe His
                325                 330                 335
Ser Phe Asn Lys Met Ile Gln Cys Asn
                340                 345
```

<210> SEQ ID NO 84
<211> LENGTH: 12
<212> TYPE: DNA
<213> ORGANISM: Artificial Sequence
<220> FEATURE:
<223> OTHER INFORMATION: Kozac consensus sequence

<400> SEQUENCE: 84
gccaccatgg ct                                                          12

<210> SEQ ID NO 85
<211> LENGTH: 12
<212> TYPE: DNA
<213> ORGANISM: Artificial Sequence
<220> FEATURE:
<223> OTHER INFORMATION: Kozac consensus sequence

<400> SEQUENCE: 85
gccaccatgg cc                                                          12

<210> SEQ ID NO 86
<211> LENGTH: 6
<212> TYPE: DNA
<213> ORGANISM: Artificial Sequence
<220> FEATURE:
<223> OTHER INFORMATION: BamHI site

<400> SEQUENCE: 86 ggatcc                                                                  6

<210> SEQ ID NO 87
<211> LENGTH: 6
<212> TYPE: DNA
<213> ORGANISM: Artificial Sequence
<220> FEATURE:
<223> OTHER INFORMATION: XhoI site

<400> SEQUENCE: 87 ctcgag                                                                  6

```
<210> SEQ ID NO 88
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 88

Gln Ala Gln Arg Asn Leu Asn Glu Leu
1               5

<210> SEQ ID NO 89
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 89

Ser Ala Leu Leu Asn Val Asp Asn Leu
1               5

<210> SEQ ID NO 90
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 90

Lys Ser Pro Ser Asn Phe Thr Ile Ile
1               5

<210> SEQ ID NO 91
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 91

Ser Asn Gln Thr Asn Gln Glu Thr Ile
1               5

<210> SEQ ID NO 92
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 92

Ile Thr Pro Glu Asn Lys Thr Leu Ile
1               5

<210> SEQ ID NO 93
<211> LENGTH: 9
<212> TYPE: PRT
<213> ORGANISM: Artificial Sequence
<220> FEATURE:
<223> OTHER INFORMATION: CD8 T cell epitope
```

```
<400> SEQUENCE: 93

Lys Leu Ile Ala Asn Asn Pro Ser Leu
1               5

<210> SEQ ID NO 94
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 94

Ser Cys Ile Leu Asn Asn Met Tyr Phe
1               5
```